(12) United States Patent
Carter et al.

(10) Patent No.: US 6,974,836 B2
(45) Date of Patent: Dec. 13, 2005

(54) DIAMINES AS MODULATORS OF CHEMOKINE RECEPTOR ACTIVITY

(75) Inventors: Percy Carter, Wilmington, DE (US); Robert Cherney, Newark, DE (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 73 days.

(21) Appl. No.: 10/027,505

(22) Filed: Dec. 20, 2001

(65) Prior Publication Data

US 2003/0060459 A1 Mar. 27, 2003

Related U.S. Application Data

(60) Provisional application No. 60/256,855, filed on Dec. 20, 2000.

(51) Int. Cl.[7] .................... C07C 237/22; C07D 209/14; A61K 31/165; A61K 31/33
(52) U.S. Cl. .................. 514/616; 514/617; 514/618; 564/154; 564/155; 564/158
(58) Field of Search ................... 564/154, 155, 564/158; 514/616, 617, 618

(56) References Cited

U.S. PATENT DOCUMENTS

| | | | |
|---|---|---|---|
| 5,538,997 A | * | 7/1996 | Billich et al. ............... 514/510 |
| 5,710,171 A | | 1/1998 | Dinsmore et al. |
| 5,770,620 A | | 6/1998 | Mjalli et al. |
| 5,981,491 A | | 11/1999 | Baxter et al. |
| 6,011,052 A | | 1/2000 | Padia et al. |
| 6,028,087 A | | 2/2000 | Bondinell et al. |
| 6,030,946 A | | 2/2000 | Klaus et al. |
| 6,048,861 A | | 4/2000 | Askew et al. |
| 6,084,065 A | | 7/2000 | Cammaggi et al. |
| 6,100,423 A | | 8/2000 | Collins et al. |
| 6,162,790 A | | 12/2000 | Bemis et al. |
| 6,706,712 B2 | | 3/2004 | Cherney |
| 2003/0216434 A1 | | 11/2003 | Cherney |
| 2004/0110736 A1 | | 6/2004 | Cherney |
| 2004/0185143 A1 | | 9/2004 | Carter et al. |
| 2004/0235835 A1 | | 11/2004 | Carter |
| 2004/0235836 A1 | | 11/2004 | Cherney |

FOREIGN PATENT DOCUMENTS

| | | | |
|---|---|---|---|
| EP | 0264795 | | 10/1987 |
| EP | 443862 | * | 8/1991 |
| EP | 0731107 | | 2/1996 |
| JP | 377869 | | 3/1991 |
| WO | 93/15047 | | 8/1993 |
| WO | 94/03479 | | 2/1994 |
| WO | 96/22966 | | 8/1996 |
| WO | 97/00894 | | 1/1997 |
| WO | WO 9708145 | | 3/1997 |
| WO | WO 97/08145 | * | 3/1997 |
| WO | 97/44329 | | 11/1997 |
| WO | 98/06703 | | 2/1998 |
| WO | 99/07351 | | 2/1999 |
| WO | 99/07678 | | 2/1999 |
| WO | 99/17790 | | 4/1999 |
| WO | 99/25686 | | 5/1999 |
| WO | 99/40913 | | 8/1999 |
| WO | 99/40914 | | 8/1999 |
| WO | WO 99/46991 | | 9/1999 |
| WO | 00/42071 | | 7/2000 |
| WO | 00/46196 | | 8/2000 |
| WO | 00/69815 | | 11/2000 |
| WO | 00/69820 | | 11/2000 |
| WO | WO 02060859 | | 8/2002 |
| WO | WO 03075853 | | 9/2003 |
| WO | WO 2004071449 | | 8/2004 |
| WO | WO 2004071460 | | 8/2004 |
| WO | WO 2004098512 | | 11/2004 |
| WO | WO 2004098516 | | 11/2004 |

OTHER PUBLICATIONS

Ruminski et al., Chem. Abstract 126:264011, 1997.*
Aleman et al., PubMed Abstract (Antivir. Ther. 4(2):109–15), 1999.*
Farber, PubMed Abstract (Braz. J. Med. Biol. Res. 31(1):11–7), Jan. 1998.*
Havlioglu et al., Slit proteins potential endogenous modulators of inflammation, Journal of Neurovirology, 8: 486–495, 2002.*
Casanova et al., PubMed Abstract (Rev Neurol. 28(9):909–15), May 1999.*
Bremner et al., Therapy of Crohn's Disease in childhood, Expert Opin. Pharmacother. 3(7):809–825, 2002.*
Beers et al., Crohn's Disease; Ulcerative Colitis; Psoriasis, The Merck Manual of Diagnosis and Therapy, Seventeenth Edition (online), 1999.*
Robinson et al., Medical Therapy of Inflammatory Bowel Disease for the 21st Century, Eur J Surg Suppl 582:90–98, 1998.*
Singh et al., Immune Therapy in inflammatory bowel disease and models of colitis, British Journal of Surgery, 88, pp. 1558–1569, 2001.*
U.S. Appl. No. 10/922,406, filed Aug. 19, 2004, Carter et al.
U.S. Appl. No. 10/923,619, filed Aug. 19, 2004, Carter et al.
U.S. Appl. No. 10/922,726, filed Aug. 19, 2004, Carter et al.

(Continued)

*Primary Examiner*—Deepak Rao
(74) *Attorney, Agent, or Firm*—Mary Van Atten

(57) ABSTRACT

The present application describes modulators of MCP-1 of formula (I):

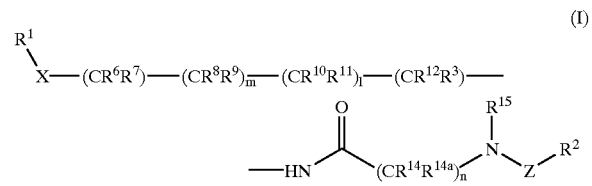

or pharmaceutically acceptable salt forms thereof, useful for the prevention of asthma, multiple sclerosis, artherosclerosis, and rheumatoid arthritis.

26 Claims, No Drawings

OTHER PUBLICATIONS

U.S. Appl. No. 10/923,538, filed Aug. 19, 2004, Carter et al.
U.S. Appl. No. 10/776,828, filed Feb. 11, 2004, Cherney et al.
Baba et al., A Small–Molecule, Nonpeptide CCR5 Antagonist With Hihgly Potent and Selective Anti–HIV–1 Activity Proc. Natl. Acad. Sci., May 1999, vol. 96, pp. 5698–5703.
Forbes, et al., CCR2B Receptor Antagonists: Conversion of a Weak HTS it to a Potent Lead Compound, Bioorganic and Medicinal Chemistry Letters, 2000, vol. 10, pp. 1803–1806.
Mirzadegan, et al. Identification of the Binding Site for a Novel Class of CCR2b Chemokine Receptor Antagonists, The Journal of Biologoical Chemistry, 2000, vol. 275 No. 33, pp. 25562–25571.
K. J. Kennedy et al., "Acute and relapsing experimental autoimmune encephalomyelitis are regulated by differential expression of the CC chemokines macrophage inflammatory protein–1α and monocyte chemotactic protein–1", Journal of Neuroimmunology, vol. 92, pp. 98–108, 1998.
Fife et al., "CC Chemokine Receptor 2 Is Critical for Induction of Experimental Autoimmune Encephalomyelitis", J. Exp. Med., vol. 192, No. 6, pp. 899–905, 2000.
Izikson et al., "Resistance to Experimental Autoimmune Encephalomyelitis in Mice Lacking the CC Chemokine Receptor (CCR)2", J. Exp. Med., vol.. 192, No. 7, pp. 1075–1080, 2000.
Tesch et al., "Monocyte Chemoattractant Protein 1–dependent Leukocytic Infiltrates Are Responsible for Autoimmune Disease in MRL–FAS$^{lpr\ Mice}$", J. Exp.; Med., vol. 190, No. 12, pp. 1813–1824, 1999.
Andres et al., "Mice with a Selective Deletion of the CC Chemokine Receptors 5 or 2 Are Protected from Dextran Sodium Sulfate–Mediated Colitis: Lack of CC Chemokine Receptor 5 Expression Results in a NK1.1$^+$Lymphocyte–Associated Th2–Type Immune Response in the Intestine," The Journal of Immunology, vol. 164, pp. 6303–6312, 2000.

Jones et al., "Potential Role of Monocyte Chemoattractant Protein 1/JE in Monocyte/Macrophage–Dependent IgA Immune Complex Alveolitis in the Rat$^{1}$", The Journal of Immunology, vol. 149, No. 6, pp. 2147–2154, 1992.
Reinecker et al., "Monocyte–Chemoattractant Protein 1 Gene Expression in Intestinal Epithelial Cells and Inflammatory Bowel Disease Mucosa", Gastroenterology, vol. 108, No. 1, pp. 40–50, 1995.
Grimm et al., "Enhanced Expression and Production of Monocyte Chemoattractant Protein–1 in Inflammatory Bowel Disease Mucosa", Journal of Leukocyte Biology, vol. 59, pp. 804–812, 1996.
Russell et al., "Early and Persistent Induction of Monocyte Chemoattractant Protein 1 in Rat Cardiac Allografts", Proc. Natl. Acad. Sci., vol. 90, pp. 6086–6090, 1993.
Antoniades et al., "Expression of Monocyte Chemoattractant Protein 1 mRNA in Human Idiopathic Pulmonary Fibrosis", Proc. Natl. Acad. Sci., vol. 89, pp. 5371–5375, 1992.
Deleuran et al., "Localization of Monocyte Chemotactic and Activating Factor (MCAF/MCP–1) in Psoriasis", Journal of Dermatological Science, vol. 13, pp. 228–236, 1996.
Gillitzer et al., "MCP–1 in mRNA Expression in Basal Keratinocytes of Psoriatic Lesions", The Journal of Investigative Dermatology, vol. 101, No. 2, pp. 127–131, 1993.
Connor et al., "Change in Coreceptor Use Correlates with Disease Progression in HIV–1–Infected Individuals", J. Exp. Med., vol. 185, No. 4, pp. 621–628, 1997.
Smith et al., "Contrasting Genetic Influence of CCR2 and CCR5 Variants of HIV–1 Infection and Disease Progression", Science, vol. 277, pp. 959–964, 1997.

* cited by examiner

US 6,974,836 B2

DIAMINES AS MODULATORS OF CHEMOKINE RECEPTOR ACTIVITY

This application claims the benefit of U.S. Provisional Application No. 60/256,855 filed Dec. 20, 2000.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, asthma, rheumatoid arthritis, atherosclerosis, and multiple sclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in: Luster, New Eng. J. Med. 1998, 338, 436–445 and Rollins, Blood 1997, 90, 909–928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in: Horuk, Trends Pharm. Sci. 1994, 15, 159–165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell 1993, 72, 415–425, and Luster, New Eng. J. Med. 1998, 338, 436–445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., Proc. Natl. Acad. Sci. USA 1994, 91, 2752–2756, and Luster, New Eng. J. Med. 1998, 338, 436–445); CCR-3 (or "CKR-3" or "CC-CKR-3") [eotaxin-1, eotaxin-2, RANTES, MCP-3, MCP-4] (Combadiere, et al., J. Biol. Chem. 1995, 270, 16491–16494, and Luster, New Eng. J. Med. 1998, 338, 436–445); CCR-4 (or "CKR-4" or "CC-CKR-4") [TARC, MIP-1α, RANTES, MCP-1] (Power, et al., J. Biol. Chem. 1995, 270, 19495–19500, and Luster, New Eng. J. Med. 1998, 338, 436–445); CCR-5 (or "CKR-5" OR "CC-CKR-5") [MIP-1α, RANTES, MIP-1β] (Sanson, et al., Biochemistry 1996, 35, 3362–3367); CCR-6 (or "CKR-6" or "CC-CKR-6") [LARC] (Baba, et al., J. Biol. Chem. 1997, 272, 14893–14898); CCR-7 (or "CKR-7" or "CC-CKR-7") [ELC] (Yoshie et al., J. Leukoc. Biol. 1997, 62, 634–644); CCR-8 (or "CKR-8" or "CC-CKR-8") [I-309, TARC, MIP-1β] (Napolitano et al., J. Immunol., 1996, 157, 2759–2763, and Bernardini, et al., Eur. J. Immunol. 1998, 28, 582–588); CCR-10 (or "CKR-10" or "CC-CKR-10") [MCP-1, MCP-3] (Bonini, et al., DNA and Cell Biol. 1997, 16, 1249–1256); and CCR-11 [MCP-1, MCP-2, and MCP-4] (Schweickert, et al., J. Biol. Chem. 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, Curr. Opin. Biotech. 1997, 8, 741–748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: Bharat K. Trivedi, et al, Ann. Reports Med. Chem. 2000, 35, 191; John Saunders and Christine M. Tarby, Drug Disc. Today 1999, 4, 80; Brett A. Premack and Thomas J. Schall, Nature Medicine 1996, 2, 1174). For example, the chemokine monocyte chemoattractant-1 (MCP-1) and its receptor CC Chekmokine Receptor 2 (CCR-2) play a pivotal role in attracting leukocytes to sites of inflammation and in subsequently activating these cells. When the chemokine MCP-1 binds to CCR-2, it induces a rapid increase in intracellular calcium concentration, increased expression of cellular adhesion molecules, cellular degranulation, and the promotion of leukocyte migration. Demonstration of the importance of the MCP-1/CCR-2 interaction has been provided by experiments with genetically modified mice. MCP-1 −/− mice had normal numbers of leukocytes and macrophages, but were unable to recruit monocytes into sites of inflammation after several different types of immune challenge (Bao Lu, et al., J. Exp. Med. 1998, 187, 601). Likewise, CCR-2 −/− mice were unable to recruit monocytes or produce interferon-γ when challenged with various exogenous agents; moreover, the leukocytes of CCR-2 null mice did not migrate in response to MCP-1 (Landin Boring, et al., J. Clin. Invest. 1997, 100, 2552), thereby demonstrating the specificity of the MCP-1/CCR-2 interaction. Two other groups have independently reported equivalent results with different strains of CCR-2 −/− mice (William A. Kuziel, et al., Proc. Natl. Acad. Sci. USA 1997, 94, 12053, and Takao Kurihara, et al., J. Exp. Med. 1997, 186, 1757). The viability and generally normal health of the MCP-1 −/− and CCR-2 −/− animals is noteworthy, in that disruption of the MCP-1/CCR-2 interaction does not induce physiological crisis. Taken together, these data lead one to the conclusion that molecules that block the actions of MCP-1 would be useful in treating a number of inflammatory and autoimmune disorders. This hypothesis has now been validated in a number of different animal disease models, as described below.

Several studies have demonstrated the potential therapeutic value of antagonism of the MCP-1/CCR2 interaction in treating rheumatoid arthritis. A DNA vaccine encoding MCP-1 was shown recently to ameliorate chronic polyadjuvant-induced arthritis in rats (Sawsan Youssef, et al., *J. Clin. Invest.* 2000, 106, 361). Likewise, inflammatory disease symptoms could be controlled via direct administration of antibodies for MCP-1 to rats with collagen-induced arthritis (Hiroomi Ogata, et al., *J. Pathol.* 1997, 182, 106), or streptococcal cell wall-induced arthritis (Ralph C. Schimmer, et al., *J. Immunol.* 1998, 160, 1466). Perhaps most significantly, a peptide antagonist of MCP-1, MCP-1 (9–76), was shown both to prevent disease onset and to reduce disease symptoms (depending on the time of administration) in the MRL-1pr mouse model of arthritis (Jiang-Hong Gong, et al., *J. Exp. Med.* 1997, 186, 131).

Three key studies have demonstrated the potential therapeutic value of antagonism of the MCP-1/CCR2 interaction in treating atherosclerosis. For example, when MCP-1 –/– mice are mated with LDL receptor-deficient mice, an 83% reduction in aortic lipid deposition was observed (Long Gu, et al., *Mol. Cell* 1998, 2, 275). Similarly, when MCP-1 was genetically ablated from mice which already overexpressed human apolipoprotein B, the resulting mice were protected from atherosclerotic lesion formation relative to the MCP-1 +/+ apoB control mice (Jennifa Gosling, et al., *J. Clin. Invest.* 1999, 103, 773). Likewise, when CCR-2 –/– mice are crossed with apolipoprotein E mice, a significant decrease in the incidence of atherosclerotic lesions was observed (Landin Boring, et al, *Nature* 1998, 394, 894).

Other studies have demonstrated the potential therapeutic value of antagonism of the MCP-1/CCR-2 interaction in treating multiple sclerosis; all of these studies have been demonstrated in experimental autoimmune encephalomyelitis (EAE), the standard animal model for multiple scelerosis. Administration of antibodies for MCP-1 to animals with EAE significantly diminished disease relapse (K. J. Kennedy, et al., *J. Neuroimmunol.* 1998, 92, 98). Furthermore, two recent reports have now shown that CCR-2 –/– mice are resistant to EAE (Brian T. Fife, et al., *J. Exp. Med.* 2000, 192, 899; Leonid Izikson, et al., *J. Exp. Med.* 2000, 192, 1075).

Other studies have demonstrated the potential therapeutic value of antagonism of the MCP-1/CCR2 interaction in treating asthma. Sequestration of MCP-1 with a neutralizing antibody in ovalbumin-challenged mice resulted in marked decrease in bronchial hyperresponsiveness and inflammation (Jose-Angel Gonzalo, et al., *J. Exp. Med.* 1998, 188, 157). It proved possible to reduce allergic airway inflammation in *Schistosoma mansoni* egg-challenged mice through the administration of antibodies for MCP-1 (Nicholas W. Lukacs, et al., J. Immunol. 1997, 158, 4398). Consistent with this, MCP-1 –/– mice displayed a reduced response to challenge with *Schistosoma mansoni* egg (Bao Lu, et al., *J. Exp. Med.* 1998, 187, 601).

Other studies have demonstrated the potential therapeutic value of antagonism of the MCP-1/CCR2 interaction in treating kidney disease. Administration of antibodies for MCP-1 in a murine model of glomerularnephritis resulted in a marked decrease in glomerular crescent formation and deposition of type I collagen (Clare M. Lloyd, et al., *J. Exp. Med.* 1997, 185, 1371). In addition, MCP-1 –/– mice with induced nephrotoxic serum nephritis showed significantly less tubular damage than their MCP-1 +/+ counterparts (Gregory H. Tesch, et al., *J. Clin. Invest.* 1999, 103, 73).

One study has demonstrated the potential therapeutic value of antagonism of the MCP-1/CCR2 interaction in treating systemic lupus erythematosus. Crossing of MCP-1 –/– mice with MRL-FAS$^{1Pr}$ mice—the latter of which have a fatal autoimmune disease that is analogous to human systemic lupus erythematosus—results mice that have less disease and longer survival than the wildtype MRL-FAS$^{1pr}$ mice (Gregory H. Tesch, et al., *J. Exp. Med.* 1999, 190, 1813).

One study has demonstrated the potential therapeutic value of antagonism of the MCP-1/CCR2 interaction in treating colitis. CCR-2 –/– mice were protected from the effects of dextran sodium sulfate-induced colitis (Pietro G. Andres, et al., *J. Immunol.* 2000, 164, 6303).

One study has demonstrated the potential therapeutic value of antagonism of the MCP-1/CCR2 interaction in treating alveolitis. When rats with IgA immune complex lung injury were treated intravenously with antibodies raised against rat MCP-1 (JE), the symptoms of alveolitis were partially aleviated (Michael L. Jones, et al., *J. Immunol.* 1992, 149, 2147).

Other studies have provided evidence that MCP-1 is overexpressed in various disease states not mentioned above. These reports provide strong correlative evidence that MCP-1 antagonists could be useful therapeutics for such diseases. Two reports described the overexpression of MCP-1 in the intestinal epithelial cells and bowel mucosa of patients with inflammatory bowel disease (H. C. Reinecker, et al., *Gastroenterology* 1995, 108, 40, and Michael C. Grimm, et al., *J. Leukoc. Biol.* 1996, 59, 804). Two reports describe the overexpression of MCP-1 rats with induced brain trauma (J. S. King, et al., *J. Neuroimmunol.* 1994, 56, 127, and Joan W. Berman, et al., *J. Immunol.* 1996, 156, 3017). Another study has demonstrated the overexpression of MCP-1 in rodent cardiac allografts, suggesting a role for MCP-1 in the pathogenesis of transplant arteriosclerosis (Mary E. Russell, et al. *Proc. Natl. Acad. Sci. USA* 1993, 90, 6086). The overexpression of MCP-1 has been noted in the lung endothelial cells of patients with idiopathic pulmonary fibrosis (Harry N. Antoniades, et al., *Proc. Natl. Acad. Sci. USA* 1992, 89, 5371). Similarly, the overexpression of MCP-1 has been noted in the skin from patients with psoriasis (M. Deleuran, et al., *J. Dermatol. Sci.* 1996, 13, 228, and R. Gillitzer, et al., *J. Invest. Dermatol.* 1993, 101, 127). Finally, a recent report has shown that MCP-1 is overexpressed in the brains and cerebrospinal fluid of patients with HIV-1-associated dementia (Alfredo Garzino-Demo, WO 99/46991).

It should also be noted that CCR-2 has been implicated as a co-receptor for some strains of HIV (B. J. Doranz, et al., *Cell* 1996, 85, 1149). It has also been determined that the use of CCR-2 as an HIV co-receptor can be correlated with disease progression (Ruth I. Connor, et al., *J. Exp. Med.* 1997, 185, 621). This finding is consistent with the recent finding that the presence of a CCR-2 mutant, CCR2-64I, is positively correlated with delayed onset of HIV in the human population (Michael W. Smith, et al., *Science* 1997, 277, 959). Although MCP-1 has not been implicated in these processes, it may be that MCP-1 antagonists that act via binding to CCR-2 may have beneficial therapeutic effects in delaying the disease progression to AIDS in HIV-infected patients.

Recently, a number of groups have described the development of small molecule antagonists of MCP-1 (reviewed in: Bharat K. Trivedi, et al, *Ann. Reports Med. Chem.* 2000, 35, 191). Workers at Teijen and Combichem reported the use of cyclic amines (A) as MCP-1 (Tatsuki Shiota, et al., WO 99/25686; Tatsuki Shiota, et al., WO 00/69815) and MIP-1α

(Christine Tarby and Wilna Moree, WO 00/69820) antagonists. These compounds are distinguished from those of the present invention (I) by the requirement for the central cyclic amine grouping.

(A)

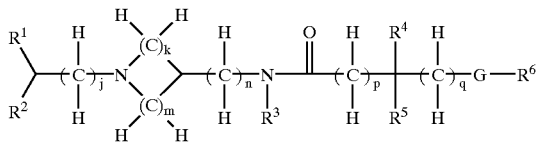

A number of other groups have also described the development of small molecule antagonists of the MCP-1/CCR-2 interaction. To date, indolopiperidines (Ian T. Forbes, et al., Bioorg. Med. Chem. Lett. 2000, 10, 1803), spiropiperidines (Tara Mirzadegan, et al., J. Biol. Chem. 2000, 275, 25562), quaternary amines (Masanori Baba, et al., Proc. Natl. Acad. Sci. 1999, 96, 5698), 2-substituted indoles (Alan Faull and Jason Kettle, WO 00/46196; Andrew John Barker, et al., WO 99/07351; Andrew John Barker, et al., WO 99/07678), pyrazolone derivatives (Janak Khimchand Padia, et al., U.S. Pat. No. 6,011,052, 2000), 2-substituted benzimidazoles (David Thomas Connor, et al., WO 98/06703), N,N-dialkylhomopiperazines (T. Shiota, et al., WO 97/44329), bicyclic pyrroles (Andrew J. Barker, et al., WO 99/40913 and Andrew J. Barker, et al., WO 99/40914), and 5-aryl pentadienamides (K. G. Carson, et al., Cambridge Health Tech Institute Chemokine Symposium, McLean, Va., USA, 1999) have all been reported as MCP-1 antagonists. The foregoing reference compounds are readily distinguished structurally from the present invention by virtue of substantial differences in the terminal functionality, the attachment functionality, or the core functionality. The prior art does not disclose nor suggest the unique combination of structural fragments that embody in the novel compounds described herein. Furthermore, the prior art does not disclose or suggest that the compounds of the present invention would be antagonists of MCP-1.

It should be noted that CCR-2 is also the receptor for the chemokines MCP-2, MCP-3, MCP-4, and MCP-5 (Luster, New Eng. J. Med. 1998, 338, 436–445). Since it is presumed that the new compounds of formula (I) described herein antagonize MCP-1 by binding to the CCR-2 receptor, it may be that these compounds of formula (I) are also effective antagonists of the actions of MCP-2, MCP-3, MCP-4, and MCP-5 that are mediated by CCR-2. Accordingly, when reference is made herein to "antagonism of MCP-1," it is to be assumed that this is equivalent to "antagonism of chemokine stimulation of CCR-2."

SUMMARY OF THE INVENTION

Accordingly, the present invention provides novel antagonists or partial agonists/antagonists of MCP-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis, multiple sclerosis, and atherosclerosis, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides diamine compounds for use in therapy.

The present invention provides the use of novel diamine compounds for the manufacture of a medicament for the treatment of inflammatory diseases.

These and other features of the invention, which will become apparent during the following detailed description, have been achieved by the inventors' discovery that compounds of formula (I):

(I)

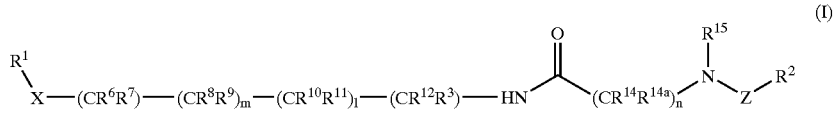

or stereoisomers or pharmaceutically acceptable salts thereof, wherein X, Z, l, m, n, s, $R^1$, $R^2$, $R^3$, $R^6$, $R^7$, $R^8$, $R^9$, $R^{10}$, $R^{11}$, $R^{12}$, $R^{14}$ and $R^{14a}$ are defined below, are effective modulators of chemokine activity.

DETAILED DESCRIPTION OF PREFERRED EMBODIMENTS

[1] Thus, in a first embodiment, the present invention provides novel compounds of formula (I):

(I)

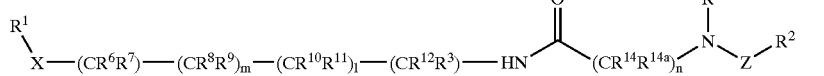

or a stereoisomer or a pharmaceutically acceptable salt thereof, wherein:

Z is selected from a bond, —C(O)—, —C(O)NH—, —C(S)NH—, —SO$_2$—, and —SO$_2$NH—;

X is selected from —NR$^{17}$—, —O—, —S—, and —CHR$^{16}$NR$^{17}$—;

R¹ is selected from a $C_{6-10}$ aryl group substituted with 0–5 R⁴ and a 5–10 membered heteroaryl system containing 1–4 heteroatoms selected from N, O, and S, substituted with 0–3 R⁴;

R² is selected from a $C_{6-10}$ aryl group substituted with 0–5 R⁵ and a 5–10 membered heteroaryl system containing 1–4 heteroatoms selected from N, O, and S, substituted with 0–3 R⁵;

R³ is selected from H, $(CRR)_qOH$, $(CRR)_qSH$, $(CRR)_q OR^{3d}$, $(CRR)_qS(O)_pR^{3d}$, $(CRR)_rC(O)R^{3b}$, $(CRR)_q NR^{3a}R^{3a}$, $(CRR)_qC(O)NR^{3a}R^{3a}$, $(CRR)_rC(O)NR^{3a}OR^{3d}$, $(CRR)_qSO_2NR^{3a}R^{3a}$, $(CRR)_rC(O)OR^{3d}$, a $(CRR)_r$—$C_{3-10}$ carbocyclic residue substituted with 0–5 R³ᵉ, and a $(CRR)_r$-5–10 membered heterocyclic system containing 1–4 heteroatoms selected from N, O, and S, substituted with 0–3 R³ᵉ;

with the proviso that R³ is not H if R⁶ is H;

alternatively, R³ and R¹² join to form a $C_{3-6}$ cycloalkyl substituted with 0–2 R³ᵍ, a $C_{5-6}$ lactam substituted with 0–2 R³ᵍ, or a $C_{5-6}$ lactone substituted with 0–2 R³ᵍ;

R³ᵃ, at each occurrence, is independently selected from H, methyl substituted with 0–1 R³ᶜ, $C_{2-6}$ alkyl substituted with 0–3 R³ᵉ, $C_{3-8}$ alkenyl substituted with 0–3 R³ᵉ, $C_{3-8}$ alkynyl substituted with 0–3 R³ᵉ, $(CH_2)_rC_{3-6}$ cycloalkyl, a $(CH_2)_r$—$C_{3-10}$ carbocyclic residue substituted with 0–5 R³ᵉ, and a $(CH_2)_r$-5–10 membered heterocyclic system containing 1–4 heteroatoms selected from N, O, and S, substituted with 0–3 R³ᵉ;

R³ᵇ, at each occurrence, is independently selected from $C_{1-6}$ alkyl substituted with 0–3 R³ᵉ, $C_{2-8}$ alkenyl substituted with 0–3 R³ᵉ, $C_{2-8}$ alkynyl substituted with 0–3 R³ᵉ, a $(CH_2)_r$—$C_{3-6}$ carbocyclic residue substituted with 0–2 R³ᵉ, and a $(CH_2)_r$-5–6 membered heterocyclic system containing 1–4 heteroatoms selected from N, O, and S, substituted with 0–3 R³ᵉ;

R³ᶜ is independently selected from —C(O)R³ᵇ, —C(O)OR³ᵈ, —C(O)NR³ᶠR³ᶠ, and $(CH_2)_r$phenyl;

R³ᵈ, at each occurrence, is independently selected from H, methyl, —CF₃, $C_{2-6}$ alkyl substituted with 0–3 R³ᵉ, $C_{3-6}$ alkenyl substituted with 0–3 R³ᵉ, $C_{3-6}$ alkynyl substituted with 0–3 R³ᵉ, a $C_{3-10}$ carbocyclic residue substituted with 0–3 R³ᵉ, and a $(CH_2)_r$-5–6 membered heterocyclic system containing 1–4 heteroatoms selected from N, O, and S, substituted with 0–3 R³ᵉ;

R³ᵉ, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, NO₂, $(CF_2)_rCF_3$, $(CH_2)_rOC_{1-5}$ alkyl, OH, SH, $(CH_2)_r SC_{1-5}$ alkyl, $(CH_2)_rNR^{3f}R^{3f}$, and $(CH_2)_r$phenyl;

R³ᶠ, at each occurrence, is selected from H, $C_{1-6}$ alkyl, and $C_{3-6}$ cycloalkyl;

R³ᵍ is selected from $(CHR)_qOH$, $(CHR)_qSH$, $(CHR)_qOR^{3d}$, $(CHR)_qS(O)_pR^{3d}$, $(CHR)_rC(O)R^{3b}$, $(CHR)_qNR^{3a}R^{3a}$, $(CHR)_qC(O)NR^{3a}R^{3a}$, $(CHR)_rC(O)NR^{3a}OR^{3d}$, $(CHR)_q SO_2NR^{3a}R^{3a}$, $(CHR)_rC(O)OR^{3d}$, and a $(CHR)_r$—$C_{3-10}$ carbocyclic residue substituted with 0–5 R³ᵉ;

R, at each occurrence, is independently selected from H, $C_{1-6}$ alkyl, $C_{2-8}$ alkenyl, $C_{2-8}$ alkynyl, $(CH_2)_rC_{3-6}$ cycloalkyl, $(CHR)_rC(O)NR^{3a}R^{3a}$, and $(CHR)_rC(O)OR^{3d}$, and $(CH_2)_r$phenyl substituted with R³ᵉ;

R⁴, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, NO₂, CN, $(CR'R')_rNR^{4a}R^{4a}$, $(CR'R')_rOH$, $(CR'R')_rO (CR'R')_rR^{4d}$, $(CR'R')_rSH$, $(CR'R')_rC(O)H$, $(CR'R')_r S (CR'R')_rR^{4d}$, $(CR'R')_rC(O)OH$, $(CR'R')_rC(O)(CR'R')_rR^{4b}$, $(CR'R')_rC(O)NR^{4a}R^{4a}$, $(CR'R')_rNR^{4f}C(O)(CR'R')_rR^{4b}$, $(CR'R')_rC(O)O(CR'R')_rR^{4d}$, $(CR'R')_rOC(O)(CR'R')_rR^{4b}$, $(CR'R')_rNR^{4f}C(O)O(CR'R')_rR^{4d}$, $(CR'R')_rOC(O)$ $NR^{4a}R^{4a}$, $(CR'R')_rNR^{6a}C(S)NR^{6a}(CR'R')_rR^{6d}$, $(CR'R')_r NR^{4a}C(O)NR^{4a}R^{4a}$, $(CR'R')_rC(=NR^{4f})NR^{4a}R^{4a}$, $(CR'R')_rNHC(=NR^{4f})NR^{4f}R^{4f}$, $(CR'R')_rS(O)_p(CR'R')_r R^{4b}$, $(CR'R')_rS(O)_2NR^{4a}R^{4a}$, $(CR'R')_rNR^{6f}S(O)_2 NR^{6a}R^{6a}$, $(CR'R')_rNR^{4f}S(O)_2(CR'R')_rR^{4b}$, $C_{1-6}$ haloalkyl, $C_{2-8}$ alkenyl substituted with 0–3 R', $C_{2-8}$ alkynyl substituted with 0–3 R', and $(CR'R')_r$phenyl substituted with 0–3 R⁴ᵉ;

alternatively, two R⁴ on adjacent atoms on R¹ may join to form a cyclic acetal;

R⁴ᵃ, at each occurrence, is independently selected from H, methyl substituted with 0–1R⁴ᵍ, $C_{2-6}$ alkyl substituted with 0–2 R⁵ᵉ, $C_{3-8}$ alkenyl substituted with 0–2 R⁵ᵉ, $C_{3-8}$ alkynyl substituted with 0–2 R⁵ᵉ, a $(CH_2)_r$—$C_{3-10}$ carbocyclic residue substituted with 0–5 R⁴ᵉ, and a $(CH_2)_r$-5–10 membered heterocyclic system containing 1–4 heteroatoms selected from N, O, and S, substituted with 0–2 R⁴ᵉ;

R⁴ᵇ, at each occurrence, is selected from $C_{1-6}$ alkyl substituted with 0–2 R⁵ᵉ, $C_{3-8}$ alkenyl substituted with 0–2 R⁵ᵉ, $C_{3-8}$ alkynyl substituted with 0–2 R⁵ᵉ, a $(CH_2)_rC_{3-6}$ carbocyclic residue substituted with 0–3 R⁴ᵉ, and a $(CH_2)_r$-5–6 membered heterocyclic system containing 1–4 heteroatoms selected from N, O, and S, substituted with 0–2 R⁴ᵉ;

R⁴ᵈ, at each occurrence, is selected from $C_{3-8}$ alkenyl substituted with 0–2 R⁵ᵉ, $C_{3-8}$ alkynyl substituted with 0–2 R⁵ᵉ, methyl, CF₃, $C_{2-6}$ alkyl substituted with 0–3 R⁴ᵉ, a $(CH_2)_r$—$C_{3-10}$ carbocyclic residue substituted with 0–3 R⁴ᵉ, and a $(CH_2)_r$-5–6 membered heterocyclic system containing 1–4 heteroatoms selected from N, O, and S, substituted with 0–3 R⁴ᵉ;

R⁴ᵉ, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, NO₂, $(CF_2)_rCF_3$, $(CH_2)_rOC_{1-5}$ alkyl, OH, SH, $(CH_2)_r SC_{1-5}$ alkyl, $(CH_2)_rNR^{4f}R^{4f}$, and $(CH_2)_r$phenyl;

R⁴ᶠ, at each occurrence, is selected from H, $C_{1-5}$ alkyl, and $C_{3-6}$ cycloalkyl, and phenyl;

R⁴ᵍ is independently selected from —C(O)R⁴ᵇ, —C(O)OR⁴ᵈ, —C(O)NR⁴ᶠR⁴ᶠ, and $(CH_2)_r$phenyl;

R⁵, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, NO₂, CN, $(CR'R')_rNR^{5a}R^{5a}$, $(CR'R')_rOH$, $(CR'R')_rO (CR'R')_rR^{5d}$, $(CR'R')_rSH$, $(CR'R')_rC(O)H$, $(CR'R')_rS (CR'R')_rR^{5d}$, $(CR'R')_rC(O)OH$, $(CR'R')_rC(O)(CR'R')_rR^{5b}$, $(CR'R')_rC(O)NR^{5a}R^{5a}$, $(CR'R')_rNR^{5f}C(O)(CR'R')_rR^{5b}$, $(CR'R')_rC(O)O(CR'R')_rR^{5d}$, $(CR'R')_rOC(O)(CR'R')_rR^{5b}$, $CR'R')_rNR^{5f}C(O)O(CR'R')_rR^{5d}$, $(CR'R')_rOC(O)NR^{5a}R^{5a}$, $(CR'R')_rNR^{5a}C(O)NR^{5a}R^{5a}$, $(CR'R')_rC(=NR^{5f}) NR^{5a}R^{5a}$, $(CR'R')_rNHC(=NR^{5f})NR^{5f}R^{5f}$, $(CR'R')_rS(O)_p (CR'R')_rR^{5b}$, $(CR'R')_rS(O)_2NR^{5a}R^{5a}$, $(CR'R')_rNR^{5a}S(O)_2 NR^{5a}R^{5a}$, $(CR'R')_rNR^{5f}S(O)_2(CR'R')_rR^{5b}$, $C_{1-6}$ haloalkyl, $C_{2-8}$ alkenyl substituted with 0–3 R', $C_{2-8}$ alkynyl substituted with 0–3 R', and $(CR'R')_r$phenyl substituted with 0–3 R⁵ᵉ;

alternatively, two R⁵ on adjacent atoms on R² may join to form a cyclic acetal;

R⁵ᵃ, at each occurrence, is independently selected from H, methyl substituted with 0–1 R⁵ᵍ, $C_{2-6}$ alkyl substituted with 0–2 R⁵ᵉ, $C_{3-8}$ alkenyl substituted with 0–2 R⁵ᵉ, $C_{3-8}$ alkynyl substituted with 0–2 R⁵ᵉ, a $(CH_2)_r$—$C_{3-10}$ carbocyclic residue substituted with 0–5 R⁵ᵉ, and a $(CH_2)_r$-5–10 membered heterocyclic system containing 1–4 heteroatoms selected from N, O, and S, substituted with 0–2 R⁵ᵉ;

R⁵ᵇ, at each occurrence, is independently selected from $C_{1-6}$ alkyl substituted with 0–2 R⁵ᵉ, $C_{3-8}$ alkenyl substituted with 0–2 $R^{5e}$, $C_{3-8}$ alkynyl substituted with 0–2 $R^{5e}$, a $(CH_2)_rC_{3-6}$ carbocyclic residue substituted with 0–3 $R^{5e}$, and a $(CH_2)_r$-5–6 membered heterocyclic system containing 1–4 heteroatoms selected from N, O, and S, substituted with 0–2 $R^{5e}$;

$R^{5d}$, at each occurrence, is independently selected from $C_{3-8}$ alkenyl substituted with 0–2 $R^{5e}$, $C_{3-8}$ alkynyl substituted with 0–2 $R^{5e}$, methyl, $CF_3$, $C_{2-6}$ alkyl substituted with 0–3 $R^{5e}$, a $(CH_2)_r$—$C_{3-10}$ carbocyclic residue substituted with 0–3 $R^{5e}$, and a $(CH_2)_r$-5–6 membered heterocyclic system containing 1–4 heteroatoms selected from N, O, and S, substituted with 0–3 $R^{5e}$;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-5}$ alkyl, and $C_{3-6}$ cycloalkyl, and phenyl;

$R^{5g}$ is independently selected from —$C(O)R^{5b}$, —$C(O)OR^{5d}$, —$C(O)NR^{5f}R^{5f}$, and $(CH_2)_r$phenyl;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, is selected from H, $C_{1-6}$ alkyl, $C_{2-6}$ alkenyl, $C_{2-6}$ alkynyl, $(CRR)_qOH$, $(CRR)_qSH$, $(CRR)_qOR^{6d}$, $(CRR)_qS(O)_pR^{6d}$, $(CRR)_rC(O)R^{6b}$, $(CRR)_rNR^{6a}R^{6a}$, $(CRR)_rC(O)NR^{6a}R^{6a}$, $(CRR)_rC(O)NR^{6a}OR^{6d}$, $(CRR)_rSO_2NR^{6a}R^{6a}$, $(CRR)_rC(O)OR^{6d}$, a $(CRR)_r$—$C_{3-10}$ carbocyclic residue substituted with 0–5 $R^{6e}$, and a $(CRR)_r$-5–10 membered heterocyclic system containing 1–4 heteroatoms selected from N, O, and S, substituted with 0–3 $R^{6e}$;

alternatively, $R^6$ and $R^7$ join to form a $C_{3-6}$ cycloalkyl substituted with 0–2 $R^{6g}$, a 5–6 membered ring lactam substituted with 0–2 $R^{6g}$, or a 5–6 membered ring lactone substituted with 0–2 $R^{6g}$;

$R^{6a}$, at each occurrence, is independently selected from H, methyl, $C_{2-6}$ alkyl substituted with 0–3 $R^{6e}$, $C_{3-8}$ alkenyl substituted with 0–3 $R^{6e}$, $C_{3-8}$ alkynyl substituted with 0–3 $R^{6e}$, $(CH_2)_rC_{3-6}$ cycloalkyl, a $(CH_2)_r$—$C_{3-10}$ carbocyclic residue substituted with 0–5 $R^{6e}$, and a $(CH_2)_r$-5–10 membered heterocyclic system containing 1–4 heteroatoms selected from N, O, and S, substituted with 0–3 $R^{6e}$;

$R^{6b}$, at each occurrence, is independently selected from $C_{1-6}$ alkyl substituted with 0–3 $R^{6e}$, $C_{2-8}$ alkenyl substituted with 0–3 $R^{6e}$, $C_{2-8}$ alkynyl substituted with 0–3 $R^{6e}$, a $(CH_2)_r$—$C_{3-6}$ carbocyclic residue substituted with 0–2 $R^{6e}$, and a $(CH_2)_r$-5–6 membered heterocyclic system containing 1–4 heteroatoms selected from N, O, and S, substituted with 0–3 $R^{6e}$;

$R^{6d}$, at each occurrence, is independently selected from H, methyl, —$CF_3$, $C_{2-6}$ alkyl substituted with 0–3 $R^{6e}$, $C_{3-6}$ alkenyl substituted with 0–3 $R^{6e}$, $C_{3-6}$ alkynyl substituted with 0–3 $R^{6e}$, a $C_{3-10}$ carbocyclic residue substituted with 0–3 $R^{6e}$, and a $(CH_2)_r$-5–6 membered heterocyclic system containing 1–4 heteroatoms selected from N, O, and S, substituted with 0–3 $R^{6e}$;

$R^{6e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{6f}R^{6f}$, and $(CH_2)_r$phenyl;

$R^{6f}$, at each occurrence, is independently selected from H, $C_{1-6}$ alkyl, and $C_{3-6}$ cycloalkyl;

$R^{6g}$ is selected from $(CHR)_qOH$, $(CHR)_qSH$, $(CHR)_qOR^{6d}$, $(CHR)_qS(O)_pR^{6d}$, $(CHR)_rC(O)R^{6b}$, $(CHR)_qNR^{6a}R^{6a}$, $(CHR)_rC(O)NR^{6a}R^{6a}$, $(CHR)_rC(O)NR^{6a}OR^{6d}$, $(CHR)_qSO_2NR^{6a}R^{6a}$, $(CHR)_rC(O)OR^{6d}$, and a $(CHR)_r$—$C_{3-10}$ carbocyclic residue substituted with 0–5 $R^{6e}$;

$R^7$, is selected from H, $C_{1-6}$ alkyl, $C_{2-6}$ alkenyl, $C_{2-6}$ alkynyl, $(CRR)_qOH$, $(CRR)_qSH$, $(CRR)_qOR^{7d}$, $(CRR)_qS(O)_pR^{7d}$, $(CRR)_rC(O)R^{7b}$, $(CRR)_rNR^{7a}R^{7a}$, $(CRR)_rC(O)NR^{7a}R^{7a}$, $(CRR)_rC(O)NR^{7a}OR^{7d}$, $(CRR)_qSO_2NR^{7a}R^{7a}$, $(CRR)_rC(O)OR^{7d}$, a $(CRR)_r$—$C_{3-10}$ carbocyclic residue substituted with 0–5 $R^{7e}$, and a $(CRR)_r$-5–10 membered heterocyclic system containing 1–4 heteroatoms selected from N, O, and S, substituted with 0–3 $R^{7e}$;

$R^{7a}$, at each occurrence, is independently selected from H, methyl, $C_{2-6}$ alkyl substituted with 0–3 $R^{7e}$, $C_{3-8}$ alkenyl substituted with 0–3 $R^{7e}$, $C_{3-8}$ alkynyl substituted with 0–3 $R^{7e}$, $(CH_2)_rC_{3-6}$ cycloalkyl, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–3 $R^{7e}$;

$R^{7b}$, at each occurrence, is independently selected from $C_{1-6}$ alkyl substituted with 0–3 $R^{7e}$, $C_{2-8}$ alkenyl substituted with 0–3 $R^{7e}$, $C_{2-8}$ alkynyl substituted with 0–3 $R^{7e}$, a $(CH_2)_r$—$C_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7d}$, at each occurrence, is independently selected from H, methyl, —$CF_3$, $C_{2-6}$ alkyl substituted with 0–3 $R^{7e}$, $C_{3-6}$ alkenyl substituted with 0–3 $R^{7e}$, $C_{3-6}$ alkynyl substituted with 0–3 $R^{7e}$, a $C_{3-10}$ carbocyclic residue substituted with 0–3 $R^{7e}$, and a $(CH_2)_r$-5–6 membered heterocyclic system containing 1–4 heteroatoms selected from N, O, and S, substituted with 0–3 $R^{7e}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{7f}R^{7f}$, and $(CH_2)_r$phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{8d}$, $(CRR)_rS(O)_pR^{8d}$, $(CRR)_rC(O)R^{8b}$, $(CRR)_rNR^{8a}R^{8a}$, $(CRR)_rC(O)NR^{8a}R^{8a}$, $(CRR)_rC(O)NR^{8a}OR^{8d}$, $(CRR)_rSO_2NR^{8a}R^{8a}$, $(CRR)_rC(O)OR^{8d}$, a $(CRR)_r$—$C_{3-10}$ carbocyclic residue substituted with 0–5 $R^8e$, and a $(CRR)_r$-5–10 membered heterocyclic system containing 1–4 heteroatoms selected from N, O, and S, substituted with 0–3 $R^{8e}$; alternatively, $R^8$ and $R^9$ join to form a $C_{3-6}$ cycloalkyl substituted with 0–2 $R^{8g}$, a 5–6 memebered ring lactam substituted with 0–2 $R^{8g}$, or a 5–6 membered ring lactone substituted with 0–2 $R^{8g}$;

$R^{8a}$, at each occurrence, is independently selected from H, methyl, $C_{2-6}$ alkyl substituted with 0–3 $R^{8e}$, $C_{3-8}$ alkenyl substituted with 0–3 $R^{8e}$, $C_{3-8}$ alkynyl substituted with 0–3 $R^{8e}$, $(CH_2)_rC_{3-6}$ cycloalkyl, a $(CH_2)_r$—$C_{3-10}$ carbocyclic residue substituted with 0–5 $R^{8e}$, and a $(CH_2)_r$-5–10 membered heterocyclic system containing 1–4 heteroatoms selected from N, O, and S, substituted with 0–3 $R^{8e}$;

$R^{8b}$, at each occurrence, is independently selected from $C_{1-6}$ alkyl substituted with 0–3 $R^{8e}$, $C_{2-8}$ alkenyl substituted with 0–3 $R^{8e}$, $C_{2-8}$ alkynyl substituted with 0–3 $R^{8e}$, a $(CH_2)_r$—$C_{3-6}$ carbocyclic residue substituted with 0–2 $R^{8e}$, and a $(CH_2)_r$-5–6 membered heterocyclic system containing 1–4 heteroatoms selected from N, O, and S, substituted with 0–3 $R^{8e}$;

$R^{8d}$, at each occurrence, is independently selected from H, methyl, —$CF_3$, $C_{2-6}$ alkyl substituted with 0–3 $R^{8e}$, $C_{3-6}$ alkenyl substituted with 0–3 $R^{8e}$, $C_{3-6}$ alkynyl substituted with 0–3 $R^{8e}$, a $C_{3-10}$ carbocyclic residue substituted with 0–3 $R^{8e}$, and a $(CH_2)_r$-5–6 membered heterocyclic system containing 1–4 heteroatoms selected from N, O, and S, substituted with 0–3 $R^{8e}$;

$R^{8e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{8f}R^{8f}$, and $(CH_2)_r$phenyl;

$R^{8f}$, at each occurrence, is independently selected from H, $C_{1-6}$ alkyl, and $C_{3-6}$ cycloalkyl;

$R^{8g}$ is selected from $(CHR)_qOH$, $(CHR)_qSH$, $(CHR)_qOR^{8d}$, $(CHR)_qS(O)_pR^{8d}$, $(CHR)_rC(O)R^{8b}$, $(CHR)_rNR^{8a}R^{8a}$, $(CHR)_rC(O)NR^{8a}R^{8a}$, $(CHR)_rC(O)NR^{8a}OR^{8d}$, $(CHR)_qSO_2NR^{8a}R^{8a}$, $(CHR)_rC(O)OR^{8d}$, and a $(CHR)_r$—$C_{3-10}$ carbocyclic residue substituted with 0–5 $R^{8e}$;

$R^9$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{9d}$, $(CRR)_rS(O)_pR^{9d}$, $(CRR)_rC(O)R^{9b}$, $(CRR)_rNR^{9a}R^{9a}$, $(CRR)_rC(O)NR^{9a}R^{9a}$, $(CRR)_rC(O)NR^{9a}OR^{9d}$, $(CRR)_rSO_2NR^{9a}R^{9a}$, $(CRR)_rC(O)OR^{9d}$, a $(CRR)_r$—$C_{3-10}$ carbocyclic residue substituted with 0–5 $R^{9e}$, and a $(CRR)_r$-5–10 membered heterocyclic system containing 1–4 heteroatoms selected from N, O, and S, substituted with 0–3 $R^{9e}$;

$R^{9a}$, at each occurrence, is independently selected from H, methyl, $C_{2-6}$ alkyl substituted with 0–3 $R^{9e}$, $C_{3-8}$ alkenyl substituted with 0–3 $R^{9e}$, $C_{3-8}$ alkynyl substituted with 0–3 $R^{9e}$, $(CH_2)_rC_{3-6}$ cycloalkyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–3 $R^{9e}$;

$R^{9b}$, at each occurrence, is independently selected from $C_{1-6}$ alkyl substituted with 0–3 $R^{9e}$, $C_{2-8}$ alkenyl substituted with 0–3 $R^{9e}$, $C_{2-8}$ alkynyl substituted with 0–3 $R^{9e}$, a $(CH_2)_r$—$C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9d}$, at each occurrence, is independently selected from H, methyl, —$CF_3$, $C_{2-6}$ alkyl substituted with 0–3 $R^{9e}$, $C_{3-6}$ alkenyl substituted with 0–3 $R^{9e}$, $C_{3-6}$ alkynyl substituted with 0–3 $R^{9e}$, a $C_{3-10}$ carbocyclic residue substituted with 0–3 $R^{9e}$, and a $(CH_2)_r$-5–6 membered heterocyclic system containing 1–4 heteroatoms selected from N, O, and S, substituted with 0–3 $R^{9e}$;

$R^{9e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{9f}R^{9f}$, and $(CH_2)_r$phenyl;

$R^{9f}$, at each occurrence, is independently selected from H, $C_{1-6}$ alkyl, and $C_{3-6}$ cycloalkyl;

$R^{10}$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{10d}$, $(CRR)_rS(O)_pR^{10}$, $(CRR)_rC(O)R^{10b}$, $(CRR)_rNR^{10a}R^{10a}$, $(CRR)_rC(O)NR^{10a}R^{10a}$, $(CRR)_rC(O)NR^{10a}OR^{10d}$, $(CRR)_rSO_2NR^{10a}R^{10a}$, $(CRR)_rC(O)OR^{10d}$, a $(CRR)_r$—$C_{3-10}$ carbocyclic residue substituted with 0–5 $R^{10e}$, and a $(CRR)_r$-5–10 membered heterocyclic system containing 1–4 heteroatoms selected from N, O, and S, substituted with 0–3 $R^{10e}$;

alternatively, $R^{10}$ and $R^{11}$ join to form a $C_{3-6}$ cycloalkyl substituted with 0–2 $R^{10g}$, a 5–6 membered ring lactam substituted with 0–2 $R^{10g}$, or a 5–6 membered ring lactone substituted with 0–2 $R^{10g}$;

$R^{10a}$, at each occurrence, is independently selected from H, methyl, $C_{2-6}$ alkyl substituted with 0–3 $R^{10e}$, $C_{3-8}$ alkenyl substituted with 0–3 $R^{10e}$, $C_{3-8}$ alkynyl substituted with 0–3 $R^{10e}$, $(CH_2)_rC_{3-6}$ cycloalkyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

$R^{10b}$, at each occurrence, is independently selected from $C_{1-6}$ alkyl substituted with 0–3 $R^{10e}$, $C_{2-8}$ alkenyl substituted with 0–3 $R^{10e}$, $C_{2-8}$ alkynyl substituted with 0–3 $R^{10e}$, a $(CH_2)_r$—$C_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10d}$, at each occurrence, is independently selected from H, methyl, —$CF_3$, $C_{2-6}$ alkyl substituted with 0–3 $R^{10e}$, $C_{3-6}$ alkenyl substituted with 0–3 $R^{10e}$, $C_{3-6}$ alkynyl substituted with 0–3 $R^{10e}$, a $C_{3-10}$ carbocyclic residue substituted with 0–3 $R^{10e}$, and a $(CH_2)_r$-5–6 membered heterocyclic system containing 1–4 heteroatoms selected from N, O, and S, substituted with 0–3 $R^{10e}$, $R^{10e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{10f}R^{10f}$, and $(CH_2)_r$phenyl;

$R^{10f}$, at each occurrence, is independently selected from H, $C_{1-6}$ alkyl, and $C_{3-6}$ cycloalkyl;

$R^{10g}$ is selected from $(CHR)_qOH$, $(CHR)_qSH$, $(CHR)_qOR^{10d}$, $(CHR)_qS(O)_pR^{10d}$, $(CHR)_rC(O)R^{10b}$, $(CHR)_qNR^{10a}R^{10a}$, $(CHR)_rC(O)NR^{10a}R^{10a}$, $(CHR)_rC(O)NR^{10a}OR^{10d}$, $(CHR)_qSO_2NR^{10a}R^{10a}$, $(CHR)_rC(O)OR^{10d}$, and a $(CHR)_r$—$C_{3-10}$ carbocyclic residue substituted with 0–5 $R^{10e}$;

$R^{11}$, is selected from H, $C_{1-6}$ alkyl, $C_{2-6}$ alkenyl, $C_{2-6}$ alkynyl, $(CRR)_rOH$, $(CRR)_rSH$, $(CRR)_rOR^{11d}$, $(CRR)_rS(O)_pR^{11d}$, $(CRR)_rC(O)R^{11b}$, $(CRR)_rNR^{11a}R^{11a}$, $(CRR)_rC(O)NR^{11a}R^{11a}$, $(CRR)_rC(O)NR^{11a}OR^{11d}$, $(CRR)_rSO_2NR^{11a}R^{11a}$, $(CRR)_rC(O)OR^{11d}$, a $(CRR)_r$—$C_{3-10}$ carbocyclic residue substituted with 0–5 $R^{11e}$, and a $(CRR)_r$-5–10 membered heterocyclic system containing 1–4 heteroatoms selected from N, O, and S, substituted with 0–3 $R^{11e}$;

$R^{11a}$, at each occurrence, is independently selected from H, methyl, $C_{2-6}$ alkyl substituted with 0–3 $R^{11e}$, $C_{3-8}$ alkenyl substituted with 0–3 $R^{11e}$, $C_{3-8}$ alkynyl substituted with 0–3 $R^{11e}$, $(CH_2)_rC_{3-6}$ cycloalkyl, a $(CH_2)_r$—$C_{3-10}$ carbocyclic residue substituted with 0–5 $R^{11e}$, and a $(CH_2)_r$-5–10 membered heterocyclic system containing 1–4 heteroatoms selected from N, O, and S, substituted with 0–3 $R^{11e}$;

$R^{11b}$, at each occurrence, is independently selected from $C_{1-6}$ alkyl substituted with 0–3 $R^{11e}$, $C_{2-8}$ alkenyl substituted with 0–3 $R^{11e}$, $C_{2-8}$ alkynyl substituted with 0–3 $R^{11e}$, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11d}$, at each occurrence, is independently selected from H, methyl, —$CF_3$, $C_{2-6}$ alkyl substituted with 0–3 $R^{11e}$, $C_{3-6}$ alkenyl substituted with 0–3 $R^{11e}$, $C_{3-6}$ alkynyl substituted with 0–3 $R^e$, a $C_{3-10}$ carbocyclic residue substituted with 0–3 $R^{11e}$, and a $(CH_2)_r$-5–6 membered heterocyclic system containing 1–4 heteroatoms selected from N, O, and S, substituted with 0–3 $R^{11e}$;

$R^{11e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{11f}R^{11f}$, and $(CH_2)_r$phenyl;

13

$R^{11f}$, at each occurrence, is independently selected from H, $C_{1-6}$ alkyl, and $C_{3-6}$ cycloalkyl;

$R^{12}$ is selected from H, $C_{1-6}$ alkyl, $C_{2-6}$ alkenyl, $C_{2-6}$ alkynyl, $(CRR)_qOH$, $(CRR)_qSH$, $(CRR)_qOR^{12d}$, $(CRR)_qS(O)_pR^{12d}$, $(CRR)_rC(O)R^{12b}$, $(CRR)_rNR^{12a}R^{12a}$, $(CRR)_rC(O)NR^{12a}R^{12a}$, $(CRR)_rC(O)NR^{12a}OR^{12d}$, $(CRR)_qSO_2NR^{12a}R^{12a}$, $(CRR)_rC(O)OR^{12d}$, a $(CRR)_r$—$C_{3-10}$ carbocyclic residue substituted with 0–5 $R^{12e}$, and a $(CRR)_r$-5–10 membered heterocyclic system containing 1–4 heteroatoms selected from N, O, and S, substituted with 0–3 $R^{12e}$;

$R^{12a}$, at each occurrence, is independently selected from H, methyl, $C_{2-6}$ alkyl substituted with 0–3 $R^{12e}$, $C_{3-8}$ alkenyl substituted with 0–3 $R^{12e}$, $C_{3-8}$ alkynyl substituted with 0–3 $R^{12e}$, $(CH_2)_rC_{3-6}$ cycloalkyl, a $(CH_2)_r$—$C_{3-10}$ carbocyclic residue substituted with 0–5 $R^{12e}$, and a $(CH_2)_r$-5–10 membered heterocyclic system containing 1–4 heteroatoms selected from N, O, and S, substituted with 0–3 $R^{12e}$;

$R^{12b}$, at each occurrence, is independently selected from $C_{1-6}$ alkyl substituted with 0–3 $R^{12e}$, $C_{2-8}$ alkenyl substituted with 0–3 $R^{12e}$, $C_{2-8}$ alkynyl substituted with 0–3 $R^{12e}$, a $(CH_2)_r$—$C_{3-6}$ carbocyclic residue substituted with 0–2 $R^{12e}$, and a $(CH_2)_r$-5–6 membered heterocyclic system containing 1–4 heteroatoms selected from N, O, and S, substituted with 0–3 $R^{12e}$;

$R^{12d}$, at each occurrence, is independently selected from H, methyl, —$CF_3$, $C_{2-6}$ alkyl substituted with 0–3 $R^{12e}$, $C_{3-6}$ alkenyl substituted with 0–3 $R^{12e}$, $C_{3-6}$ alkynyl substituted with 0–3 $R^{12e}$, a $C_{3-10}$ carbocyclic residue substituted with 0–3 $R^{12e}$, and a $(CH_2)_r$-5–6 membered heterocyclic system containing 1–4 heteroatoms selected from N, O, and S, substituted with 0–3 $R^{12e}$;

$R^{12e}$, at each occurrence, is independently selected from $C_{1-6}$ alkyl, $C_{2-8}$ alkenyl, $C_{2-8}$ alkynyl, $C_{3-6}$ cycloalkyl, Cl, F. Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{14}$ and $R^{14a}$ are independently selected from H, and $C_{1-4}$alkyl substituted with 0–1 $R^{14b}$, alternatively, $R^{14}$ and $R^{14a}$ can join to form a $C_{3-6}$ cycloalkyl;

$R^{14b}$, at each occurrence, is independently selected from —OH, —SH, —$NR^{14c}R^{14c}$, —$C(O)NR^{14c}R^{14c}$, —NHC(O)$R^{14c}$ and phenyl;

$R^{14c}$ is selected from H, $C_{1-4}$ alkyl and $C_{3-6}$ cycloalkyl;

$R^{15}$ is selected from H, $C_{1-4}$ alkyl, and $C_{3-6}$ cycloalkyl;

$R^{16}$ is selected from H, $C_{1-4}$ alkyl substituted with 0–3 $R^{16a}$, and $C_{3-6}$ cycloalkyl substituted with 0–3 $R^{16a}$;

$R^{16a}$ is selected from $C_{1-4}$ alkyl, —OH, —SH, —$NR^{16c}R^{16c}$, —$C(O)NR^{16c}R^{16c}$, and —NHC(O)$R^{16c}$;

$R^{16c}$ is selected from H, $C_{1-4}$ alkyl and $C_{3-6}$ cycloalkyl;

$R^{17}$ is selected from H, $C_{1-4}$ alkyl, and $C_{3-4}$ cycloalkyl;

n is selected from 1 and 2;

l is selected from 0 and 1;

m is selected from 0 and 1;

p, at each occurrence, is selected from 0, 1, or 2;

q, at each occurrence, is selected from 1, 2, 3, or 4; and r, at each occurrence, is selected from 0, 1, 2, or 3 or 4.

[2] In another embodiment, the present invention provides novel compounds of formula (I), wherein:

Z is selected from a bond, —C(O)—, —C(O)NH—, —C(S)NH—, —$SO_2$—, and —$SO_2NH$—;

X is selected from —$NR^{17}$—, —O—, —S—, and —$CHR^{16}NR^{17}$—;

14

$R^1$ is selected from a $C_{6-10}$ aryl group substituted with 0–5 $R^4$ and a 5–10 membered heteroaryl system containing 1–4 heteroatoms selected from N, O, and S, substituted with 0–3 $R^4$;

$R^2$ is selected from a $C_{6-10}$ aryl group substituted with 0–5 $R^5$ and a 5–10 membered heteroaryl system containing 1–4 heteroatoms selected from N, O, and S, substituted with 0–3 $R^5$;

$R^3$ is selected from $(CRR)_qOH$, $(CRR)_qSH$, $(CRR)_qOR^{3d}$, $(CRR)_qS(O)_pR^{3d}$, $(CRR)_rC(O)R^{3b}$, $(CRR)_qNR^{3a}R^{3a}$, $(CRR)_rC(O)NR^{3a}R^{3a}$, $(CRR)_rC(O)NR^{3a}OR^{3d}$, $(CRR)_qSO_2NR^{3a}R^{3a}$, $(CRR)_rC(O)OR^{3d}$, a $(CRR)_r$—$C_{3-10}$ carbocyclic residue substituted with 0–5 $R^{3e}$, and a $(CRR)_r$-5–10 membered heterocyclic system containing 1–4 heteroatoms selected from N, O, and S, substituted with 0–3 $R^{3e}$;

alternatively, $R^3$ and $R^{12}$ join to form a $C_{3-6}$ cycloalkyl substituted with 0–2 $R^{3g}$, a $C_{5-6}$ lactam substituted with 0–2 $R^{3g}$, or a $C_{5-6}$ lactone substituted with 0–2 $R^{3g}$;

$R^{3a}$, at each occurrence, is independently selected from H, methyl substituted with 0–1 $R^{3c}$, $C_{2-6}$ alkyl substituted with 0–3 $R^{3e}$, $C_{3-8}$ alkenyl substituted with 0–3 $R^{3e}$, $C_{3-8}$ alkynyl substituted with 0–3 $R^{3e}$, $(CH_2)_rC_{3-6}$ cycloalkyl, a $(CH_2)_r$—$C_{3-10}$ carbocyclic residue substituted with 0–5 $R^{3e}$, and a $(CH_2)_r$-5–10 membered heterocyclic system containing 1–4 heteroatoms selected from N, O, and S, substituted with 0–3 $R^{3e}$;

$R^{3b}$, at each occurrence, is independently selected from $C_{1-6}$ alkyl substituted with 0–3 $R^{3e}$, $C_{2-8}$ alkenyl substituted with 0–3 $R^{3e}$, $C_{2-8}$ alkynyl substituted with 0–3 $R^{3e}$, a $(CH_2)_r$—$C_{3-6}$ carbocyclic residue substituted with 0–2 $R^{3e}$, and a $(CH_2)_r$-5–6 membered heterocyclic system containing 1–4 heteroatoms selected from N, O, and S, substituted with 0–3 $R^{3e}$;

$R^{3c}$ is independently selected from —$C(O)R^{3b}$, —$C(O)OR^{3d}$, —$C(O)NR^{3f}R^{3f}$, and $(CH_2)_r$phenyl;

$R^{3d}$, at each occurrence, is independently selected from H, methyl, —$CF_3$, $C_{2-6}$ alkyl substituted with 0–3 $R^{3e}$, $C_{3-6}$ alkenyl substituted with 0–3 $R^{3e}$, $C_{3-6}$ alkynyl substituted with 0–3 $R^{3e}$, a $C_{3-10}$ carbocyclic residue substituted with 0–3 $R^{3e}$, and a $(CH_2)_r$-5–6 membered heterocyclic system containing 1–4 heteroatoms selected from N, O, and S, substituted with 0–3 $R^{3e}$;

$R^{3e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{3f}R^{3f}$, and $(CH_2)_r$phenyl;

$R^{3f}$, at each occurrence, is selected from H, $C_{1-6}$ alkyl, and $C_{3-6}$ cycloalkyl;

$R^{3g}$ is selected from $(CHR)_qOH$, $(CHR)_qSH$, $(CHR)_qOR^{3d}$, $(CHR)_qS(O)_pR^{3d}$, $(CHR)_rC(O)R^{3b}$, $(CHR)_qNR^{3a}R^{3a}$, $(CHR)_rC(O)NR^{3a}R^{3a}$, $(CHR)_rC(O)NR^{3a}OR^{3d}$, $(CHR)_qSO_2NR^{3a}R^{3a}$, $(CHR)_rC(O)OR^{3d}$, and a $(CHR)_r$—$C_{3-10}$ carbocyclic residue substituted with 0–5 $R^{3e}$;

R, at each occurrence, is independently selected from H, $C_{1-6}$ alkyl, $C_{2-8}$ alkenyl, $C_{2-8}$ alkynyl, $(CH_2)_rC_{3-6}$ cycloalkyl, $(CHR)_rC(O)NR^{3a}R^{3a}$, and $(CHR)_rC(O)OR^{3d}$, and $(CH_2)_r$phenyl substituted with $R^{3e}$;

$R^4$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{4a}R^{4a}$, $(CR'R')_rOH$, $(CR'R')_rO(CR'R')_rR^{4d}$, $(CR'R')_rSH$, $(CR'R')_rC(O)H$, $(CR'R')_rSR^{4d}$, $(CR'R')_rC(O)OH$, $(CR'R')_rC(O)(CR'R')_rR^{4b}$, $(CR'R')_rC(O)NR^{4a}R^{4a}$, $(CR'R')_rNR^{4f}C(O)$ $(CR'R')_rR^{4b}$, $(CR'R')_rC(O)O(CR'R')_rR^{4d}$, $(CR'R')_rOC(O)(CR'R')_rR^{4b}$, $(CR'R')_rNR^{4f}C(O)O(CR'R')_rR^{4d}$, $(CR'R')_rOC(O)NR^{4a}R^{4a}$, $(CR'R')_rNR^{6a}C(S)NR^{6a}(CR'R')_rR^{6d}$, $(CR'R')_r$ NR$^{4a}$C(O)NR$^{4a}$R$^{4a}$, (CR'R')$_r$C(=NR$^{4f}$)NR$^{4a}$R$^{4a}$, (CR'R')$_r$NHC(=NR$^{4f}$)NR$^{4f}$R$^{4f}$, (CR'R')$_r$S(O)$_p$(CR'R')$_r$R$^{4b}$, (CR'R')$_r$S(O)$_2$NR$^{4a}$R$^{4a}$, (CR'R')$_r$NR$^{6f}$S(O)$_2$NR$^{6a}$R$^{6a}$, (CR'R')$_r$NR$^{4f}$S(O)$_2$(CR'R')$_r$R$^{4b}$, C$_{1-6}$ haloalkyl, C$_{2-8}$ alkenyl substituted with 0–3 R', C$_{2-8}$ alkynyl substituted with 0–3 R', and (CR'R')$_r$phenyl substituted with 0–3 R$^{4e}$;

alternatively, two R$^4$ on adjacent atoms on R$^1$ may join to form a cyclic acetal;

R$^{4a}$, at each occurrence, is independently selected from H, methyl substituted with 0–1R$^{4g}$, C$_{2-6}$ alkyl substituted with 0–2 R$^{5e}$, C$_{3-8}$ alkenyl substituted with 0–2 R$^{5e}$, C$_{3-8}$ alkynyl substituted with 0–2 R$^{5e}$, a (CH$_2$)$_r$—C$_{3-10}$ carbocyclic residue substituted with 0–5 R$^{4e}$, and a (CH$_2$)$_r$-5–10 membered heterocyclic system containing 1–4 heteroatoms selected from N, O, and S, substituted with 0–2 R$^{4e}$;

R$^{4b}$, at each occurrence, is selected from C$_{1-6}$ alkyl substituted with 0–2 R$^{5e}$, C$_{3-8}$ alkenyl substituted with 0–2 R$^{5e}$, C$_{3-8}$ alkynyl substituted with 0–2 R$^{5e}$, a (CH$_2$)$_r$C$_{3-6}$ carbocyclic residue substituted with 0–3 R$^{4e}$, and a (CH$_2$)$_r$-5–6 membered heterocyclic system containing 1–4 heteroatoms selected from N, O, and S, substituted with 0–2 R$^{4e}$;

R$^{4d}$, at each occurrence, is selected from C$_{3-8}$ alkenyl substituted with 0–2 R$^{5e}$, C$_{3-8}$ alkynyl substituted with 0–2 R$^{5e}$, methyl, CF$_3$, C$_{2-6}$ alkyl substituted with 0–3 R$^{4e}$, a (CH$_2$)$_r$—C$_{3-10}$ carbocyclic residue substituted with 0–3 R$^{4e}$, and a (CH$_2$)$_r$-5–6 membered heterocyclic system containing 1–4 heteroatoms selected from N, O, and S, substituted with 0–3 R$^{4e}$;

R$^{4e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, and (CH$_2$)$_r$phenyl;

R$^{4f}$, at each occurrence, is selected from H, C$_{1-5}$ alkyl, and C$_{3-6}$ cycloalkyl, and phenyl;

R$^{4g}$ is independently selected from —C(O)R$^{4b}$, —C(O)OR$^{4d}$, —C(O)NR$^{4f}$R$^{4f}$, and (CH$_2$)$_r$phenyl;

R$^5$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{5a}$R$^{5a}$, (CR'R')$_r$OH, (CR'R')$_r$O(CR'R')$_r$R$^{5d}$, (CR'R')$_r$SH, (CR'R')$_r$C(O)H, (CR'R')$_r$S(CR'R')$_r$R$^{5d}$, (CR'R')$_r$C(O)OH, (CR'R')$_r$C(O)(CR'R')$_r$R$^{5b}$, (CR'R')$_r$C(O)NR$^{5a}$R$^{5a}$, (CR'R')$_r$NR$^{5f}$C(O)(CR'R')$_r$R$^{5b}$, (CR'R')$_r$C(O)O(CR'R')$_r$R$^{5d}$, (CR'R')$_r$OC(O)(CR'R')$_r$R$^{5b}$, (CR'R')$_r$NR$^{5f}$C(O)O(CR'R')$_r$R$^{5d}$, (CR'R')$_r$OC(O)NR$^{5a}$R$^{5a}$, (CR'R')$_r$NR$^{5a}$C(O)NR$^{5a}$R$^{5a}$, (CR'R')$_r$C(=NR$^{5f}$)NR$^{5a}$R$^{5a}$, (CR'R')$_r$NHC(=NR$^{5f}$)NR$^{5f}$R$^{5f}$, (CR'R')$_r$S(O)$_p$(CR'R')$_r$R$^{5b}$, (CR'R')$_r$S(O)$_2$NR$^{5a}$R$^{5a}$, (CR'R')$_r$NR$^{5a}$S(O)$_2$NR$^{5a}$R$^{5a}$, (CR'R')$_r$NR$^{5f}$S(O)$_2$(CR'R')$_r$R$^{5b}$, C$_{1-6}$ haloalkyl, C$_{2-8}$ alkenyl substituted with 0–3 R', C$_{2-8}$ alkynyl substituted with 0–3 R', and (CR'R')$_r$phenyl substituted with 0–3 R$^{5e}$;

alternatively, two R$^5$ on adjacent atoms on R$^2$ may join to form a cyclic acetal;

R$^{5a}$, at each occurrence, is independently selected from H, methyl substituted with 0–1 R$^{5g}$, C$_{2-6}$ alkyl substituted with 0–2 R$^{5e}$, C$_{3-8}$ alkenyl substituted with 0–2 R$^{5e}$, C$_{3-8}$ alkynyl substituted with 0–2 R$^{5e}$, a (CH$_2$)$_r$—C$_{3-10}$ carbocyclic residue substituted with 0–5 R$^{5e}$, and a (CH$_2$)$_r$-5–10 membered heterocyclic system containing 1–4 heteroatoms selected from N, O, and S, substituted with 0–2 R$^{5e}$;

R$^{5b}$, at each occurrence, is independently selected from C$_{1-6}$ alkyl substituted with 0–2 R$^{5e}$, C$_{3-8}$ alkenyl substituted with 0–2 R$^{5e}$, C$_{3-8}$ alkynyl substituted with 0–2 R$^{5e}$, a (CH$_2$)$_r$C$_{3-6}$ carbocyclic residue substituted with 0–3 R$^{5e}$, and a (CH$_2$)$_r$-5–6 membered heterocyclic system containing 1–4 heteroatoms selected from N, O, and S, substituted with 0–2 R$^{5e}$;

R$^{5d}$, at each occurrence, is independently selected from C$_{3-8}$ alkenyl substituted with 0–2 R$^{5e}$, C$_{3-8}$ alkynyl substituted with 0–2 R$^{5e}$, methyl, CF$_3$, C$_{2-6}$ alkyl substituted with 0–3 R$^{5e}$, a (CH$_2$)$_r$—C$_{3-10}$ carbocyclic residue substituted with 0–3 R$^{5e}$, and a (CH$_2$)$_r$-5–6 membered heterocyclic system containing 1–4 heteroatoms selected from N, O, and S, substituted with 0–3 R$^{5e}$;

R$^{5e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{5f}$R$^{5f}$, and (CH$_2$)$_r$phenyl;

R$^{5f}$, at each occurrence, is selected from H, C$_{1-5}$ alkyl, and C$_{3-6}$ cycloalkyl, and phenyl;

R$^{5g}$ is independently selected from —C(O)R$^{5b}$, —C(O)OR$^{5d}$, —C(O)NR$^{5f}$R$^{5f}$, and (CH$_2$)$_r$phenyl;

R', at each occurrence, is selected from H, C$_{1-6}$ alkyl, C$_{2-8}$ alkenyl, C$_{2-8}$ alkynyl, (CH$_2$)$_r$C$_{3-6}$ cycloalkyl, and (CH$_2$)$_r$phenyl substituted with R$^{5e}$;

R$^6$, is selected from H, C$_{1-6}$ alkyl, C$_{2-6}$ alkenyl, C$_{2-6}$ alkynyl, (CRR)$_q$OH, (CRR)$_q$SH, (CRR)$_q$OR$^{6d}$, (CRR)$_q$S(O)$_p$R$^{6d}$, (CRR)$_q$C(O)R$^{6b}$, (CRR)$_r$NR$^{6a}$R$^{6a}$, (CRR)$_r$C(O)NR$^{6a}$R$^{6a}$, (CRR)$_r$C(O)NR$^{6a}$OR$^{6d}$, (CRR)SO$_2$NR$^{6a}$R$^{6a}$, (CRR)$_r$C(O)OR$^{6d}$, a (CRR)$_r$—C$_{3-10}$ carbocyclic residue substituted with 0–5 R$^{6e}$, and a (CRR)$_r$-5–10 membered heterocyclic system containing 1–4 heteroatoms selected from N, O, and S, substituted with 0–3 R$^{6e}$;

alternatively, R$^6$ and R$^7$ join to form a C$_{3-6}$ cycloalkyl substituted with 0–2 R$^{6g}$, a 5–6 membered ring lactam substituted with 0–2 R$^{6g}$, or a 5–6 membered ring lactone substituted with 0–2 R$^{6g}$;

R$^{6a}$, at each occurrence, is independently selected from H, methyl, C$_{2-6}$ alkyl substituted with 0–3 R$^{6e}$, C$_{3-8}$ alkenyl substituted with 0–3 R$^{6e}$, C$_{3-8}$ alkynyl substituted with 0–3 R$^{6e}$, (CH$_2$)$_r$C$_{3-6}$ cycloalkyl, a (CH$_2$)$_r$—C$_{3-10}$ carbocyclic residue substituted with 0–5 R$^{6e}$, and a (CH$_2$)$_r$-5–10 membered heterocyclic system containing 1–4 heteroatoms selected from N, O, and S, substituted with 0–3 R$^{6e}$;

R$^{6b}$, at each occurrence, is independently selected from C$_{1-6}$ alkyl substituted with 0–3 R$^{6e}$, C$_{2-8}$ alkenyl substituted with 0–3 R$^{6e}$, C$_{2-8}$ alkynyl substituted with 0–3 R$^{6e}$, a (CH$_2$)$_r$—C$_{3-6}$ carbocyclic residue substituted with 0–2 R$^{6e}$, and a (CH$_2$)$_r$-5–6 membered heterocyclic system containing 1–4 heteroatoms selected from N, O, and S, substituted with 0–3 R$^{6e}$;

R$^{6d}$, at each occurrence, is independently selected from H, methyl, —CF$_3$, C$_{2-6}$ alkyl substituted with 0–3 R$^{6e}$, C$_{3-6}$ alkenyl substituted with 0–3 R$^{6e}$, C$_{3-6}$ alkynyl substituted with 0–3 R$^{6e}$, a C$_{3-10}$ carbocyclic residue substituted with 0–3 R$^{6e}$, and a (CH$_2$)$_r$-5–6 membered heterocyclic system containing 1–4 heteroatoms selected from N, O, and S, substituted with 0–3 R$^{6e}$;

R$^{6e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{6f}$R$^{6f}$, and (CH$_2$)$_r$phenyl;

R$^{6f}$, at each occurrence, is independently selected from H, C$_{1-6}$ alkyl, and C$_{3-6}$ cycloalkyl;

R$^{6g}$ is selected from (CHR)$_q$OH, (CHR)$_q$SH, (CHR)$_q$OR$^{6d}$, (CHR)$_q$S(O)$_p$R$^{6d}$, (CHR)$_q$C(O)R$^{6b}$, (CHR)$_q$NR$^{6a}$R$^{6a}$, (CHR)$_q$C(O)NR$^{6a}$R$^{6a}$, (CHR)$_r$C(O)NR$^{6a}$OR$^{6d}$, (CHR)$_q$SO$_2$NR$^{6a}$R$^{6a}$, (CHR)$_r$C(O)OR$^{6d}$, and a (CHR)$_r$—C$_{3-10}$ carbocyclic residue substituted with 0–5 R$^{6e}$;

R$^7$, is selected from H, C$_{1-6}$ alkyl, C$_{2-6}$ alkenyl, C$_{2-6}$ alkynyl, (CRR)$_q$OH, (CRR)$_q$SH, (CRR)$_q$OR$^{7d}$, (CRR)$_q$S(O)$_p$R$^{7d}$, (CRR)$_r$C(O)R$^{7b}$, (CRR)$_r$NR$^{7a}$R$^{7a}$, (CRR)$_r$C(O)NR$^{7a}$R$^{7a}$, (CRR)$_r$C(O)NR$^{7a}$OR$^{7d}$, (CRR)$_q$SO$_2$NR$^{7a}$R$^{7a}$, (CRR)$_r$C(O)OR$^{7d}$, a (CRR)$_r$—C$_{3-10}$ carbocyclic residue substituted with 0–5 R$^{7e}$, and a (CRR)$_r$-5–10 membered heterocyclic system containing 1–4 heteroatoms selected from N, O, and S, substituted with 0–3 R$^{7e}$;

R$^{7a}$, at each occurrence, is independently selected from H, methyl, C$_{2-6}$ alkyl substituted with 0–3 R$^{7e}$, C$_{3-8}$ alkenyl substituted with 0–3 R$^{7e}$, C$_{3-8}$ alkynyl substituted with 0–3 R$^{7e}$, (CH$_2$)$_r$C$_{3-6}$ cycloalkyl, a (CH$_2$)$_r$—C$_{3-10}$ carbocyclic residue substituted with 0–5 R$^{7e}$, and a (CH$_2$)$_r$-5–10 membered heterocyclic system containing 1–4 heteroatoms selected from N, O, and S, substituted with 0–3 R$^{7e}$;

R$^{7b}$, at each occurrence, is independently selected from C$_{1-6}$ alkyl substituted with 0–3 R$^{7e}$, C$_{2-8}$ alkenyl substituted with 0–3 R$^{7e}$, C$_{2-8}$ alkynyl substituted with 0–3 R$^{7e}$, a (CH$_2$)$_r$—C$_{3-6}$ carbocyclic residue substituted with 0–2 R$^{7e}$, and a (CH$_2$)$_r$-5–6 membered heterocyclic system containing 1–4 heteroatoms selected from N, O, and S, substituted with 0–3 R$^{7e}$;

R$^{7d}$, at each occurrence, is independently selected from H, methyl, —CF$_3$, C$_{2-6}$ alkyl substituted with 0–3 R$^{7e}$, C$_{3-6}$ alkenyl substituted with 0–3 R$^{7e}$, C$_{3-6}$ alkynyl substituted with 0–3 R$^{7e}$, a C$_{3-10}$ carbocyclic residue substituted with 0–3 R$^{7e}$, and a (CH$_2$)$_r$-5–6 membered heterocyclic system containing 1–4 heteroatoms selected from N, O, and S, substituted with 0–3 R$^{7e}$;

R$^{7e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is independently selected from H, C$_{1-6}$ alkyl, and C$_{3-6}$ cycloalkyl;

R$^8$ is selected from H, C$_{1-6}$ alkyl, C$_{2-6}$ alkenyl, C$_{2-6}$ alkynyl, (CRR)$_r$OH, (CRR)$_r$SH, (CRR)$_r$OR$^{8d}$, (CRR)$_r$S(O)$_p$R$^{8d}$, (CRR)$_r$C(O)R$^{8b}$, (CRR)$_r$NR$^{8a}$R$^{8a}$, (CRR)$_r$C(O)NR$^{8a}$R$^{8a}$, (CRR)$_r$C(O)NR$^{8a}$OR$^{8d}$, (CRR)$_r$SO$_2$NR$^{8a}$R$^{8a}$, (CRR)$_r$C(O)OR$^{8d}$, a (CRR)$_r$—C$_{3-10}$ carbocyclic residue substituted with 0–5 R$^{8e}$, and a (CRR)$_r$-5–10 membered heterocyclic system containing 1–4 heteroatoms selected from N, O, and S, substituted with 0–3 R$^{8e}$;

alternatively, R$^8$ and R$^9$ join to form a C$_{3-6}$ cycloalkyl substituted with 0–2 R$^{8g}$, a 5–6 memebered ring lactam substituted with 0–2 R$^{8g}$, or a 5–6 membered ring lactone substituted with 0–2 R$^{8g}$;

R$^{8a}$, at each occurrence, is independently selected from H, methyl, C$_{2-6}$ alkyl substituted with 0–3 R$^{8e}$, C$_{3-8}$ alkenyl substituted with 0–3 R$^{8e}$, C$_{3-8}$ alkynyl substituted with 0–3 R$^{8e}$, (CH$_2$)$_r$C$_{3-6}$ cycloalkyl, a (CH$_2$)$_r$—C$_{3-10}$ carbocyclic residue substituted with 0–5 R$^{8e}$, and a (CH$_2$)$_r$-5–10 membered heterocyclic system containing 1–4 heteroatoms selected from N, O, and S, substituted with 0–3 R$^{8e}$;

R$^{8b}$, at each occurrence, is independently selected from C$_{1-6}$ alkyl substituted with 0–3 R$^{8e}$, C$_{2-8}$ alkenyl substituted with 0–3 R$^{8e}$, C$_{2-8}$ alkynyl substituted with 0–3 R$^{8e}$, a (CH$_2$)$_r$—C$_{3-6}$ carbocyclic residue substituted with 0–2 R$^{8e}$, and a (CH$_2$)$_r$-5–6 membered heterocyclic system containing 1–4 heteroatoms selected from N, O, and S, substituted with 0–3 R$^{8e}$;

R$^{8d}$, at each occurrence, is independently selected from H, methyl, —CF$_3$, C$_{2-6}$ alkyl substituted with 0–3 R$^{8e}$, C$_{3-6}$ alkenyl substituted with 0–3 R$^{8e}$, C$_{3-6}$ alkynyl substituted with 0–3 R$^{8e}$, a C$_{3-10}$ carbocyclic residue substituted with 0–3 R$^{8e}$, and a (CH$_2$)$_r$-5–6 membered heterocyclic system containing 1–4 heteroatoms selected from N, O, and S, substituted with 0–3 R$^{8e}$;

R$^{8e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{8f}$R$^{8f}$, and (CH$_2$)$_r$phenyl;

R$^{8f}$, at each occurrence, is independently selected from H, C$_{1-6}$ alkyl, and C$_{3-6}$ cycloalkyl;

R$^{8g}$ is selected from (CHR)$_q$OH, (CHR)$_q$SH, (CHR)$_q$OR$^{8d}$, (CHR)$_q$S(O)$_p$R$^{8d}$, (CHR)$_r$C(O)R$^{8b}$, (CHR)$_r$NR$^{8a}$R$^{8a}$, (CHR)$_r$C(O)NR$^{8a}$R$^{8a}$, (CHR)$_r$C(O)NR$^{8a}$OR$^{8d}$, (CHR)$_q$SO$_2$NR$^{8a}$R$^{8a}$, (CHR)$_r$C(O)OR$^{8d}$, and a (CHR)$_r$—C$_{3-10}$ carbocyclic residue substituted with 0–5 R$^{8e}$;

R$^9$ is selected from H, C$_{1-6}$ alkyl, C$_{2-6}$ alkenyl, C$_{2-6}$ alkynyl, (CRR)$_r$OH, (CRR)$_r$SH, (CRR)$_r$OR$^{9d}$, (CRR)$_r$S(O)$_p$R$^{9d}$, (CRR)$_r$C(O)R$^{9b}$, (CRR)$_r$NR$^{9a}$R$^{9a}$, (CRR)$_r$C(O)NR$^{9a}$R$^{9a}$, (CRR)$_r$C(O)NR$^{9a}$OR$^{9d}$, (CRR)$_r$SO$_2$NR$^{9a}$R$^{9a}$, (CRR)$_r$C(O)OR$^{9d}$, a (CRR)$_r$—C$_{3-10}$ carbocyclic residue substituted with 0–5 R$^{9e}$, and a (CRR)$_r$-5–10 membered heterocyclic system containing 1–4 heteroatoms selected from N, O, and S, substituted with 0–3 R$^{9e}$;

R$^{9a}$, at each occurrence, is independently selected from H, methyl, C$_{2-6}$ alkyl substituted with 0–3 R$^{9e}$, C$_{3-8}$ alkenyl substituted with 0–3 R$^{9e}$, C$_{3-8}$ alkynyl substituted with 0–3 R$^{9e}$, (CH$_2$)$_r$C$_{3-6}$ cycloalkyl, a (CH$_2$)$_r$—C$_{3-10}$ carbocyclic residue substituted with 0–5 R$^{9e}$, and a (CH$_2$)$_r$-5–10 membered heterocyclic system containing 1–4 heteroatoms selected from N, O, and S, substituted with 0–3 R$^{9e}$;

R$^{9b}$, at each occurrence, is independently selected from C$_{1-6}$ alkyl substituted with 0–3 R$^{9e}$, C$_{2-8}$ alkenyl substituted with 0–3 R$^{9e}$, C$_{2-8}$ alkynyl substituted with 0–3 R$^{9e}$, a (CH$_2$)$_r$—C$_{3-6}$ carbocyclic residue substituted with 0–2 R$^{9e}$, and a (CH$_2$)$_r$-5–6 membered heterocyclic system containing 1–4 heteroatoms selected from N, O, and S, substituted with 0–3 R$^{9e}$;

R$^{9d}$, at each occurrence, is independently selected from H, methyl, —CF$_3$, C$_{2-6}$ alkyl substituted with 0–3 R$^{9e}$, C$_{3-6}$ alkenyl substituted with 0–3 R$^{9e}$, C$_{3-6}$ alkynyl substituted with 0–3 R$^{9e}$, a C$_{3-10}$ carbocyclic residue substituted with 0–3 R$^{9e}$, and a (CH$_2$)$_r$-5–6 membered heterocyclic system containing 1–4 heteroatoms selected from N, O, and S, substituted with 0–3 R$^{9e}$;

R$^{9e}$, at each occurrence, is independently selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, —O—C$_{1-6}$ alkyl, SH, (CH$_2$)$_r$SC$_{1-5}$ alkyl, (CH$_2$)$_r$NR$^{9f}$R$^{9f}$, and (CH$_2$)$_r$phenyl;

R$^{9f}$, at each occurrence, is independently selected from H, C$_{1-6}$ alkyl, and C$_{3-6}$ cycloalkyl;

R$^{10}$ is selected from H, C$_{1-6}$ alkyl, C$_{2-6}$ alkenyl, C$_{2-6}$ alkynyl, (CRR)$_r$OH, (CRR)$_r$SH, (CRR)$_r$OR$^{10d}$, (CRR)$_r$S(O)$_p$R$^{10d}$, (CRR)$_r$C(O)R$^{10b}$, (CRR)$_r$NR$^{10a}$R$^{10a}$, (CRR)$_r$C(O)NR$^{10a}$R$^{10a}$, (CRR)$_r$C(O)NR$^{10a}$OR$^{10d}$, (CRR)$_r$SO$_2$NR$^{10a}$R$^{10a}$, (CRR)$_r$C(O)OR$^{10d}$, a (CRR)$_r$—C$_{3-10}$ carbocyclic residue substituted with 0–5 R$^{10e}$, and a (CRR)$_r$-5–10 membered heterocyclic system containing 1–4 heteroatoms selected from N, O, and S, substituted with 0–3 R$^{10e}$;

alternatively, R$^{10}$ and R$^{11}$ join to form a C$_{3-6}$ cycloalkyl substituted with 0–2 R$^{10g}$, a 5–6 membered ring lactam substituted with 0–2 R$^{10g}$, or a 5–6 membered ring lactone substituted with 0–2 R$^{10g}$;

R$^{10a}$, at each occurrence, is independently selected from H, methyl, C$_{2-6}$ alkyl substituted with 0–3 R$^{10e}$, C$_{3-8}$ alkenyl substituted with 0–3 R$^{10e}$, C$_{3-8}$ alkynyl substituted with 0–3 R$^{10e}$, (CH$_2$)$_r$C$_{3-6}$ cycloalkyl, a (CH$_2$)$_r$—C$_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

$R^{10b}$, at each occurrence, is independently selected from $C_{1-6}$ alkyl substituted with 0–3 $R^{10e}$, $C_{2-8}$ alkenyl substituted with 0–3 $R^{10e}$, $C_{2-8}$ alkynyl substituted with 0–3 $R^{10e}$, a $(CH_2)_r$—$C_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10d}$, at each occurrence, is independently selected from H, methyl, —$CF_3$, $C_{2-6}$ alkyl substituted with 0–3 $R^{10e}$, $C_{3-6}$ alkenyl substituted with 0–3 $R^{10e}$, $C_{3-6}$ alkynyl substituted with 0–3 $R^{10e}$, a $C_{3-10}$ carbocyclic residue substituted with 0–3 $R^{10e}$, and a $(CH_2)_r$-5–6 membered heterocyclic system containing 1–4 heteroatoms selected from N, O, and S, substituted with 0–3 $R^{10e}$;

$R^{10e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_r NR^{10f}R^{10f}$, and $(CH_2)_r$phenyl;

$R^{10f}$, at each occurrence, is independently selected from H, $C_{1-6}$ alkyl, and $C_{3-6}$ cycloalkyl;

$R^{10g}$ is selected from $(CHR)_qOH$, $(CHR)_qSH$, $(CHR)_q OR^{10d}$, $(CHR)_qS(O)_pR^{10d}$, $(CHR)_rC(O)R^{10b}$, $(CHR)_q NR^{10a}R^{10a}$, $(CHR)_rC(O)NR^{10a}R^{10a}$, $(CHR)_rC(O) NR^{10a}OR^{10d}$, $(CHR)_qSO_2NR^{10a}R^{10a}$, $(CHR)_rC(O) OR^{10d}$, and a $(CHR)_r$—$C_{3-10}$ carbocyclic residue substituted with 0–5 $R^{10e}$;

$R^{11}$, is selected from H, $C_{1-6}$ alkyl, $C_{2-6}$ alkenyl, $C_{2-6}$ alkynyl, $(CRR)_rOH$, $(CRR)_rSH$, $(CRR)_rOR^{11d}$, $(CRR)_rS (O)_pR^{11d}$, $(CRR)_rC(O)R^{11b}$, $(CRR)_rNR^{11a}R^{11a}$, $(CRR)_rC (O)NR^{11a}R^{11a}$, $(CRR)_rC(O)NR^{11a}OR^{11d}$, $(CRR)_r SO_2NR^{11a}R^{11a}$, $(CRR)_rC(O)OR^{11d}$, a $(CRR)_r$—$C_{3-10}$ carbocyclic residue substituted with 0–5 $R^{11e}$, and a $(CRR)_r$-5–10 membered heterocyclic system containing 1–4 heteroatoms selected from N, O, and S, substituted with 0–3 $R^{11e}$;

$R^{11a}$, at each occurrence, is independently selected from H, methyl, $C_{2-6}$ alkyl substituted with 0–3 $R^{11e}$, $C_{3-8}$ alkenyl substituted with 0–3 $R^{11e}$, $C_{3-8}$ alkynyl substituted with 0–3 $R^{11e}$, $(CH_2)_rC_{3-6}$ cycloalkyl, a $(CH_2)_r$—$C_{3-10}$ carbocyclic residue substituted with 0–5 $R^{11e}$, and a $(CH_2)_r$-5–10 membered heterocyclic system containing 1–4 heteroatoms selected from N, O, and S, substituted with 0–3 $R^{11e}$;

$R^{11b}$, at each occurrence, is independently selected from $C_{1-6}$ alkyl substituted with 0–3 $R^{11e}$, $C_{2-8}$ alkenyl substituted with 0–3 $R^{11e}$, $C_{2-8}$ alkynyl substituted with 0–3 $R^{11e}$, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11d}$, at each occurrence, is independently selected from H, methyl, —$CF_3$, $C_{2-6}$ alkyl substituted with 0–3 $R^{11e}$, $C_{3-6}$ alkenyl substituted with 0–3 $R^{11e}$, $C_{3-6}$ alkynyl substituted with 0–3 $R^{11e}$, a $C_{3-10}$ carbocyclic residue substituted with 0–3 $R^{11e}$, and a $(CH_2)_r$-5–6 membered heterocyclic system containing 1–4 heteroatoms selected from N, O, and S, substituted with 0–3 $R^{11e}$;

$R^{11e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_r NR^{11f}R^{11f}$, and $(CH_2)_r$phenyl;

$R^{11f}$, at each occurrence, is independently selected from H, $C_{1-6}$ alkyl, and $C_{3-6}$ cycloalkyl;

$R^{12}$ is selected from H, $C_{1-6}$ alkyl, $C_{2-6}$ alkenyl, $C_{2-6}$ alkynyl, $(CRR)_qOH$, $(CRR)_qSH$, $(CRR)_qOR^{12d}$, $(CRR)_qS (O)_pR^{12d}$, $(CRR)_rC(O)R^{12b}$, $(CRR)_rNR^{12a}R^{12a}$, $(CRR)_rC (O)NR^{12a}R^{12a}$, $(CRR)_rC(O)NR^{12a}OR^{12d}$, $(CRR)_q SO_2NR^{12a}R^{12a}$, $(CRR)_rC(O)OR^{12d}$, a $(CRR)_r$—$C_{3-10}$ carbocyclic residue substituted with 0–5 $R^{12e}$, and a $(CRR)_r$-5–10 membered heterocyclic system containing 1–4 heteroatoms selected from N, O, and S, substituted with 0–3 $R^{12e}$;

$R^{12a}$, at each occurrence, is independently selected from H, methyl, $C_{2-6}$ alkyl substituted with 0–3 $R^{12e}$, $C_{3-8}$ alkenyl substituted with 0–3 $R^{12e}$, $C_{3-8}$ alkynyl substituted with 0–3 $R^{12e}$, $(CH_2)_rC_{3-6}$ cycloalkyl, a $(CH_2)_r$—$C_{3-10}$ carbocyclic residue substituted with 0–5 $R^{12e}$, and a $(CH_2)_r$-5–10 membered heterocyclic system containing 1–4 heteroatoms selected from N, O, and S, substituted with 0–3 $R^{12e}$;

$R^{12b}$, at each occurrence, is independently selected from $C_{1-6}$ alkyl substituted with 0–3 $R^{12e}$, $C_{2-8}$ alkenyl substituted with 0–3 $R^{12e}$, $C_{2-8}$ alkynyl substituted with 0–3 $R^{12e}$, a $(CH_2)_r$—$C_{3-6}$ carbocyclic residue substituted with 0–2 $R^{12e}$, and a $(CH_2)_r$-5–6 membered heterocyclic system containing 1–4 heteroatoms selected from N, O, and S, substituted with 0–3 $R^{12e}$;

$R^{12d}$, at each occurrence, is independently selected from H, methyl, —$CF_3$, $C_{2-6}$ alkyl substituted with 0–3 $R^{12e}$, $C_{3-6}$ alkenyl substituted with 0–3 $R^{12e}$, $C_{3-6}$ alkynyl substituted with 0–3 $R^{12e}$, a $C_{3-10}$ carbocyclic residue substituted with 0–3 $R^{12e}$, and a $(CH_2)_r$-5–6 membered heterocyclic system containing 1–4 heteroatoms selected from N, O, and S, substituted with 0–3 $R^{12e}$;

$R^{12e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC1$-5 alkyl, OH, —O—$C_{1-6}$ alkyl, SH, $(CH_2)_rSC_{1-5}$ alkyl, $(CH_2)_r NR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{14}$ and $R^{14a}$ are independently selected from H, and $C_{1-4}$alkyl substituted with 0–1 $R^{14b}$, alternatively, $R^{14}$ and $R^{14a}$ can join to form a $C_{3-6}$ cycloalkyl;

$R^{14b}$, at each occurrence, is independently selected from —OH, —SH, —$NR^{14c}R^{14c}$, —$C(O)NR^{14c}R^{14c}$, —NHC (O)$R^{14c}$ and phenyl;

$R^{14c}$ is selected from H, $C_{1-4}$ alkyl and $C_{3-6}$ cycloalkyl;

$R^{15}$ is selected from H, $C_{1-4}$ alkyl, and $C_{3-6}$ cycloalkyl;

$R^{16}$ is selected from H, $C_{1-4}$ alkyl substituted with 0–3 $R^{16a}$, and $C_{3-6}$ cycloalkyl substituted with 0–3 $R^{16a}$;

$R^{16a}$ is selected from $C_{1-4}$ alkyl, —OH, —SH, —$NR^{16c}R^{16c}$, —$C(O)NR^{16c}R^{16c}$, and —NHC(O)$R^{16c}$;

$R^{16c}$ is selected from H, $C_{1-4}$ alkyl and $C_{3-6}$ cycloalkyl;

$R^{17}$ is selected from H, $C_{1-4}$ alkyl, and $C_{3-4}$ cycloalkyl;

n is selected from 1 and 2;

l is selected from 0 and 1;

m is selected from 0 and 1;

p, at each occurrence, is selected from 0, 1, or 2;

q, at each occurrence, is selected from 1, 2, 3, or 4; and r, at each occurrence, is selected from 0, 1, 2, 3, or 4.

[3] In another embodiment, the present invention provides novel compounds of formula (I), wherein:

$R^{14}$ and $R^{14a}$ are H;

$R^{15}$ is H; and n is 1.

[4] In another embodiment, the present invention provides novel compounds of formula (I), wherein:
$R^{16}$ is selected from H, $C_{1-4}$ alkyl substituted with 0–1 $R^{16a}$, wherein the alkyl is selected from methyl, ethyl, propyl, i-propyl, butyl, i-butyl, and s-butyl, and $C_{3-4}$ cycloalkyl substituted with 0–3 $R^{16a}$ wherein the cycloalkyl is selected from cyclopropyl and cyclobutyl;
$R^{16a}$ is selected from methyl, ethyl, propyl, i-propyl, —OH, —SH, —NR$^{16c}$R$^{16c}$, —C(O)NR$^{16c}$R$^{16c}$, and —NHC(O)NR$^{16c}$; and
$R^{17}$ is selected from H, methyl, ethyl, propyl, and i-propyl.

[5] In another embodiment, the present invention provides novel compounds of formula (I), wherein:
$R^9$ and $R^{11}$ are H; and
$R^8$ and $R^{10}$ are independently selected from H, $C_{1-6}$ alkyl, $C_{2-6}$ alkenyl, $C_{2-6}$ alkynyl, a $(CH_2)_r$—$C_{3-10}$ carbocyclic residue wherein the carbocyclic residue is selected from cyclopropyl, cyclobutyl, cyclopentyl, cyclohexyl, phenyl and naphthyl.

[6] In another embodiment, the present invention provides novel compounds of formula (I), wherein:
$R^3$ is selected from $(CRR)_qOH$, $(CRR)_qSH$, $(CRR)_qOR^{3d}$, $(CRR)_qS(O)_pR^{3d}$, $(CRR)_rC(O)R^{3b}$, $(CRR)_qNR^{3a}R^{3a}$, $(CRR)_rC(O)NR^{3a}R^{3a}$, $(CRR)_rC(O)NR^{3a}OR^{3d}$, $(CRR)_qSO_2NR^{3a}R^{3a}$, $(CRR)_rC(O)OR^{3d}$, a $(CRR)_r$—$C_{3-10}$ carbocyclic residue substituted with 0–5 $R^{3e}$, and a $(CRR)_r$-5–10 membered heterocyclic system containing 1–4 heteroatoms selected from N, O, and S, substituted with 0–3 $R^{3e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, pyrrolidinyl, tetrahydrofuranyl, tetrahydrothiophenyl, 1,2,4-triazolyl, 1,2,3-triazolyl, tetrazolyl, thiadiazolyl, thiazolyl, oxazolyl, pyrazinyl, and pyrimidinyl;
$R^6$ is selected from H, $(CRR)_qOH$, $(CRR)_qSH$, $(CRR)_qOR^{6d}$, $(CRR)_qS(O)_pR^{6d}$, $(CRR)_rC(O)R^{6b}$, $(CRR)_qNR^{6a}R^{6a}$, $(CRR)_rC(O)NR^{6a}R^{6a}$, $(CRR)_rC(O)NR^{6a}OR^{6d}$, $(CRR)_qSO_2NR^{6a}R^{6a}$, $(CRR)_rC(O)OR^{6d}$, a $(CRR)_r$—$C_{6-10}$ carbocyclic residue substituted with 0–5 $R^{6e}$, and a $(CRR)_r$-5–10 membered heterocyclic system containing 1–4 heteroatoms selected from N, O, and S, substituted with 0–6 $R^{6e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, pyrrolidinyl, tetrahydrofuranyl, tetrahydrothiophenyl, 1,2,4-triazolyl, 1,2,6-triazolyl, tetrazolyl, thiadiazolyl, thiazolyl, oxazolyl, pyrazinyl, and pyrimidinyl;
$R^7$ is H;
$R^{12}$ is selected from H, methyl, ethyl, and propyl;
alternatively, $R^3$ and $R^{12}$ join to form a $C_{3-6}$ cycloalkyl substituted with 0–2 $R^{3g}$, a $C_{5-6}$ lactam substituted with 0–2 $R^{3g}$, or a $C_{5-6}$ lactone substituted with 0–2 $R^{3g}$.

[7] In another embodiment, the present invention provides novel compounds of formula (I), wherein:
$R^1$ is selected from phenyl substituted with 0–3 $R^4$ and a 5–10 membered heteroaryl system substituted with 0–3 $R^4$, wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridinyl, pyrimidinyl, pyrrolyl, quinazolinyl, quinolinyl, thiazolyl, thienyl, and tetrazolyl;
$R^2$ is selected from phenyl substituted with 0–3 $R^5$ and a 5–10 membered heteroaryl system containing 1–4 heteroatoms substituted with 0–3 $R^5$, wherein the heteroaryl system is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridinyl, pyrimidinyl, pyrrolyl, quinazolinyl, quinolinyl, thiazolyl, thienyl, and tetrazolyl.

[8] In another embodiment, the present invention provides novel compounds of formula (I), wherein:
X is CHR$^{16}$NR$^{17}$;
$R^4$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, NO$_2$, CN, $(CR'R')_rNR^{4a}R^{4a}$, $(CR'R')_rOH$, $(CR'R')_rOR^{4d}$, $(CR'R')_rSH$, $(CR'R')_rSR^{4d}$, $(CR'R')_rC(O)OH$, $(CR'R')_rC(O)R^{4b}$, $(CR'R')_rC(O)NR^{4a}R^{4a}$, $(CR'R')_rNR^{4f}C(O)R^{4b}$, $(CR'R')_rC(O)OR^{4d}$, $(CR'R')_rOC(O)R^{4b}$, $(CR'R')_rNR^{4f}C(O)OR^{4d}$, $(CR'R')_rOC(O)NR^{4a}R^{4a}$, $(CR'R')_rNR^{4a}C(O)NR^{4a}R^{4a}$, $(CR'R')_rS(O)_pR^{4b}$, $(CR'R')_rS(O)_2NR^{4a}R^{4a}$, $(CR'R')_rNR^{4f}S(O)_2R^{4b}$, $(CR'R')_rNR^{4f}S(O)_2NR^{4a}R^{4a}$, $C_{1-6}$ haloalkyl, and $(CR'R')_r$phenyl substituted with 0–3 $R^{4e}$;
alternatively, two $R^4$ on adjacent atoms join to form —O—(CH$_2$)—O—;
$R^{4a}$, at each occurrence, is independently selected from H, methyl, ethyl, propyl, i-propyl, butyl, s-butyl, i-butyl, t-butyl, pentyl, hexyl, allyl, propargyl, and a (CH$_2$)$_r$—$C_{3-6}$ carbocyclic residue selected from cyclopropyl, cyclobutyl, cyclopentyl and cyclohexyl;
$R^{4b}$, at each occurrence, is selected from methyl, ethyl, propyl, i-propyl, butyl, s-butyl, i-butyl, t-butyl, pentyl, hexyl, allyl, propargyl, a (CH$_2$)$_r$—$C_{3-6}$ carbocyclic residue substituted with 0–3 $R^{4e}$, wherein the carbocyclic residue is selected from cyclopropyl, cyclobutyl, cyclopentyl and cyclohexyl, and a (CH$_2$)$_r$-5–6 membered heterocyclic system containing 1–4 heteroatoms selected from N, O, and S, substituted with 0–2 $R^{4e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;
$R^{4d}$, at each occurrence, is selected from H, methyl, CF$_3$, ethyl, propyl, i-propyl, butyl, s-butyl, i-butyl, t-butyl, pentyl, hexyl, allyl, propargyl, and a (CH$_2$)$_r$—$C_{3-6}$ carbocyclic residue selected from cyclopropyl, cyclobutyl, cyclopentyl and cyclohexyl;
$R^{4e}$, at each occurrence, is selected from $C_{1-6}$ alkyl, $C_{2-8}$ alkenyl, $C_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, and (CH$_2$)$_r$phenyl;
$R^{4f}$, at each occurrence, is selected from H, methyl, ethyl, propyl, i-propyl, butyl, and cyclopropyl, cyclobutyl, and phenyl;
$R^5$, at each occurrence, is selected from methyl, ethyl, propyl, i-propyl, butyl, i-butyl, s- butyl, t-butyl, pentyl, hexyl, (CR'R')$_r$C$_{3-6}$ cycloalkyl, Cl, Br, I, F, NO$_2$, CN, (CR'R')$_r$NR$^{5a}$R$^{5a}$, (CR'R')$_r$OH, (CR'R'$^7$)$_r$OR$^{5d}$, (CR'R')$_r$ SH, $(CR'R')_rC(O)H$, $(CR'R')_rSR^{5d}$, $(CR'R')_rC(O)OH$, $(CR'R')_rC(O)R^{5b}$, $(CR'R')_rC(O)NR^{5a}R^{5a}$, $(CR'R')_rNR^{5f}C(O)R^{5b}$, $(CR'R')_rC(O)OR^{5d}$, $(CR'R')_rOC(O)R^{5b}$, $(CR'R')_rNR^{5f}C(O)OR^{5d}$, $(CR'R')_rOC(O)NR^{5a}R^{5a}$, $(CR'R')_rNR^{5a}C(O)NR^{5a}R^{5a}$, $(CR'R')_rNR^{7a}C(O)NR^{7a}R^{7a}$, $(CR'R')_r NR^{7a}C(O)O(CR'R')_rR^{7d}$, $(CR'R')_rS(O)_pR^{5b}$, $(CR'R')_rS(O)_2NR^{5a}R^{5a}$, $(CR'R')_rNR^{5f}S(O)_2R^{5b}$, $C_{1-6}$ haloalkyl, and $(CHR')_r$phenyl substituted with 0–3 $R^{5e}$;

alternatively, two $R^5$ on adjacent atoms join to form —O—$(CH_2)$—O—;

$R^{5a}$, at each occurrence, is independently selected from H, methyl, ethyl, propyl, i-propyl, butyl, s-butyl, i-butyl, t-butyl, pentyl, hexyl, allyl, propargyl, and a $(CH_2)_r$—$C_{3-10}$ carbocyclic residue substituted with 0–1 $R^{5e}$, wherein the carbocyclic residue is selected from cyclopropyl, cyclobutyl, cyclopentyl, cyclohexyl, phenyl and naphthyl;

$R^{5b}$, at each occurrence, is selected from methyl, ethyl, propyl, i-propyl, butyl, s-butyl, i-butyl, t-butyl, pentyl, hexyl, allyl, propargyl, a $(CH_2)_r$—$C_{3-6}$ carbocyclic residue selected from cyclopropyl, cyclobutyl, cyclopentyl, cyclohexyl, and phenyl; and a $(CH_2)_r$-5–6 membered heterocyclic system containing 1–4 heteroatoms selected from N, O, and S, wherein the heterocyclic system is selected from pyridinyl, thiophenyl, furanyl, indazolyl, azetidinyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, morphlinyl, piperidinyl, pyrrolyl, 2,5-dihydropyrrolyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{5d}$, at each occurrence, is selected from H, methyl, $CF_3$, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{4f}R^{4f}$, and $(CH_2)_r$phenyl; and $R^{5f}$, at each occurrence, is selected from H, methyl, ethyl, propyl, i-propyl, butyl, and cyclopropyl, cyclobutyl, and phenyl.

[9] In another embodiment, the present invention provides novel compounds of formula (I), wherein:

$R^5$ is selected from methyl, ethyl, propyl, i-propyl, butyl, i-butyl, s-butyl, pentyl, hexyl, $CF_3$, $CF_2CF_3$, $CF_2H$, $OCF_3$, Cl, Br, I, F, $SCF_3$, $NR^{5a}R^{5a}$, $NHC(O)OR^{5a}$, $NHC(O)R^{5b}$, and $NHC(Q)NHR^{5a}$; and $R^{12}$ is selected from H and methyl.

[10] In another embodiment, the present invention provides compounds of formula (I), wherein Z is —C(O)—;

X is —$CHR^{16}NR^{17}$—;

$R^1$ is selected from phenyl substituted with 0–3 $R^4$, and a 5–10 membered heteroaryl system substituted with 0–2 $R^4$, wherein the heteroaryl is selected from indolyl, and pyridyl;

$R^2$ is phenyl substituted with 0–2 $R^5$;

$R^3$ is selected from $(CRR)_qOH$, $(CRR)_qOR^{3d}$, $(CH_2)_rC(O)OH$, $(CH_2)_rC(O)NR^{3a}R^{3a}$, $(CHR)_rC(O)NR^{3a}OR^{3d}$, $(CH_2)C(O)R^{3b}$, $(CH_2)_rC(O)OR^{3d}$, and $(CH_2)$-phenyl;

alternatively, $R^3$ and $R^{12}$ join to form cyclopropyl, cyclopentyl or cyclohexyl;

$R^{3a}$ is selected from H, methyl, ethyl, propyl, i-propyl, butyl, i-butyl, s-butyl, t-butyl, allyl, $CH_2CF_3$, $C(CH_3)CH_2CH_2OH$, cyclopropyl, 1-methylcyclopropyl, cyclobutyl, cyclopentyl, cyclohexyl, phenyl, and benzyl;

$R^{3b}$ is selected from pyrrolidinyl, pyrrolid-3-enyl, and morpholinyl;

$R^{3d}$ is selected from methyl, ethyl, propyl, i-propyl, butyl, i-butyl, t-butyl and benzyl;

R is selected from H, methyl, ethyl, propyl, i-propyl, butyl, i-butyl, s-butyl, pentyl, neopentyl, phenyl and benzyl;

$R^4$ is selected from methyl, ethyl, propyl, i-propyl, butyl, ethylene, $OCH_3$, $OCF_3$, $SCH_3$, $SO_2CH_3$, Cl, F, Br, CN;

alternatively, two $R^4$ join to form —O—$(CH_2)$—O—;

$R^6$ is selected from H, methyl, ethyl, propyl, i-propyl, butyl, $C(O)OCH_3$, $C(O)NHCH_2CH_3$;

$R^7$, $R^9$, and $R^{11}$ are H;

$R^8$ is H;

$R^{10}$ is selected from H and methyl;

$R^{16}$ is selected from H and methyl;

$R^{17}$ is selected from H and methyl;

m is 0 or 1;

l is 0 or 1 r is 0 or 1; and q is 1.

[11] In another embodiment, the present invention provides compounds of formula (I), wherein $R^3$ is H; and $R^6$, is selected from $C_{1-6}$ alkyl, $C_{2-6}$ alkenyl, $C_{2-6}$ alkynyl, $(CRR)_qOH$, $(CRR)_qSH$, $(CRR)_qOR^{6d}$, $(CRR)_qS(O)_pR^{6d}$, $(CRR)_rC(O)R^{6b}$, $(CRR)_rNR^{6a}R^{6a}$, $(CRR)_rC(O)NR^{6a}R^{6a}$, $(CRR)_rC(O)NR^{6a}OR^{6d}$, $(CRR)SO_2NR^{6a}R^{6a}$, $(CRR)_rC(O)OR^{6d}$, a $(CRR)_r$—$C_{3-10}$ carbocyclic residue substituted with 0–5 $R^{6e}$, and a $(CRR)_r$-5–10 membered heterocyclic system containing 1–4 heteroatoms selected from N, O, and S, substituted with 0–3 $R^{6e}$.

[12] In another embodiment, the present invention provides compounds of formula (I), wherein $R^{14}$ and $R^{14a}$ are H;

$R^{15}$ is H;

n is 1;

$R^{16}$ is selected from H, $C_{1-4}$ alkyl substituted with 0–1 $R^{16a}$, wherein the alkyl is selected from methyl, ethyl, propyl, i-propyl, butyl, i-butyl, and s-butyl, and $C_{3-4}$ cycloalkyl substituted with 0–3 $R^{16a}$ wherein the cycloalkyl is selected from cyclopropyl and cyclobutyl;

$R^{16a}$ is selected from methyl, ethyl, propyl, i-propyl, —OH, —SH, —$NR^{16c}R^{16c}$, —$C(O)NR^{16c}R^{16c}$, and —$NHC(O)R^{16c}$;

$R^{17}$ is selected from H, methyl, ethyl, propyl, and i-propyl;

$R^9$ and $R^{11}$ are H; and $R^8$ and $R^{10}$ are independently selected from H, $C_{1-6}$ alkyl, $C_{2-6}$ alkenyl, $C_{2-6}$ alkynyl, a $(CH_2)_r$—$C_{3-10}$ carbocyclic residue wherein the carbocyclic residue is selected from cyclopropyl, cyclobutyl, cyclopentyl, cyclohexyl, phenyl and naphthyl.

[13] In another embodiment, the present invention provides compounds of formula (I), wherein X is $CHR^{16}NR^{17}$;

$R^5$ is selected from methyl, ethyl, propyl, i-propyl, butyl, i-butyl, s-butyl, pentyl, hexyl, $CF_3$, $CF_2CF_3$, $CF_2H$, $OCF_3$, Cl, Br, I, F, $SCF_3$, $NR^{5a}R^{5a}$, $NHC(O)OR^{5a}$, $NHC(O)R^{5b}$, and $NHC(O)NHR^{5a}$; and $R^{12}$ is selected from H and methyl;

Z is —C(O)—;

$R^1$ is selected from phenyl substituted with 0–3 $R^4$, and a 5–10 membered heteroaryl system substituted with 0–2 $R^4$, wherein the heteroaryl is selected from indolyl, and pyridyl;

$R^2$ is phenyl substituted with 0–2 $R^5$;

R³ is selected from (CRR)$_q$OH, (CRR)$_q$OR$^{3d}$, (CH$_2$)$_r$C(O)OH, (CH$_2$)$_r$C(O)NR$^{3a}$R$^{3a}$, (CHR)$_r$C(O)NR$^{3a}$OR$^{3d}$, (CH$_2$)$_r$C(O)R$^{3b}$, (CH$_2$)$_r$C(O)OR$^{3d}$, and (CH$_2$)-phenyl;

alternatively, R³ and R¹² join to form cyclopropyl, cyclopentyl or cyclohexyl;

R$^{3a}$ is selected from H, methyl, ethyl, propyl, i-propyl, butyl, i-butyl, s-butyl, t-butyl, allyl, CH$_2$CF$_3$, C(CH$_3$)CH$_2$CH$_2$OH, cyclopropyl, 1-methylcyclopropyl, cyclobutyl, cyclopentyl, cyclohexyl, phenyl, and benzyl;

R$^{3b}$ is selected from pyrrolidinyl, pyrrolid-3-enyl, and morpholinyl;

R$^{3d}$ is selected from methyl, ethyl, propyl, i-propyl, butyl, i-butyl, t-butyl and benzyl;

R is selected from H, methyl, ethyl, propyl, i-propyl, butyl, i-butyl, s-butyl, pentyl, neopentyl, phenyl and benzyl;

R⁴ is selected from methyl, ethyl, propyl, i-propyl, butyl, ethylene, OCH$_3$, OCF$_3$, SCH$_3$, SO$_2$CH$_3$, Cl, F, Br, CN;

alternatively, two R⁴ join to form —O—(CH$_2$)—O—;

R⁶ is selected from H, methyl, ethyl, propyl, i-propyl, butyl, C(O)OCH$_3$, C(O)NHCH$_2$CH$_3$;

R⁷, R⁹, and R¹¹ are H;

R⁸ is H;

R¹⁰ is selected from H and methyl;

R¹⁶ is selected from H and methyl;

R¹⁷ is selected from H and methyl;

m is 0 or 1;

l is 0 or 1 r is 0 or 1; and q is 1.

[14] In another embodiment, the present invention provides novel compounds of formula (I), wherein the compound is selected from:

Methyl (2S)-3-[[(2,4-dimethylphenyl)methyl]amino]-2-[[[[3-(trifluoromethyl)benzoyl]amino]acetyl]amino]-propanoate;

Methyl (2R)-3-[[(2,4-dimethylphenyl)methyl]amino]-2-[[[[3-(trifluoromethyl)benzoyl]amino]acetyl]amino]-propanoate;

(2S)-3-[[(2,4-dimethylphenyl)methyl]amino]-2-[[[[3-(trifluoromethyl)benzoyl amino]acetyl]amino]-propanoic acid;

(2S)-N-Methyl-3-[[(2,4-dimethylphenyl)methyl]amino]-2-[[[[3-(trifluoromethyl)benzoyl]amino]acetyl]amino]-propanamide;

(2S)-3-[[(2,4-dimethylphenyl)methyl]amino]-2-[[[[3-(trifluoromethyl)benzoyl]amino]acetyl]amino]-propanamide;

(2R)-3-[[(2,4-dimethylphenyl)methyl]amino]-2-[[[[3-(trifluoromethyl)benzoyl]amino]acetyl]amino]-propanamide;

(2S)-N-Ethyl-3-[[(2,4-dimethylphenyl)methyl]amino]-2-[[[[3-(trifluoromethyl)benzoyl]amino]acetyl]amino]-propanamide;

(2S)-N-Benzyl-3-[[(2,4-dimethylphenyl)methyl]amino]-2-[[[[3-(trifluoromethyl)benzoyl]amino]acetyl]amino]-propanamide;

(2S)-N-Isopropyl-3-[[(2,4-dimethylphenyl)methyl]amino]-2-[[[[3-(trifluoromethyl)benzoyl]amino]acetyl]amino]-propanamide;

(2S)-N-tert-Butyl-3-[[(2,4-dimethylphenyl)methyl]amino]-2-[[[[3-(trifluoromethyl)benzoyl]amino]acetyl]amino]-propanamide;

(2S)-N-Cyclopropyl-3-[[(2,4-dimethylphenyl)methyl]amino]-2-[[[[3-(trifluoromethyl)benzoyl]amino]acetyl]amino]-propanamide;

(2S)-N-Cyclobutyl-3-[[(2,4-dimethylphenyl)methyl]amino]-2-[[[[3-(trifluoromethyl)benzoyl]amino]acetyl]amino]-propanamide;

(2S)-N-Phenyl-3-[[(2,4-dimethylphenyl)methyl]amino]-2-[[[[3-(trifluoromethyl)benzoyl]amino]acetyl]amino]-propanamide;

(2S)-N,N-Dimethyl-3-[[(2,4-dimethylphenyl)methyl]amino]-2-[[[[3-(trifluoromethyl)benzoyl]amino]acetyl]amino]-propanamide;

(2S)-N-Methyl,N-methoxy-3-[[(2,4-dimethylphenyl)methyl]amino]-2-[[[[3-(trifluoromethyl)benzoyl]amino]acetyl]amino]-propanamide;

Methyl (2S)-3-[[(4-chlorophenyl)methyl]amino]-2-[[[[3-(trifluoromethyl)benzoyl]amino]acetyl]amino]-propanoate;

(2S)-3-[[(4-chlorophenyl)methyl]amino]-2-[[[[3-(trifluoromethyl)benzoyl]amino]acetyl]amino]-propanamide;

(2S)-N-Ethyl-3-[[(4-chlorophenyl)methyl]amino]-2-[[[[3-(trifluoromethyl)benzoyl]amino]acetyl]amino]-propanamide;

Methyl (2S)-3-[[(1S/R)-1-(4-chlorophenyl)ethyl]amino]-2-[[[[3-(trifluoromethyl)benzoyl]amino]acetyl]amino]-propanoate;

Methyl (2S)-3-[[(1S/R)-1-(2,4-dimethylphenyl)ethyl]amino]-2-[[[[3-(trifluoromethyl)benzoyl]amino]acetyl]amino]-propanoate;

Methyl (2S)-3-[(1H-indol-3-ylmethyl)amino]-2-[[[[3-(trifluoromethyl)benzoyl]amino]acetyl]amino]-propanoate;

(2S)-3-[(1H-indol-3-ylmethyl)amino]-2-[[[[3-(trifluoromethyl)benzoyl]amino]acetyl]amino]-propanamide;

Methyl (2S)-3-[(1,3-benzodioxol-5-ylmethyl)amino]-2-[[[[3-(trifluoromethyl)benzoyl]amino]acetyl]amino]-propanoate;

Methyl (2S)-3-[[(4-bromophenyl)methyl]amino]-2-[[[[3-(trifluoromethyl)benzoyl]amino]acetyl]amino]-propanoate;

Methyl (2S)-2-[[[[2-[[(1,1-dimethylethoxy)carbonyl]amino]-5-(trifluoromethyl)benzoyl]amino]acetyl]amino]-3-[[(2,4-dimethylphenyl)methyl]amino]-propanoate;

Methyl (2S)-2-[[[[2-amino-5-(trifluoromethyl)benzoyl]amino]acetyl]amino]-3-[[(2,4-dimethylphenyl)methyl]amino]-propanoate;

(2S)-2-[[[[2-amino-5-(trifluoromethyl)benzoyl]amino]acetyl]amino]-3-[[(2,4-dimethylphenyl)methyl]amino]-propanamide;

N-[2-[[(1S)-2-[[(2,4-dimethylphenyl)methyl]amino]-1-(hydroxymethyl)ethyl]amino]-2-oxoethyl]-3-(trifluoromethyl)benzamide;

N-[2-[[(-1R)-2-[[(2,4-dimethylphenyl)methyl]amino]-1-(hydroxymethyl)ethyl]amino]-2-oxoethyl]-3-(trifluoromethyl)benzamide;

N-[2-[[(1S, 2S/R)-1-[[[(2,4-dimethylphenyl)methyl]amino]methyl]-2-hydroxypropyl]amino]-2-oxoethyl]-3-(trifluoromethyl)benzamide;

tert-Butyl (3R)-4-[[(2,4-dimethylphenyl)methyl]amino]-3-[[[[3-(trifluoromethyl)benzoyl]amino]acetyl]amino]-butanoate;

N-[2-[[(-1R)-2-[[(2,4-dimethylphenyl)methyl]amino]-1-(phenylmethyl)ethyl]amino]-2-oxoethyl]-3-(trifluoromethyl)benzamide;

(2S)-N-tert-Butyl-2-[[[[2-[[(1,1-dimethylethoxy)carbonyl]amino]-5-(trifluoromethyl)benzoyl]amino]acetyl]amino]-3-[[(2,4-dimethylphenyl)methyl]amino]-propanamide;

(2S)-N-tert-Butyl-2-[[[[2-amino-5-(trifluoromethyl)benzoyl]amino]acetyl]amino]-3-[[(2,4-dimethylphenyl)methyl]amino]-propanamide;

(2S)-N-tert-Butyl-3-[[(4-bromo, 2-methylphenyl)methyl]amino]-2-[[[[2-[[(1,1-dimethylethoxy)carbonyl]amino]-5-(trifluoromethyl)benzoyl]amino]acetyl]amino]-propanamide;

(2S)-N-tert-Butyl-2-[[[[2-amino-5-(trifluoromethyl) benzoyl]amino]acetyl]amino]-3-[[(4-bromo, 2-methylphenyl)methyl]amino]-propanamide;

N-[2-[[(1S, 2S)-1-[[[(2,4-dimethylphenyl)methyl]amino] methyl]-2-hydroxy-3-(methyl)butyl]amino]-2-oxoethyl]-3-(trifluoromethyl)benzamide;

N-[2-[[(1S, 2R)-1-[[[(2,4-dimethylphenyl)methyl]amino] methyl]-2-hydroxy-3-(methyl)butyl]amino]-2-oxoethyl]-3-(trifluoromethyl)benzamide;

N-[2-[[(1S, 2S)-1-[[[(2,4-dimethylphenyl)methyl]amino] methyl]-2-hydroxy-2-(phenyl)ethyl]amino]-2-oxoethyl]-3-(trifluoromethyl)benzamide;

N-[2-[[(1S, 2R)-1-[[[(2,4-dimethylphenyl)methyl]amino] methyl]-2-hydroxy-2-(phenyl)ethyl]amino]-2-oxoethyl]-3-(trifluoromethyl)benzamide;

N-[2-[[(1S, 2S)-1-[[[(2,4-dimethylphenyl)methyl]amino] methyl]-2-hydroxy-3-(phenyl)propyl]amino]-2-oxoethyl]-3-(trifluoromethyl)benzamide;

N-[2-[[(1S, 2R)-1-[[[(2,4-dimethylphenyl)methyl]amino] methyl]-2-hydroxy-3-(phenyl)propyl]amino]-2-oxoethyl]-3-(trifluoromethyl)benzamide;

N-[2-[[(1S, 2S)-1-[[[(2,4-dimethylphenyl)methyl]amino] methyl]-2-hydroxy-4-(methyl)pentyl]amino]-2-oxoethyl]-3-(trifluoromethyl)benzamide;

N-[2-[[(1S, 2R)-1-[[[(2,4-dimethylphenyl)methyl]amino] methyl]-2-hydroxy-4-(methyl)pentyl]amino]-2-oxoethyl]-3-(trifluoromethyl)benzamide;

N-[2-[[(1S, 2S)-1-[[[(2,4-dimethylphenyl)methyl]amino] methyl]-2-(hydroxy)butyl]amino]-2-oxoethyl]-3-(trifluoromethyl)benzamide;

N-[2-[[(1S, 2R)-1-[[[(2,4-dimethylphenyl)methyl]amino] methyl]-2-(hydroxy)butyl]amino]-2-oxoethyl]-3-(trifluoromethyl)benzamide;

N-[2-[[(1S, 2S)-1-[[[(2,4-dimethylphenyl)methyl]amino] methyl]-2-(hydroxy)butyl]amino]-2-oxoethyl]-2-[[(1,1-dimethylethoxy)carbonyl]amino]-5-(trifluoromethyl)benzamide;

N-[2-[[(1S, 2S)-1-[[[(2,4-dimethylphenyl)methyl]amino] methyl]-2-(hydroxy)butyl]amino]-2-oxoethyl]-2-amino-5-(trifluoromethyl)benzamide;

N-[2-[[(1S, 2S)-1-[[[(2,4-dimethylphenyl)methyl]amino] methyl]-2-hydroxy-4-(methyl)pentyl]amino]-2-oxoethyl]-2-[[(1,1-dimethylethoxy)carbonyl]amino]-5-(trifluoromethyl)benzamide;

N-[2-[[(1S, 2R)-1-[[[(2,4-dimethylphenyl)methyl]amino] methyl]-2-hydroxy-4-(methyl)pentyl]amino]-2-oxoethyl]-2-[[(1,1-dimethylethoxy)carbonyl]amino]-5-(trifluoromethyl)benzamide;

N-[2-[[(1S, 2S)-1-[[[(2,4-dimethylphenyl)methyl]amino] methyl]-2-hydroxy-4-(methyl)pentyl]amino]-2-oxoethyl]-2-amino-5-(trifluoromethyl)benzamide;

N-[2-[[(1S, 2R)-1-[[[(2,4-dimethylphenyl)methyl]amino] methyl]-2-hydroxy-4-(methyl)pentyl]amino]-2-oxoethyl]-2-amino-5-(trifluoromethyl)benzamide;

N-[2-[[(1S, 2S)-1-[[[(2,4-dimethylphenyl)methyl]amino] methyl]-4,4-dimethyl-2-(hydroxy)pentyl]amino]-2-oxoethyl]-3-(trifluoromethyl)benzamide;

N-[2-[[(1S, 2R)-1-[[[(2,4-dimethylphenyl)methyl]amino] methyl]-4,4-dimethyl-2-(hydroxy)pentyl]amino]-2-oxoethyl]-3-(trifluoromethyl)benzamide;

N-[2-[[(1S, 2S)-1-[[[(2,4-dimethylphenyl)methyl]amino] methyl]-2-(hydroxy)pentyl]amino]-2-oxoethyl]-3-(trifluoromethyl)benzamide;

N-[2-[[(1S, 2R)-1-[[[(2,4-dimethylphenyl)methyl]amino] methyl]-2-(hydroxy)pentyl]amino]-2-oxoethyl]-3-(trifluoromethyl)benzamide;

N-[2-[[(1S, 2S)-1-[[[(2,4-dimethylphenyl)methyl]amino] methyl]-2-(hydroxy)pentyl]amino]-2-oxoethyl]-2-[[(1,1-dimethylethoxy)carbonyl]amino]-5-(trifluoromethyl)benzamide;

N-[2-[[(1S, 2R)-1-[[[(2,4-dimethylphenyl)methyl]amino]methyl]-2-(hydroxy)pentyl]amino]-2-oxoethyl]-2-[[(1,1-dimethylethoxy)carbonyl]amino]-5-(trifluoromethyl)benzamide;

N-[2-[[(1S, 2S)-1-[[[(2,4-dimethylphenyl)methyl]amino] methyl]-2-(hydroxy)pentyl]amino]-2-oxoethyl]-2-amino-5-(trifluoromethyl)benzamide;

N-[2-[[(1S, 2R)-1-[[[(2,4-dimethylphenyl) methyl]amino] methyl]-2-(hydroxy)pentyl ]amino ]-2-oxoethyl ]-2-amino-5-(trifluoromethyl)benzamide;

N-[2-[[(1S, 2S)-1-[[[(2,4-dimethylphenyl)methyl]amino] methyl]-2-(hydroxy)pentyl]amino]-2-oxoethyl]-3-amino-5-(trifluoromethyl)benzamide;

N-[2-[[(1S, 2R)-1-[[[(2,4-dimethylphenyl)methyl]amino] methyl]-2-(hydroxy)pentyl]amino]-2-oxoethyl]-3-amino-5-(trifluoromethyl)benzamide;

N-[2-[[(1S, 2S)-1-[[[(2,4-dimethylphenyl)methyl]amino] methyl]-2-(hydroxy)pentyl]amino]-2-oxoethyl]-2-[[(ethylamino)carbonyl]amino]-5-(trifluoromethyl) benzamide;

N-[2-[[(1S, 2R)-1-[[[(2,4-dimethylphenyl)methyl]amino] methyl]-2-(hydroxy)pentyl]amino]-2-oxoethyl]-2-[[(ethylamino) carbonyl]amino]-5-(trifluoromethyl) benzamide;

N-[2-[[(1S, 2S)-1-[[[(2,4-dimethylphenyl)methyl]amino]methyl]-2-(hydroxy)pentyl]amino]-2-oxoethyl]-2-[[(isopropylamino) carbonyl]amino]-5-(trifluoromethyl)benzamide;

N-[2-[[(1S, 2R)-1-[[[(2,4-dimethylphenyl)methyl]amino] methyl]-2-(hydroxy)pentyl]amino]-2-oxoethyl]-2-[[(isopropylamino) carbonyl]amino]-5-(trifluoromethyl) benzamide;

N-[2-[[(1S, 2S)-1-[[[(2,4-dimethylphenyl)methyl]amino] methyl]-2-(hydroxy)pentyl]amino]-2-oxoethyl]-2-[(1-pyrrolidinylcarbonyl)amino]-5-(trifluoromethyl) benzamide;

N-[2-[[(1S, 2S)-1-[[[(2,4-dimethylphenyl)methyl]amino] methyl]-2-(hydroxy)pentyl]amino]-2-oxoethyl]-2-[(1-azetidinylcarbonyl)amino]-5-(trifluoromethyl) benzamide;

N-[2-[[(1S, 2S)-1-[[[(2,4-dimethylphenyl)methyl]amino] methyl]-2-(hydroxy)pentyl]amino]-2-oxoethyl]-2-[[(methylamino)carbonyl]amino]-5-(trifluoromethyl) benzamide;

N-[2-[[(1S, 2R)-1-[[[(2,4-dimethylphenyl)methyl]amino] methyl]-2-(hydroxy)pentyl]amino]-2-oxoethyl]-2-[[(4-mopholinylcarbonyl)]amino]-5-(trifluoromethyl) benzamide;

N-[2-[[(1S, 2R)-1-[[[(2,4-dimethylphenyl)methyl]amino] methyl]-2-(hydroxy)pentyl]amino]-2-oxoethyl]-2-[[(1-piperazinylcarbonyl)]amino]-5-(trifluoromethyl) benzamide;

N-[2-[[(1S, 2S)-1-[[[(4-ethylphenyl)methyl]amino]methyl]-2-(hydroxy)pentyl]amino]-2-oxoethyl]-2-[[(1,1-dimethylethoxy)carbonyl]amino]-5-(trifluoromethyl) benzamide;

N-[2-[[(1S, 2S)-1-[[[(4-ethylphenyl)methyl]amino]methyl]-2-(hydroxy)pentyl]amino]-2-oxoethyl]-2-amino-5-(trifluoromethyl)benzamide;

N-[2-[[(1S, 2S)-1-[[[(4-ethylphenyl)methyl]amino]methyl]-2-(hydroxy)pentyl]amino]-2-oxoethyl]-2-[[(isopropylamino) carbonyl]amino]-5-(trifluoromethyl) benzamide;

N-[2-[[(1S, 2S)-1-[[[(4-ethylphenyl)methyl]amino]methyl]-2-(hydroxy)pentyl]amino]-2-oxoethyl]-2-[(4-morpholinylcarbonyl)amino]-5-(trifluoromethyl) benzamide;

N-[2-[[(1S, 2S)-1-[[[(4-dimethylamino-2-methylphenyl)
methyl]amino]methyl]-2-(hydroxy)pentyl]amino]-2-
oxoethyl]-2-[[(1,1-dimethylethoxy)carbonyl]amino]-5-
(trifluoromethyl)benzamide;

N-[2-[[(1S, 2S)-1-[[[(4-dimethylamino-2-methylphenyl)
methyl]amino]methyl]-2-(hydroxy)pentyl]amino]-2-
oxoethyl]-2-amino-5-(trifluoromethyl)benzamide;

N-[2-[[(1S, 2S)-1-[[[(2,4-dimethylphenyl)methyl]amino]
methyl]-2-(hydroxy)pentyl]amino]-2-oxoethyl]-2-(tert-
butyl)amino-5-(trifluoromethyl)benzamide;

N-[2-[[(1S, 2S)-1-[[[(2,4-dimethylphenyl)methyl]amino]
methyl]-2-(hydroxy)pentyl]amino]-2-oxoethyl]-2-
isopropylamino-5-(trifluoromethyl)benzamide;

N-[2-[[(1S, 2S)-1-[[[(2,4-dimethylphenyl)methyl]amino]
methyl]-2-(hydroxy)pentyl]amino]-2-oxoethyl]-2-
benzylamino-5-(trifluoromethyl)benzamide;

N-[2-[[(1S, 2S)-1-[[[(2,4-dimethylphenyl)methyl]amino]
methyl]-2-(methoxy)pentyl]amino]-2-oxoethyl]-2-[[(1,1-
dimethylethoxy)carbonyl]amino]-5-(trifluoromethyl)
benzamide;

N-[2-[[(1S, 2S)-1-[[[(2,4-dimethylphenyl)methyl]amino]
methyl]-2-(methoxy)pentyl]amino]-2-oxoethyl]-2-
amino-5-(trifluoromethyl)benzamide;

N-[2-[[(S)-1-[[[(2,4-dimethylphenyl)methyl]amino]
methyl]-2-hydroxy-2-(methyl)propyl]amino]-2-
oxoethyl]-2-[[(1,1-dimethylethoxy)carbonyl]amino]-5-
(trifluoromethyl)benzamide;

N-[2-[[(S)-1-[[[(2,4-dimethylphenyl)methyl]amino]
methyl]-2-hydroxy-2-(methyl)propyl]amino]-2-
oxoethyl]-2-amino-5-(trifluoromethyl)benzamide;

N-[2-[[(S)-1-[[[(2,4-dimethylphenyl)methyl]amino]
methyl]-2-hydroxy-2-(ethyl)butyl]amino]-2-oxoethyl]-2-
[[(1,1-dimethylethoxy)carbonyl]amino]-5-
(trifluoromethyl)benzamide;

N-[2-[[(S)-1-[[[(2,4-dimethylphenyl)methyl]amino]
methyl]-2-hydroxy-2-(ethyl)butyl]amino]-2-oxoethyl]-2-
amino-5-(trifluoromethyl)benzamide;

N-[2-[[(S)-1-[[[(2,4-dimethylphenyl)methyl]amino]
methyl]-2-hydroxy-2-(propyl)pentyl]amino]-2-
oxoethyl]-2-[[(1,1-dimethylethoxy)carbonyl]amino]-5-
(trifluoromethyl)benzamide;

N-[2-[[(S)-1-[[[(2,4-dimethylphenyl)methyl]amino]
methyl]-2-hydroxy-2-(propyl)pentyl]amino]-2-
oxoethyl]-2-amino-5-(trifluoromethyl)benzamide;

N-[2-[[(S)-2-[[(2,4-dimethylphenyl)methyl]amino]-1-
(hydroxycyclopentyl)ethyl]amino]-2-oxoethyl]-2-[[(1,1-
dimethylethoxy)carbonyl]amino]-5-(trifluoromethyl)
benzamide;

N-[2-[[(S)-1-[[(S)-2-[[(2,4-dimethylphenyl)methyl]amino]-
1-(hydroxycyclopentyl)ethyl]amino]-2-oxoethyl]-2-
amino-5-(trifluoromethyl)benzamide;

(2S)-N-tert-Butyl-3-[[(2,4-dimethylphenyl)methyl]amino]-
2-[[[[3-(trifluoromethoxy)benzoyl]amino]acetyl]amino]-
propanamide;

(2S)-N-tert-Butyl-3-[[(2,4-dimethylphenyl)methyl]amino]-
2-[[[[3-(difluoromethyl)benzoyl]amino]acetyl]amino]-
propanamide;

(2S)-N-tert-Butyl-3-[[(2,4-dimethylphenyl)methyl]amino]-
2-[[[[3-(trifluoromethylthio)benzoyl]amino]acetyl]
amino]-propanamide;

(2S)-N-tert-Butyl-3-[[(2,4-dimethylphenyl)methyl]amino]-
2-[[[[3-(pentafluoroethyl)benzoyl]amino]acetyl]amino]-
propanamide;

(2S)-N-tert-Butyl-2-[[[[2-amino-5-(trifluoromethoxy)
benzoyl]amino]acetyl]amino]-3-[[(2,4-dimethylphenyl)
methyl]amino]-propanamide;

(2S)-N-tert-Butyl-2-[[[[2-amino-5-(methyl)benzoyl]amino]
acetyl]amino]-3-[[(2,4-dimethylphenyl)methyl]amino]-
propanamide;

(2S)-N-tert-Butyl-3-[[(2,4-dimethylphenyl)methyl]amino]-
2-[[[[2-ethylamino-5-(trifluoromethyl)benzoyl]amino]
acetyl]amino]-propanamide;

(2S)-N-tert-Butyl-3-[[(2,4-dimethylphenyl)methyl]amino]-
2-[[[[2-propylamino-5-(trifluoromethyl)benzoyl]amino]
acetyl]amino]-propanamide;

(2S)-N-tert-Butyl-3-[[(2,4-dimethylphenyl)methyl]amino]-
2-[[[[2-isobutylamino-5-(trifluoromethyl)benzoyl]amino]
acetyl]amino]-propanamide;

(2S)-N-tert-Butyl-2-[[[[2-butylamino-5-(trifluoromethyl)
benzoyl]amino]acetyl]amino]-3-[[(2,4-dimethylphenyl)
methyl]amino]-propanamide;

(2S)-N-tert-Butyl-2-[[[[2-cyclohexylamino-5-
(trifluoromethyl)benzoyl]amino]acetyl]amino]-3-[[(2,4-
dimethylphenyl)methyl]amino]-propanamide;

(2S)-N-tert-Butyl-3-[[(2,4-dimethylphenyl)methyl]amino]-
2-[[[[2-isopropylamino-5-(trifluoromethyl)benzoyl]
amino]acetyl]amino]-propanamide;

(2S)-N-tert-Butyl-3-[[(2,4-dimethylphenyl)methyl]amino]-
2-[[[[2-(tert-butyl)amino-5-(trifluoromethyl)benzoyl]
amino]acetyl]amino]-propanamide;

(2S)-N-tert-Butyl-3-[[(2,4-dimethylphenyl)methyl]amino]-
2-[[[[2-(methylaminocarbonyl)amino-5-(trifluoromethyl)
benzoyl]amino]acetyl]amino]-propanamide;

(2S)-N-tert-Butyl-3-[[(2,4-dimethylphenyl)methyl]amino]-
2-[[[[2-(isopropoxycarbonyl)amino-5-(trifluoromethyl)
benzoyl]amino]acetyl]amino]-propanamide;

(2S)-N-tert-Butyl-3-[[(2,4-dimethylphenyl)methyl]amino]-
2-[[[[2-(isopropylaminocarbonyl) amino-5-
(trifluoromethyl)benzoyl]amino]acetyl]amino]-
propanamide;

(2S)-N-tert-Butyl-2-[[[[2-(cyclohexylcarbonyl)amino-5-
(trifluoromethyl)benzoyl]amino]acetyl]amino]-3-[[(2,4-
dimethylphenyl)methyl]amino]-propanamide;

(2S)-N-tert-Butyl-2-[[[[2-benzylamino-5-(trifluoromethyl)
benzoyl]amino]acetyl]amino]-3-[[(2,4-dimethylphenyl)
methyl]amino]-propanamide;

(2S)-N-tert-Butyl-2-[[[[2-(para-chloro)benzylamino-5-
(trifluoromethyl)benzoyl]amino]acetyl]amino]-3-[[(2,4-
dimethylphenyl)methyl]amino]-propanamide;

(2S)-N-tert-Butyl-2-[[[[2-[(beta-napthyl)methyl]amino-5-
(trifluoromethyl)benzoyl]amino]acetyl]amino]-3-[[(2,4-
dimethylphenyl)methyl]amino]-propanamide;

(2S)-N-tert-Butyl-2-[[[[2-(meta-methyl)benzylamino-5-
(trifluoromethyl)benzoyl]amino]acetyl]amino]-3-[[(2,4-
dimethylphenyl)methyl]amino]-propanamide;

(2S)-N-tert-Butyl-2-[[[[2-(para-methyl)benzylamino-5-
(trifluoromethyl)benzoyl]amino]acetyl]amino]-3-[[(2,4-
dimethylphenyl)methyl]amino]-propanamide;

(2S)-N-tert-Butyl-2-[[[[2-(ortho-methyl)benzylamino-5-
(trifluoromethyl)benzoyl]amino]acetyl]amino]-3-[[(2,4-
dimethylphenyl)methyl]amino]-propanamide;

(2S)-N-tert-Butyl-3-[[(2,4-dimethylphenyl)methyl]amino]-
2-[[[[2-(para-trifluoromethyl)benzylamino-5-
(trifluoromethyl)benzoyl]amino]acetyl]amino]-
propanamide;

(2S)-N-tert-Butyl-2-[[[[3-amino-5-(trifluoromethyl)
benzoyl]amino]acetyl]amino]-3-[[(2,4-dimethylphenyl)
methyl]amino]-propanamide;

(2S)-N-tert-Butyl-2-[[[[3-benzylamino-5-(trifluoromethyl)
benzoyl]amino]acetyl]amino]-3-[[(2,4-dimethylphenyl)
methyl]amino]-propanamide;

(2S)-N-tert-Butyl-2-[[[[3-methylamino-5-(trifluoromethyl)
benzoyl]amino]acetyl]amino]-3-[[(2,4-dimethylphenyl)
methyl]amino]-propanamide;

(2S)-N-tert-Butyl-2-[[[[3-ethylamino-5-(trifluoromethyl)
benzoyl]amino]acetyl]amino]-3-[[(2,4-dimethylphenyl)
methyl]amino]-propanamide;

(2S)-N-tert-Butyl-2-[[[[3-isobutylamino-5-(trifluoromethyl)
benzoyl]amino]acetyl]amino]-3-[[(2,4-dimethylphenyl)
methyl]amino]-propanamide;
(2S)-N-tert-Butyl-2-[[[[3-propylamino-5-(trifluoromethyl)
benzoyl]amino]acetyl]amino]-3-[[(2,4-dimethylphenyl)
methyl]amino]-propanamide;
(2S)-N-tert-Butyl-2-[[[[3-butylamino-5-(trifluoromethyl)
benzoyl]amino]acetyl]amino]-3-[[(2,4-dimethylphenyl)
methyl]amino]-propanamide;
(2S)-N-tert-Butyl-2-[[[[3-(trifluoromethylcarbonyl)amino-
5-(trifluoromethyl)benzoyl]amino]acetyl]amino]-3-[[(2,
4-dimethylphenyl)methyl]amino]-propanamide;
(2S)-N-tert-Butyl-2-[[[[3-(ethoxycarbonyl)amino-5-
(trifluoromethyl)benzoyl]amino]acetyl]amino]-3-[[(2,4-
dimethylphenyl)methyl]amino]-propanamide;
(2S)-2-[[[[2-amino-5-(trifluoromethyl)benzoyl]amino]
acetyl]amino]-3-[[(2-methyl-4-bromophenyl)methyl]
amino]-propanamide;
(2S)-2-[[[[2-amino-5-(trifluoromethyl)benzoyl]amino]
acetyl]amino]-3-[[(4-bromophenyl)methyl]amino]-
propanamide;
(2S)-N-tert-Butyl-3-[[(4-methylphenyl)methyl]amino]-2-
[[[[3-(trifluoromethyl)benzoyl]amino]acetyl]amino]-
propanamide;
(2S)-N-tert-Butyl-3-[[(4-bromophenyl)methyl]amino]-2-
[[[[3-(trifluoromethyl)benzoyl]amino]acetyl]amino]-
propanamide;
(2S)-N-tert-Butyl-3-[[(4-bromo-2-methylphenyl)methyl]
amino]-2-[[[[3-(trifluoromethyl)benzoyl]amino]acetyl]
amino]-propanamide;
(2S)-N-tert-Butyl-3-[[(4-methoxyphenyl)methyl]amino]-2-
[[[[3-(trifluoromethyl)benzoyl]amino]acetyl]amino]-
propanamide;
(2S)-N-tert-Butyl-3-[[(4-methoxy-2-methylphenyl)methyl]
amino]-2-[[[[3-(trifluoromethyl)benzoyl]amino]acetyl]
amino]-propanamide;
(2S)-N-tert-Butyl-3-[[(2-methoxypyridin-5-yl)methyl]
amino]-2-[[[[3-(trifluoromethyl)benzoyl]amino]acetyl]
amino]-propanamide;
(2S)-N-tert-Butyl-3-[[(2,3-dimethyl-4-methoxy-phenyl)
methyl]amino]-2-[[[[3-(trifluoromethyl)benzoyl]amino]
acetyl]amino]-propanamide;
(2S)-N-tert-Butyl-3-[[(4-cyano-2-methylphenyl)methyl]
amino]-2-[[[[3-(trifluoromethyl)benzoyl]amino]acetyl]
amino]-propanamide;
(2S)-N-tert-Butyl-3-[[(4-ethylphenyl)methyl]amino]-2-
[[[[3-(trifluoromethyl)benzoyl]amino]acetyl]amino]-
propanamide;
(2S)-N-tert-Butyl-3-[[(2-methyl-4-vinylphenyl)methyl]
amino]-2-[[[[3-(trifluoromethyl)benzoyl]amino]acetyl]
amino]-propanamide;
(2S)-N-tert-Butyl-3-[[(4-ethyl-2-methylphenyl)methyl]
amino]-2-[[[[3-(trifluoromethyl)benzoyl]amino]acetyl]
amino]-propanamide;
(2S)-N-tert-Butyl-3-[[(4-isopropylphenyl)methyl]amino]-2-
[[[[3-(trifluoromethyl)benzoyl]amino]acetyl]amino]-
propanamide;
(2S)-N-tert-Butyl-3-[[(4-butylphenyl)methyl]amino]-2-
[[[[3-(trifluoromethyl)benzoyl]amino]acetyl]amino]-
propanamide;
(2S)-N-tert-Butyl-3-[[(4-dimethylaminophenyl)methyl]
amino]-2-[[[[3-(trifluoromethyl)benzoyl]amino]acetyl]
amino]-propanamide;
(2S)-N-tert-Butyl-3-[[(4-dimethylamino-2-methylphenyl)
methyl]amino]-2-[[[[3-(trifluoromethyl)benzoyl]amino]
acetyl]amino]-propanamide;
(2S)-N-tert-Butyl-3-[[(4-methylthiophenyl)methyl]amino]-
2-[[[[3-(trifluoromethyl)benzoyl]amino]acetyl]amino]-
propanamide;

(2S)-N-tert-Butyl-3-[[(4-methylsulfonylphenyl)methyl]
amino]-2-[[[[3-(trifluoromethyl)benzoyl]amino]acetyl]
amino]-propanamide;
(2S)-N-tert-Butyl-3-[[(4-trifluoromethoxyphenyl)methyl]
amino]-2-[[[[3-(trifluoromethyl)benzoyl]amino]acetyl]
amino]-propanamide;
(2S)-N-tert-Butyl-3-[[(3-amino-4-methylphenyl)methyl]
amino]-2-[[[[3-(trifluoromethyl)benzoyl]amino]acetyl]
amino]-propanamide;
(2S)-N-tert-Butyl-3-[[(indol-3-yl)methyl]amino]-2-[[[[3-
(trifluoromethyl)benzoyl]amino]acetyl]amino]-
propanamide;
(2S)-N-tert-Butyl-3-[[(2-methylphenyl)methyl]amino]-2-
[[[[3-(trifluoromethyl)benzoyl]amino]acetyl]amino]-
propanamide;
(2S)-N-tert-Butyl-3-[[(2-ethylphenyl)methyl]amino]-2-
[[[[3-(trifluoromethyl)benzoyl]amino]acetyl]amino]-
propanamide;
(2R)-N-Ethyl-3-[[(2,4-dimethylphenyl)methyl]amino]-2-
[[[[3-(trifluoromethyl)benzoyl]amino]acetyl]amino]-
propanamide;
(2R)-N-tert-Butyl-3-[[(2,4-dimethylphenyl)methyl]amino]-
2-[[[[3-(trifluoromethyl)benzoyl]amino]acetyl]amino]-
propanamide;
(2R)-N-[(2-methyl)hydroxyprop-2-yl]-3-[[(2,4-
dimethylphenyl)methyl]amino]-2-[[[[3-(trifluoromethyl)
benzoyl]amino]acetyl]amino]-propanamide;
(2S)-N-tert-Amyl-3-[[(2,4-dimethylphenyl)methyl]amino]-
2-[[[[3-(trifluoromethyl)benzoyl]amino]acetyl]amino]-
propanamide;
(2S)-N-[(2-methyl)hydroxyprop-2-yl]-3-[[(2,4-
dimethylphenyl)methyl]amino]-2-[[[[3-(trifluoromethyl)
benzoyl]amino]acetyl]amino]-propanamide;
(2S)-N-[(1-methyl)cycloprop-1-yl]-3-[[(2,4-
dimethylphenyl)methyl]amino]-2-[[[[3-(trifluoromethyl)
benzoyl]amino]acetyl]amino]-propanamide;
(2S)-N-Cyclopentyl-3-[[(2,4-dimethylphenyl)methyl]
amino]-2-[[[[3-(trifluoromethyl)benzoyl]amino]acetyl]
amino]-propanamide;
(2S)-N-Cyclohexyl-3-[[(2,4-dimethylphenyl)methyl]
amino]-2-[[[[3-(trifluoromethyl)benzoyl]amino]acetyl]
amino]-propanamide;
(2S)-N-(β, β, β,-Trifluoro)ethyl-3-[[(2,4-dimethylphenyl)
methyl]amino]-2-[[[[3-(trifluoromethyl)benzoyl]amino]
acetyl]amino]-propanamide;
(2S)-N-Allyl-3-[[(2,4-dimethylphenyl)methyl]amino]-2-
[[[[3-(trifluoromethyl)benzoyl]amino]acetyl]amino]-
propanamide;
(2S)-N-Cyclopropylmethyl-3-[[(2,4-dimethylphenyl)
methyl]amino]-2-[[[[3-(trifluoromethyl)benzoyl]amino]
acetyl]amino]-propanamide;
N-[2-[[(2S)-3-[[(2,4-dimethylphenyl)methyl]amino]-1-
(pyrrolid-3-enyl)-1-oxopropyl-2-amino]-2-oxoethyl]-3-
(trifluoromethyl)benzamide;
N-[2-[[(2S)-3-[[(2,4-dimethylphenyl)methyl]amino]-1-
(pyrrolidinyl)-1-oxopropyl-2-amino]-2-oxoethyl]-3-
(trifluoromethyl)benzamide;
N-[2-[[(2S)-3-[[(2,4-dimethylphenyl)methyl]amino]-1-
(morpholinyl)-1-oxopropyl-2-amino]-2-oxoethyl]-3-
(trifluoromethyl)benzamide;
(2S)-N-Isobutyl-3-[[(2,4-dimethylphenyl)methyl]amino]-2-
[[[[3-(trifluoromethyl)benzoyl]amino]acetyl]amino]-
propanamide;
(2S)-N-sec-Butyl-3-[[(2,4-dimethylphenyl)methyl]amino]-
2-[[[[3-(trifluoromethyl)benzoyl]amino]acetyl]amino]-
propanamide;
(2S)-N-tert-Butyl-4-[[(2,4-dimethylphenyl)methyl]amino]-
3-[[[[3-(trifluoromethyl)benzoyl]amino]acetyl]amino]-
butanamide;

(2S, 3R)-N-Ethyl-3-[[(2,4-dimethylphenyl)methyl]amino]-2-[[[[3-(trifluoromethyl)benzoyl]amino]acetyl]amino]-butanamide;
(2S, 3R)-N-Ethyl-3-[[(4-bromophenyl)methyl]amino]-2-[[[[3-(trifluoromethyl)benzoyl]amino]acetyl]amino]-butanamide;
Methyl (2R)-2-[[(2,4-dimethylphenyl)methyl]amino]-3-[[[[3-(trifluoromethyl)benzoyl]amino]acetyl]amino]-propanoate;
(2R)-N-Ethyl-2-[[(2,4-dimethylphenyl)methyl]amino]-3-[[[[3-(trifluoromethyl)benzoyl]amino]acetyl]amino]-propanamide;
Methyl (2S)-4-[[(2,4-dimethylphenyl)methyl]amino]-2-[[[[3-(trifluoromethyl)benzoyl]amino]acetyl]amino]-butanoate;
(2S)-4-[[(2,4-dimethylphenyl)methyl]amino]-2-[[[[3-(trifluoromethyl)benzoyl]amino]acetyl]amino]-butanamide;
(2S)-N-Ethyl-4-[[(2,4-dimethylphenyl)methyl]amino]-2-[[[[3-(trifluoromethyl)benzoyl]amino]acetyl]amino]-butanamide;
(2S)-N-Ethyl-4-[[(2,4-dimethylphenyl)methyl]methylamino]-2-[[[[3-(trifluoromethyl)benzoyl]amino]acetyl]amino]-butanamide;
(2S)-N-tert-Butyl-2-[[[[2-[[(1,1-dimethylethoxy)carbonyl]amino]-5-(trifluoromethyl)benzoyl]amino]acetyl]amino]-4-[[(2,4-dimethylphenyl)methyl]amino]-butanamide;
(2S)-N-tert-Butyl-2-[[[[2-[[(1,1-dimethylethoxy)carbonyl]amino]-5-(trifluoromethyl)benzoyl]amino]acetyl]amino]-4-[[(2,4-dimethylphenyl)methyl]methylamino]-butanamide;
(2S)-N-tert-Butyl-2-[[[[2-amino-5-(trifluoromethyl)benzoyl]amino]acetyl]amino]-4-[[(2,4-dimethylphenyl)methyl]amino]-butanamide;
(2S)-N-tert-Butyl-2-[[[[2-amino-5-(trifluoromethyl)benzoyl]amino]acetyl]amino]-4-[[(2,4-dimethylphenyl)methyl]methylamino]-butanamide;
(2S)-N-tert-Butyl-2-[[[[3-amino-5-(trifluoromethyl)benzoyl]amino]acetyl]amino]-4-[[(2,4-dimethylphenyl)methyl]amino]-butanamide;
(2S)-N-tert-Butyl-2-[[[[3-amino-5-(trifluoromethyl)benzoyl]amino]acetyl]amino]-4-[[(4-ethylphenyl)methyl]amino]-butanamide;
(2S)-N-tert-Butyl-4-[[(2,4-dimethylphenyl)methyl]amino]-2-[[[[3-(trifluoromethyl)benzoyl]amino]acetyl]amino]-butanamide;
(2S)-N-tert-Butyl-4-[[(4-ethylphenyl)methyl]amino]-2-[[[[3-(trifluoromethyl)benzoyl]amino]acetyl]amino]-butanamide;
(2S)-N-Ethyl-5-[[(2,4-dimethylphenyl)methyl]amino]-2-[[[[3-(trifluoromethyl)benzoyl]amino]acetyl]amino]-pentanamide;
N-[2-[[(1S, 2S/R)-1-[[[(2,4-dimethylphenyl)methyl]methylamino]methyl]-2-hydroxy-3-(methyl)butyl]amino]-2-oxoethyl]-3-(trifluoromethyl)benzamide;
N-[2-[[(1S, 2S)-1-[[[(2,4-dimethylphenyl)methyl]methylamino]methyl]-2-(hydroxy)pentyl]amino]-2-oxoethyl]-2-[[(isopropylamino) carbonyl]amino]-5-(trifluoromethyl)benzamide;
N-[2-[[(1S, 2S)-1-[[[(2,4-dimethylphenyl)methyl]isopropylamino]methyl]-2-(hydroxy)pentyl]amino]-2-oxoethyl]-2-[[(isopropylamino) carbonyl]amino]-5-(trifluoromethyl)benzamide;
N-[2-[[(1S, 2S)-1-[[[(4-ethylphenyl)methyl]methylamino]methyl]-2-(hydroxy)pentyl]amino]-2-oxoethyl]-2-[[(isopropylamino) carbonyl]amino]-5-(trifluoromethyl)benzamide;
N-[2-[[(1S, 2S)-1-[[[(4-ethylphenyl)methyl]isopropylamino]methyl]-2-(hydroxy)pentyl]amino]-2-oxoethyl]-2-[[(isopropylamino) carbonyl]amino]-5-(trifluoromethyl)benzamide;
(2S)-N-tert-Butyl-3-[[(2,4-dimethylphenyl)methyl]methylamino]-2-[[[[3-(trifluoromethyl)benzoyl]amino]acetyl]amino]-propanamide;
N-[2-[[1-[[[(2,4-dimethylphenyl)methyl]amino]methyl]cyclohexyl]amino]-2-oxoethyl]-3-(trifluoromethyl)benzamide;
N-[2-[[1-[[[(4-chlorophenyl)methyl]amino]methyl]cyclohexyl]amino]-2-oxoethyl]-3-(trifluoromethyl)benzamide;
N-[2-[[1-[[[(2,4-dimethylphenyl)methyl]amino]methyl]cyclopentyl]amino]-2–2-oxoethyl]-3-(trifluoromethyl)benzamide;
N-[2-[[1-[[[(2,4-dimethylphenyl)methyl]amino]methyl]cyclopentyl]amino1-2-oxoethyl]-2-[[(1,1-dimethylethoxy) carbonyl]amino]-5-(trifluoromethyl)benzamide;
N-[2-[[1-[[[(2,4-dimethylphenyl)methyl]amino]methyl]cyclopropyl]amino]-2-oxoethyl]-2-[[(1,1-dimethylethoxy)carbonyl]amino]-5-(trifluoromethyl)benzamide;
N-[2-[[1-[[[(2,4-dimethylphenyl)methyl]amino]methyl]cyclopropyl]amino]-2-oxoethyl]-2-amino-5-(trifluoromethyl)benzamide; and
(2S)-N-Ethyl-3-[[(2,4-dimethylphenyl)methyl]amino]-2-[[[[2-amino-5-(trifluoromethyl)benzoyl]amino]acetyl]amino]-2-methyl-propanamide.

In another embodiment, the present invention is directed to a pharmaceutical composition, comprising a pharmaceutically acceptable carrier and a therapeutically effective amount of a compound of Formula (I).

In another embodiment, the present invention is directed to a method for modulation of chemokine or chemokine receptor activity comprising administering to a patient in need thereof a therapeutically effective amount of a compound of Formula (I).

In another embodiment, the present invention is directed to a method for modulation of MCP-1, MCP-2, MCP-3 and MCP-4, and MCP-5 activity that is mediated by the CCR2 receptor comprising administering to a patient in need thereof a therapeutically effective amount of a compound of Formula (I).

In another embodiment, the present invention is directed to a method for modulation of MCP-1 activity comprising administering to a patient in need thereof a therapeutically effective amount of a compound of Formula (I).

In another embodiment, the present invention is directed to a method for treating or preventing disorders, comprising administering to a patient in need thereof a therapeutically effective amount of a compound of Formula (I), said disorders being selected from osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a method for treating or preventing disorders, of Formula (I), wherein said disorders being selected from psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a method for treating or preventing disorders, of Formula (I), wherein said disorders being selected from alveolitis, colitis, systemic lupus erythematosus, nephrotoxic serum nephritis, glomerularnephritis, asthma, multiple sclerosis, artherosclerosis, and rheumatoid arthritis.

In another embodiment, the present invention is directed to a method for treating or preventing disorders, of Formula (I), wherein said disorders being selected from asthma, multiple sclerosis, artherosclerosis, and rheumatoid arthritis.

In another embodiment, the present invention is directed to a method for treating or preventing rheumatoid arthritis, comprising administering to a patient in need thereof a therapeutically effective amount of a compound of Formula (I).

In another embodiment, the present invention is directed to a method for treating or preventing multiple sclerosis, comprising administering to a patient in need thereof a therapeutically effective amount of a compound of Formula (I).

In another embodiment, the present invention is directed to a method for treating or preventing atherosclerosis, comprising administering to a patient in need thereof a therapeutically effective amount of a compound of Formula (I).

In another embodiment, the present invention is directed to a method for treating or preventing asthma, comprising administering to a patient in need thereof a therapeutically effective amount of a compound of Formula (I).

In another embodiment, the present invention is directed to a method for treating or preventing inflammatory diseases, comprising administering to a patient in need thereof a therapeutically effective amount of a compound of Formula (I).

In another embodiment, the present invention is directed to a method for modulation of CCR2 activity comprising administering to a patient in need thereof a therapeutically effective amount of a compound of Formula (I).

In another embodiment, Z is —C(O)—.

In another embodiment, X is —CHR$^{16}$NR$^{17}$—; and

R$^{16}$ is selected from H, C$_{1-4}$ alkyl substituted with 0–1 R$^{16a}$, wherein the alkyl is selected from methyl, ethyl, propyl, i-propyl, butyl, i-butyl, and s-butyl, and C$_{3-4}$ cycloalkyl substituted with 0–3 R$^{16a}$ wherein the cycloalkyl is selected from cyclopropyl and cyclobutyl;

R$^{16a}$ is selected from methyl, ethyl, propyl, i-propyl, —OH, —SH, NR$^{16c}$R$^{16c}$, —C(O)NR$^{16c}$R$^{16c}$, and —NHC(O)R$^{16c}$; and R$^{17}$ is selected from H, methyl, ethyl, propyl, and i-propyl.

In another embodiment, R$^7$, R$^8$, R$^9$, and R$^{11}$ are H;

R$^{10}$ is selected from H and methyl;

R$^{16}$ is selected from H and methyl;

R$^{17}$ is selected from H and methyl;

m is 0 or 1; and l is 0 or 1.

In another embodiment, R$^3$ is selected from (CRR)$_q$OH, (CRR)$_q$SH, (CRR)$_q$OR$^{3d}$, (CRR)$_q$S(O)$_p$R$^{3d}$, (CRR)$_r$C(O)R$^{3b}$, (CRR)$_q$NR$^{3a}$R$^{3a}$, (CRR)$_r$C(O)NR$^{3a}$R$^{3a}$, (CRR)$_r$C(O)NR$^{3a}$OR$^{3d}$, (CRR)$_q$SO$_2$NR$^{3a}$R$^{3a}$, (CRR)$_r$C(O)OR$^{3d}$, a (CRR)$_r$—C$_{3-10}$ carbocyclic residue substituted with 0–5 R$^{3e}$, and a (CRR)$_r$-5–10 membered heterocyclic system containing 1–4 heteroatoms selected from N, O, and S, substituted with 0–3 R$^{3e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

alternatively, R$^3$ and R$^{12}$ join to form a C$_{3-6}$ cycloalkyl substituted with 0–2 R$^{3g}$, a C$_{5-6}$ lactam substituted with 0–2 R$^{3g}$, or a C$_{5-6}$ lactone substituted with 0–2 R$^{3g}$.

In another embodiment, R$^3$ is selected from (CRR)$_q$OH, (CH$_2$)$_r$C(O) OH, (CH$_2$)$_r$C(O)NR$^{3a}$R$^{3a}$, (CHR)$_r$C(O)NR$^{3a}$OR$^{3d}$, (CH$_2$)$_r$C(O)R$^{3b}$, (CH$_2$)$_r$C(O)OR$^{3d}$, and (CH$_2$)-phenyl.

In another embodiment, R$^3$ is H and R$^6$, is selected from C$_{1-6}$ alkyl, C$_{2-6}$ alkenyl, C$_{2-6}$ alkynyl, (CRR)$_q$OH, (CRR)$_q$SH, (CRR)$_q$OR$^{6d}$, (CRR)$_q$S(O)$_p$R$^{6d}$, (CRR)$_r$C(O)R$^{6b}$, (CRR)$_q$NR$^{6a}$R$^{6a}$, (CRR)$_r$C(O)NR$^{6a}$R$^{6a}$, (CRR)$_r$C(O)NR$^{6a}$OR$^{6d}$, (CRR)SO$_2$NR$^{6a}$R$^{6a}$, (CRR)$_r$C(O)OR$^{6d}$, a (CRR)$_r$—C$_{3-10}$ carbocyclic residue substituted with 0–5 R$^{6e}$, and a (CRR)$_r$-5–10 membered heterocyclic system containing 1–4 heteroatoms selected from N, O, and S, substituted with 0–3 R$^{6e}$.

In another embodiment, R$^6$ is selected from H, (CRR)$_q$OH, (CRR)$_q$SH, (CRR)$_q$OR$^{6d}$, (CRR)$_q$S(O)$_p$R$^{6d}$, (CRR)$_r$C(O)R$^{6b}$, (CRR)$_q$NR$^{6a}$R$^{6a}$, (CRR)$_r$C(O)NR$^{6a}$R$^{6a}$, (CRR)$_r$C(O)NR$^{6a}$OR$^{6d}$, (CRR)$_q$SO$_2$NR$^{6a}$R$^{6a}$, (CRR)$_r$C(O)OR$^{6d}$, a (CR R)$_r$—C$_{6-10}$ carbocyclic residue substituted with 0–5 R$^{6e}$, and a (CRR)$_r$-5–10 membered heterocyclic system containing 1–4 heteroatoms selected from N, O, and S, substituted with 0–6 R$^{6e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,6-triazolyl, tetrazolyl, thiadiazolyl, thiazolyl, oxazolyl, pyrazinyl, and pyrimidinyl.

In another embodiment, R$^1$ is selected from phenyl substituted with 0–3 R$^4$ and a 5–10 membered heteroaryl system substituted with 0–3 R$^4$, wherein the heteroaryl is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, R$^1$ is selected from phenyl substituted with 0–2 R$^4$, indolyl, and pyridyl.

In another embodiment, R$^2$ is selected from phenyl substituted with 0–3 R$^5$ and a 5–10 membered heteroaryl system containing 1–4 heteroatoms substituted with 0–3 R$^5$, wherein the heteroaryl system is selected from benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

In another embodiment, R$^2$ is phenyl substituted with 0–2 R$^5$.

In another embodiment, R$^4$, at each occurrence, is selected from C$_{1-8}$ alkyl, C$_{2-8}$ alkenyl, C$_{2-8}$ alkynyl, (CR'R')$_r$C$_{3-6}$ cycloalkyl, Cl, Br, I, F, NO$_2$, CN, (CR'R')$_r$NR$^{4a}$R$^{4a}$, (CR'R')$_r$OH, (CR'R')$_r$OR$^{4d}$, (CR'R')$_r$SH, (CR'R')$_r$SR$^{4d}$, (CR'R')$_r$C(O)OH, (CR'R I)$_r$C(O)R$^{4b}$, (CR'R')$_r$C(O)

NR$^{4a}$R$^{4a}$, (CR'R')$_r$NR$^{4f}$C(O)R$^{4b}$, (CR'R')$_r$C(O)OR$^{4d}$, (CR'R')$_r$OC(O)R$^{4b}$, (CR'R')$_r$NR$^{4f}$C(O)OR$^{4d}$, (CR'R')$_r$OC(O)NR$^{4a}$R$^{4a}$, (CR'R')$_r$NR$^{4a}$C(O)NR$^{4a}$R$^{4a}$, (CR'R')$_r$S(O)$_p$R$^{4b}$, (CR'R')$_r$S(O)$_2$NR$^{4a}$R$^{4a}$, (CR'R')$_r$NR$^{4f}$S(O)$_2$R$^{4b}$, (CR'R')$_r$NR$^{4f}$S(O)$_2$NR$^{4a}$R$^{4a}$, C$_{1-6}$ haloalkyl, and (CR'R')$_r$ phenyl substituted with 0–3 R$^{4e}$;

alternatively, two R$^4$ on adjacent atoms join to form —O—(CH$_2$)—O—;

R$^{4a}$, at each occurrence, is independently selected from H, methyl, ethyl, propyl, i-propyl, butyl, s-butyl, i-butyl, t-butyl, pentyl, hexyl, allyl, propargyl, and a (CH$_2$)$_r$—C$_{3-6}$ carbocyclic residue selected from cyclopropyl, cyclobutyl, cyclopentyl and cyclohexyl;

R$^{4b}$, at each occurrence, is selected from methyl, ethyl, propyl, i-propyl, butyl, s-butyl, i-butyl, t-butyl, pentyl, hexyl, allyl, propargyl, a (CH$_2$)$_r$—C$_{3-6}$ carbocyclic residue substituted with 0–3 R$^{4e}$, wherein the carbocyclic residue is selected from cyclopropyl, cyclobutyl, cyclopentyl and cyclohexyl, and a (CH$_2$)$_r$-5–6 membered heterocyclic system containing 1–4 heteroatoms selected from N, O, and S, substituted with 0–2 R$^{4e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

R$^{4d}$, at each occurrence, is selected from H, methyl, CF$_3$, ethyl, propyl, i-propyl, butyl, s-butyl, i-butyl, t-butyl, pentyl, hexyl, allyl, propargyl, and a (CH$_2$)$_r$—C$_{3-6}$ carbocyclic residue selected from cyclopropyl, cyclobutyl, cyclopentyl and cyclohexyl;

R$^{4e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, and (CH$_2$)$_r$phenyl;

R$^{4f}$, at each occurrence, is selected from H, methyl, ethyl, propyl, i-propyl, butyl, and cyclopropyl, cyclobutyl, and phenyl.

In another embodiment, R$^4$ is selected from methyl, ethyl, propyl, i-propyl, butyl, ethylene, OCH$_3$, OCF$_3$, SCH$_3$, SO$_2$CH$_3$, Cl, F, Br, and CN;

alternatively, two R$^4$ join to form —O—(CH$_2$)—O—.

In another embodiment, R$^5$, at each occurrence, is selected from methyl, ethyl, propyl, i-propyl, butyl, i-butyl, s-butyl, t-butyl, pentyl, hexyl, (CR'R')$_r$C$_{3-6}$ cycloalkyl, Cl, Br, I, F, NO$_2$, CN, (CR'R')$_r$NR$^{5a}$R$^{5a}$, (CR'R')$_r$OH, (CR'R')$_r$ OR$^{5d}$, (CR'R')$_r$SH, (CR'R')$_r$C(O)H, (CR'R')$_r$SR$^{5d}$, (CR'R')$_r$C(O)OH, (CR'R')$_r$C(O)R$^{5b}$, (CR'R')$_r$C(O)NR$^{5a}$R$^{5a}$, (CR'R')$_r$NR$^{5f}$C(O)R$^{5b}$, (CR'R')$_r$C(O)OR$^{5d}$, (CR'R')$_r$OC(O)R$^{5b}$, (CR'R')$_r$NR$^{5f}$C(O)OR$^{5d}$, (CR'R')$_r$OC(O)NR$^{5a}$R$^{5a}$, (CR'R')$_r$NR$^{5a}$C(O)NR$^{5a}$R$^{5a}$, (CR'R')$_r$NR$^{7a}$C(O)NR$^{7a}$R$^{7a}$, (CR'R')$_r$NR$^{7a}$C(O)O(CR'R')$_r$R$^{7d}$, (CR'R')$_r$S(O)$_p$R$^{5b}$, (CR'R')$_r$S(O)$_2$NR$^{5a}$R$^{5a}$, (CR'R')$_r$NR$^{5f}$S(O)$_2$R$^{5b}$, C$_{1-6}$ haloalkyl, and (CHR')$_r$phenyl substituted with 0–3 R$^{5e}$;

alternatively, two R$^5$ on adjacent atoms join to form —O—(CH$_2$)—O—;

R$^{5a}$, at each occurrence, is independently selected from H, methyl, ethyl, propyl, i-propyl, butyl, s-butyl, i-butyl, t-butyl, pentyl, hexyl, allyl, propargyl, and a (CH$_2$)$_r$—C$_{3-6}$ carbocyclic residue selected from cyclopropyl, cyclobutyl, cyclopentyl and cyclohexyl;

R$^{5b}$, at each occurrence, is selected from methyl, ethyl, propyl, i-propyl, butyl, s-butyl, i-butyl, t-butyl, pentyl, hexyl, allyl, propargyl, and a (CH$_2$)$_r$—C$_{3-6}$ carbocyclic residue selected from cyclopropyl, cyclobutyl, cyclopentyl and cyclohexyl;

R$^{5d}$, at each occurrence, is selected from H, methyl, CF$_3$, ethyl, propyl, i-propyl, butyl, s-butyl, i-butyl, t-butyl, pentyl, hexyl, allyl, propargyl, and a (CH$_2$)$_r$—C$_{3-6}$ carbocyclic residue selected from cyclopropyl, cyclobutyl, cyclopentyl and cyclohexyl;

R$^{5e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, and (CH$_2$)$_r$phenyl; and R$^{5f}$, at each occurrence, is selected from H, methyl, ethyl, propyl, i-propyl, butyl, and cyclopropyl, cyclobutyl, and phenyl.

In another embodiment, R$^5$ is selected from methyl, ethyl, propyl, i-propyl, butyl, i-butyl, s-butyl, pentyl, hexyl, CF$_3$, CF$_2$CF$_3$, CF$_2$H, OCF$_3$, Cl, Br, I, F, SCF$_3$, NR$^{5a}$R$^{5a}$, NHC(O)OR$^{5a}$, NHC(O)R$^{5b}$, and NHC(O)NHR$^{5a}$.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., R$^a$) occurs more than one time in any constituent or formula for a compound, its definition at each occurrence is independent of its definition at every other occurrence. Thus, for example, if a group is shown to be substituted with 0–2 R$^a$, then said group may optionally be substituted with up to two R$^a$ groups and R$^a$ at each occurrence is selected independently from the definition of R$^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl", is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5–6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, azetidinyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, morphlinyl, piperidinyl, pyrrolyl, 2,5-dihydropyrrolyl, pyrrazolyl, 1,2,4-triazolyl, 1,2,3-triazolyl, tetrazolyl, thiadiazolyl, thiazolyl, oxazolyl, pyrazinyl, and pyrimidinyl. Also included are fused ring and spiro compounds containing, for example, the above heterocycles.

Examples of heteroaryls are 1-indazole, 2H,6H-1,5,2-dithiazinyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyridazinyl, pyridyl, pyridinyl, pyrimidinyl, pyrrolyl, quinazolinyl, quinolinyl, thiazolyl, thienyl, and tetrazolyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or in combination with other active ingredients effective to inhibit MCP-1 or effective to treat or prevent inflammatory disorders.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1999).

Compounds of formula 1.5 are available as shown in Scheme 1. A differentially protected diamine 1.1 is singly deprotected and coupled with a carboxylic acid 1.2 to provide the amide 1.3. For substrates with acid sensitive groups at $R^3$ (i.e. tert-butyl esters or ethers), a selective removal of the N-Boc group is still readily achieved (Frank S. Gibson, et al, J. Org. Chem. 1994, 59, 3216). If the central spacer is an α-amino acid, than a more optimal protocol involves stepwise coupling as shown (1.1→1.6→1.3). The other terminus of the diamine subunit of 1.3 is revealed by hydrogenation, and the nascent amine is readily conjugated with aldehydes 1.7 ($R^{16}$=H) and ketones 1.7 under reductive conditions (MeOH, NaCNBH$_3$ or THF, AcOH, NaHB(OAc)$_3$) to provide the desired secondary amine 1.5. The chemistry shown in Scheme 1 is quite general, and a wide array of amino acids 1.8, amino acid conjugates 1.2, aldehydes 1.7 (R$^{16}$=H), and ketones 1.7 are commercially available. Thus, the primary challenge in producing compounds of formula 1.5 lies in the synthesis of the differentially protected diamines 1.1. Accordingly, the syntheses of a number of important representative embodiments of 1.1 are illustrated in Schemes 2–15.

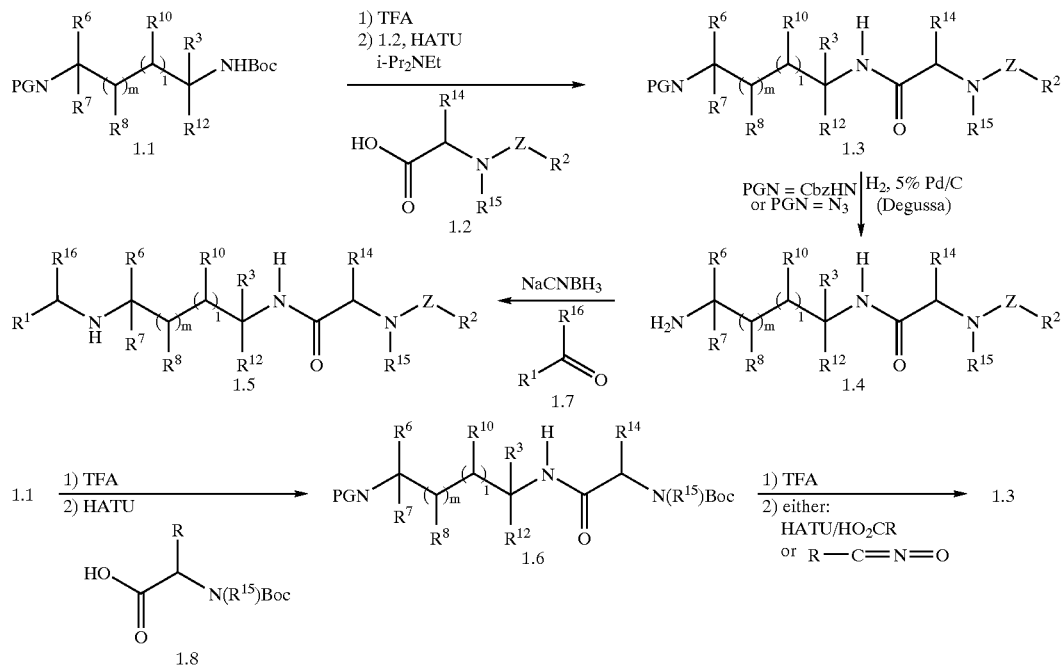

Singly substituted variants of 1.1 (R$^3$≠H) are readily available as shown in Scheme 2. Compounds of formula 2.1—namely L- or D-N$_\alpha$-Boc, N$_\omega$-Cbz-diaminopropionic acid, diaminobutyric acid, and ornithine—are commercially available and are readily converted into esters 2.2 and amides 2.3 using a number of standard synthetic methods (two of which are illustrated). It is possible to synthesize a wide variety of other singly substituted variants of 1.1 (R$^3$≠H or C(O)X) from L- or D-α, β, or γ-amino acids 2.4. The α-amino acids are available from commercial sources, and the β- and γ-amino acids are readily prepared from the α-amino acids (Tobias Hintermann, et al., *Helv. Chim. Acta.* 1998, 81, 983). Selective reduction of the carboxylic acid of 2.5 to the alcohol in the presence of other sensitive functionality (e.g. esters) is accomplished by initial conversion of the acid to the succinimide ester, followed by low temperature reduction (NaBH$_4$, EtOH, 0° C., 5 min). Simple transformation of the alcohol to the azide via the mesylate provides 2.5.

Scheme 2

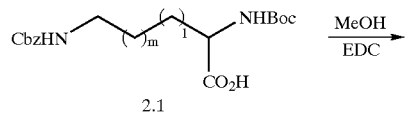

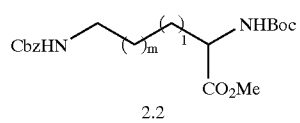

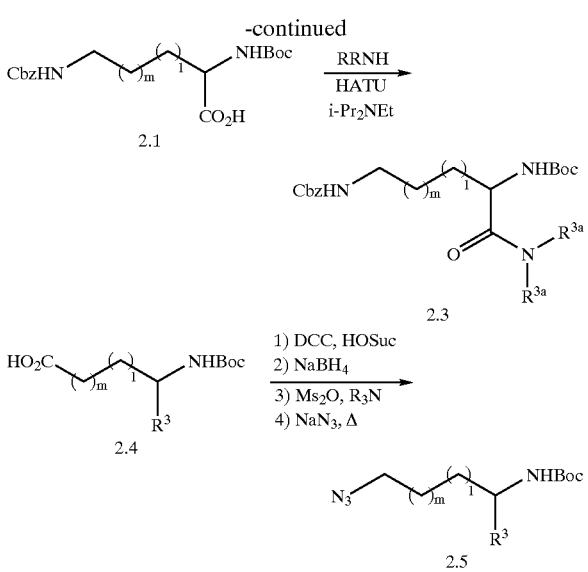

Doubly substituted variants of 1.1 (R$^3$, R$^{12}$≠H) are available as shown in Schemes 3 and 4. The methodology for the synthesis of L- and D-α-alkylserines 3.1 has been described in the literature (Dieter Seebach and Johannes Aebi, *Tetrahedron Lett.* 1984, 25, 2545). Sequential functionalization of the amine, acid, and alcohol functionalities affords mesylate 3.2. This mesylate can be reacted with either sodium azide to give the masked α, β-diamine 3.3 or with sodium cyanide to give nitrile 3.4. Hydrogenation of 3.4 and protection of the resultant amine affords protected α, γ-diamine 3.5, which is easily converted into the amide 3.6 if desired. Alternatively, 3.1 can be doubly homologated using standard chemistry to give 3.8 via the intermediacy of the unsaturated ester 3.7. Note that this sequence (3.1→3.7→3.8) capitalizes on the presence of the $R^{12}$ group to modulate the reactivity of the ester towards bases and reducing agents. Displacement of the mesylate of 3.8 with sodium azide affords the selectively protected α, δ-diamine 3.9, which can be subsequently transformed to the amide 3.10 if desired.

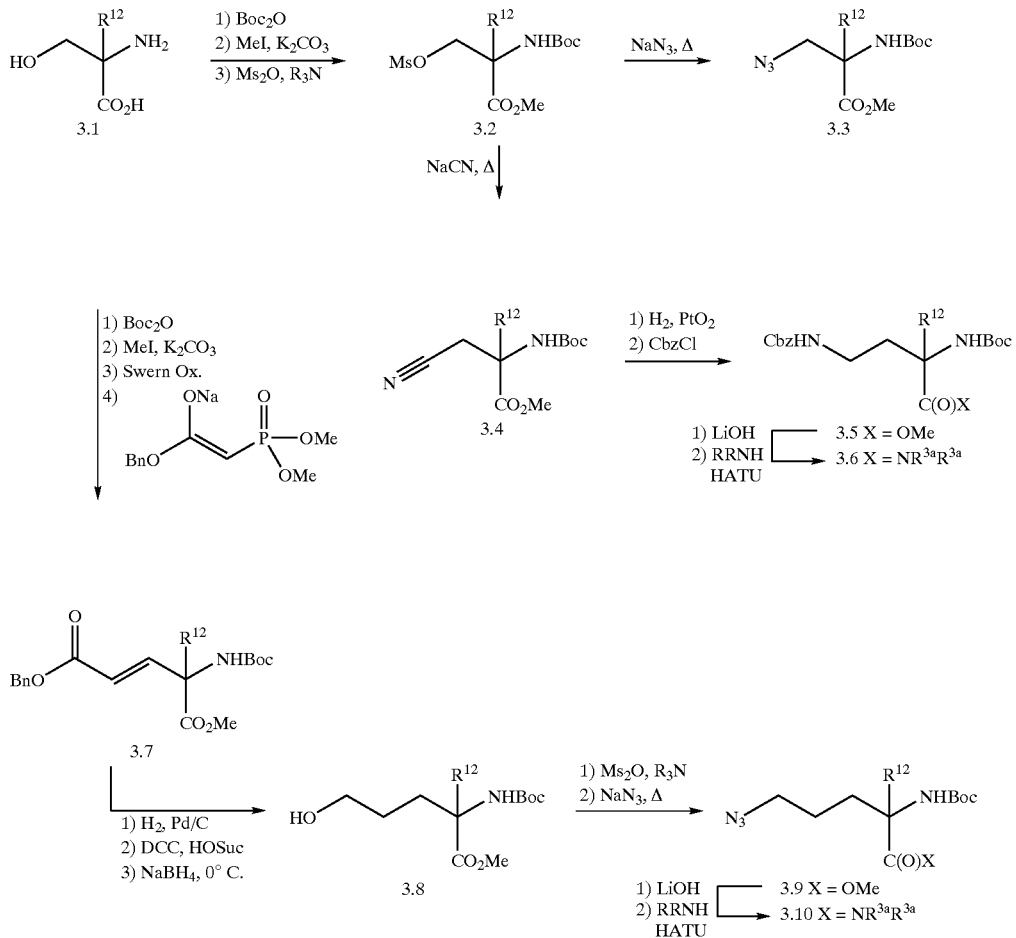

Scheme 3

It is possible to synthesize a wide variety of other doubly substituted variants of 1.1 ($R^3$, $R^{12}$≠H; $R^3$≠C(O)X) from L- or D-α-alkyl-α-, β-, or γ-amino acids 4.1 (Scheme 4) using the same methodology that was described above for the sequence shown in Scheme 2 (2.4→2.5). The enantioselective synthesis of α-alkyl-α-amino acids 4.1 (l=m=0) has been described by a number of authors (cf. André Charette and Christophe Mellon, *Tetrahedron* 1998, 54, 10525 for leading references). These compounds can be readily transformed into the β- and γ-homologues of 4.1 (l=1, m=0 and l=m=1, respectively) using the same chemistry that has been described for α-unsubstituted-α-amino acids (Tobias Hintermann, et al., *Helv. Chim. Acta.* 1998, 81, 983) as shown in the lower portion of Scheme 4.

Scheme 4

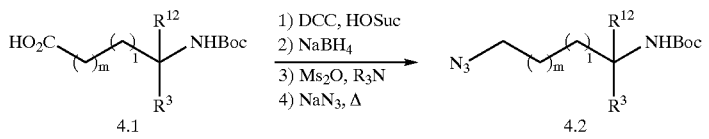

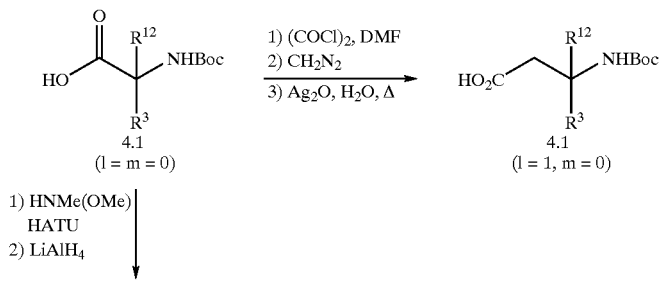

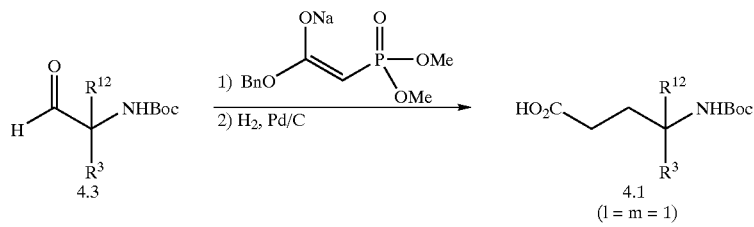

Doubly substituted variants of 1.1 ($R^3 \neq H$, $R^6$ or $R^{10} \neq H$) are available as shown in Schemes 5 and 6. A variety of syn β-hydroxy-α-amino acids 5.1 are available in homochiral form from either commercial sources ($R^6$=Me) or by synthesis (cf. Adam J. Morgan, et al., *Org. Lett.* 1999, 1, 1949 for leading references). Protection of the amine group as its tert-butyl carbamate is followed by standard amide formation to afford 5.2. Installation of the second protected amine functionality may be accomplished using either Mitsonobu chemistry (illustrated) or a more conventional approach ($Ms_2O$; then $NaN_3$) to afford the anti β-azido-α-amino amide 5.3. If the syn isomer of the β-azido-α-amino amide 5.3 is desired, than the stereochemistry of the β-hydroxyl group of 5.2 can be inverted (p-$NO_2PhCO_2H$, $Ph_3P$, DEAD; then LiOH) before installation of the azide. Either isomer of the amide 5.3 can be readily converted to the ester via methanolysis of the imide derivative (D. L. Flynn, et al., *J. Org. Chem.* 1983, 48, 2424). The γ- and δ-homologues of 5.4 are synthesized from a different starting material, namely the β-alkyl-γ-hydroxy-α-amino ester 5.5, which is available via the alkylation of suitably protected aspartic acid derivatives (Jean-Pierre Wolf and Henry Rapoport, *J. Org. Chem.* 1989, 54, 3164). The mesylate derivative of 5.5 is displaced with sodium azide or with sodium cyanide; both of these products may then be hydrogenated and then treated with acid to give the α, γ- and α, δ-diamino acids 5.6 and 5.11. Selective protection of the terminal amine of either 5.6 or 5.11 is accomplished after initial treatment with Cu(II) (Andre Rosowsky and Joel E. Wright, *J. Org. Chem.* 1983, 48, 1539). Subsequent protection of the α-amine, decomplexation of the copper with EDTA, and amidation or esterification of the carboxylic acid provides access to any of the final products 5.8, 5.9, 5.13, or 5.14.

Scheme 5

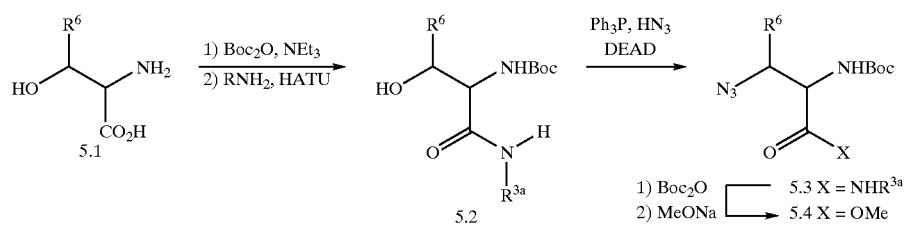

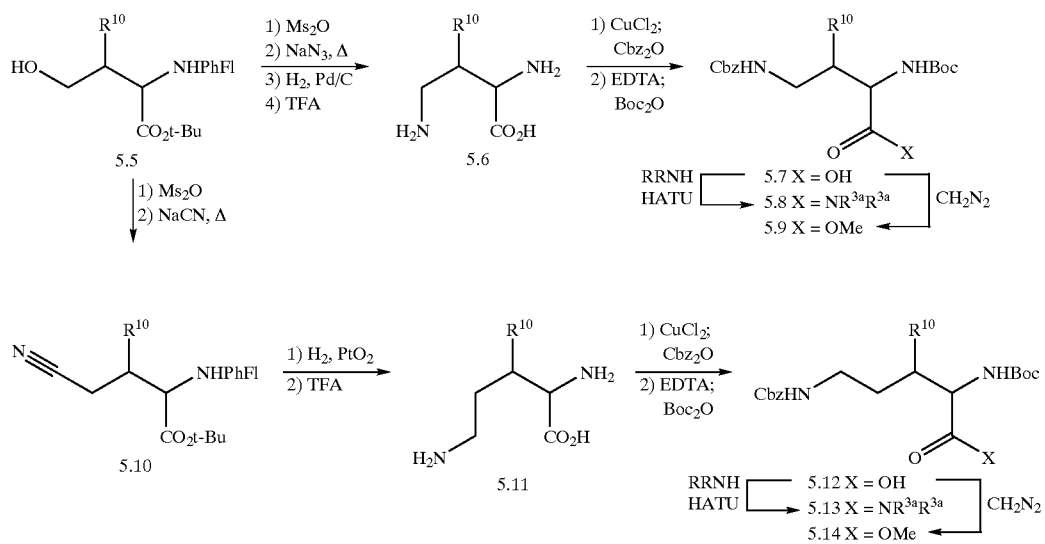

It is possible to synthesize a wide variety of other doubly substituted variants of 1.1 ($R^6$ or $R^{10} \neq H$; $R^3 \neq H$ or C(O)X) from α-amino acids as shown in Scheme 6. Formation of the U-amino ketone 6.2 from the α-amino acid 6.1 is easily accomplished via Grignard addition to the α-amino Weinreb amide. The ketone 6.2 is reduced to the alcohol and reacted with mesyl anhyrdide to give the secondary mesylate 6.3. This mesylate is reacted with either sodium azide to afford the masked α, β-diamine 6.4, or with sodium cyanide to give nitrile 6.5. The nitrile is readily reduced and protected to provide the protected α, γ-diamine 6.6. Alternatively, the ketone 6.2 may be homologated under standard Horner-Wadsworth-Emmons conditions to give the unsaturated ester, which may then be reduced to the saturated acid 6.7. This acid is readily converted to the protected α, δ-diamine 6.9 using the same methodology that was described above for the sequence shown in Scheme 2 (2.4→2.5).

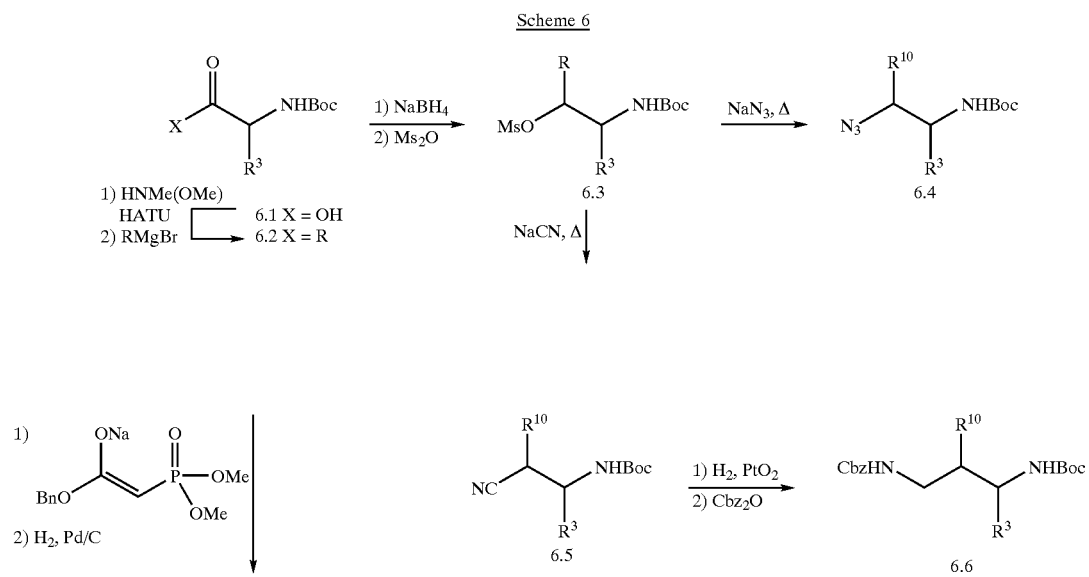

-continued

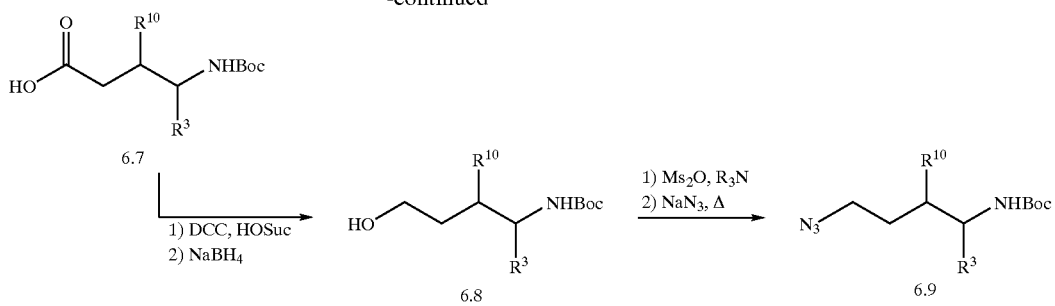

Doubly substituted variants of 1.1 ($R^6$ or $R^8 \neq H$; $R^3 \neq H$) are available as shown in Schemes 7 and 8. Any diastereomer of the carboxylic acid 7.1 is available from the alkylation of a suitably protected glutamic acid derivative (Zong-Qiang Tian, et al, *J. Org. Chem.* 1997, 62, 514). The acid of 7.1 is converted into a carbamate-protected amine using a Curtius rearrangement; subsequent deprotection of the pthalimide protecting group gives the monoprotected α,γ-diamine 7.2. Acid-mediated cleavage of the tert-butyl ester can be followed by N-Boc protection to give the acid 7.3, which may be readily transformed into either the amide 7.4 or the methyl ester 7.5. Alternatively, the key intermediate 7.1 can be converted into the azide 7.6 using the same methodology that was described above for the sequence shown in Scheme 2 (2.4→2.5). Appropriate protecting group manipulation would then afford the masked α,δ-diamino acid 7.7, which can be converted into the amide 7.8 or the ester 7.9 using standard chemistry.

latter is readily transformed into the protected α,δ-diamine 8.5 via hydrogenation and N-protection.

Scheme 8

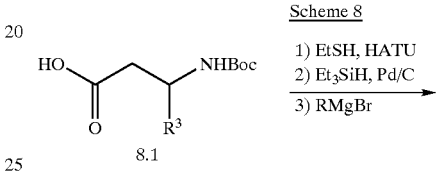

Scheme 7

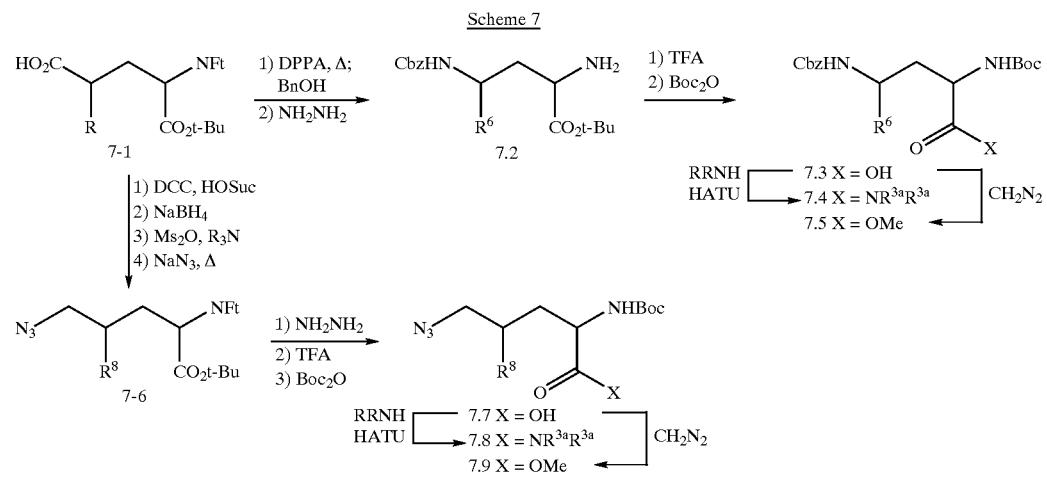

Pt = pthaloyl

It is possible to synthesize a wide variety of other doubly substituted variants of 1.1 ($R^6$ or $R^8 \neq H$; $R^3 \neq H$ or C(O)X) from β-amino acids as shown in Scheme 8. Conversion of the readily available (cf. David A. Evans, et al., *J. Org. Chem.* 1999, 64, 6411 for leading references) carboxylic acid 8.1 to the aldehyde may be accomplished under mild conditions (T. Fukuyama, et al., *J. Am. Chem. Soc.* 1990, 112, 7050) such that any ester functionality in R is not affected. Reaction of the resultant aldehyde with a single equivalent of Grignard reagent at low temperature affords the secondary alcohol 8.2. The key alcohol 8.2 can be converted into the γ-azido amine 8.3 or the nitrile 8.4; the -continued

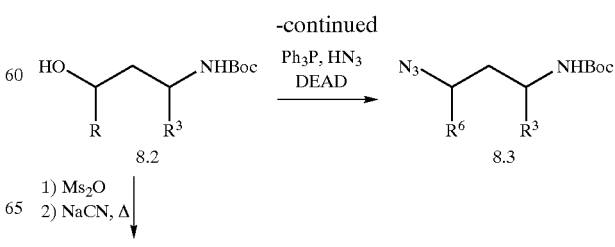

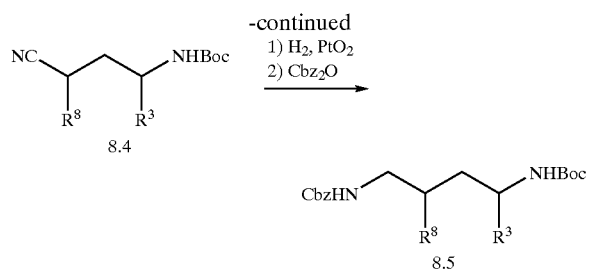

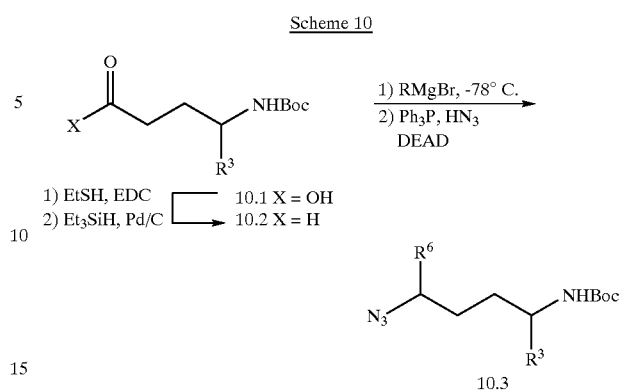

Doubly substituted variants of 1.1 ($R^3$, $R^6 \neq H$) are available as shown in Schemes 9 and 10. Pyrroglutamic acid 9.1, which is commercially available in either antipode, may be N-protected and C-amidated to give 9.2. Reaction of 9.2 with a Grignard reagent gives the ketone (Tomihisa Ohta, et al., *Chem. Lett.* 1987, 2091), which may be reduced to give the alcohol 9.3. Conversion of the alcohol to the azide provides the masked α, δ-diamine 9.4. If desired, the amide of 9.4 may be saponified to give 9.5 via the imide (David A. Evans, et al., *Tetrahedron Lett.* 1997, 38, 4535); the nascent acid is easily transformed into the ester 9.7 or another amide 9.6 using standard chemistry.

Schemes 2–10 have illustrated how to prepare a number of doubly substituted variants of 1.1 ($R^3 \neq H$; $R^3 = C(O)X$ or $R^3 \neq C(O)X$) in a regio- and stereoselective fashion. Given this instruction, it will be apparent to one skilled in the art of organic synthesis how to prepare the analogous triply substituted variants of 1.1 using the appropriate combination of the chemistry presented in Schemes 2–10.

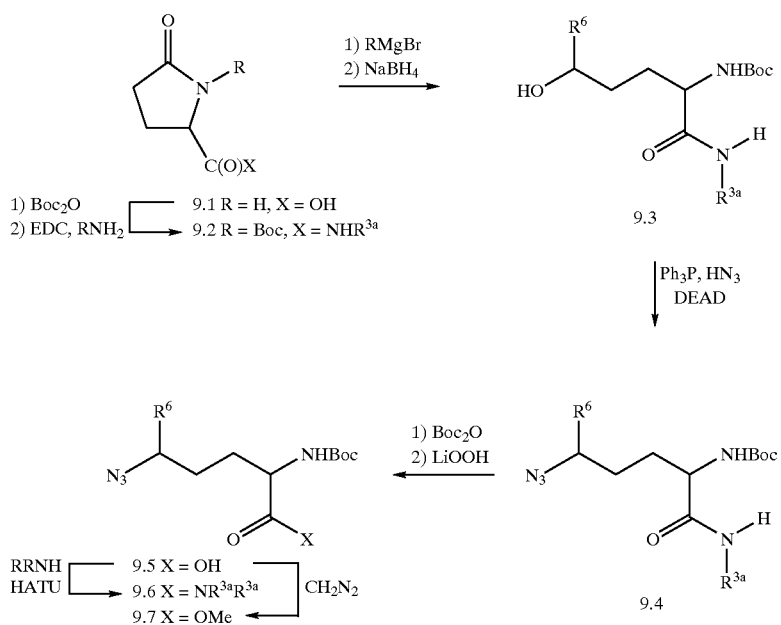

It is possible to synthesize a wide variety of other doubly substituted variants of 1.1 ($R^6 \neq H$; $R^3 \neq H$ or $C(O)X$) from γ-amino acids as shown in Scheme 10. Conversion of the readily available (Tobias Hintermann, et al., *Helv. Chim. Acta.* 1998, 81, 983) carboxylic acid 10.1 to the aldehyde may be accomplished under mild conditions. Reaction of the aldehyde with a single equivalent of Grignard reagent at low temperature would then afford the secondary alcohol, which can be readily transformed into the masked α, δ-diamine 10.3 using Mitsonobu chemistry.

Singly, doubly, and triply substituted variants of 1.1 ($R^3 = C(O)X$) can be converted into other variants of 1.1 that contain a hydroxyl functionality as shown in Scheme 11. Carboxylic acids of formula 11.1 are available as shown in Schemes 2–10; if the synthesis of only the methyl ester has been illustrated, than the methyl ester may be converted into the acid 11.1 via saponification (LiOH, THF/MeOH/H$_2$O). Conversion of the acid into the Weinreb amide and reaction with a Grignard reagent provides ketone 11.3. This ketone may either be reacted with another Grignard reagent (R=R or R≠R) to afford the tertiary alcohol 11.4 or reduced with sodium borohydride (or other reducing agent) to provide the secondary alcohol 11.5. If desired, the alcohol could be further transformed to provide 11.6.

Scheme 11

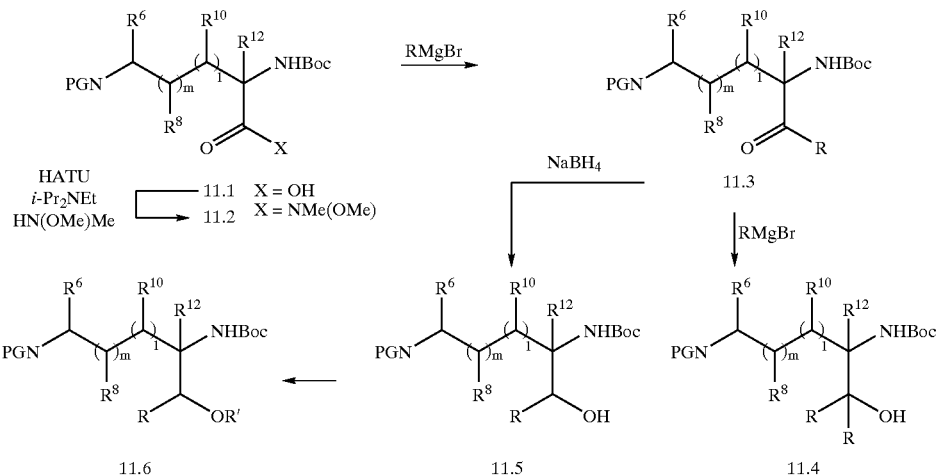

Varients of protected diamine 1.1 that contain a spirocyclic group ($R^3$ and $R^{12}$ conjugated in a ring) are available as shown in Schemes 12–15. Cyclic ketone 12.1 is converted into the α-amino nitrile 12.2 using classical Strecker chemistry (T. A. Keating and R. W. Armstrong, *J. Am. Chem. Soc.* 1996, 118, 2574). Under certain circumstances, this amine may be incorporated directly into the chemistry shown in Scheme 1 (cf. Example 39); alternatively, the amine can be protected, the nitrile hydrogenated, and the nascent amine protected to give the doubly protected α, β-diamine 12.3. The ketone 12.1 may also be homologated using a Hornor-Wadsworth-Emmons reaction to provide enoate 12.4, which is readily reacted with ammonia and then protected to afford the key β-amino ester 12.5. This intermediate can be converted into the protected α, β-diamine via ester saponification and Curtius rearrangement. Alternatively, the ester of 12.5 may be reduced, and the resultant primary alcohol derivatized as the mesylate to afford 12.6. The mesylate 12.6 may be reacted with sodium azide (DMSO, heat) to give the masked α, γ-diamine 12.7. Alternatively, the mesylate 12.6 may be reacted with sodium cyanide to give the nitrile, which may then be hydrogenated and reacted with dibenzyl carbonate to give the protected α, δ-diamine 12.8.

Scheme 12

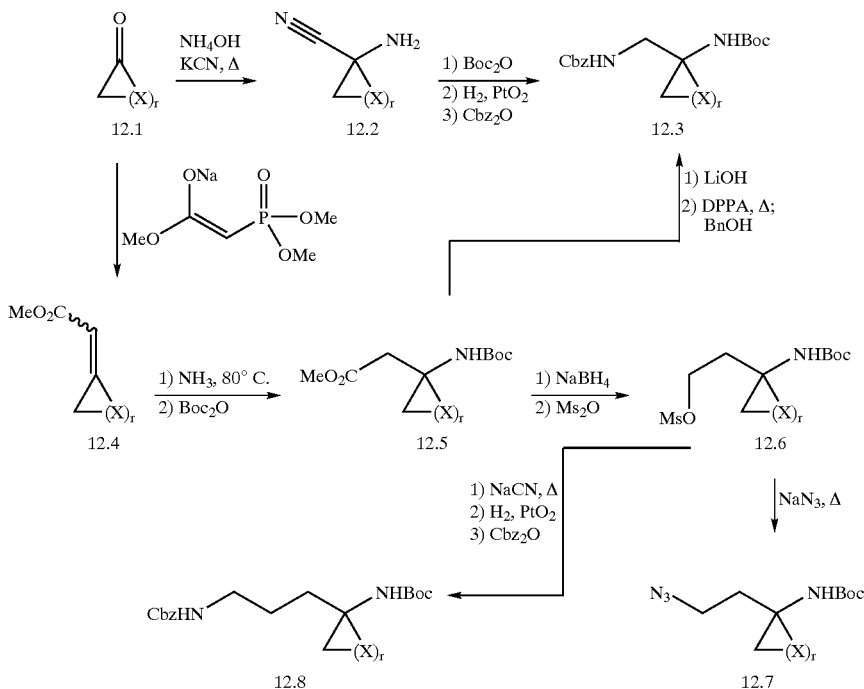

The preparation of the two key intermediates for the synthesis of the target compounds 14.5, 14.7, 15.3, and 15.5 (all variants of 1.1) is shown in Scheme 13. Trapping of the enolate derived from 13.1 with an alkyl bromide containing a pendant olefin affords compound 13.2 (Dieter Seebach and Johannes Aebi, *Tetrahedron Lett.* 1984, 25, 2545). Hydrolysis of 13.2 with refluxing 6N HCl, followed by N-protection with tert-butyl dicarbonate affords the β-hydroxy acid 13.4. This latter compound is readily functionalized to provide the fully protected synthon 13.6, which may be utilized in the chemistry described in Scheme 14. Alternatively, the enolate of 13.1 can be reacted with a diiodoalkane; the resultant primary iodide is readily displaced with sodium azide to give 13.3 (for highly analogous chemistry, cf. Amos B. Smith, III, et al., *Tetrahedron Lett.* 1997, 38, 3809). The primary azide 13.3 may be transformed into the fully protected synthon 13.7 using the chemistry described above; this compound is ready for incorporation into Scheme 15. If desired, the enantiomer of 13.1 may be synthesized from D-serine and utilized in Scheme 13 to afford the enantiomers of 13.6 and 13.7.

Scheme 13

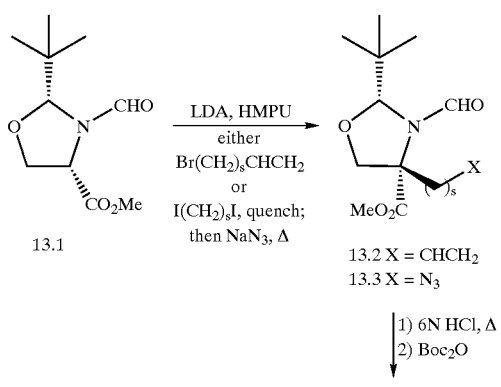

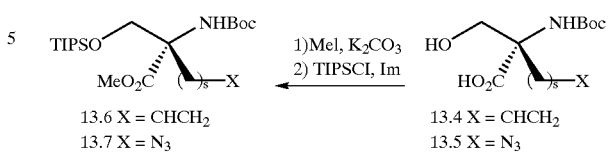

Varients of protected diamine 1.1 that contain an oxygenated spirocyclic group ($R^3$ and $R^{12}$ conjugated in a ring) are available as shown in Scheme 14. Oxidation of the terminal olefin of 13.6 to the corresponding methyl ester 14.1 may be achieved using known chemistry (David A. Evans and Eric B. Sjogren, *Tetrahedron Lett.* 1986, 27, 4961). Dieckman cyclization of the diester 14.1 under basic conditions provides the β-ketoester 14.2. If desired, the β-ketoester may be alkylated under mild conditions (carbonate, alkyl iodide); the resultant product and its precursor may both be transformed into ketones 14.3 ($R^{3g} \neq H$ and $R^{3g} = H$, respectively) by saponification and decarboxylation. Compounds of formula 14.3 are readily reduced and deprotected to give the diol; the primary alcohol can be derivatized selectively in the presence of the secondary alcohol through the use of tosyl chloride under carefully controlled conditions (pyridine, 0° C.). The resultant lynchpin tosylate 14.4 may be reacted with sodium azide to afford the masked α, β-diamine 14.5. Alternatively, the tosylate of 14.4 may be displaced with sodium cyanide; reduction of the resultant nitrile and protection of the nascent amine affords the protectd α, γ-diamine 14.7.

Scheme 14

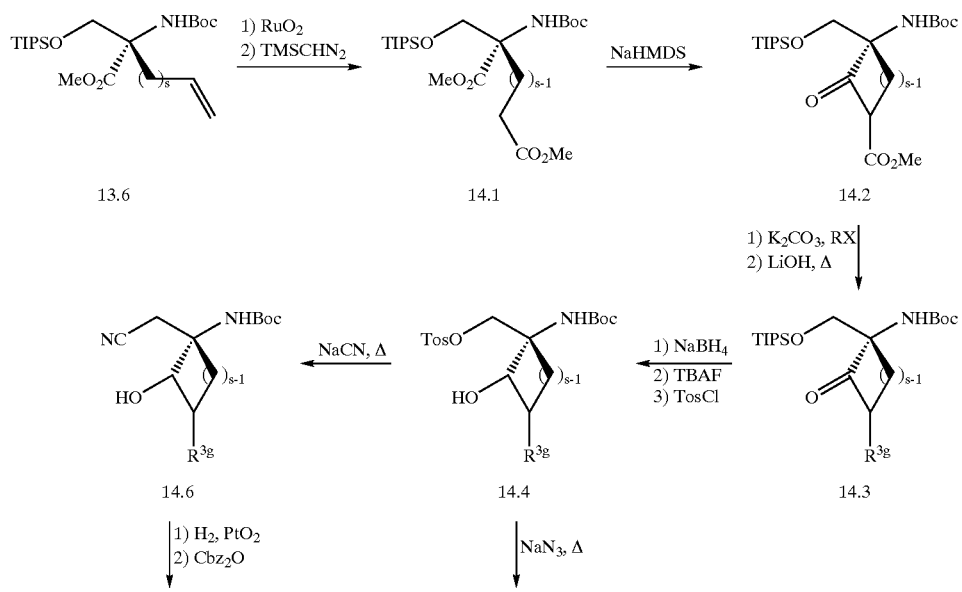

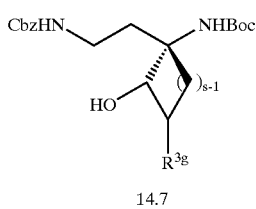
14.7

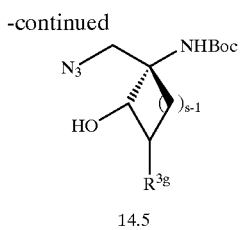
14.5

Varients of protected diamine 1.1 that contain a spirocyclic lactam ($R^3$ and $R^{12}$ conjugated into a lactam) are available as shown in Scheme 15. Saponification of the methyl ester of 13.7, followed by hydrogenolysis of the azide provides the amino acid 15.1 ($R^{3g}$=H). If desired, this amine may be monoalkylated under reductive amination conditions to give the N-alkylated amino acid 15.1 ($R^{3g} \neq H$). Cyclization of the amino acid using DCC affords lactam 15.2, which is readily deprotected and tosylated to afford the key intermediate 15.4. The tosylate 15.3 may be reacted with sodium azide to afford the masked α, β-diamine 15.4. Alternatively, the tosylate of 15.4 may be displaced with sodium cyanide; reduction of the resultant nitrile and protection of the nascent amine affords the protectd α, γ-diamine 15.5. One skilled in the art will readily appreciate that the lactone analogs of compounds 15.4 and 15.5 can be synthesized by using similar chemistry, allowing for a change in the electrophile in Scheme 13.

cally pure material. When required, separation of racemic material can be achieved by HPLC using a chiral column or by a resolution using a resolving agent such as camphonic chloride (Steven D. Young, et al, *Antimicrobial Agents and Chemotheraphy* 1995, 2602). Likewise, separation of diastereomers of target compounds can be achieved by HPLC using either an achiral or chiral column. If desired, alcohol diastereomers may be readily interconverted using Mitsonobu conditions (p-NO$_2$PhCO$_2$H, Ph$_3$P, DEAD). If a particular alcohol diastereomer is preferred, the precursor ketone can be reduced using a chiral reducing agent (e.g. E. J. Corey and Christopher J. Helal, *Angew. Chem. Int. Ed.* 1998, 37, 1986) in order to favor the production of one diastereomer over the other. A number of the variants of the target compounds of formula 1.5 may be elaborated into other desirable compounds as shown in Schemes 16–19. In the specific instance of compounds of formula 16.1, the ester Scheme 15

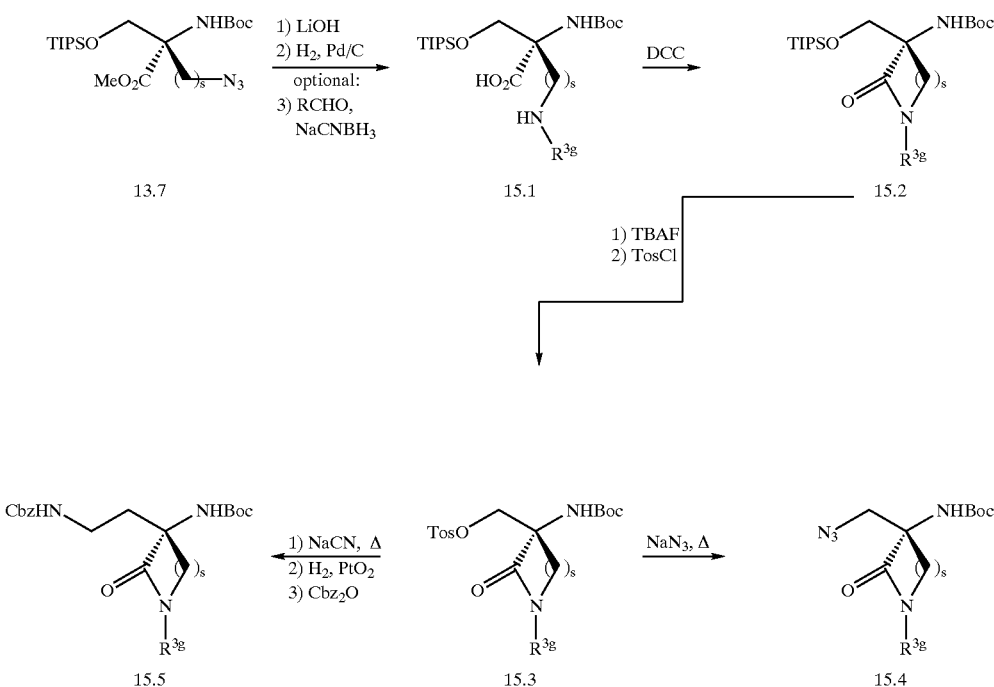

As will be apparent to one skilled in the art, the instruction given above (Schemes 2–15) on the synthesis of embodiments of 1.1 usually provides for the synthesis of enantiomerically pure material, but not necessarily diastereomerically pure material. When required, separation of racemic may either be reduced or hydrolyzed to give the alcohol 16.4 or the acid 16.2, respectively. The carboxylic acid 16.2 may be coupled with amines without significant epimerization using HATU to afford the amide 16.3.

Scheme 16

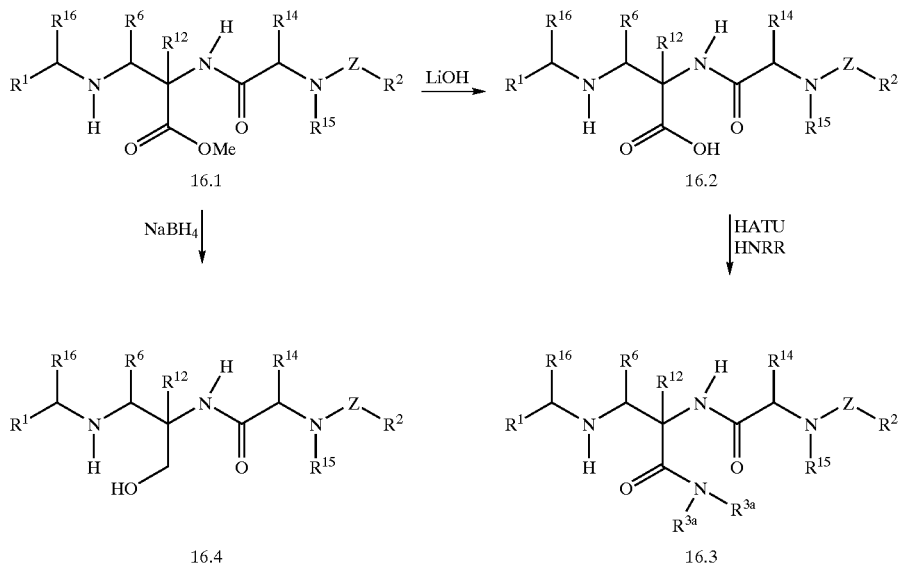

The chemistry described in Scheme 16 is not readily applied to the mainchain homologs of 16.1. The mainchain homologs of amide 16.3 are most easily prepared from the amidated diamine variants of 1.1 (cf. Schemes 2, 3, 5, 7, and 9). For the mainchain homologs of alcohol 16.4, the alternative strategy shown in Scheme 17 must be utilized. Compounds of formula 17.1, which still have one nitrogen of the core diamine in protected form, may be reduced with sodium borohydride to give alcohol 17.2. Hydrogenation of 17.2 affords the free amine 17.4, which is alkylated readily under reductive conditions to give 17.6. If desired, the mainchain homologs of carboxylic acid 16.2 may be prepared using analogous chemistry, except that the ester of 17.1 is saponified to give the corresponding carboxylic acid 17.3 before being hydrogenated and alkylated to give 17.7.

Scheme 17

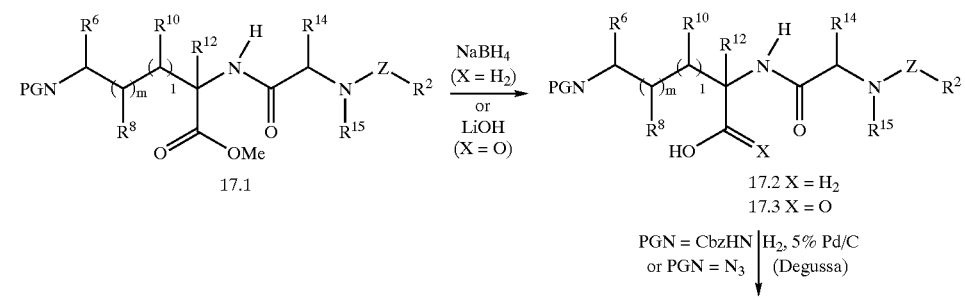

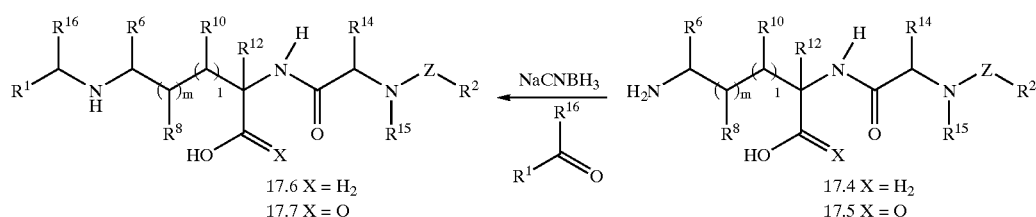

The chemistry described in Scheme 16 is not readily applied to the sidechain homologs of 16.1, and so the alternative strategy shown in Scheme 18 must be utilized. Compounds of formula 18.1, which still have one nitrogen of the core diamine in protected form, may be deprotected with TFA and amidated under standard conditions to provide compounds of formula 18.2. These are then hydrogenated and alkylated to afford the desired compounds of formula 18.4.

Scheme 18

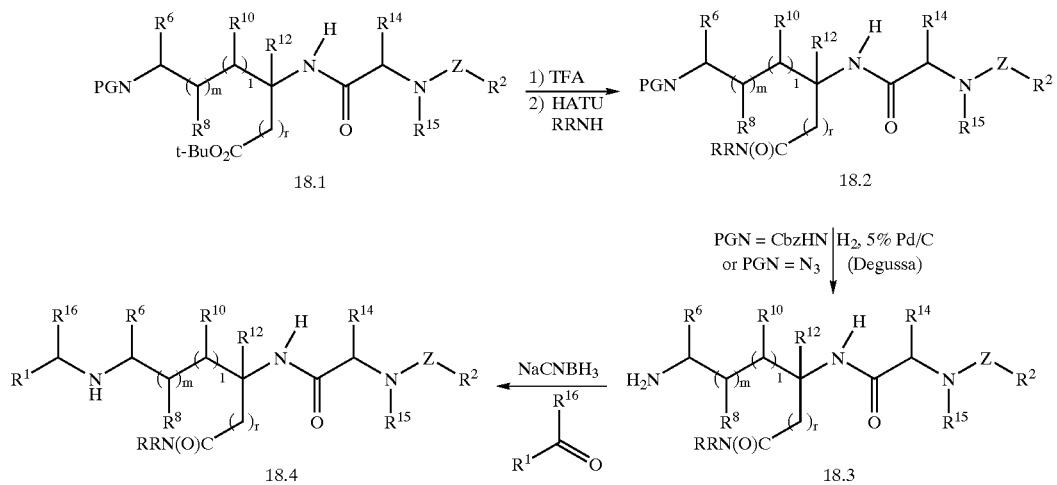

If desired, the compounds of formulas 19.1 and 19.3, both specific embodiements of formula 1.5, may be further transformed as shown in Scheme 19. Selective N-protection of the secondary nitrogen of either 19.1 or 19.3 under biphasic conditions is followed by Dess-Martin oxidation of the alcohol and deprotection of the benzyl carbamate to provide the amino ketones 19.1 and 19.4.

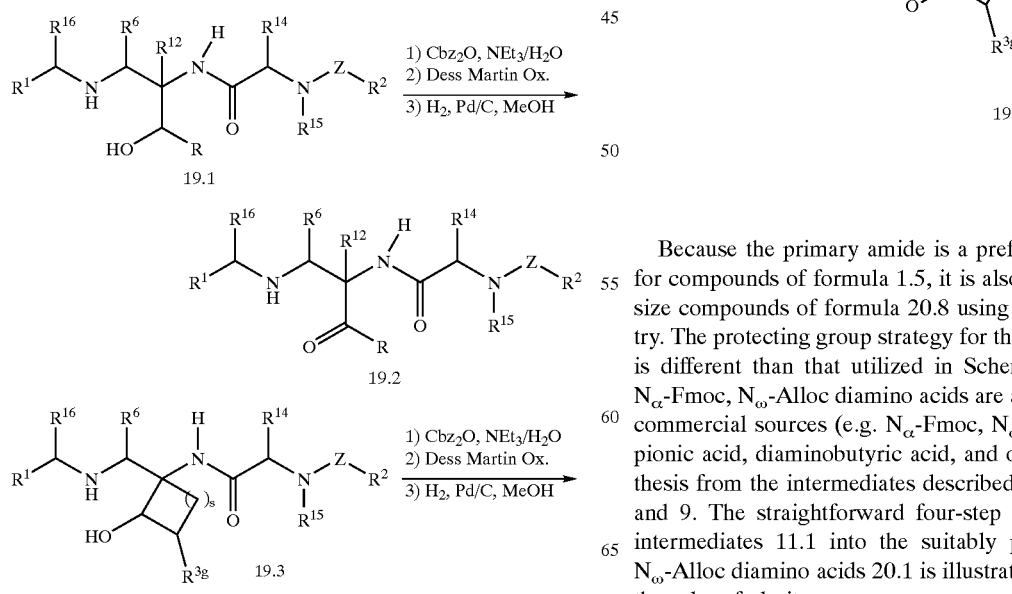

Because the primary amide is a preferred $R^3$ substituent for compounds of formula 1.5, it is also possible to synthesize compounds of formula 20.8 using solid-phase chemistry. The protecting group strategy for the diamino acids 20.1 is different than that utilized in Scheme 1. The requisite $N_\alpha$-Fmoc, $N_\omega$-Alloc diamino acids are available from either commercial sources (e.g. $N_\alpha$-Fmoc, $N_\omega$-Alloc diaminopropionic acid, diaminobutyric acid, and ornithine) or by synthesis from the intermediates described in Schemes 3, 5, 7, and 9. The straightforward four-step conversion of these intermediates 11.1 into the suitably protected $N_\alpha$-Fmoc, $N_\omega$-Alloc diamino acids 20.1 is illustrated in Scheme 21 for the sake of clarity.

Scheme 20

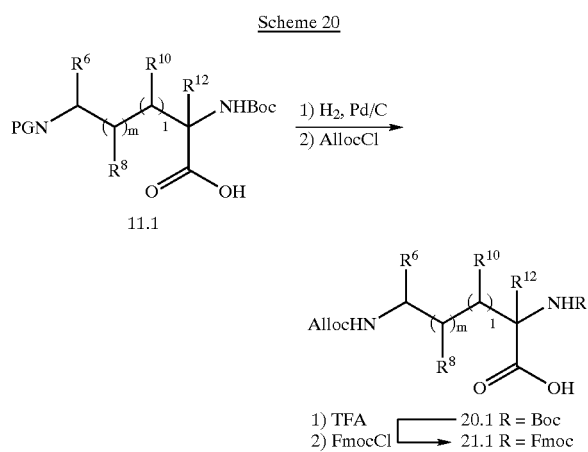

Once obtained, compounds of formula 20.1 may be attached to an appropriate amine resin (e.g. Rink or PAL), deprotected, coupled with amino acids 20.3, deprotected, and coupled with carboxylic acids 20.5 to give the resin bound polyamide 20.6. If desired, this sequence (20.1→20.2→20.4→20.6) may be performed on an automated peptide synthesizer. Deprotection of the $N_\omega$-Alloc group using $Pd(PPh_3)_4$ and N-methyl morpholine is followed by reductive amination of the resin-bound amine (Jeremy Green, *J. Org. Chem.* 1995, 60, 4287). Liberation of the desired primary amide 20.8 from the resin is accomplished via treatment with 5% $Et_3SiH/TFA$. It is apparent to one skilled in the art of organic synthesis that large compound libraries (>100 compounds) can be prepared using this chemistry, given the wide variety of $N_\alpha$-Fmoc amino acids 20.3, carboxylic acids 20.5, and aldehydes 20.7 that are available from commercial sources and by synthesis.

Scheme 21

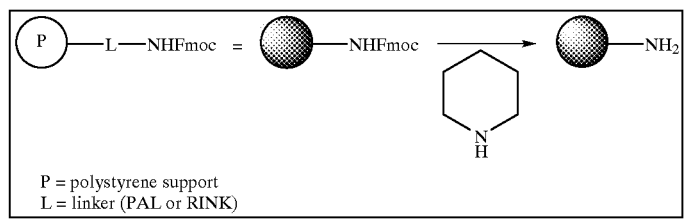

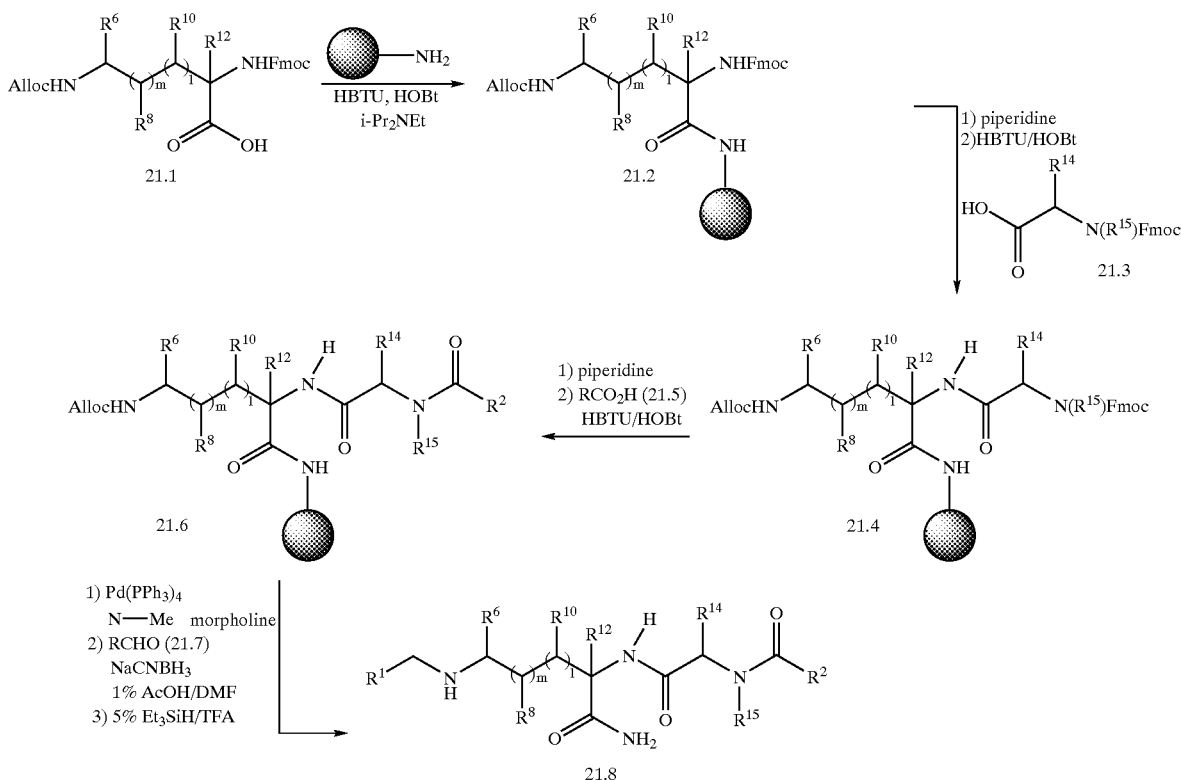

Because N-alkyl- and N,N-alkylamides are preferred $R^3$ substituents for compounds of formula 1.5, it is also possible to synthesize compounds of formula 22.5 using solid-phase chemistry, as shown in Scheme 22. In this instance, the chemistry is highly analogous to that described above for Scheme 21. The only differences come in the resin-loading step (21.1→22.1), and the resin-release step (22.4→22.5), both of which are performed according to the protocols of Ellman (Bradley J. Backes and Jonathon A. Ellman, *J. Org. Chem.* 1999, 64, 2322). It is apparent to one skilled in the art of organic synthesis that large compound libraries (>100 compounds) can be prepared using this chemistry, given the wide variety of $N_\alpha$-Fmoc amino acids 20.3, carboxylic acids 20.5, aldehydes 20.7, and amines that are available from commercial sources and by synthesis.

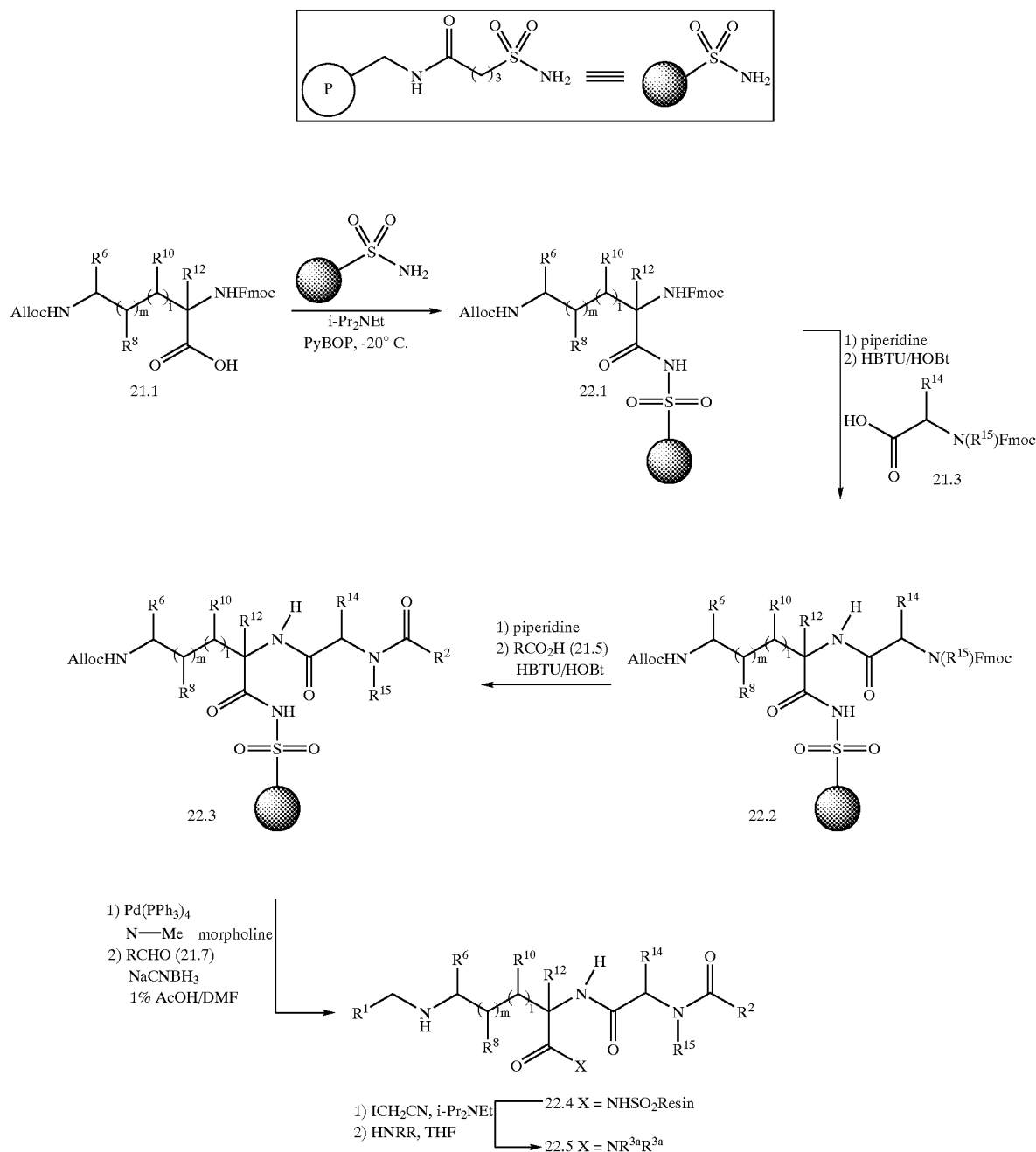

As will be readily appreciated by one skilled in the art of organic synthesis, there is an element of pseudosymmetry present in compounds of formula 1.1. Thus, one can synthesize more compounds of formula 1.5 than are available from the reaction sequence shown in Scheme 1 without changing the protecting group scheme of the many intermediates of formula 1.1, the syntheses of which have already been detailed in Schemes 2–15. As shown in Scheme 23, hydrogenation of 1.1 and coupling of the nascent amine with acid 1.2 provides amide 23.1. Alternatively, compounds of formula 23.1 may be accessed using a stepwise approach (cf. Scheme 23, 1.1→23.3→23.1). Acid-mediated removal of the N-Boc group from 23.1 is followed by reductive amination to provide compounds of formula 23.2. If one allows for a simple change in the designation of the sidechain R groups, than these compounds of formula 23.2 are actually embodiments of compounds of formula 1.5, as is clearly illustrated in Scheme 23 (see also Example 35).

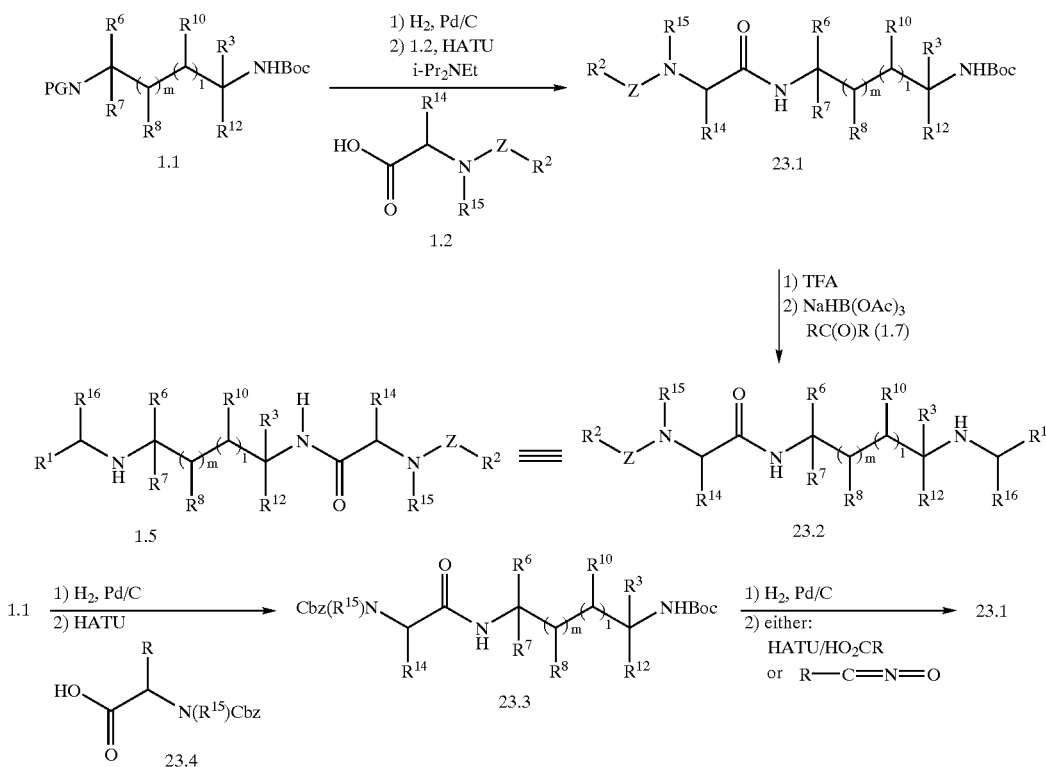

Finally, it should be noted that 1.5 and its various embodiments (e.g. 16.3, 16.4, 17.6, 17.7, 18.4, 21.8, and 22.5) can be alkylated selectively under reductive amination conditions to provide compounds 24.1.

Scheme 24

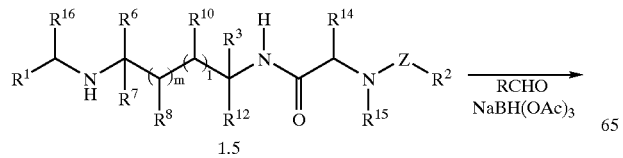

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "°C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

Methyl (2S)-3-[[(2,4-dimethylphenyl)methyl]amino]-2-[[[[3-(trifluoromethyl)benzoyl]amino]acetyl]amino]-propanoate (1a) tert-Butyl glycine hydrochloride (6.6 g, 50 mmol) was suspended in methylene chloride and metatrifluoromethyl benzoic acid (9.5 g, 50 mmol) was added, followed by N,N-diisopropylethylamine (17.5 mL, 100 mmol), EDC (10.2 g, 53 mmol), and DMAP (300 mg, 2.5 mmol). The reaction was stirred for 12 hrs at RT and partitioned between EtOAc and 1 N HCl. The organic phase was washed with brine, dried ($Na_2SO_4$), filtered, and concentrated in vacuo. The material was purified via flash chromatography to give tert-Butyl (3-trifluoromethylbenzoyl)glycine as a clear and colorless oil (12 g), which was dissolved in methylene chloride (40 mL), cooled to 0° C., and treated with trifluoroacetic acid (20 mL). The reaction was stirred for 3.5 hrs at RT and concentrated in vacuo. The material was redissolved in methylene chloride and concentrated again; this procedure was repeated three more times to give the desired carboxylic acid 1.2 (Z=—C(O)—, $R^2$=3-trifluoromethylphenyl, all other R=H; 8.9 g). $^1$H-NMR (300 MHz): δ 8.03 (s, 1H), 7.94 (d, 1H, J=7.7 Hz), 7.66 (d, 1H, J=7.7 Hz), 7.48 (t, 1H, J=7.9 Hz), 4.08 (s, 2H).

(1b) A solution of (S)-$N_\alpha$-Boc,$N_\beta$-Cbz-diaminopropionic acid DCHA salt (S)-2.1 (l=m=0; 5.07 g, 9.77 mmol) in methylene chloride was treated successively with EDC (1.96 g, 10.3 mmol) and methanol (0.79 mL, 19.5 mmol). The reaction was stirred at RT for 4 hrs and partitioned between EtOAc and 1 N hydrochloric acid. The aqueous phase was extracted with EtOAc (2×). The organic extracts were combined, washed with brine, dried ($Na_2SO_4$), filtered, and concentrated in vacuo. The material was purifed by flash chromatography to give the desired ester (S)-2.2 (l=m=0; 1.86 g). MS found: $(M+Na)^+$=375.2.

(1c) The ester (S)-2.2 (l=m=0) was dissolved in methylene chloride (40 mL), treated with trifluoroacetic acid (20 mL), and stirred at room temperature for 1.5 hrs before being concentrated in vacuo. The material was redissolved in methylene chloride and concentrated again; this procedure was repeated three more times to give the desired amine (quantitative). A solution of the amine (5.28 mmol) in methylene chloride was charged with carboxylic acid 1.2 (Z=—C(O)—, $R^2$=3-trifluoromethylphenyl, all other R=H; 5.6 mmol), BOP (2.5 g, 5.7 mmol), and N,N-diisopropylethylamine (2.1 mL, 12 mmol). The reaction was stirred at RT for 12 hrs and partitioned between EtOAc and sat. $NaHCO_3$. The organic extracts were washed with brine, dried ($Na_2SO_4$), filtered, and concentrated in vacuo. The material was purifed by flash chromatography to give the desired amide (S)-1.3 (l=m=0, PGN=CbzHN, $R^3$=$CO_2$Me, Z=—C(O)—, $R^2$=3-trifluoromethylphenyl, all other R=H; 2.01 g). MS found: $(M+Na)^+$=504.2.

(1d) A solution of the amide (S)-1.3 (PGN=CbzHN, l=m=0, $R^3$=$CO_2$Me, Z=—C(O)—, $R^2$=3-trifluoromethylphenyl, all other R=H; 0.25 g, 0.53 mmol) in methanol was charged with 5% Pd/C, Degussa type (ca. 0.1 g). The vessel was purged with hydrogen and stirred under 1 atm of hydrogen for 7 hrs before being filtered and concentrated in vacuo. This material was dissolved in methanol and treated with 2,4-dimethylbenzaldehyde (0.09 mL) and sodium cyanoborohydride (40 mg). The reaction was stirred for 12 hrs at RT and quenched with sat. $NaHCO_3$. The resultant mixture was extracted with EtOAc (2×). The organic extracts were combined, washed with brine, dried ($Na_2SO_4$), filtered, and concentrated in vacuo. The material was purifed by flash chromatography to give one pure fraction of the title compound (S)-1.5 (l=m=0, $R^1$=2,4-dimethylphenyl, $R^3$=$CO_2$Me, Z=—C(O)—, $R^2$=3-trifluoromethylphenyl, all other R=H; 20 mg). MS found: $(M+H)^+$=466.3.

Example 2

Methyl (2R)-3-[[(2,4-dimethylphenyl)methyl]amino]-2-[[[[3-(trifluoromethyl)benzoyl]amino]acetyl]amino]-propanoate (2a) (R)-$N_\alpha$-Boc,$N_\beta$-Cbz-diaminopropionic acid DCHA salt (R)-2.1 (l=m=0; 2.6 g, 5.07 mmol) was incorporated into the above procedure (1b) to give (R)-2.2 (l=m=0; 0.82 g), which was subsequently incorporated into procedures (1c) & (1d). Purification by RP-HPLC provided the title compound (R)-1.5 (l=m=0, $R^1$=2,4-dimethylphenyl, $R^3$=$CO_2$Me, Z=—C(O)—, $R^2$=3-trifluoromethylphenyl, all other R=H; 85 mg). MS found: $(M+H)^+$=466.3.

Example 3

(2S)-3-[[(2,4-dimethylphenyl)methyl]amino]-2-[[[[3-(trifluoromethyl)benzoyl]amino]acetyl]amino]-propanoic acid (3a) To a solution of ester (S)-1.5 (l=m=0, $R^1$=2,4-dimethylphenyl, $R^3$=$CO_2$Me, Z=—C(O)—, $R^2$=3-trifluoromethylphenyl, all other R=H; 40 mg) in 2:2:1 THF:MeOH:$H_2O$ was added LiOH (ca. 40 mg). The reaction was stirred at RT for 12 hrs, quenched with 1 N HCl and extracted with EtOAc (3×). The organic extracts were combined, washed with brine, dried ($MgSO_4$), filtered, and concentrated in vacuo. The material was purifed by reverse phase HPLC to give the desired acid (S)-16.2 ($R^1$=2,4-dimethylphenyl, Z=—C(O)—, $R^2$=3-trifluoromethylphenyl, all other R=H; 29 mg). MS found: $(M+H)^+$=452.3.

Example 4

(2S)-N-Methyl-3-[[(2,4-dimethylphenyl)methyl]amino]-2-[[[[3-(trifluoromethyl)benzoyl]amino]acetyl]amino]-propanamide (4a) To a solution of acid (S)-16.2 ($R^1$=2,4-dimethylphenyl, $R^2$=3-trifluoromethylphenyl, all other R=H; 24 mg, 0.04 mmol) in 4:1 methylene chloride/DMF was added methylamine hydrochloride (14 mg, 0.21 mmol), N,N-diisopropylethylamine (0.05 mL, 0.29 mmol), and HATU (19 mg, 0.05 mmol). The reaction was stirred for 12 hrs at RT and then filtered and concentrated in vacuo. The material was purified by reverse phase HPLC to give the desired amide (S)-16.3 ($R^1$=2,4-dimethylphenyl, —C(O)N($R^{3a}$)$_2$=—C(O)NHMe, Z=—C(O)—, $R^2$=3-trifluoromethylphenyl, all other R=H; 12 mg). Exact MS calcd for $C_{23}H_{28}F_3N_4O_3$, the formula for $(M+H)^+$= 465.2113. Found: 465.2114.

Example 5

(2S)-3-[[(2,4-dimethylphenyl)methyl]amino]-2-[[[[3-(trifluoromethyl)benzoyl]amino]acetyl]amino]-propanamide (5a) Ammonia (22 μL of a 2.0 M solution) was incorporated into the above procedure (4a) to give the title amide (S)-16.3 ($R^1$=2,4-dimethylphenyl, =C(O)N($R^{3a}$)$_2$=—C(O)NH$_2$, Z=—C(O)—, $R^2$=3-trifluoromethylphenyl, all other R=H; 5.0 mg). Exact MS calcd for $C_{22}H_{26}F_3N_4O_3$, the formula for $(M+H)^+$=451.1957. Found: 451.1958.

Example 6

(2R)-3-[[(2,4-dimethylphenyl)methyl]amino]-2-[[[[3-(trifluoromethyl)benzoyl]amino]acetyl]amino]-propanamide (6a) (S)-1.5 (l=m=0, $R^1$=2,4-dimethylphenyl, $R^2$=3-trifluoromethylphenyl, all other R=H; 60 mg) was incorporated into the above procedure (3a) to give (R)-16.2 ($R^1$= 2,4-dimethylphenyl, Z=—C(O)—, $R^2$=3-trifluoromethylphenyl, all other R=H; 55 mg). MS found: $(M+H)^+$=452.3.

(6b) Ammonia (0.23 mL of a 2.0 M solution) and (R)-16.2 ($R^1$=2,4-dimethylphenyl, $R^2$=3-trifluoromethylphenyl, all other R=H; 52 mg) were incorporated into the above procedure (4a) to give the title amide (R)-16.3 ($R^1$=2,4-dimethylphenyl, —C(O)N($R^{3a}$)$_2$=—C(O)NH$_2$, Z=—C(O)—, $R^2$=3-trifluoromethylphenyl, all other R=H; 24 mg). Exact MS calcd for $C_{22}H_{26}F_3N_4O_3$, the formula for (M+H)$^+$=451.1957. Found: 451.1967.

Example 7

(2S)-N-Ethyl-3-[[(2,4-dimethylphenyl)methyl]amino]-2-[[[[3-(trifluoromethyl)benzoyl]amino]acetyl]amino]-propanamide (7a) Ethylamine (22 μL of a 2.0 M solution) was incorporated into the above procedure (4a) to give the title amide (S)-16.3 ($R^1$=2,4-dimethylphenyl, —C(O)N($R^{3a}$)$_2$=—C(O)NHEt, Z=—C(O)—, $R^2$=3-trifluoromethylphenyl, all other R=H; 5.5 mg). Exact MS calcd for $C_{24}H_{30}F_3N_4O_3$, the formula for (M+H)$^+$=479.2270. Found: 479.2266.

Example 8

(2S)-N-Benzyl-3-[[(2,4-dimethylphenyl)methyl]amino]-2-[[[[3-(trifluoromethyl)benzoyl]amino]acetyl]amino]-propanamide (8a) Benzyl amine (4.8 μL) was incorporated into the above procedure (4a) to give the title amide (S)-16.3 ($R^1$=2,4-dimethylphenyl, —C(O)N($R^{3a}$)$_2$=—C(O)NHBn, Z=—C(O)—, $R^2$=3-trifluoromethylphenyl, all other R=H; 4.5 mg). Exact MS calcd for $C_{29}H_{32}F_3N_4O_3$, the formula for (M+H)$^+$=541.2427. Found: 541.2431.

Example 9

(2S)-N-Isopropyl-3-[[(2,4-dimethylphenyl)methyl]amino]-2-[[[[3-(trifluoromethyl)benzoyl]amino]acetyl]amino]-propanamide (9a) Isopropylamine (3.8 μL) was incorporated into the above procedure (4a) to give the title amide (S)-16.3 ($R^1$=2,4-dimethylphenyl, —C(O)N($R^{3a}$)$_2$=—C(O)NHi-Pr, Z=—C(O)—, $R^2$=3-trifluoromethylphenyl, all other R=H; 2.0 mg). Exact MS calcd for $C_{25}H_{32}F_3N_4O_3$, the formula for (M+H)$^+$=493.2427. Found: 493.2450.

Example 10

(2S)-N-tert-Butyl-3-[[(2,4-dimethylphenyl)methyl]amino]-2-[[[[3-(trifluoromethyl)benzoyl]amino]acetyl]amino]-propanamide (10a) tert-Butylamine (40 μL) was incorporated into the above procedure (4a) to give the title amide (S)-16.3 ($R^1$=2,4-dimethylphenyl, —C(O)N($R^{3a}$)$_2$=—C(O)NHt-Bu, Z=—C(O)—, $R^2$=3-trifluoromethylphenyl, all other R=H; 10 mg). Exact MS calcd for $C_{26}H_{34}F_3N_4O_3$, the formula for (M+H)$^+$=507.2583. Found: 507.2577.

Example 11

(2S)-N-Cyclopropyl-3-[[(2,4-dimethylphenyl)methyl]amino]-2-[[[[3-(trifluoromethyl)benzoyl]amino]acetyl]amino]-propanamide (11a) Cyclopropylamine (40 μL) was incorporated into the above procedure (4a) to give the title amide (S)-16.3 ($R^1$=2,4-dimethylphenyl, —C(O)N($R^{3a}$)$_2$=—C(O)NHc-Pr, Z=—C(O)—, $R^2$=3-trifluoromethylphenyl, all other R=H; 5 mg). Exact MS calcd for $C_{25}H_{30}F_3N_4O_3$, the formula for (M+H)$^+$=491.2270. Found: 491.2260.

Example 12

(2S)-N-Cyclobutyl-3-[[(2,4-dimethylphenyl)methyl]amino]-2-[[[[3-(trifluoromethyl)benzoyl]amino]acetyl]amino]-propanamide (12a) Cyclobutylamine (50 μL) was incorporated into the above procedure (4a) to give the title amide (S)-16.3 ($R^1$=2,4-dimethylphenyl, —C(O)N($R^{3a}$)$_2$=—C(O)NHc-Bu, Z=—C(O)—, $R^2$=3-trifluoromethylphenyl, all other R=H; 20 mg). Exact MS calcd for $C_{26}H_{32}F_3N_4O_3$, the formula for (M+H)$^+$=505.2427. Found: 505.2430.

Example 13

(2S)-N-Phenyl-3-[[(2,4-dimethylphenyl)methyl]amino]-2-[[[[3-(trifluoromethyl)benzoyl]amino]acetyl]amino]-propanamide (13a) Aniline (4.0 μL) was incorporated into the above procedure (4a) to give the title amide (S)-16.3 ($R^1$=2,4-dimethyiphenyl, C(O)N($R^{3a}$)$_2$=—C(O)NHPh, Z=—C(O)—, $R^2$=3-trifluoromethylphenyl, all other R=H; 1.3 mg). MS found: (M+H)$^+$=527.3.

Example 14

(2S)-N,N-Dimethyl-3-[[(2,4-dimethylphenyl)methyl]amino]-2-[[[[3-(trifluoromethyl)benzoyl]amino]acetyl]amino]-propanamide (14a) N,N-Dimethyl amine (18.0 mg of the hydrochloride salt) was incorporated into the above procedure (4a) to give the title amide (S)-16.3 ($R^1$=2,4-dimethylphenyl, —C(O)N($R^{3a}$)$_2$=—C(O)NMe$_2$, Z=—C(O)—, $R^2$=3-trifluoromethylphenyl, all other R=H; 5 mg). Exact MS calcd for $C_{24}H_{30}F_3N_4O_3$, the formula for (M+H)$^+$=479.2270. Found: 479.2267.

Example 15

(2S)-N-Methyl,N-methoxy-3-[[(2,4-dimethylphenyl)methyl]amino]-2-[[[[3-(trifluoromethyl)benzoyl]aminoacetyl]amino]-propanamide (15a) N,O-Dimethylhydroxylamine (17.5 mg of the hydrochloride salt) was incorporated into the above procedure (4a) to give the title amide (S)-16.3 ($R^1$=2,4-dimethylphenyl, —C(O)N($R^{3a}$)$_2$=—C(O)N(OMe)Me, Z=—C(O)—, $R^2$=3-trifluoromethylphenyl, all other R=H; 20 mg). Exact MS calcd for $C_{24}H_{30}F_3N_4O_4$, the formula for (M+H)$^+$=495.2219. Found: 495.2230.

Example 16

Methyl (2S)-3-[[(4-chlorophenyl)methyl]amino]-2-[[[[3-(trifluoromethyl)benzoyl]amino]acetyl]amino]-propanoate (16a) para-Chlorobenzaldehyde (71 mg, 0.51 mmol) was incorporated into the above procedure (1d) to give the title ester (S)-1.5 (l=m=0, $R^1$=4-chlorophenyl, $R^3$=$CO_2$Me, Z=—C(O)—, $R^2$=3-trifluoromethylphenyl, all other R=H; 59 mg). Exact MS calcd for $C_{21}H_{22}F_3Cl_1N_3O_4$, the formula for (M+H)$^+$=472.1251. Found: 472.1239.

Example 17

(2S)-3-[[(4-chlorophenyl)methyl]amino]-2-[[[[3-(trifluoromethyl)benzoyl]amino]acetyl]amino]-propanamide (17a) (S)-1.5 (l=m=0, $R^1$=4-chlorophenyl, $R^3$=$CO_2$Me, Z=—C(O)—, $R^2$=3-trifluoromethylphenyl, all other R=H;

51 mg, 0.09 mmol) was incorporated into the above procedure (3a) to give the crude carboxylic acid (S)-16.2 ($R^1$=4-chlorophenyl, Z=—C(O)—, $R^2$=3-trifluoromethylphenyl, all other R=H; 47 mg). This material was not characterized, but rather taken directly into procedures (17b) and (18a).

(17b) Ammonia (0.2 mL of a 2.0 M solution) and (S)-16.2 ($R^1$=4-chlorophenyl, Z=—C(O)—, $R^2$=3-trifluoromethylphenyl, all other R=H; 23 mg) were incorporated into the above procedure (4a) to give the title amide (S)-16.3 ($R^1$=4-chlorophenyl, —C(O)N($R^{3a}$)$_2$=—C(O)NH$_2$, Z=—C(O)—, $R^2$=3-trifluoromethylphenyl, all other R=H; 6.5 mg). Exact MS calcd for $C_{20}H_{21}Cl_1F_3N_4O_3$, the formula for (M+H)$^+$=457.1254. Found: 457.1257.

Example 18

(2S)-N-Ethyl-3-[[(4-chlorophenyl)methyl]amino]-2-[[[[3-(trifluoromethyl)benzoyl]amino]acetyl]amino]-propanamide (18a) Ethylamine (0.18 mL of a 2.0 M solution) and (S)-16.2 (R1=4-chlorophenyl, R2=3-trifluoromethylphenyl, all other R=H; 23 mg) were incorporated into the above procedure (4a) to give the title amide (S)-16.3 ($R^1$=4-chlorophenyl, —C(O)N($R^{3a}$)$_2$=—C(O)NHEt, Z=—C(O)—, $R^2$=3-trifluoromethylphenyl, all other R=H; 7.0 mg). Exact MS calcd for $C_{22}H_{25}Cl_1F_3N_4O_3$, the formula for (M+H)$^+$=485.1567. Found: 485.1577.

Example 19

Methyl (2S)-3-[[(1S/R)-1-(4-chlorophenyl)ethyl]amino]-2-[[[[3-(trifluoromethyl)benzoyl]amino]acetyl]amino]-propanoate (19a) The free amine (212 mg, 0.61 mmol) derived from the hydrogenation of (S)-1.3 (l=m=0, $R^3$=CO$_2$Me, Z=—C(O)—, $R^2$=3-trifluoromethylphenyl, all other R=H; cf. procedure (1d) above) was combined with THF (6 mL), glacial acetic acid (0.12 mL), para-chloroacetophenone (142 mg, 0.92 mmol), and sodium triacetoxyborohydride (390 mg, 1.83 mmol). The reaction was stirred for 20 hrs at RT and quenched with sat. NaHCO$_3$. The resultant mixture was extracted with EtOAc (1×). The organic extracts were washed with brine, dried (Na$_2$SO$_4$), filtered, and concentrated in vacuo. The material was purifed by HPLC to give the title ester (1'S/R, 2S)-1.5 (l=m=0, $R^1$=4-chlorophenyl, $R^{16}$=methyl, $R^3$=CO$_2$Me, Z=—C(O)—, $R^2$=3-trifluoromethylphenyl, all other R=H; 54 mg). Exact MS calcd for $C_{22}H_{24}Cl_1F_3N_3O_4$, the formula for (M+H)$^+$=486.1407. Found: 486.1406.

Example 20

Methyl (2S)-3-[[(1S/R)-1-(2,4-dimethylphenyl)ethyl]amino]-2-[[[[3-(trifluoromethyl)benzoyl]amino]acetyl]amino]-propanoate (20a) The free amine (323 mg, 0.93 mmol) derived from the hydrogenation of (S)-1.3 (l=m=0, $R^3$=CO$_2$Me, Z=—C(O)—, $R^2$=3-trifluoromethylphenyl, all other R=H; cf. procedure (1d) above was dissolved in THF (2.0 mL), and the resultant solution was charged sequentially with 2,4-dimethylacetophenone (0.2 mL, 1.35 mmol), powdered 4 Å molecular sieves (202 mg), and glacial acetic acid (0.13 mL). The reaction was stirred at room temperature for 30 minutes before being treated with sodium triacetoxyborohydride (527 mg, 2.5 mmol). The reaction was stirred for 30 h at room temperature before being quenched with NaHCO3. The resultant mixture was extracted with EtOAc (2×), and the organic extracts were washed with water (1×), washed with brine (1×), dried (MgSO$_4$), filtered, and concentrated in vacuo. The material was purifed by HPLC to give the title ester (1'S/R, 2S)-1.5 (l=m=0, $R^1$=2,4-dimethylphenyl, $R^{16}$=methyl, $R^3$=CO$_2$Me, Z=—C(O)—, $R^2$=3-trifluoromethylphenyl, all other R=H; 30 mg). Exact MS calcd for $C_{24}H_{29}F_3N_3O_4$, the formula for (M+H)$^+$=480.2110. Found: 480.2117.

Example 21

Methyl (2S)-3-[(1H-indol-3-ylmethyl)amino]-2-[[[[3-(trifluoromethyl)benzoyl]amino]acetyl]amino]-propanoate (21a) Indole-3-carboxaldehyde (43 mg, 0.296 mmol) was incorporated into the above procedure (1d) to give the title ester (S)-1.5 (l=m=0, $R^1$=1H-indol-3-yl, $R^3$=CO$_2$Me, Z=—C(O)—, $R^2$=3-trifluoromethylphenyl, all other R=H; 35 mg). $^1$H-NMR (300 MHz, CD$_3$OD): δ 8.18 (s, 1H), 8.07 (d, 1H, J=7.8 Hz), 7.88 (d, 1H, J=8.1 Hz), 7.74–7.63 (m, 2H), 7.51–7.05 (m, 5H), 4.97 (dd, 1H, J=9.2, 4.4 Hz), 4.57 (d, 1H, J=14 Hz), 4.49 (d, 1H, J=14 Hz), 4.11 (d, 1H, J=17 Hz), 4.05 (d, 1H, J=17 Hz), 3.76 (s, 3H), 3.64 (dd, 1H, J=13, 4.8 Hz), 3.37 (dd, 1H, J=13, 9.1 Hz).

Example 22

(2S)-3-[(1H-indol-3-ylmethyl)amino]-2-[[[[3-(trifluoromethyl)benzoyl]amino]acetyl]amino]-propanamide (22a) (S)-1.5 (l=m=0, $R^1$=1H-indol-3-yl, $R^3$=CO$_2$Me, Z=—C(O)—, $R^2$=3-trifluoromethylphenyl, all other R=H; 33 mg) was incorporated into the above procedure (3a) to give (S)-16.2 ($R^1$=1H-indol-3-yl, Z=—C(O)—, $R^2$=3-trifluoromethylphenyl, all other R=H; 15 mg). MS found: (M+Na)$^+$=494.2.

(22b) Ammonia (0.1 mL of a 2.0 M solution) and (S)-16.2 ($R^1$=1H-indol-3-yl, Z=—C(O)—, $R^2$=3-trifluoromethylphenyl, all other R=H; 10.6 mg) were incorporated into the above procedure (4a) to give the title amide (S)-16.3 ($R^1$=1H-indol-3-yl, —C(O)N($R^{3a}$)$_2$=—C(O)NH$_2$, Z=—C(O)—, $R^2$=3-trifluoromethylphenyl, all other R=H; 0.5 mg). MS found: (M+H)$^+$=462.2.

Example 23

Methyl (2S)-3-[(1,3-benzodioxol-5-ylmethyl)amino]-2-[[[[3-(trifluoromethyl)benzoyl]amino]acetyl]amino]-propanoate (23a) Piperonal (46 mg, 0.31 mmol) was incorporated into the above procedure (1d) to give the title ester (S)-1.5 (l=m=0, $R^1$=1,3-benzodioxol-5-yl, $R^3$=CO$_2$Me, Z=—C(O)—, $R^2$=3-trifluoromethylphenyl, all other R=H; 25 mg). Exact MS calcd for $C_{22}H_{23}F_3N_3O_6$, the formula for (M+H)$^+$=482.1539. Found: 482.1537.

Example 24

Methyl (2S)-3-[[(4-bromophenyl)methyl]amino]-2-[[[[3-(trifluoromethyl)benzoyl]amino]acetyl]amino]-propanoate (24a) para-Bromobenzaldehyde (59 mg, 0.32 mmol) was incorporated into the above procedure (1d) to give the title ester (S)-1.5 (l=m=0, $R^1$=4-bromophenyl, $R^3$=CO$_2$Me, Z=—C(O)—, $R^2$=3-trifluoromethylphenyl, all other R=H;

40 mg). Exact MS calcd for $C_{21}H_{22}F_3Br_1N_3O_4$, the formula for $(M+H)^+=516.0746$. Found: 516.0756.

Example 25

Methyl (2S)-2-[[[[2-[[(1,1-dimethylethoxy)carbonyl]amino]-5-(trifluoromethyl)benzoyl]amino]acetyl]amino]-3-[[(2,4-dimethylphenyl)methyl]amino]-propanoate (25a) A solution of the ester (S)-2.2 (l=m=0; 2.25 g, 6.39 mmol; cf. Example 1) in dioxane (32 mL) was treated with 4 N HCl/dioxane (32 mL) and stirred for 12 h at room temperature before being concentrated in vacuo. The residue was dissolved in chloroform and concentrated in vacuo; this procedure was repeated twice more to give the amine (1.42). MS found: $(M+H)^+=253.3$. A solution of the amine (6.3 mmol) in 4:1 methylene chloride/DMF (55 mL) was charged with N-Boc glycine (1.1 g, 6.2 mmol), BOP (2.7 g, 6.2 mmol), and N,N-diisopropylethylamine (2.9 mL, 17 mmol). The reaction was stirred at RT for 12 hrs and partitioned between EtOAc and sat. $NaHCO_3$. The organic extracts were washed with brine, dried ($Na_2SO_4$), filtered, and concentrated in vacuo. The material was purifed by flash chromatography to give the desired amide (S)-1.6 (l=m=0, $R^3=CO_2Me$, all other R=H; 1.75 g). MS found: $(M+Na)^+=432.1$.

(25b) To a solution of the carbamate (S)-1.6 (l=m=0, $R^3=CO_2Me$, all other R=H; 1.14 g) in methylene chloride (20 mL) was added TFA (5 mL). The reaction was stirred for 3 h at room temperature and concentrated in vacuo. The residue was dissolved in benzene and the solution was concentrated in vacuo; this was repeated twice to give the desired amine (806 mg). MS found: $(M+H)^+=310.2$. A solution of the amine (140 mg, 0.46 mmol) in 5:1 methylene chloride/DMF (6 mL) was charged with N-Boc-2-amino-5-(trifluoromethyl)benzoic acid (S. Takagishi, et al., *Synlett* 1992, 360; 156 mg, 0.51 mmol), BOP (223 mg, 0.51 mmol), and N,N-diisopropylethylamine (0.2 mL, 1.1 mmol). The reaction was stirred at RT for 12 hrs and partitioned between EtOAc and sat. $NaHCO_3$. The organic extracts were washed with brine, dried ($Na_2SO_4$), filtered, and concentrated in vacuo. The material was purifed by flash chromatography to give the desired amide (S)-1.3 (l=m=0, PGN=CbzHN, $R^3=CO_2Me$, Z=—C(O)—, $R^2$=N-Boc-2-amino-5-(trifluoromethyl)phenyl, all other R=H; 78 mg). MS found: $(M+Na)^+=619.2$.

(25c) The amide (S)-1.3 (l=m=0, PGN=CbzHN, $R^3=CO_2Me$, Z=—C(O)—, $R^2$=N-Boc-2-amino-5-(trifluoromethyl)phenyl, all other R=H; 78 mg) was incorporated into the above procedure (1d) to afford the title compound (S)-1.5 (l=m=0, $R^1$=2,4-dimethylphenyl, $R^3=CO_2Me$, Z=—C(O)—, $R^2$=N-Boc-2-amino-5-(trifluoromethyl)phenyl, all other R=H; 62 mg). MS Found: $(M+H)^+=581.3$.

Example 26

Methyl (2S)-2-[[[[2-amino-5-(trifluoromethyl)benzoyl]amino]acetyl]amino]-3-[[(2,4-dimethylphenyl)methyl]amino]-propanoate (26a) To a solution of the carbamate (S)-1.5 (l=m=0, $R^1$=2,4-dimethylphenyl, $R^3=CO_2Me$, Z=—C(O)—, $R^2$=N-Boc-2-amino-5-(trifluoromethyl)phenyl, all other R=H; 20 mg) in methylene chloride (20 mL) was added TFA (5 mL). The reaction was stirred for 3 h at room temperature and concentrated in vacuo. The residue was dissolved in benzene and the solution was concentrated in vacuo; this was repeated twice. The residue was purified by reverse phase HPLC to give the title compound (S)-1.5 (l=m=0, $R^1$=2,4-dimethylphenyl, $R^3=CO_2Me$, Z=—C(O)—, $R^2$=2-amino-5-(trifluoromethyl)phenyl, all other R=H; 7.1 mg). MS found: $(M+H)^+=481.2$.

Example 27

(2S)-2-[[[[2-amino-5-(trifluoromethyl)benzoyl]amino]acetyl]amino]-3-[[(2,4-dimethylphenyl)methyl]amino]-propanamide (27a) Using an Applied Biosystems 431A peptide synthesizer setup for the FastMOC protocol (piperidine deprotection cycles, HBTU/HOBT/DIEA coupling cycles, NMP as solvent), Fmoc-PAL resin (PE Biosystems, 0.39 mmol/gram; 0.64 g, 0.25 mmol), (S)-$N_\alpha$-Fmoc, $N_\beta$-Alloc-diaminopropionic acid (0.41 g, 1.0 mmol), $N_\alpha$-Fmoc glycine (0.28 g, 1.0 mmol), and N-Boc-2-amino-5-(trifluoromethyl)benzoic acid (S. Takagishi, et al., *Synlett* 1992, 360; 0.25, 1.0 mmol) were combined to provide resin bound (S)-21.6 (l=m=0, $R^2$=N-Boc-2-amino-5-(trifluoromethyl)phenyl, all other R=H; 600 mg).

(27b) The resin (S)-21.6 (l=m=0, $R^2$=2-amino-5-(trifluoromethyl)phenyl, all other R=H; 0.21 g) was loaded into a fritted peptide synthesis vessel and swelled in 37:2:1 $CHCl_3$/AcOH/N-methyl morpholine (2 mL). The suspension was charged with a solution of $Pd(PPh_3)_3$ (150 mg) in 37:2:1 $CHCl_3$/AcOH/N-methyl morpholine (2 mL), agitated for 2 h at room temperature, and then drained in vacuo. The remaining resin was washed consecutively with 0.5% N,N-diisopropylethylamine/DMF (4 mL), 0.5% sodium diethyldithiocarbamate/DMF (4 mL), methanol (4 mL), methylene chloride (4 mL), methanol (4 mL), and methylene chloride (4 mL) to provide the resin-bound free amine. This resin tested positive in the ninhydrin free amine test. The entirety of the remaining resin was suspended in 1% AcOH/dimethylacetamide (4 mL); the resulting suspension was charged with 2,4-dimethylbenzaldehyde (50 μL) and agitated for 15 min. The suspension was treated with sodium cyanoborohydride (ca. 20 mg) and agitated for 12 h at room temperature. The solution was drained in vacuo and the resin was resuspended in 1% AcOH/dimethylacetamide (4 mL). The suspension was treated with sodium cyanoborohydride (ca. 20 mg) and agitated for 3 h at room temperature. The solution was drained in vacuo and the resin was washed with methanol (4 mL), methylene chloride (4 mL), methanol (4 mL), and methylene chloride (4 mL) to provide the resin-bound benzylamine. The entirety of this resin was suspended in 95:5 TFA/$H_2O$ (3 mL), and the resulting suspension was charged with triethylsilane (50 μL) and agitated for 2 h at room temperature. The solution was drained in vacuo, and the resin was washed with TFA (2 mL) and methylene chloride (2×5 mL). The filtrate was concentrated in vacuo. The residue was dissolved in methylene chloride and the resulting solution was concentrated in vacuo; this procedure was repeated. The residue was purified by reverse phase HPLC to afford the title compound (S)-21.8 (l=m=0, $R^1$=2,4-dimethylphenyl, $R^2$=2-amino-5-(trifluoromethyl)phenyl, all other R=H; 1.3 mg). MS Found: $(M+H)^+=466.3$.

Example 28

N-[2-[[(1S)-2-[[(2,4-dimethylphenyl)methyl]amino]-1-(hydroxymethyl)ethyl]amino]-2-oxoethyl]-3-(trifluoromethyl)benzamide (28a) To a solution of the ester (S)-1.5 (l=m=0, $R^1$=2,4-dimethylphenyl, $R^3=CO_2Me$, Z=—C(O)—, $R^2$=3- trifluoromethylphenyl, all other R=H; 15 mg) in methanol was added sodium borohydride (ca. 3 equivs). The reaction was stirred for 12 hrs at RT, quenched with sat. NaHCO$_3$, and extracted with EtOAc (2×). The organic extracts were combined, washed with brine, dried (Na$_2$SO$_4$), filtered, and concentrated in vacuo to give the title compound (S)-16.4 (R$^1$=2,4-dimethylphenyl, Z=—C(O)—, R$^2$=3-trifluoromethylphenyl, all other R=H; 12 mg). MS found: (M+H)$^+$=438.3.

Example 29

N-[2-[[(1R)-2-[[(2,4-dimethylphenyl)methyl]amino]-1-(hydroxymethyl)ethyl]amino]-2-oxoethyl]-3-(trifluoromethyl)benzamide (29a) (R)-1.5 (l=m=0, R$^1$=2,4-dimethylphenyl, R$^3$=CO$_2$Me, Z=—C(O)—, R$^2$=3-trifluoromethylphenyl, all other R=H; 24 mg) was incorporated into the above procedure (28a) to give the title compound (R)-16.4 (R$^1$=2,4-dimethylphenyl, Z=—C(O)—, R$^2$=3-trifluoromethylphenyl, all other R=H; 3.2 mg). MS found: (M+H)$^+$=438.2.

Example 30

N-[2-[[(1S, 2S/R)-1-[[[(2,4-dimethylphenyl)methyl]amino]methyl]-2-hydroxypropyl]amino]-2-oxoethyl]-3-(trifluoromethyl)benzamide (30a) To a solution of (S)-N$_\alpha$-Boc, N$_\beta$-Cbz-diaminopropionic acid DCHA salt (1.13 g, 2.17 mmol) in CH$_2$Cl$_2$ (50 mL) was added N,N-diisopropylethylamine (1.0 mL, 5.4 mmol), N,O-dimethylhydroxylamine hydrochloride (222 mg, 2.3 mmol), and HATU (866 mg, 2.3 mmol). The reaction was stirred for 12 h at room temperature and partitioned between EtOAc and sat. NH$_4$Cl. The aqueous phase was back-extracted with EtOAc (2×). The organic extracts were combined, washed with sat. NaHCO$_3$ (1×), washed with brine (1×), dried (MgSO$_4$), filtered, and concentrated in vacuo. The residue was purified via flash chromatography to afford (S)-11.2 (l=m=0, PGN=CbzHN, all other R=H; 840 mg).

(30b) The Weinreb amide (S)-11.2 (l=m=0, PGN=CbzHN, all other R=H; 310 mg) was dissolved in THF (8 mL), and the resulting solution was cooled to 0° C. and charged with methyl magnesium bromide (2.2 mL of a 3.0 M solution). The reaction was stirred at room temperature for 2.5 h before being recooled to 0° C. and quenched with the slow addition of sat. NH$_4$Cl. The mixture was partitioned between EtOAc and half-sat. NH$_4$Cl, and the organic phase was washed with brine (1×), dried (MgSO$_4$), filtered, and concentrated in vacuo to provide the methyl ketone (S)-11.3 (l=m=0, PGN=CbzHN, R=methyl, all other R=H; 248 mg).

(30c) The methyl ketone (S)-11.3 (l=m=0, PGN=CbzHN, R=methyl, all other R=H; 248 mg) was dissolved in THF (8 mL), and the resultant solution was charged with EtOH (6 mL), cooled to 0° C., and treated with sodium borohydride (56 mg). The reaction was stirred at room temperature for 2 h and quenched successively with acetone and sat. NH$_4$Cl. The mixture was partitioned between EtOAc and half-sat. NH$_4$Cl, and the organic phase was washed with brine (1×), dried (MgSO$_4$), filtered, and concentrated in vacuo to provide the alcohol (2S, 3S/R)-11.5 (l=m=0, PGN=CbzHN, R=methyl, all other R=H; 227 mg).

(30d) The alcohol (2S, 3S/R)-11.5 (l=m=0, PGN=CbzHN, R=methyl, all other R=H; 227 mg) was incorporated into the procedures (1c) and (1d) to provide the title compound (1S, 2S/R)-1.5 (l=m=0, R$^1$=2,4-dimethylphenyl, R$^3$=—CH(OH)CH$_3$, Z=—C(O)—, R$^2$=3-(trifluoromethyl)phenyl, all other R=H; 5 mg). Exact MS calculated for C$_{23}$H$_{29}$F$_3$N$_3$O$_3$, the formula for (M+H)$^+$=452.2161. Found 452.2167.

Example 31 tert-Butyl (3R)-4-[[(2,4-dimethylphenyl)methyl]amino]-3-[[[[3-(trifluoromethyl)benzoyl]amino]acetyl]amino]-butanoate (31a) To a cooled (0° C.) suspension of D-Boc-Asp(OtBu)-OH (R)-2.4 (l=m=0, R$^3$=CH$_2$CO$_2$tBu; 2.04 g, 7.05 mmol) in EtOAc (28 mL) was added N-hydroxysuccinimide (974 mg, 8.5 mmol) and DCC (1.75 g, 8.5 mmol). The reaction was stirred for 2 h and then filtered. The filtrate was diluted with EtOAc and washed with sat. NaHCO$_3$ (1×) and brine (1×). The organic phase was dried (MgSO$_4$), filtered, and concentrated in vacuo. The product ester was dissolved in THF (12 mL), and the resultant solution was cooled to 0° C. and charged successively with sodium borohydride (293 mg, 7.8 mmol) and ethanol (3.0 mL). The reaction was stirred for 30 min at 0° C. and then quenched with sat. NH$_4$Cl. The mixture was extracted with EtOAc (2×), and the organic extracts were dried (MgSO$_4$), filtered, and concentrated in vacuo to provide the tert-butyl N$_\beta$-Boc (R)-3-amino-4-hydroxybutanoate (1.48 g), which was carried on to (31b) without further purification. A small sample could be purified by flash chromatography for characterization. $^1$H-NMR (300 MHz, CD$_3$OD): δ 3.96–3.92 (m, 1H), 3.51 (dd, 1H, J=11, 5.5 Hz), 3.42 (dd, 1H, J=11, 6.2 Hz), 2.53 (dd, 1H, J=15, 5.5 Hz), 2.30 (dd, 1H, J=15, 8.4 Hz), 1.45 (s, 9H), 1.43 (s, 9H).

(31b) To a cooled (0° C.) solution of the crude tert-butyl N$_\beta$-Boc (R)-3-amino-4-hydroxybutanoate (1.48 g, 5.38 mmol) in CH$_2$Cl$_2$ (75 mL) was added 2,6-lutidine (658 µL, 5.7 mmol) and methanesulfonic anhydride (1.25 g, 7.16 mmol). The reaction was stirred for 3 h at room temperature before being partitioned between EtOAc and sat. NH$_4$Cl. The organic phase was washed with brine, dried (Na$_2$SO$_4$), filtered, and concentrated in vacuo to give the mesylate (715 mg). A sample could be purified for characterization by flash chromatography. $^1$H-NMR (300 MHz, CDCl$_3$): δ 5.19 (d, 1H, J=8.4 Hz), 4.30 (d, 2H, J=5.1 Hz), 4.29–4.23 (m, 1H), 3.04 (s, 3H), 2.56 (d, 2H, J=5.8 Hz), 1.46 (s, 9H), 1.44 (s, 9H).

(31c) The mesylate (715 mg, 2.03 mmol) was dissolved in DMSO (38 mL), and the resultant solution was charged with sodium azide (660 mg, 10.1 mmol) and heated at 65° C. for 14 h. The reaction was filtered, absorbed onto silica gel, and eluted with 80% EtOAc/hexanes to give the azide (R)-2.5 (l=m=0, R=CH$_2$CO$_2$tBu; 562 mg). $^1$H-NMR (300 MHz, CDCl$_3$): δ 5.12 (bs, 1H), 4.10–4.05 (m, 1H), 3.55–3.39 (m, 2H), 2.49 (d, 5.9 Hz), 1.46 (s, 9H), 1.44 (s, 9H).

(31d) The carbamate (R)-2.5 (l=m=0, R$^3$=CH$_2$CO$_2$tBu; 562 mg) was charged with a solution of anhydrous HCl in EtOAc (prepared from 760 uL of MeOH and 1.33 mL of acetyl chloride in 19 mL of EtOAc), stirred for 12 h at room temperature, and concentrated in vacuo. The residue was diluted with EtOAc and washed with water (1×) and brine (1×). The organic phase was dried (Na$_2$SO$_4$), filtered, and concentrated in vacuo to give the amine (260 mg). This crude product was dissolved in CH$_2$Cl$_2$ (12 mL), and the resultant solution was charged successively with 1.2 (Z=—C(O)—, R$^2$=3-trifluoromethylphenyl; 321 mg, 1.3 mmol), N,N-diisopropylethylamine (453 mL, 2.6 mmol), and BOP (633 mg, 1.4 mmol). The reaction was stirred at room temperature for 14 h and then partitioned between EtOAc and 1N HCl. The organic phase was washed successively with water, sat. NaHCO$_3$, water, and brine. The organic phase was then dried (MgSO$_4$), filtered, and concentrated in vacuo to give (R)-1.3 (l=m=0, PGN=N$_3$, R$^3$=CH$_2$CO$_2$tBu, Z=—C(O)—, R$^2$=3-(trifluoromethyl)phenyl, all other R=H; 493 mg). MS found: (M+Na)$^+$=452.2.

(31e) The azide (R)-1.3 (l=m=0, PGN=N$_3$, R$^3$=CH$_2$CO$_2$tBu, Z=—C(O)—, R$^2$=3-(trifluoromethyl)phenyl, all other R=H; 493 mg) was incorporated into the above procedure (1d) to give 161 mg of pure product after flash chromatography. A small sample was removed and further purified by RP-HPLC to give the title compound (R)-1.5 (l=m=0, R$^1$=2,4-dimethylphenyl, R$^3$=CH$_2$CO$_2$tBu, Z=—C(O)—, R$^2$=3-(trifluoromethyl)phenyl, all other R=H). Exact MS calcd for C$_{27}$H$_{35}$F$_3$N$_3$O$_4$, the formula for (M+H)$^+$=522.2580. Found: 522.2575.

Example 32

N-[2-[[(1R)-2-[[(2,4-dimethylphenyl)methyl]amino]-1-(phenylmethyl)ethyl]amino]-2-oxoethyl]-3-(trifluoromethyl)benzamide (32a) D-N$_\alpha$-Boc phenylalanine (R)-2.4 (l=m=0, R$^3$=CH$_2$Ph; 2.65 g) was incorporated into the above procedure (31a), and the product alcohol (1.91 g) was carried on through procedures (31b)–(31e) to give the title compound (S)-1.5 (l=m=0, R$^1$=2,4-dimethylphenyl, R$^3$=CH$_2$Ph, Z=—C(O)—, R$^2$=3-(trifluoromethyl)phenyl, all other R=H; 2 mg). Exact MS calcd for C$_{28}$H$_{31}$F$_3$N$_3$O$_2$, the formula for (M+H)$^+$=498.2368. Found: 498.2370.

Example 33

(2S)-N-tert-Butyl-2-[[[[2-[[(1,1-dimethylethoxy)carbonyl]amino]-5-(trifluoromethyl)benzoyl]amino]acetyl]amino]-3-[[(2,4-dimethylphenyl)methyl]amino]-propanamide (33a) A solution of (S)-N$_\alpha$-Boc,N$_\beta$-Cbz-diaminopropionic acid DCHA salt (S)-2.1 (l=m=0; 5.01 g, 9.6 mmol) in 90 mL of 8:1 methylene chloride/DMF was treated successively with HATU (3.84 g, 10.1 mmol) and then tert-butyl amine (3.0 mL, 28.8 mmol). The reaction was stirred at RT for 14 hrs and partitioned between EtOAc and 1 N hydrochloric acid. The organic phase was washed with 5% NaHCO$_3$ and brine before being dried (MgSO$_4$), filtered, and concentrated in vacuo. The product was diluted with EtOAc, dried again (Na$_2$SO$_4$), filtered, and concentrated in vacuo to give the desired amide (S)-2.3 (l=m=0, C(O)N(R$^{3a}$)$_2$=—C(O)NHt-Bu; 7.7 g). MS found: (M+Na)$^+$=416.

(33b) The carbamate (S)-2.3 (l=m=0, —C(O)N(R$^{3a}$)$_2$=—C(O)NHt-Bu; 7.7 mmol) was dissolved in 90 mL of 2:1 methylene chloride/TFA and stirred at RT for 3 h before being concentrated in vacuo. The residue was dissolved in methylene chloride and concentrated in vacuo; this procedure was repeated twice more to give the amine (10 g). MS found: (M+H)$^+$=294.2. A solution of the amine (estimated as 9.6 mmol) in 6:1 methylene chloride/DMF (70 mL) was charged with N,N-diisopropylethylamine (9.0 mL, 48 mmol), N$_\alpha$-Boc glycine (1.86 g, 10.6 mmol), and BOP (4.7 g, 10.6 mmol). The reaction was stirred at RT for 3 days and diluted with EtOAc. The organic extracts were washed with sat. NH$_4$Cl (2×) and brine (1×), dried (Na$_2$SO$_4$), filtered, and concentrated in vacuo. The material was purifed by flash chromatography to give the desired amide (S)-1.6 (l=m=0, PGN=CbzHN, R$^3$=CONHt-Bu, all other R=H; 4.5 g). MS found: (M+Na)$^+$=473.2.

(33c) To a solution of the carbamate (S)-1.6 (l=m=0, PGN=CbzHN, R$^3$=CONHt-Bu, all other R=H; 0.53 g) in methylene chloride (10 mL) was added TFA (4 mL). The reaction was stirred for 3 h at RT and concentrated in vacuo. The residue was dissolved in methlyene chloride and the solution was concentrated in vacuo; this was repeated twice. The residue was dissolved in benzene and the solution was concentrated in vacuo; this was repeated twice. The residue was dissolved in methlyene chloride and the solution was concentrated in vacuo; this was repeated twice to give the desired amine. MS found: (M+H)$^+$=351.2. A solution of the amine (estimated 0.8 mmol) in methylene chloride (6 mL) was charged successively with N,N-diisopropylethylamine (0.9 mL, 5.2 mmol), a suspension of N-Boc-2-amino-5-(trifluoromethyl)benzoic acid (S. Takagishi, et al., *Synlett* 1992, 360; 233 mg, 0.76 mmol) in methylene chloride (4 mL; 2 mL DMF rinse), and HATU (320 mg, 0.84 mmol). The reaction was stirred at RT for 4.5 h and diluted with EtOAc. The organic phase was washed with sat. NH$_4$Cl (2×), 5% NaHCO$_3$ (1×), and brine (1×), before being dried (Na$_2$SO$_4$), filtered, and concentrated in vacuo to give the desired amide (S)-1.3 (l=m=0, PGN=CbzHN, R$^3$=CONHt-Bu, Z=—C(O)—, R$^2$=N-Boc-2-amino-5-(trifluoromethyl)phenyl, all other R=H; assumed quantitative). MS found: (M+H)$^+$=660.5.

(33d) A solution of the amide (S)-1.3 (l=m=0, PGN=CbzHN, R$^3$=CONHt-Bu, Z=—C(O)—, R$^2$=N-Boc-2-amino-5-(trifluoromethyl)phenyl, all other R=H; assumed 0.8 mmol) in MeOH (10 mL) was charged with 5% Pd/C, Degussa (100 mg). The reaction vessel was purged with hydrogen gas (2×) and stirred under hydrogen (1 atm) for 10 h before being filtered and concentrated in vacuo to give the amine (S)-1.4 (l=m=0, R$^3$=CONHt-Bu, Z=—C(O)—, R$^2$=N-Boc-2-amino-5-(trifluoromethyl)phenyl, all other R=H; assumed 0.8 mmol) as a light yellow oil. MS found: (M+H)$^+$=504.4

(33e) A solution of the amine (S)-1.4 (l=m=0, R$^3$=CONHt-Bu, Z=—C(O)—, R$^2$=N-Boc-2-amino-5-(trifluoromethyl)phenyl, all other R=H; assumed 0.35 mmol) in MeOH (4 mL) was charged with 2,4-dimethylbenzaldehyde (0.05 mL, 0.35 mmol) and stirred for 8 min at RT before being charged with sodium cyanoborohydride (44 mg, 0.70 mmol) and stirred for 4 h at RT. The reaction was quenched with the addition of sat. NaHCO$_3$ and then extracted with EtOAc (2×). The organic extracts were combined, washed with brine, dried (MgSO$_4$), filtered, and concentrated in vacuo. The crude product was purified by reverse-phase HPLC to afford the title compound (S)-1.5 (l=m=0, R$^1$=2,4-dimethylphenyl, R$^3$=CONHt-Bu, Z=—C(O)—, R$^2$=N-Boc-2-amino-5-(trifluoromethyl)phenyl, all other R=H; 12 mg) as a white powder after lyopholization. Exact MS calcd for C$_{31}$H$_{43}$F$_3$N$_5$O$_5$, the formula for (M+H)$^+$=622.3216. Found: 622.3219.

Example 34

(2S)-N-tert-Butyl-2-[[[[2-amino-5-(trifluoromethyl)benzoyl]amino]acetyl]amino]-3-[[(2,4-dimethylphenyl)methyl]amino]-propanamide (34a) A solution of (S)-1.5 (l=m=0, R$^1$=2,4-dimethylphenyl, R$^3$=CONHt-Bu, Z=—C(O)—, R$^2$=N-Boc-2-amino-5-(trifluoromethyl)phenyl, all other R=H; 5 mg) in methylene chloride (8 mL) was charged with TFA (4 mL) and stirred at RT for 3 h before being concentrated in vacuo. The residue was dissolved in methylene chloride and the solution was concentrated in vacuo. The crude product was purified by reverse-phase HPLC to afford the title compound (S)-1.5 (l=m=0, R$^1$=2,4-dimethylphenyl, R$^3$=CONHt-Bu, Z=—C(O)—, R$^2$=2-amino-5-(trifluoromethyl)phenyl, all other R=H; 5 mg) as a white powder after lyophilization. Exact MS calcd for C$_{26}$H$_{35}$F$_3$N$_5$O$_3$, the formula for (M+H)$^+$=522.2692. Found: 522.2707.

Example 35

(2S)-N-tert-Butyl-3-[[(4-bromo, 2-methylphenyl) methyl]amino]-2-[[[[2-[[(1,1-dimethylethoxy) carbonyl]amino]-5-(trifluoromethyl)benzoyl]amino] acetyl]amino]-propanamide (35a) 4-Bromo, 2-methylbenzaldehyde (M. I. Dawson, et al., *J. Med. Chem.* 1984, 27, 1516–1531; 0.05 mL) was incorporated into the above procedure (33e) to provide the title compound (S)-1.5 (l=m=0, R$^1$=4-bromo,2-methylphenyl, R$^3$=CONHt-Bu, Z=—C(O)—, R$^2$=N-Boc-2-amino-5-(trifluoromethyl)phenyl, all other R=H; 11 mg) as a white powder after lyopholization. Exact MS calcd for C$_{30}$H$_{40}$Br$_1$F$_3$N$_5$O$_5$, the formula for (M+H)$^+$=686.2165. Found: 686.2173.

Example 36

(2S)-N-tert-Butyl-2-[[[[2-amino-5-(trifluoromethyl) benzoyl]amino]acetyl]amino]-3-[[(4-bromo, 2-methylphenyl)methyl]amino]-propanamide (36a) The compound (S)-1.5 (l=m=0, R$^1$=4-bromo,2-methylphenyl, R$^3$=CONHt-Bu, Z=—C(O)—, R$^2$=N-Boc-2-amino-5-(trifluoromethyl)phenyl, all other R=H; 5 mg) was incorporated into the above procedure (35a) to afford the title compound (S)-1.5 (l=m=0, R$^1$=4-bromo,2-methylphenyl, R$^3$=CONHt-Bu, Z=—C(O)—, R$^2$=2-amino-5-(trifluoromethyl)phenyl, all other R=H; 3 mg) as a white powder after lyopholization. Exact MS calcd for C$_{30}$H$_{40}$Br$_1$F$_3$N$_5$O$_5$, the formula for (M+H)$^+$=586.1641. Found: 586.1635.

Example 37

N-[2-[[(1S, 2S)-1-[[[(2,4-dimethylphenyl)methyl] amino]methyl]-2-hydroxy-3-(methyl)butyl]amino]-2-oxoethyl]-3-(trifluoromethyl)benzamide (37a) The Weinreb amide (S)-11.2 (l=m=0, PGN=CbzHN, all other R=H; cf. procedure (30a); 365 mg, 0.96 mmol) and iso-propylmagnesium bromide (2.9 mL of a 2.0 M solution in THF) were incorporated into the above procedure (30b). The resultant product was carried through procedure (30c) to provide (2S, 3S/R)-11.5 (l=m=0, PGN=CbzHN, R=iso-propyl, all other R=H; assumed 0.96 mmol). MS found: (M+Na)$^+$=389.1.

(37b) The alcohol (2S, 3S/R)-11.5 (l=m=0, PGN=CbzHN, R=iso-propyl, all other R=H; assumed 0.96 mmol) was incorporated into the procedures (1c) and (1d) to provide (1S, 2S/R)-1.5 (l=m=0, R$^1$=2,4-dimethylphenyl, R$^3$=—CH(OH)i-Pr, Z=—C(O)—, R$^2$=3-(trifluoromethyl)phenyl, all other R=H; 120 mg). MS found: (M+H)$^+$=480.5.

(37c) To a solution of the amine (1S, 2S/R)-1.5 (l=m=0, R$^1$=2,4-dimethylphenyl, R$^3$=—CH(OH)i-Pr, Z=—C(O)—, R$^2$=3-(trifluoromethyl)phenyl, all other R=H; ca. 0.4 mmol) in 4 mL of 1:1 THF/H$_2$O was added triethylamine (0.07 mL, 0.5 mmol) and di-tert-butyldicarbonate (110 mg, 0.5 mmol). The reaction was stirred for 3 days at RT and then partitioned between EtOAc and sat. NaHCO$_3$. The organic phase was washed with sat. NaCl, dried (Na$_2$SO$_4$), filtered, and concentrated in vacuo. The crude product was purified by flash chromatography in order to separate the two diastereomers, which were deprotected independently as described below in procedures (37d) and (38a).

(37d) The minor diastereomer from procedure (37c) was dissolved in methylene chloride (4 mL) and treated with TFA (2 mL). The reaction was stirred for 3 h at RT before being concentrated in vacuo. The residue was dissolved in methylene chloride and the solution was concentrated in vacuo; this procedure was repeated once more. The crude product thus obtained was purified by RP-HPLC to afford the title compound (1S, 2S)-1.5 (l=m=0, R$^1$=2,4-dimethylphenyl, R$^3$=—CH(OH)i-Pr, Z=—C(O)—, R$^2$=3-(trifluoromethyl)phenyl, all other R=H; 120 mg) as a white powder after lyopholization. MS found: (M+H)$^+$=480.5.

Example 38

N-[2-[[(1S, 2R)-1-[[[(2,4-dimethylphenyl)methyl] amino]methyl]-2-hydroxy-3-(methyl)butyl]amino]-2-oxoethyl]-3-(trifluoromethyl)benzamide (38a) The major diastereomer obtained from procedure (37c) was processed according to procedure (37d). The crude product thus obtained was purified by RP-HPLC to afford the title compound (1S, 2R)-1.5 (l=m=0, R$^1$=2,4-dimethylphenyl, R$^3$=—CH(OH)i-Pr, Z=—C(O)—, R$^2$=3-(trifluoromethyl)phenyl, all other R=H; 120 mg) as a white powder after lyopholization. MS found: (M+H)$^+$=480.5.

Example 39

N-[2-[[(1S, 2S)-1-[[[(2,4-dimethylphenyl)methyl] amino]methyl]-2-hydroxy-2-(phenyl)ethyl]amino]-2-oxoethyl]-3-(trifluoromethyl)benzamide (39a) The Weinreb amide (S)-11.2 (l=m=0, PGN=CbzHN, all other R=H; cf. procedure (30a); 403 mg, 1.06 mmol) and phenylmagnesium bromide (6.4 mL of a 1.0 M solution in THF) were incorporated into the above procedure (30b). The resultant product was carried through procedure (30c) to provide (2S, 3S/R)-11.5 (l=m=0, PGN=CbzHN, R=phenyl, all other R=H; assumed 1.06 mmol). MS found: (M+Na)$^+$=421.1.

(39b) The alcohol (2S, 3S/R)-11.5 (l=m=0, PGN=CbzHN, R=phenyl, all other R=H; assumed 1.06 mmol) was incorporated into the procedures (1c) and (1d) to provide (1S, 2S/R)-1.5 (l=m=0, R$^1$=2,4-dimethylphenyl, R$^3$=—CH(OH)Ph, Z=—C(O)—, R$^2$=3-(trifluoromethyl)phenyl, all other R=H; 63 mg) as a white powder after lyopholization. MS found: (M+H)$^+$=514.2.

(39c) The diastereomeric mixture of alcohols (1S, 2S/R)-1.5 (l=m=0, R$^1$=2,4-dimethylphenyl, R$^3$=—CH(OH)Ph, Z=—C(O)—, R$^2$=3-(trifluoromethyl)phenyl, all other R=H) was purified further by HPLC with a chiral column (Chiracel OD) in order to separate the two diastereomers. The second peak to elute from the column (minor diastereomer) was the title compound (1S, 2S)-1.5 (l=m=0, R$^1$=2,4-dimethylphenyl, R$^3$=—CH(OH)Ph. Z=—C(O)—, R$^2$=3-(trifluoromethyl)phenyl, all other R=H).

Example 40

N-[2-[[(1S, 2R)-1-[[[(2,4-dimethylphenyl)methyl] amino]methyl]-2-hydroxy-2-(phenyl)ethyl]amino]-2-oxoethyl]-3-(trifluoromethyl)benzamide (40a) The diastereomeric mixture of alcohols (1S, 2S/R)-1.5 (l=m=0, R$^1$=2,4-dimethylphenyl, R$^3$=—CH(OH)Ph, Z=—C(O)—, R$^2$=3-(trifluoromethyl)phenyl, all other R=H)

obtained from procedure (39b) was purified further by HPLC with a chiral column (Chiracel OD) in order to separate the two diastereomers. The first peak to elute from the column (major diastereomer) was the title compound (1S, 2R)-1.5 (l=m=0, R$^1$=2,4-dimethylphenyl, R$^3$=—CH(OH)Ph, Z=—C(O)—, R$^2$=3-(trifluoromethyl)phenyl, all other R=H).

Example 41

N-[2-[[(1S, 2S)-1-[[[(2,4-dimethylphenyl)methyl]amino]methyl]-2-hydroxy-3-(phenyl)propyl]amino]-2-oxoethyl]-3-(trifluoromethyl)benzamide

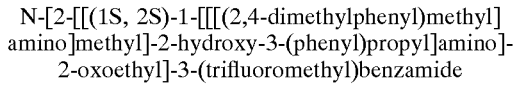

(41a) The Weinreb amide (S)-11.2 (l=m=0, PGN=CbzHN, all other R=H; cf. procedure (30a); 311 mg, 0.82 mmol) and benzylmagnesium bromide (2.5 mL of a 2.0 M solution in THF) were incorporated into the above procedure (30b). The resultant product was carried through procedure (30c) to provide (2S, 3S/R)-11.5 (l=m=0, PGN=CbzHN, R=benzyl, all other R=H; assumed 0.82 mmol).

(41b) The alcohol (2S, 3S/R)-11.5 (l=m=0, PGN=CbzHN, R=phenyl, all other R=H; assumed 0.82 mmol) was incorporated into the procedures (1c) and (1d) to provide (1S, 2S/R)-1.5 (l=m=0, R$^1$=2,4-dimethylphenyl, R$^3$=—CH(OH)CH$_2$Ph, Z=—C(O)—, R$^2$=3-(trifluoromethyl)phenyl, all other R=H; 40 mg) as a white powder after RP-HPLC and lyopholization. MS found: (M+H)$^+$=528.2.

(41c) The unpurified mixture of diastereomers (1S, 2S/R)-1.5 (l=m=0, R$^1$=2,4-dimethylphenyl, R$^3$=—CH(OH)CH$_2$Ph, Z=—C(O)—, R$^2$=3-(trifluoromethyl)phenyl, all other R=H; assumed 0.4 mmol) was incorporated into the above procedure (37c). The crude product was purified by flash chromatography in order to separate the two diastereomers, which were deprotected independently as described below in procedures (41d) and (42a).

(41d) The minor product from procedure (41c) was incorporated into procedure (37d) to provide the title compound (1S, 2S)-1.5 (l=m=0, R$^1$=2,4-dimethylphenyl, R$^3$=—CH(OH)CH$_2$Ph, Z=—C(O)—, R$^2$=3-(trifluoromethyl)phenyl, all other R=H; 10 mg) as a white powder after RP-HPLC and lyopholization. MS found: (M+H)$^+$=528.5.

Example 42

N-[2-[[(1S, 2R)-1-[[[(2,4-dimethylphenyl)methyl]amino]methyl]-2-hydroxy-3-(phenyl)propyl]amino]-2-oxoethyl]-3-(trifluoromethyl)benzamide (42a) The major product from procedure (41c) was incorporated into procedure (37d) to provide the title compound (1S, 2R)-1.5 (l=m=0, R$^1$=2,4-dimethylphenyl, R$^3$=—CH(OH)CH$_2$Ph, Z=—C(O)—, R$^2$=3-(trifluoromethyl)phenyl, all other R=H; 10 mg) as a white powder after RP-HPLC and lyopholization. MS found: (M+H)$^+$=528.5.

Example 43

N-[2-[[(1S, 2S)-1-[[[(2,4-dimethylphenyl)methyl]amino]methyl]-2-hydroxy-4-(methyl)pentyl]amino]-2-oxoethyl]-3-(trifluoromethyl)benzamide (43a) The Weinreb amide (S)-11.2 (l=m=0, PGN=CbzHN, all other R=H; cf. procedure (30a); 540 mg, 1.42 mmol) and isobutylmagnesium bromide (4.3 mL of a 2.0 M solution in Et$_2$O) were incorporated into the above procedure (30b). The resultant product was carried through procedure (30c) to provide (2S, 3S/R)-11.5 (l=m=0, PGN=CbzHN, R=iso-butyl, all other R=H; assumed 1.4 mmol). MS found: (M+Na)$^+$=403.3.

(43b) The alcohol (2S, 3S/R)-11.5 (l=m=0, PGN=CbzHN, R=iso-butyl, all other R=H; assumed 1.4 mmol) was incorporated into the procedures (1c) and (1d) to provide (1S, 2S/R)-1.5 (l=m=0, R$^1$=2,4-dimethylphenyl, R$^3$=—CH(OH)CH$_2$i-Pr, Z=—C(O)—, R$^2$=3-(trifluoromethyl)phenyl, all other R=H; 33 mg) as a white powder after RP-HPLC and lyopholization. MS found: (M+H)$^+$=480.5.

(43c) The unpurified mixture of diastereomers (1S, 2S/R)-1.5 (l=m=0, R$^1$=2,4-dimethylphenyl, R$^3$=—CH(OH)CH$_2$i-Pr, Z=—C(O)—, R$^2$=3-(trifluoromethyl)phenyl, all other R=H; assumed 0.4 mmol) was incorporated into the above procedure (37c). The crude product was purified by flash chromatography in order to separate the two diastereomers, which were deprotected independently as described below in procedures (43d) and (44a).

(43d) The minor product from procedure (43c) was incorporated into procedure (37d) to provide the title compound (1S, 2S)-1.5 (l=m=0, R$^1$=2,4-dimethylphenyl, R$^3$=—CH(OH)CH$_2$i-Pr, Z=—C(O)—, R$^2$=3-(trifluoromethyl)phenyl, all other R=H; 10 mg) as a white powder after RP-HPLC and lyopholization. MS found: (M+H)$^+$=480.5.

Example 44

N-[2-[[(1S, 2R)-1-[[[(2,4-dimethylphenyl)methyl]amino]methyl]-2-hydroxy-4-(methyl)pentyl]amino]-2-oxoethyl]-3-(trifluoromethyl)benzamide

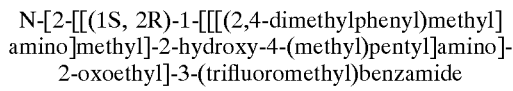

(44a) The major product from procedure (43c) was incorporated into procedure (37d) to provide the title compound (1S, 2R)-1.5 (l=m=0, R$^1$=2,4-dimethylphenyl, R$^3$=—CH(OH)CH$_2$i-Pr, Z=—C(O)—, R$^2$=3-(trifluoromethyl)phenyl, all other R=H; 10 mg) as a white powder after RP-HPLC and lyopholization. MS found: (M+H)$^+$=480.5.

Example 45

N-[2-[[(1S, 2S)-1-[[[(2,4-dimethylphenyl)methyl]amino]methyl]-2-(hydroxy)butyl]amino]-2-oxoethyl]-3-(trifluoromethyl)benzamide

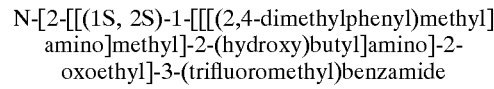

(45a) The Weinreb amide (S)-11.2 (l=m=0, PGN=CbzHN, all other R=H; cf. procedure (30a); 530 mg, 1.39 mmol) and ethylmagnesium bromide (4.2 mL of a 2.0 M solution in THF) were incorporated into the above procedure (30b). The resultant product was carried through procedure (30c) to provide (2S, 3S/R)-11.5 (l=m=0, PGN=CbzHN, R=ethyl, all other R=H; assumed 1.4 mmol). MS found: (M+Na)$^+$=375.2.

(45b) The mixture of diastereomers (2S, 3S/R)-11.5 (l=m=0, PGN=CbzHN, R=ethyl, all other R=H; assumed 1.4 mmol) was dissolved in 2:1 acetone/dimethoxypropane (15 mL) and the resultant solution was charged with a pinch of camphorsulfonic acid. The reaction was stirred for 14 h at RT, quenched with 0.2 mL of triethylamine, and concentrated in vacuo. The residue was purified by flash chromatography to provide the N, O-acetal (274 mg). MS found: (M+Na)$^+$=415.1.

(45c) The N, O-acetal (274 mg, 0.68 mmol) was incorporated into procedure (1d) to provide the benzyl amine. MS found: (M+H)$^+$=377.5. This material was not purified, but rather dissolved in 10 mL of 1:1 THF/H$_2$O. The solution was charged with triethylamine (0.19 mL, 1.36 mmol) and then treated with dibenzyldicarbonate (234 mg, 0.82 mmol). The reaction was stirred for 3 days at RT and then partitioned between EtOAc and sat. NH$_4$Cl. The organic phase was washed with brine, dried (MgSO$_4$), filtered, and concentrated in vacuo. The residue was purified by flash chroma-

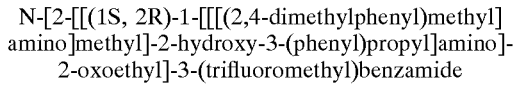

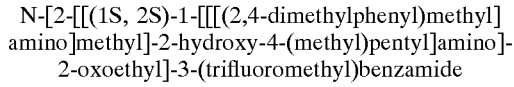

tography in order to separate the two diastereomers. The MS found for each diastereomer was identical: (M+Na)⁺=533.2.

(45d) The faster-eluting diastereomer (minor product, 47 mg, 0.09 mmol) obtained from procedure (45c) was dissolved in THF (2 mL), H₂O (1 mL), and glacial acetic acid (4 mL). The solution was stirred for 96 h at RT and then partitioned between EtOAc and sat. NaHCO₃. The organic phase was washed with 5% NaHCO₃ (1×) and brine (1×) before being dried (Na₂SO₄), filtered, and concentrated in vacuo to provide (2S, 3S)-11.5 (l=m=0, PGN=2,4-Me₂PhCH₂-(Cbz)N, R ethyl, all other R=H; assumed 0.09 mmol). MS found: (M+H)⁺=471.3.

(45e) The compound (2S, 3S)-11.5 (l=m=0, PGN=2,4-Me₂PhCH₂-(Cbz)N, R=ethyl, all other R=H; assumed 0.9 mmol) was incorporated into the above procedure (1c) to afford (1S, 2S)-1.4 (l=m=0, PGN=2,4-Me₂PhCH₂(Cbz)N, R³=—CH(OH)Et, Z=—C(O)—, R²=3-(trifluoromethyl)phenyl, all other R=H; assumed 0.09 mmol) as a crude product. MS found: (M+Na)⁺=622.2. This material was dissolved in MeOH (3 mL) and the solution was charged with 5% Pd/C, Degussa (12 mg). The reaction vessel was purged with hydrogen, and the reaction was stirred under hydrogen (1 atm) for 14 h at RT. The reaction was filtered and concentrated in vacuo. The residue was purified by RP-HPLC to afford the title compound (1S, 2S)-1.5 (l=m=0, R¹=2,4-dimethylphenyl, R³=—CH(OH)Et, Z=—C(O)—, R²=3-(trifluoromethyl)phenyl, all other R=H; 10 mg) as a white powder after lyophilization. Exact MS calcd for C₂₄H₃₁F₃N₃O₃, the formula for (M+H)⁺=466.2318. Found: 466.2342.

Example 46

N-[2-[[(1S, 2R)-1-[[[(2,4-dimethylphenyl)methyl]amino]methyl]-2-(hydroxy)butyl]amino]-2-oxoethyl]-3-(trifluoromethyl)benzamide

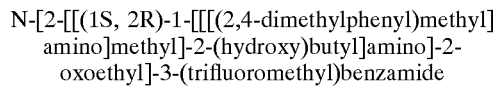

(46a) The faster-eluting diastereomer (major product, 85 mg, 0.22 mmol) obtained from procedure (45c) was incorporated into procedures (45d) and (45e). The resultant residue was purified by RP-HPLC to afford the title compound (1S, 2R)-1.5 (l=m=0, R¹=2,4-dimethylphenyl, R³=—CH(OH)Et, Z=—C(O)—, R²=3-(trifluoromethyl)phenyl, all other R=H; 20 mg) as a white powder after lyophilization. Exact MS calcd for C₂₄H₃₁F₃N₃O₃, the formula for (M+H)⁺=466.2318. Found: 466.2317.

Example 47

N-[2-[[(1S, 2S)-1-[[[(2,4-dimethylphenyl)methyl]amino]methyl]-2-(hydroxy)butyl]amino]-2-oxoethyl]-2-[[(1,1-dimethylethoxy)carbonyl]amino]-5-(trifluoromethyl)benzamide

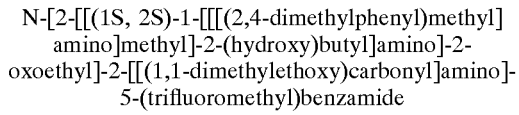

(47a) A solution of H-Gly-OBn (p-Tos salt; 6.0 g, 17.9 mmol) in DMF (45 mL) was charged successively with N,N-diisopropylethylamine (12.4 mL, 71.5 mmol), N-Boc-2-amino-5-(trifluoromethyl)benzoic acid (S. Takagishi, et al., Synlett 1992, 360; 6.0 g, 19.7 mmol), and BOP (8.69 g, 19.7 mmol). The reaction was stirred at RT for 3 days, diluted with EtOAc, and washed with brine (pH 5, 1×), H₂O (1×), sat. NaHCO₃ (1×), and brine (1×). The organic phase was dried (MgSO₄), filtered, and concentrated in vacuo. The residue was purified by flash chromatography to provide the amide (5.78 g, 12.8 mmol). MS found: (M+Na)⁺=475.3. This material was dissolved in MeOH (50 mL) and the solution was charged with 10% Pd/C, Degussa (1.0 g). The vessel was purged with hydrogen, and the reaction was stirred under hydrogen (1 atm) for 3 h before being filtered. The filtrate was concentrated in vacuo to afford 1.2 (Z=—C(O)—, R²=N-Boc 2-amino-5-(trifluoromethyl)benzoic acid, all other R=H; 4.56 g) as a white solid. MS found: (M–H)⁻=361.3.

(47b) Both 1.2 (Z=—C(O)—, R²=N-Boc 2-amino-5-(trifluoromethyl)benzoic acid, all other R=H; 73 mg, 0.2 mmol) and the compound (2S, 3S)-11.5 (l=m=0, PGN=2,4-Me₂PhCH₂(Cbz)N, R=ethyl, all other R=H; cf. procedure (45d); 86 mg, 0.18 mmol) were incorporated into the above procedure (1c) to afford (1S, 2S)-1.4 (l=m=0, PGN=2,4-Me₂PhCH₂(Cbz)N, R³=—CH(OH)Et, Z=—C(O)—, R²=N-Boc 2-amino-5-(trifluoromethyl)phenyl, all other R=H; assumed 0.18 mmol) after flash chromatography. This material was dissolved in MeOH (5 mL) and the solution was charged with 5% Pd/C, Degussa (20 mg). The reaction vessel was purged with hydrogen, and the reaction was stirred under hydrogen (1 atm) for 45 min at RT. The reaction was filtered and concentrated in vacuo to afford the title compound (1S, 2S)-1.5 (l=m=0, R¹=2,4-dimethylphenyl, R³=—CH(OH)Et, Z=—C(O)—, R²=N-Boc 2-amino-5-(trifluoromethyl)phenyl, all other R=H; 80 mg). MS found: (M+H)⁺=581.4.

Example 48

N-[2-[[(1S, 2S)-1-[[[(2,4-dimethylphenyl)methyl]amino]methyl]-2-(hydroxy)butyl]amino]-2-oxoethyl]-2-amino-5-(trifluoromethyl)benzamide

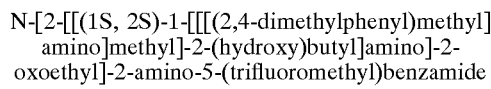

(48a) The compound (1S, 2S)-1.5 (l=m=0, R¹=2,4-dimethylphenyl, R³=—CH(OH)Et, Z=—C(O)—, R²=N-Boc 2-amino-5-(trifluoromethyl)phenyl, all other R=H; 75 mg) was dissolved in 6 mL of 2:1 methylene chloride/TFA and stirred at RT for 80 min before being concentrated in vacuo. The residue was purified by RP-HPLC to afford the title compound (1S, 2S)-1.5 (l=m=0, R¹=2,4-dimethylphenyl, R³=—CH(OH)Et, Z=—C(O)—, R²=2-amino-5-(trifluoromethyl)phenyl, all other R=H; 60 mg) as a white powder after lyophilization. Exact MS calcd for C₂₄H₃₂F₃N₄O₃, the formula for (M+H)⁺=481.2426. Found: 481.2407.

Example 49

N-[2-[[(1S, 2S)-1-[[[(2,4-dimethylphenyl)methyl]amino]methyl]-2-hydroxy-4-(methyl)pentyl]amino]-2-oxoethyl]-2-[[(1,1-dimethylethoxy)carbonyl]amino]-5-(trifluoromethyl)benzamide

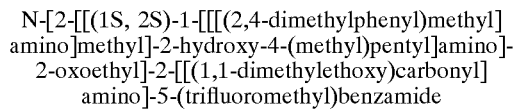

(49a) The crude product mixture from procedure (43a) was purified by flash chromatography to provide separation of the two diastereomers (2S, 3S)- and (2S, 3R)-11.5 (l=m=0, PGN=CbzHN, R=iso-butyl, all other R=H). The minor, faster-eluting (2S, 3S)-isomer (95 mg, 0.25 mmol), was combined with 1.2 (Z=—C(O)—, R²=N-Boc 2-amino-5-(trifluoromethyl)benzoic acid, all other R=H; cf. procedure (47a); 94 mg, 0.26 mmol) in procedure (1c). The product from this reaction was then taken through procedure (1d). RP-HPLC afforded the title compound (1S, 2S)-1.5 (l=m=0, R¹=2,4-dimethylphenyl, R³=—CH(OH)i-Bu, Z=—C(O)—, R²=N-Boc 2-amino-5-(trifluoromethyl)phenyl, all other R=H; 10 mg) as a white powder after lyopholization. Exact MS calcd for C₃₁H₄₄F₃N₄O₅, the formula for (M+H)⁺=609.3264. Found: 609.3267.

Example 50

N-[2-[[(1S, 2R)-1-[[[(2,4-dimethylphenyl)methyl]amino]methyl]-2-hydroxy-4-(methyl)pentyl]amino]-2-oxoethyl]-2-[[(1,1-dimethylethoxy)carbonyl]amino]-5-(trifluoromethyl)benzamide

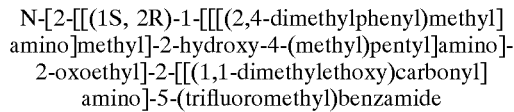

(50a) The major, slower-eluting (2S, 3R)-isomer (86 mg, 0.35 mmol) from procedure (49a) was taken through procedure (1d). The product was combined with 1.2 (Z=—C(O)—, R²=N-Boc 2-amino-5-(trifluoromethyl)benzoic acid, all other R=H; cf. procedure (47a); 31 mg, 0.09 mmol) in procedure (1c). RP-HPLC afforded the title compound (1S, 2R)-1.5 (l=m=0, R¹=2,4-dimethylphenyl, R³=—CH(OH)i-Bu, Z=—C(O)—, R²=N-Boc 2-amino-5-(trifluoromethyl)phenyl, all other R=H; 5 mg) as a white powder after lyopholization. Exact MS calcd for $C_{31}H_{44}F_3N_4O_5$, the formula for (M+H)⁺=609.3264. Found: 609.3250.

Example 51

N-[2-[[(1S, 2S)-1-[[[(2,4-dimethylphenyl)methyl]amino]methyl]-2-hydroxy-4-(methyl)pentyl]amino]-2-oxoethyl]-2-amino-5-(trifluoromethyl)benzamide (51a) The product from procedure (49a) was taken through procedure (48a) and then purified by RP-HPLC to afford the title compound (1S, 2S)-1.5 (l=m=0, R¹=2,4-dimethylphenyl, R³=—CH(OH)i-Bu, Z=—C(O)—, R²=2-amino-5-(trifluoromethyl)phenyl, all other R=H; 3 mg). MS found: (M+H)⁺=509.3.

Example 52

N-[2-[[(1S, 2R)-1-[[[(2,4-dimethylphenyl)methyl]amino]methyl]-2-hydroxy-4-(methyl)pentyl]amino]-2-oxoethyl]-2-amino-5-(trifluoromethyl)benzamide (52a) The product from procedure (50a) was taken through procedure (48a) and then purified by RP-HPLC to afford the title compound (1S, 2R)-1.5 (l=m=0, R¹=2,4-dimethylphenyl, R³=—CH(OH)i-Bu, Z=—C(O)—, R²=2-amino-5-(trifluoromethyl)phenyl, all other R=H; 10 mg) as a white powder after lyopholization. MS found: (M+H)⁺= 509.5.

Example 53

N-[2-[[(1S, 2S)-1-[[[(2,4-dimethylphenyl)methyl]amino]methyl]-4,4-dimethyl-2-(hydroxy)pentyl]amino]-2-oxoethyl]-3-(trifluoromethyl)benzamide (53a) The Weinreb amide (S)-11.2 (l=m=0, PGN=CbzHN, all other R=H; cf. procedure (30a); 850 mg, 2.23 mmol) and neopentylmagnesium bromide (13.4 mL of a 1.0 M solution in THF) were incorporated into the above procedure (30b). The resultant product was carried through procedure (30c). The crude mixture of diastereomeric alcohols were separated by flash chromatography to provide (2S, 3S)-11.5 (l=m=0, PGN=CbzHN, R=CH₂t-Bu, all other R=H; 31 mg) and (2S, 3R)-11.5 (l=m=0, PGN=CbzHN, R=CH₂t-Bu, all other R=H; 199 mg).

(53b) The (2S, 3S)-diastereomer from (53a) was carried through procedures (1c) and (1d). The crude product was purified by RP-HPLC to afford the title compound (1S, 2S)-1.5 (l=m=O, R¹=2,4-dimethylphenyl, R³=—CH(OH)CH₂t-Bu, Z=—C(O)—, R²⁻³-(trifluoromethyl)phenyl, all other R=H; 5 mg) as a white powder after lyopholization. Exact MS calcd for $C_{27}H_{37}F_3N_3O_3$, the formula for (M+H)⁺=508.2787. Found: 508.2778.

Example 54

N-[2-[[(1S, 2R)-1-[[[(2,4-dimethylphenyl)methyl]amino]methyl]-4,4-dimethyl-2-(hydroxy)pentyl]amino]-2-oxoethyl]-3-(trifluoromethyl)benzamide (54a) The (2S, 3R)-diastereomer from (53a) was carried through procedures (1c) and (1d). The crude product was purified by RP-HPLC to afford the title compound (1S, 2S)-1.5 (l=m=0, R¹=2,4-dimethylphenyl, R³=—CH(OH)CH₂t-Bu, Z=—C(O)—, R²=3-(trifluoromethyl)phenyl, all other R=H; 10 mg) as a white powder after lyopholization. Exact MS calcd for $C_{27}H_{37}F_3N_3O_3$, the formula for (M+H)⁺=508.2787. Found: 508.2774.

Example 55

N-[2-[[(1S, 2S)-1-[[[(2,4-dimethylphenyl)methyl]amino]methyl]-2-(hydroxy)pentyl]amino]-2-oxoethyl]-3-(trifluoromethyl)benzamide (55a) The Weinreb amide (S)-11.2 (l=m=0, PGN=CbzHN, all other R=H; cf. procedure (30a); 894 mg, 2.34 mmol) and propylmagnesium bromide (7.0 mL of a 2.0 M solution in Et₂O) were incorporated into the above procedure (30b). The resultant product was carried through procedure (30c). The crude mixture of diastereomeric alcohols was then carried through procedure (1d). The product (632 mg) was dissolved in THF (27 mL) and the solution was charged with triethylamine (0.72 mL, 5.41 mmol) and dibenzyldicarbonate (618 mg, 2.16 mmol). The reaction was stirred for 14 h, concentrated in vacuo, dissolved in EtOAc, and washed with 1N HCl (1×), H₂O (1×), and brine (1×). The organic extract was dried (Na₂SO₄), filtered, and concentrated in vacuo to afford the mixture of diastereomers as an oil (188 mg). The mixture was separated by repeated flash chromatography (SiO₂) to provide pure fractions of (2S, 3S)- and (2S, 3R)-11.5 (l=m=0, PGN=2,4-Me₂Bn(Cbz)N, R=propyl, all other R=H), as well as fractions that contained both diastereomers.

(55b) The (2S, 3S)-diastereomer (29 mg, 0.074 mmol) from (55a) was carried through procedure (1c). The crude product (43 mg) was dissolved in MeOH (2 mL) and the solution was charged with 5% Pd/C, Degussa (9 mg). The vessel was purged with hydrogen and the reaction was stirred under hydrogen (1 atm) for 14 h before it was filtered and concentrated in vacuo. The residue was purified by RP-HPLC to afford the title compound (1S, 2S)-1.5 (l=m=0, R¹=2,4-dimethylphenyl, R³=—CH(OH)n-propyl, Z=—C(O)—, R²=3-(trifluoromethyl)phenyl, all other R=H; 5 mg) as a white powder after lyopholization. Exact MS calcd for $C_{25}H_{33}F_3N_3O_3$, the formula for (M+H)⁺=480.2474. Found: 480.2480.

Example 56

N-[2-[[(1S, 2R)-1-[[[(2,4-dimethylphenyl)methyl]amino]methyl]-2-(hydroxy)pentyl]amino]-2-oxoethyl]-3-(trifluoromethyl) benzamide (56a) The (2S, 3R)-diastereomer (30 mg, 0.078 mmol) from (55a) was carried through procedure (1c). The crude product was dissolved in MeOH (3 mL) and the solution was charged with 5% Pd/C, Degussa (10 mg). The vessel was purged with hydrogen and the reaction was stirred under hydrogen (1 atm) for 14 h before it was filtered and concentrated in vacuo. The residue was purified by RP-HPLC to afford the title compound (1S, 2R)-1.5 (l=m=0, R¹=2,4-dimethylphenyl, R³=—CH(OH)n-propyl, Z=—C(O)—, R²=3-(trifluoromethyl)phenyl, all other R=H; 8 mg) as a white powder after lyopholization. Exact MS calcd for $C_{25}H_{33}F_3N_3O_3$, the formula for (M+H)⁺=480.2474. Found: 480.2478.

Example 57

N-[2-[[(1S, 2S)-1-[[[(2,4-dimethylphenyl)methyl]amino]methyl]-2-(hydroxy)pentyl]amino]-2-oxoethyl]-2-[[(1,1-dimethylethoxy)carbonyl]amino]-5-(trifluoromethyl)benzamide (57a) An purified, but incompletely separated mixture of diastereomers (128 mg, 0.33 mmol) from procedure (55a)

was combined with 1.2 (Z=—C(O)—, $R^2$=N-Boc 2-amino-5-(trifluoromethyl)benzoic acid, all other R=H; cf. procedure (47a); 87 mg, 0.33 mmol) in procedure (1c). The residue thus obtained was purified by flash chromatography to separate the alcohol diastereomers.

(57b) The minor diastereomer (25 mg, 0.03 mmol) from (57a) was dissolved in in MeOH (2 mL) and the solution was charged with 5% Pd/C, Degussa (5 mg). The vessel was purged with hydrogen and the reaction was stirred under hydrogen (1 atm) for 14 h before it was filtered and concentrated in vacuo. The residue was purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=N-Boc 2-amino-5-(trifluoromethyl)phenyl, all other R=H; 7 mg). MS found: $(M+H)^+$=595.5.

Example 58

N-[2-[[(1S, 2R)-1-[[[(2,4-dimethylphenyl)methyl]amino]methyl]-2-(hydroxy)pentyl]amino]-2-oxoethyl]-2-[[(1,1-dimethylethoxy)carbonyl]amino]-5-(trifluoromethyl)benzamide (58a) The major diastereomer (75 mg, 0.10 mmol) from (57a) was dissolved in in MeOH (3 mL) and the solution was charged with 5% Pd/C, Degussa (15 mg). The vessel was purged with hydrogen and the reaction was stirred under hydrogen (1 atm) for 14 h before it was filtered and concentrated in vacuo. The residue was purified by RP-HPLC to afford the title compound (1S, 2R)-1.5 (l=m=0, $R^1$=2,4-dimethylphenyl, $R^3$=—CH(OH)n-propyl, Z=—C(O)—, $R^2$=N-Boc 2-amino-5-(trifluoromethyl)phenyl, all other R=H; 20 mg). Exact MS calcd for $C_{30}H_{42}F_3N_4O_5$, the formula for $(M+H)^+$=595.3107. Found: 595.3110.

Example 59

N-[2-[[(1S, 2S)-1-[[[(2,4-dimethylphenyl)methyl]amino]methyl]-2-(hydroxy)pentyl]amino]-2-oxoethyl]-2-amino-5-(trifluoromethyl)benzamide (59a) The product (5 mg) from procedure (57b) was carried through procedure (48a) to afford the title compound (1S, 2S)-1.5 (l=m=0, $R^1$=2,4-dimethylphenyl, $R^3$=—CH(OH)n-propyl, Z=—C(O)—, $R^2$=2-amino-5-(trifluoromethyl)phenyl, all other R=H; 1 mg) after RP-HPLC and lyopholization. MS found: $(M+H)^+$=495.4.

Example 60

N-[2-[[(1S, 2R)-1-[[[(2,4-dimethylphenyl)methyl]amino]methyl]-2-(hydroxy)pentyl]amino]-2-oxoethyl]-2-amino-5-(trifluoromethyl)benzamide (60a) The product (15 mg) from procedure (58a) was carried through procedure (48a) to afford the title compound (1S, 2R)-1.5 (l=m=0, $R^1$=2,4-dimethylphenyl, $R^3$=—CH(OH)n-propyl, Z=—C(O)—, $R^2$=2-amino-5-(trifluoromethyl)phenyl, all other R=H; 3 mg) after RP-HPLC and lyopholization. Exact MS calcd for $C_{25}H_{34}F_3N_4O_3$, the formula for $(M+H)^+$=495.2583. Found: 495.2584.

Example 61

N-[2-[[(1S, 2S)-1-[[[(2,4-dimethylphenyl)methyl]amino]methyl]-2-(hydroxy)pentyl]amino]-2-oxoethyl]-3-amino-5-(trifluoromethyl)benzamide (61a) A solution of 3-nitro-5(trifluoromethyl)benzoic acid (7.71 g, 32.8 mmol) and glycine tert-butyl ester (5.23 g, 32.4 mmol) in methylene chloride (330 mL) was charged with N,N-diisopropylethylamine (5.5 mL, 31.8 mmol) and BOP (14.6 g, 32.9 mmol). The reaction was stirred at RT for 14 h, concentrated in vacuo, and diluted with EtOAc (1 L). The organic phase was washed successively with sat. $NH_4Cl$, sat. $NaHCO_3$, and brine before being dried ($Na_2SO_4$), filtered, and concentrated in vacuo. The residue was purified by flash chromatography ($SiO_2$, 50% EtOAc/hexanes) to afford the tert-Butyl (3-trifluoromethylbenzoyl)glycine as an oil. A portion (1.0 g, 2.65 mmol) of this material was dissolved in methylene chloride (8 mL) before being treated with TFA (4 mL). The reaction was stirred for 1 h at RT and then concentrated in vacuo. The residue was dissolved in methlyene chloride and concentrated again; this procedure was repeated twice more to afford the title compound 1.2 (Z=—C(O)—, $R^2$=3-amino-5-(trifluoromethyl)phenyl, all other R=H; 0.77 g) as a white solid. MS found: $(M–H)^-$=291.1.

(61b) A cooled (0° C.) solution of the Weinreb amide (S)-11.2 (l=m=0, PGN=CbzHN, all other R=H; 7.7 g, 20 mmol) in THF (100 mL) was treated with propylmagnesium bromide (50 mL of a 2.0 M solution in THF). The reaction was allowed to warm to RT over 2 h and then recooled to 0° C. before being quenched with the addition of sat. $NH_4Cl$. The mixture was diluted with $H_2O$ and extracted with EtOAc (2×). The organic phase was washed with brine, dried ($Na_2SO_4$), filtered, and concentrated in vacuo. The resultant ketone was dissolved in THF (70 mL) and EtOH (30 mL). The solution was cooled to 0° C., charged with sodium borohydride (1.5 g, 40 mmol), and then stirred at RT for 3 h before being quenched with sat. $NaHCO_3$. The mixture was extracted with EtOAc (2×), and the organic phase was washed with brine, dried ($Na_2SO_4$), filtered, and concentrated in vacuo. The residue was purified by repeated flash chromatography ($SiO_2$) to provide (2S, 3S)- and (2S, 3R)-11.5 (l=m=0, PGN=CbzHN, R=propyl, all other R=H) in a circa 1:10 ratio. MS found: $(M+Na)^+$=389.4.

(61c) The minor, (2S, 3S)-diastereomer (84 mg, 0.22 mmol) from (61b) and 1.2 (Z=—C(O)—, $R^2$=3-amino-5-(trifluoromethyl)phenyl, all other R=H; 64 mg, 0.22 mmol) were combined in procedure (1c). The resultant product was taken through procedure (1d) and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=3-amino-5-(trifluoromethyl)phenyl, all other R=H; 15 mg). Exact MS calcd for $C_{25}H_{34}F_3N_4O_3$, the formula for $(M+H)^+$=495.2583. Found: 495.2584.

Example 62

N-[2-[[(1S, 2R)-1-[[[(2,4-dimethylphenyl)methyl]amino]methyl]-2-(hydroxy)pentyl]amino]-2-oxoethyl]-3-amino-5-(trifluoromethyl)benzamide (62a) The major, (2S, 3R)-diastereomer (194 mg, 0.73 mmol) from (61b) and 1.2 (Z=—C(O)—, $R^2$=3-amino-5-(trifluoromethyl)phenyl, all other R=H; cf. procedure (61a); 218 mg, 0.61 mmol) were combined in procedure (1c). The resultant product was taken through procedure (1d) and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=3-amino-5-(trifluoromethyl)phenyl, all other R=H; 15 mg). Exact MS calcd for $C_{25}H_{34}F_3N_4O_3$, the formula for $(M+H)^+$=495.2583. Found: 495.2586.

Example 63

N-[2-[[(1S, 2S)-1-[[[(2,4-dimethylphenyl)methyl]amino]methyl]-2-(hydroxy)pentyl]amino]-2-oxoethyl]-2-[[(ethylamino)carbonyl]amino]-5-(trifluoromethyl)benzamide (63a) N-Boc 2-amino-5-(trifluoromethyl)benzoic acid (S. Takagishi, et al., *Synlett* 1992, 360; 5.1 g, 17 mmol) was dissolved in DMF (42 mL) and the solution was charged with allyl bromide (3.8 mL, 44 mmol) and potassium carbonate (3.4 g, 25 mmol). The slurry was stirred for 14 h at RT, diluted with EtOAc, and washed successively with brine, water, and brine. The organic phase was dried ($Na_2SO_4$), filtered, and concentrated in vacuo to provide the allyl ester as a white solid. This material was dissolved in methylene chloride (30 mL) and TFA (15 mL) and stirred at RT for 2 h before being concentrated in vacuo. The residue was dissolved in methylene chloride and the solution was concentrated in vacuo; this procedure was repeated twice. The residue was purified by flash chromatography ($SiO_2$) to provide the amine as an oil (contaminated with some DMF). The amine (ca. 15.7 mmol) was dissolved in THF (30 mL) and added dropwise to a solution of disphosgene (5.6 mL, 47 mmol) in THF (30 mL). The reaction was stirred for 14 h at RT and concentrated in vacuo to afford a brown solid. A portion (2.4 g, ca. 7.7 mmol) of the brown solid was dissolved in THF (40 mL) and the solution was charged with ethylamine (20 mL of a 2.0 M solution in THF). The reaction was stirred for 14 h at RT and then diluted with EtOAc. The organic phase was washed successively with 1N HCl (2×) and brine (1×) before being dried ($Na_2SO_4$), filtered, and concentrated in vacuo to give a white solid. This material (1.8 g, ca. 5.7 mmol) was dissolved in acetonitrile (25 mL) and DMF (20 mL). The solution was charged with pyrolidine (1.0 mL, 12 mmol) and $Ph(PPh_3)_4$ (140 mg, 0.17 mmol) and then stirred for 2 h at RT before being concentrated in vacuo. The residue was diluted with EtOAc and this was washed successively with 1N HCl (2×) and brine (1×) before being dried ($Na_2SO_4$), filtered, and concentrated in vacuo. The residue was triturated with methylene chloride to afford pure 2-[[(ethylamino)carbonyl]amino]-5-(trifluoromethyl)benzoic acid (0.89 g). $^1$H-NMR (300 MHz, $d_4$-MeOH): δ 8.59 (d, 1 H, J=9.6 Hz), 8.26 (d, 1 H, J=1.5 Hz), 7.72 (dd, 1 H, J=9.2, 1.8 Hz), 3.23 (q, 2 H, J=7.3 Hz), 1.17 (t, 3 H, J=7.2 Hz).

(63b) The 2-[[(ethylamino)carbonyl]amino]-5-(trifluoromethyl)benzoic acid (0.88 g, 3.2 mmol) was incorporated into procedure (47a) to provide 1.2 (Z=—C(O)—, $R^2$=2-(ethylaminocarbonyl)amino-5-(trifluoromethyl) benzoic acid, all other R=H; 0.70 g) as a white solid. $^1$H-NMR (300 MHz, $d_4$-MeOH): δ 8.46 (d, 1 H, J=8.8 Hz), 7.95 (d, 1 H, J=1.1 Hz), 7.68 (dd, 1 H, J=8.9, 1.6 Hz), 4.09 (s, 2 H), 3.22 (q, 2 H, J=7.3 Hz), 1.15 (t, 3 H, J=7.2 Hz).

(63c) The minor, (2S, 3S)-diastereomer (63 mg, 0.17 mmol) from (61b) and 1.2 (Z=—C(O)—, $R^2$=2-(ethylaminocarbonyl)amino-5-(trifluoromethyl)phenyl, all other R=H; 55 mg, 0.17 mmol) were combined in procedure (1c). The resultant product was taken through procedure (1d) and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=2-(ethylaminocarbonyl)amino-5-(trifluoromethyl)phenyl, all other R=H; 28 mg). Exact MS calcd for $C_{28}H_{39}F_3N_5O_4$, the formula for $(M+H)^+$=566.2954. Found: 566.2978.

Example 64

N-[2-[[(1S, 2R)-1-[[[(2,4-dimethylphenyl)methyl]amino]methyl]-2-(hydroxy)pentyl]amino]-2-oxoethyl]-2-[[(ethylamino)carbonyl]amino]-5-(trifluoromethyl)benzamide (64a) The major, (2S, 3R)-diastereomer (100 mg, 0.26 mmol) from (61b) and 1.2 (Z=—C(O)—, $R^2$=2-(ethylaminocarbonyl)amino-5-(trifluoromethyl)phenyl, all other R=H; cf. procedure (63b); 91 mg, 0.26 mmol) were combined in procedure (1c). The resultant product was taken through procedure (1d) and then purified by RP-HPLC to afford the title compound (1S, 2R)-1.5 (l=m=0, $R^1$=2,4-dimethylphenyl, $R^3$=—CH(OH)n-propyl, Z=—C(O)—, $R^2$=2-(ethylaminocarbonyl)amino-5-(trifluoromethyl) phenyl, all other R=H; 50 mg). Exact MS calcd for $C_{28}H_{39}F_3N_5O_4$, the formula for $(M+H)^+$=566.2954. Found: 566.2959.

Example 65

N-[2-[[(1S, 2S)-1-[[[(2,4-dimethylphenyl)methyl]amino]methyl]-2-(hydroxy)pentyl]amino]-2-oxoethyl]-2-[[(isopropylamino)carbonyl]amino]-5-(trifluoromethyl)benzamide (65a) Isopropylamine was incorporated into procedure (63a) to afford 2-[[(isopropylamino)carbonyl]amino]-5-(trifluoromethyl)benzoic acid, which was then carried through procedure (63b) to afford 1.2 (Z=—C(O)—, $R^2$=2-(isopropylaminocarbonyl)amino-5-(trifluoromethyl)phenyl, all other R=H). This material (59 mg, 0.17 mmol) and the minor, (2S, 3S)-diastereomer (65 mg, 0.17 mmol) from (61b) were combined in procedure (1c). The resultant product was taken through procedure (1d) and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=2-(isopropylaminocarbonyl)amino-5-(trifluoromethyl)phenyl, all other R=H; 30 mg). Exact MS calcd for $C_{29}H_{41}F_3N_5O_4$, the formula for $(M+H)^+$=580.3111. Found: 580.3116.

Example 66

N-[2-[[(1S, 2R)-1-[[[(2,4-dimethylphenyl)methyl]amino]methyl]-2-(hydroxy)pentyl]amino]-2-oxoethyl]-2-[[(isopropylamino)carbonyl]amino]-5-(trifluoromethyl)benzamide (66a) The major, (2S, 3R)-diastereomer (100 mg, 0.26 mmol) from (61b) and 1.2 (Z=—C(O)—, $R^2$=2-(isopropylaminocarbonyl)amino-5-(trifluoromethyl)phenyl, all other R=H; cf. procedure (65a); 92 mg, 0.26 mmol) were combined in procedure (1c). The resultant product was taken through procedure (1d) and then purified by RP-HPLC to afford the title compound (1S, 2R)-1.5 (l=m=0, $R^1$=2,4-dimethylphenyl, $R^3$ —CH(OH)n-propyl, Z=—C(O)—, $R^2$=2-(isopropylaminocarbonyl)amino-5-(trifluoromethyl) phenyl, all other R=H; 30 mg). Exact MS calcd for $C_{29}H_{41}F_3N_5O_4$, the formula for $(H+H)^+$=580.3111. Found: 580.3113.

Example 67

N-[2-[[(1S, 2S)-1-[[[(2,4-dimethylphenyl)methyl]amino]methyl]-2-(hydroxy)pentyl]amino]-2-oxoethyl]-2-[(1-pyrrolidinylcarbonyl)amino]-5-(trifluoromethyl)benzamide (67a) Pyrrolidine was incorporated into procedure (63a) to afford 2-[(1-pyrrolidinylcarbonyl)amino]-5-(trifluoromethyl)benzoic acid, which was then carried through procedure (63b) to afford 1.2 (Z=—C(O)—, $R^2$=2-(1-pyrrolidinylcarbonyl)amino-5-(trifluoromethyl)phenyl, all other R=H). This material (93 mg, 0.26 mmol) and the minor, (2S, 3S)-diastereomer (98 mg, 0.26 mmol) from (61b) were combined in procedure (1c). The resultant product was taken through procedure (1d) and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=2-(1-pyrrolidinylcarbonyl)amino-5-(trifluoromethyl)phenyl, all other R=H; 10 mg). Exact MS calcd for $C_{30}H_{41}F_3N_5O_4$, the formula for $(M+H)^+$=592.3111. Found: 592.3133.

Example 68

N-[2-[[(1S, 2S)-1-[[[(2,4-dimethylphenyl)methyl]amino]methyl]-2-(hydroxy)pentyl]amino]-2-oxoethyl]-2-[(1-azetidinylcarbonyl)amino]-5-(trifluoromethyl)benzamide (68a) A cooled (0° C.) solution of the Weinreb amide (S)-11.2 (l=m=0, PGN=CbzHN, all other R=H; 5.27 g, 13.8 mmol) in THF (20 mL) was treated with propynylmagnesium bromide (110 mL of a 0.5 M solution in THF). The reaction was stirred at RT for 3 h and recooled to 0° C. before being quenched with the addition of sat. $NH_4Cl$. The reaction was diluted with $H_2O$ and extracted with EtOAc (2×). The organic phase was washed with brine, dried ($Na_2SO_4$), filtered, and concentrated in vacuo. The resultant ketone was dissolved in THF (2 mL) and treated with (R)-Alpine Borane (Aldrich Chemical Co.; 5.5 mL of neat liquid). The reaction was stirred for 7 days at RT, concentrated in vacuo, and treated with ethanolamine (1.2 mL). After stirring for 10 min at RT, the residue was diluted with $Et_2O$ and the resultant solid was removed by suction filtration. The solution was concentrated in vacuo and the residue was purified by flash chromatography ($SiO_2$) to provide (2S, 3S)-11.5 (l=m=0, PGN=CbzHN, R=propynyl, all other R=H) as a yellow oil. MS found: $(M+Na)^+$=385.3.

(68b) Azetidine was incorporated into procedure (63a) to afford 2-[(1-azetidinylcarbonyl)amino]-5-(trifluoromethyl)benzoic acid, which was then carried through procedure (63b) to afford 1.2 (Z=—C(O)—, $R^2$=2-(1-azetidinylcarbonyl)amino-5-(trifluoromethyl)phenyl, all other R=H). This material (61 mg, 0.18 mmol) and (2S, 3S)-11.5 (l=m=0, PGN=CbzHN, R=propynyl, all other R=H; cf. procedure (68a); 67 mg, 0.18 mmol) were combined in procedure (1c). The resultant product was taken through procedure (1d) and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=2-(1-azetidinylcarbonyl)amino-5-(trifluoromethyl)phenyl, all other R=H; 10 mg). Exact MS calcd for $C_{29}H_{39}F_3N_5O_4$, the formula for $(M+H)^+$=578.2954. Found: 578.2977.

Example 69

N-[2-[[(1S, 2S)-1-[[[(2,4-dimethylphenyl)methyl]amino]methyl]-2-(hydroxy)pentyl]amino]-2-oxoethyl]-2-[[(methylamino)carbonyl]amino]-5-(trifluoromethyl)benzamide (69a) Methylamine was incorporated into procedure (63a) to afford 2-[[(methylamino)carbonyl]amino]-5-(trifluoromethyl)benzoic acid, which was then carried through procedure (63b) to afford 1.2 (Z=—C(O)—, $R^2$=2-(methylaminocarbonyl)amino-5-(trifluoromethyl)phenyl, all other R=H). This material (56 mg, 0.18 mmol) and (2S, 3S)-11.5 (l=m=0, PGN=CbzHN, R=propynyl, all other R=H; cf. procedure (68a); 67 mg, 0.18 mmol) were combined in procedure (1c). The resultant product was taken through procedure (1d) and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=2-(methylaminocarbonyl)amino-5-(trifluoromethyl)phenyl, all other R=H; 5 mg). Exact MS calcd for $C_{27}H_{37}F_3N_5O_4$, the formula for $(M+H)^+$=552.2798. Found: 552.2822.

Example 70

N-[2-[[(1S, 2R)-1-[[[(2,4-dimethylphenyl)methyl]amino]methyl]-2-(hydroxy)pentyl]amino]-2-oxoethyl]-2-[[(4-mopholinylcarbonyl)]amino]-5-(trifluoromethyl)benzamide (70a) N-Boc glycine (36 mg, 0.21 mmol) and (2S, 3S)-11.5 (l=m=0, PGN=CbzHN, R=propynyl, all other R=H; cf. procedure (68a); 78 mg, 0.21 mmol) were combined in procedure (1c) to afford (1S, 2S)-1.6 (l=m=0, PGN=CbzHN, $R^3$=—CH(OH)n-propyl, all other R=H; 84 mg). MS found: $(M+H)^+$=420.5.

(70b) Morpholine was incorporated into procedure (63a) to afford 2-[(4-morpholinylcarbonyl)amino]-5-(trifluoromethyl)benzoic acid, a portion (69 mg, 0.18 mmol) of which which was then combined with (1S, 2S)-1.6 (l=m=0, PGN=CbzHN, $R^3$=—CH(OH)n-propyl, all other R=H; cf. procedure (70a); 69 mg, 0.18 mmol) and carried through procedure (1c). A portion (32 mg, 0.06 mmol) of the resultant product was taken through procedure (1d) and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=2-(4-morpholinylcarbonyl)amino-5-(trifluoromethyl)phenyl, all other R=H; 3 mg). Exact MS calcd for $C_{30}H_{41}F_3N_5O_5$, the formula for $(M+H)^+$=608.3060. Found: 608.3048.

Example 71

N-[2-[[(1S, 2R)-1-[[[(2,4-dimethylphenyl)methyl]amino]methyl]-2-(hydroxy)pentyl]amino]-2-oxoethyl]-2-[[(1-piperazinylcarbonyl)]amino]-5-(trifluoromethyl)benzamide (71a) Piperazine was incorporated into procedure (63a) to afford 2-[[(N-Boc 1-piperazinyl)carbonyl]amino]-5-(trifluoromethyl)benzoic acid, a portion (130 mg, 0.28 mmol) of which which was then combined with (1S, 2S)-1.6 (l=m=0, PGN=CbzHN, $R^3$=—CH(OH)n-propyl, all other R=H; cf. procedure (70a); 103 mg, 0.28 mmol) and carried through procedure (1c). The resultant product was taken through procedures (1d) and (48a), and then purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=2-(1-piperazinylcarbonyl)amino-5-(trifluoromethyl)phenyl, all other R=H; 3 mg). Exact MS calcd for $C_{30}H_{42}F_3N_6O_4$, the formula for $(M+H)^+$=607.3220. Found: 607.3227.

Example 72

N-[2-[[(1S, 2S)-1-[[[(4-ethylphenyl)methyl]amino]methyl]-2-(hydroxy)pentyl]amino]-2-oxoethyl]-2-[[(1,1-dimethylethoxy)carbonyl]amino]-5-(trifluoromethyl)benzamide (72a) The compound 1.2 (Z=—C(O)—, $R^2$=N-Boc 2-amino-5-(trifluoromethyl)benzoic acid, all other R=H; cf. procedure (47a); 68.4 mg, 0.26 mmol) and (2S, 3S)-11.5 (l=m=0, PGN=CbzHN, R=propynyl, all other R=H; cf. procedure (68a); 110 mg, 0.30 mmol) were combined in procedure (1c). A portion (24 mg, 0.05 mmol) of the resultant product was combined with paraethylbenzaldehyde (0.007 mL, 0.05 mmol) and taken through procedure (1d). The crude product was purified by RP-HPLC to afford the title compound (1S, 2S)-1.5 (l=m=0, $R^1$=4-ethylphenyl, $R^3$=—CH(OH)n-propyl, Z=—C(O)—, $R^2$=N-Boc 2-amino-5-(trifluoromethyl)phenyl, all other R=H; 12 mg). Exact MS calcd for $C_{30}H_{42}F_3N_4O_5$, the formula for $(M+H)^+$=595.3107. Found: 595.3128.

Example 73

N-[2-[[(1S, 2S)-1-[[[(4-ethylphenyl)methyl]amino]methyl]-2-(hydroxy)pentyl]amino]-2-oxoethyl]-2-amino-5-(trifluoromethyl)benzamide (73a) A sample of (1S, 2S)-1.5 (l=m=0, $R^1$=4-ethylphenyl, $R^3$=—CH(OH)n-propyl, Z=—C(O)—, $R^2$=N-Boc 2-amino-5-(trifluoromethyl)phenyl, all other R=H; cf. procedure (72a); 8 mg) was taken through procedure (48a). The residue was purified by RP-HPLC to afford the title compound (1S, 2S)-1.5 (l=m=0, $R^1$=4-ethylphenyl, $R^3$=—CH(OH)n-propyl, Z=—C(O)—, $R^2$=2-amino-5-(trifluoromethyl)phenyl, all other R=H; 3 mg). Exact MS calcd for $C_{25}H_{34}F_3N_4O_3$, the formula for $(M+H)^+$=495.2583. Found: 495.2591.

Example 74

N-[2-[[(1S, 2S)-1-[[[(4-ethylphenyl)methyl]amino]methyl]-2-(hydroxy)pentyl]amino]-2-oxoethyl]-2-[[(isopropylamino)carbonyl]amino]-5-(trifluoromethyl)benzamide (74a) The compound 1.2 (Z=—C(O)—, $R^2$=2-(isopropylaminocarbonyl)amino-5-(trifluoromethyl)phenyl, all other R=H; cf. procedure (65a); 0.93 g, 2.67 mmol) and (2S, 3S)-11.5 (l=m=0, PGN=CbzHN, R=propynyl, all other R=H; cf. procedure (68a); 1.0 g, 2.76 mmol) were combined in procedure (1c). A portion (52 mg, 0.11 mmol) of the resultant product was combined with 4-ethylbenzaldehyde (0.015 mL, 0.11 mmol) and taken through procedure (1d). The crude product was purified by RP-HPLC to afford the title compound (1S, 2S)-1.5 (l=m=0, $R^1$=4-ethylphenyl, $R^3$=—CH(OH)n-propyl, Z=—C(O)—, $R^2$=2-(isopropylaminocarbonyl)amino-5-(trifluoromethyl)phenyl, all other R=H; 20 mg). Exact MS calcd for $C_{29}H_{41}F_3N_5O_4$, the formula for $(M+H)^+$=580.3111. Found: 580.3131.

Example 75

N-[2-[[(1S, 2S)-1-[[[(4-ethylphenyl)methyl]amino]methyl]-2-(hydroxy)pentyl]amino]-2-oxoethyl]-2-[(4-morpholinylcarbonyl)amino]-5-(trifluoromethyl)benzamide (75a) The compound 2-[(4-morpholinylcarbonyl)amino]-5-(trifluoromethyl)benzoic acid (cf. procedure (70b); 69 mg, 0.18 mmol) was combined with (1S, 2S)-1.6 (l=m=0, PGN=CbzHN, $R^3$=—CH(OH)n-propyl, all other R=H; cf. procedure (70a); 69 mg, 0.18 mmol) and carried through procedure (1c). A portion (32 mg, 0.06 mmol) of the resultant product was combined with 4-ethylbenzaldehyde (0.009 mL, 0.06 mmol) and taken through procedure (1d). The crude product was purified by RP-HPLC to afford the title compound (1S, 2S)-1.5 (l=m=0, $R^1$=4-ethylphenyl, $R^3$=—CH(OH)n-propyl, Z=—C(O)—, $R^2$=2-(4-morpholinylcarbonyl)amino-5-(trifluoromethyl)phenyl, all other R=H; 3 mg). MS found: $(M+H)^+$=608.5.

Example 76

N-[2-[[(1S, 2S)-1-[[[(4-dimethylamino-2-methylphenyl)methyl]amino]methyl]-2-(hydroxy)pentyl]amino]-2-oxoethyl]-2-[[(1,1-dimethylethoxy)carbonyl]amino]-5-(trifluoromethyl)benzamide (76a) The compound 1.2 (Z=—C(O)—, $R^2$=N-Boc 2-amino-5-(trifluoromethyl)benzoic acid, all other R=H; cf. procedure (47a); 68.4 mg, 0.26 mmol) and (2S, 3S)-11.5 (l=m=0, PGN=CbzHN, R=propynyl, all other R=H; cf. procedure (68a); 110 mg, 0.30 mmol) were combined in procedure (1c). A portion (24 mg, 0.05 mmol) of the resultant product was combined with 4-dimethylamino-2-methylbenzaldehyde (8.3 mg, 0.05 mmol) and taken through procedure (1d). The crude product was purified by RP-HPLC to afford the title compound (1S, 2S)-1.5 (l=m=0, $R^1$=4-dimethylamino-2-methylphenyl, $R^3$=—CH(OH)n-propyl, Z=—C(O)—, $R^2$=N-Boc 2-amino-5-(trifluoromethyl)phenyl, all other R=H; 10 mg). MS found: $(M+H)^+$=624.6.

Example 77

N-[2-[[(1S, 2S)-1-[[[(4-dimethylamino-2-methylphenyl)methyl]amino]methyl]-2-(hydroxy)pentyl]amino]-2-oxoethyl]-2-amino-5-(trifluoromethyl)benzamide (77a) A sample of (1S, 2S)-1.5 (l=m=0, $R^1$=4-dimethylamino-2-methylphenyl, $R^3$=—CH(OH)n-propyl, Z=—C(O)—, $R^2$=N-Boc 2-amino -5-(trifluoromethyl)phenyl, all other R=H; cf. procedure (76a); 7 mg) was taken through procedure (48a). The residue was purified by RP-HPLC to afford the title compound (1S, 2S)-1.5 (l=m=0, $R^1$=4-dimethylamino-2-methylphenyl, $R^3$=—CH(OH)n-propyl, Z=—C(O)—, $R^2$=2-amino-5-(trifluoromethyl)phenyl, all other R=H; 3 mg). Exact MS calcd for $C_{26}H_{37}F_3N_5O_3$, the formula for $(M+H)^+$=524.2848. Found: 524.2864.

Example 78

N-[2-[[(1S, 2S)-1-[[[(2,4-dimethyphenyl)methyl]amino]methyl]-2-(hydroxy)pentyl]amino]-2-oxoethyl]-2-(tert-butyl)amino-5-(trifluoromethyl)benzamide (78a) Allyl bromide (2.8 mL), [2-fluoro-5-(trifluoromethyl)]benzoic acid (5.5 g), and potassium carbonate (4.6 g) were dissolved in DMF (90 mL). The reaction was stirred for 12 h and diluted with water and EtOAc. The organic layer was washed with 2% LiCl solution, dried, filtered, and concentrated to provide allyl [2-fluoro-5-(trifluoromethyl)] benzoate (6.4 g). This material was dissolved in DMF (25 mL) and the solution was charged with tert-butylamine (16 mL) and potassium carbonate (7.4 g). The mixture was warmed to 40° C., stirred for 36 h, and diluted with water and EtOAc. The organic layer was washed with 2% LiCl solution, dried, filtered and concentrated to provide allyl [2-(tert-butylamino)-5-(trifluoromethyl)]benzoate (7.6 g). This material was combined with pyrrolidine (2.3 mL) and dissolved in acetonitrile (150 mL). The solution was degassed with nitrogen, and then tetrakis (triphenylphosphino) palladium(0) was added. This mixture was stirred for 8 h, and concentrated. The residue was dissolved in EtOAc and washed with 1 N HCl solution and water. The organic layer was dried, filtered, and concentrated. Flash chromatography of the resulting residue provided 2-(tert-butylamino)-5-(trifluoromethyl)]benzoic acid (4.6 g). MS found: $(M-H)^-$=260.2.

(78b) The 2-(tert-butylamino)-5-(trifluoromethyl)] benzoic acid was carried through procedure (47a) to afford 1.2 (Z=—C(O)—, $R^2$=2-(tert-butyl)amino-5-(trifluoromethyl)benzoic acid, all other R=H). A portion (56 mg, 0.18 mmol) of this material was combined with (2S, 3S)-11.5 (l=m=0, PGN=CbzHN, R=propynyl, all other R=H; cf. procedure (68a); 67 mg, 0.18 mmol) and incorporated in procedure (1c). The product was carried through procedure (1d). The crude product was purified by RP-HPLC to afford the title compound (1S, 2S)-1.5 (l=m=0, $R^1$=4-ethylphenyl, $R^3$=—CH(OH)n-propyl, Z=—C(O)—, $R^2$=2-(tert-butyl)amino-5-(trifluoromethyl)phenyl, all other R=H; 10 mg). Exact MS calcd for $C_{29}H_{42}F_3N_4O_3$, the formula for $(M+H)^+$=551.3209. Found: 551.3225.

Example 79

N-[2-[[(1S, 2S)-1-[[[(2,4-dimethylphenyl)methyl]amino]methyl]-2-(hydroxy)pentyl]amino]-2-oxoethyl]-2-isopropylamino-5-(trifluoromethyl)benzamide (79a) Isopropylamine (4.0 mL) was dissolved in THF (20 mL). This solution was cooled to 0° C. and n-butyllithium (2.5 M, 20 mL) was added. The reaction was stirred for 90 min and then transferred to a solution of 2-fluoro-5-(trifluoromethyl)benzoic acid (4.2 g) in THF (40 mL) at −78° C. This mixture was stirred for 15 min and then quenched with aqueous $NH_4Cl$. The mixture was extracted with EtOAc (3×), and the organic layer was dried, filtered, and concentrated in vacuo. Flash chromatography of the resulting residue provided 2-isopropylamino-5-(trifluoromethyl)benzoic acid (2.4 g). MS found: $(M+H)^+$= 248.2.

(79b) The 2-isopropylamino-5-(trifluoromethyl)]benzoic acid was carried through procedure (47a) to afford 1.2 (Z=—C(O)—, $R^2$=2-isopropylamino-5-(trifluoromethyl)benzoic acid, all other R=H). A portion (61 mg, 0.18 mmol) of this material was combined with (2S, 3S)-11.5 (l=m=0, PGN=CbzHN, R=propynyl, all other R=H; cf. procedure (68a); 67 mg, 0.18 mmol) and incorporated in procedure (1c). The product was carried through procedure (1d). The crude product was purified by RP-HPLC to afford the title compound (1S, 2S)-1.5 (l=m=0, $R^1$=4-ethylphenyl, $R^3$=—CH(OH)n-propyl, Z=—C(O)—, $R^2$=2-isopropylamino-5-(trifluoromethyl)phenyl, all other R=H; 10 mg). Exact MS calcd for $C_{28}H_{40}F_3N_4O_3$, the formula for $(M+H)^+$= 537.3053. Found: 537.3074.

Example 80

N-[2-[[(1S, 2S)-1-E[[(2,4-dimethylphenyl)methyl]amino]methyl]-2-(hydroxy)pentyl]amino]-2-oxoethyl]-2-benzylamino-5-(trifluoromethyl)benzamide (80a) N-Boc 2-amino-5-(trifluoromethyl)benzoic acid (S. Takagishi, et al., *Synlett* 1992, 360; 3.0 g) was dissolved in DMF prior to the addition of $K_2CO_3$ (2.4 g) and iodomethane (0.8 mL). After 1.5 h, the solution was diluted with EtOAc and was washed with brine solution followed by 1N HCl solution. The organic layer was then washed with $Na_2CO_3$ solution, water, and brine. The organic layer was dried ($MgSO_4$), filtered, and concentrated to give the ester as an off-white solid (3.03 g). A portion of this solid was dissolved in TFA (3.3 mL) and cooled to 0° C. prior to the addition of TFAA (0.97 mL). After 10 min, crushed ice was added. After an additional 30 min, the solid was collected and washed with water. The solid was dried to give the TFA amide (970 mg). A portion of this solid (583 mg) was dissolved in DMF (12 mL), and the solution was charged with $K_2CO_3$ (511 mg) and benzyl bromide (0.24 mL). The reaction was stirred 18 h before it was diluted with EtOAc and washed with 1N HCl and brine. The EtOAc was dried ($MgSO_4$), filtered, and concentrated in vacuo. The resulting residue was dissolve in THF (10 mL) prior to addition of 1N LiOH (10 mL) and 20 drops of MeOH. After 18 h, the THF was removed and the solution was made acidic (pH=5) with 1N HCl. This solution was extracted with EtOAc. The organic layer was washed with brine, dried, filtered, and concentrated to give 2-benzylamino-5-trifluoromethylbenzoic acid (500 mg). MS found: $(2M-H)^-$=589.1.

(80b) The compound from procedure (80a), 2-benzylamino-5-(trifluoromethyl)benzoic acid (58 mg, 0.20 mmol), was combined with (1S, 2S)-1.6 (l=m=0, PGN=CbzHN, $R^3$=—CH(OH)n-propyl, all other R=H; cf. procedure (70a); 64 mg, 0.20 mmol) and carried through procedures (1c) and (1d). The crude product was purified by RP-HPLC to afford the title compound (1S, 2S)-1.5 (l=m=0, $R^1$=2,4-dimethylphenyl, $R^3$=—CH(OH)n-propyl, Z=—C(O)—, $R^2$=2-benzylamino-5-(trifluoromethyl)phenyl, all other R=H; 5 mg). MS found: $(M+H)^+$=585.6.

Example 81

N-[2-[[(1S, 2S)-1-[[[(2,4-dimethylphenyl)methyl]amino]methyl]-2-(methoxy)pentyl]amino]-2-oxoethyl]-2-[[(1,1-dimethylethoxy)carbonyl]amino]-5-(trifluoromethyl)benzamide (81a) To a cooled (0° C.), light-protected solution of (2S, 3S)-11.5 (l=m=0, PGN=CbzHN, R=propynyl, all other R=H; cf. procedure (68a); 0.27 g, 0.75 mmol) in methylene chloride (8 mL) was added $Me_3OBF_3$ (0.15 g, 1.0 mmol) and then proton sponge (0.21 g, 0.98 mmol). The reaction was stirred for 2 days in the dark and then diluted with methylene chloride and filtered through a pad of Celite. The filtrate was washed with 1N HCl (2×) and brine (1×), and then dried ($MgSO_4$), filtered, and concentrated in vacuo. The residue was purified via flash chromatography ($SiO_2$) to afford the desired (2S, 3S)-11.6 (l=m=0, PGN=CbzHN, R=propynyl, R'=Me, all other R=H; 49 mg). MS found: $(M+Na)^+$=399.4.

(81b) The compound 1.2 (Z=—C(O)—, $R^2$=N-Boc 2-amino-5-(trifluoromethyl)benzoic acid, all other R=H; cf. procedure (47a); 54 mg, 0.15 mmol) and (2S, 3S)-11.6 (l=m=0, PGN=CbzHN, R=propynyl, R'=Me, all other R=H; cf. procedure (81a); 49 mg, 0.13 mmol) were combined in procedure (1c). The product was taken through procedure (1d), and the resultant product was purified by RP-HPLC to afford the title compound (1S, 2S)-1.5 (l=m=0, $R^1$=2,4-dimethylphenyl, $R^3$=—CH(OMe)n-propyl, Z=—C(O)—, $R^2$=N-Boc 2-amino -5-(trifluoromethyl)phenyl, all other R=H; 15 mg). Exact MS calcd for $C_{31}H_{44}F_3N_4O_5$, the formula for $(M+H)^+$=609.3264. Found: 609.3270.

Example 82

N-[2-[[(1S, 2S)-1-[[[(2,4-dimethylphenyl)methyl]amino]methyl]-2-(methoxy)pentyl]amino]-2-oxoethyl]-2-amino-5-(trifluoromethyl)benzamide (82a) A sample of (1S, 2S)-1.5 (l=m=0, $R^1$=2,4-dimethylphenyl, $R^3$=—CH(OMe)n-propyl, Z=—C(O)—, $R^2$=N-Boc 2-amino -5-(trifluoromethyl)phenyl, all other R=H; 11 mg) from procedure (81b) was taken through procedure (48a). The resultant product was purified by RP-HPLC to afford the title compound (1S, 2S)-1.5 (l=m=0, $R^1$=2,4-dimethylphenyl, $R^3$=—CH(OMe)n-propyl, Z=—C(O)—, $R^2$=2-amino-5-(trifluoromethyl)phenyl, all other R=H; 10 mg). MS found: $(M+H)^+$=509.5.

Example 83

N-[2-[[(S)-1-[[[(2,4-dimethylphenyl)methyl]amino]methyl]-2-hydroxy-2-(methyl)propyl]amino]-2-oxoethyl]-2-[[(1,1-dimethylethoxy)carbonyl]amino]-5-(trifluoromethyl)benzamide (83a) To a cooled (−78° C.) solution of the Weinreb amide (S)-11.2 (l=m=0, PGN=CbzHN, all other R=H; 0.26 g, 0.69 mmol) in THF (7 mL) was added methyl lithium (4.0 mL of a 1.0 M solution in THF). The reaction was stirred for 2 h at −78° C. and 30 min at RT. The mixture was recooled to −78° C. and quenched with sat. $NH_4Cl$. The mixture was diluted with EtOAc, washed with sat. $NH_4Cl$ (2×) and brine (1×), and dried ($Na_2SO_4$), filtered, and concentrated in vacuo. The residue was resubjected to the identical procedure, including the aqueous workup, and the resultant residue was purified by flash chromatography to afford the desired (S)-11.4 (l=m=0, PGN=CbzHN, R=R"=methyl, all other R=H; 74 mg). MS found: $(M+Na)^+$=375.4.

(83b) The compound 1.2 (Z=—C(O)—, $R^2$=N-Boc 2-amino-5-(trifluoromethyl)benzoic acid, all other R=H; cf. procedure (47a); 88 mg, 0.24 mmol) and (S)-11.4 (l=m=0, PGN=CbzHN, R=R"=methyl, all other R=H; cf. procedure (83a); 74 mg, 0.21 mmol) were combined in procedure (1c). The product was taken through procedure (1d), and the resultant product was purified by RP-HPLC to afford the title compound (S)-1.5 (l=m=0, $R^1$=2,4-dimethylphenyl, $R^3$=—C(OH)Me$_2$, Z=—C(O)—, $R^2$=N-Boc 2-amino-5-(trifluoromethyl)phenyl, all other R=H; 10 mg). Exact MS calcd for $C_{29}H_{40}F_3N_4O_5$, the formula for $(M+H)^+$=581.2951. Found: 581.2940.

Example 84

N-[2-[[(S)-1-[[[(2,4-dimethylphenyl)methyl]amino]methyl]-2-hydroxy-2-(methyl)propyl]amino]-2-oxoethyl]-2-amino-5-(trifluoromethyl)benzamide (84a) A sample of (S)-1.5 (l=m=0, $R^1$=2,4-dimethylphenyl, $R^3$=—C(OH)Me$_2$, Z=—C(O)—, $R^2$=N-Boc 2-amino -5-(trifluoromethyl)phenyl, all other R=H; 11 mg) from procedure (83b) was taken through procedure (48a). The resultant product was purified by RP-HPLC to afford the title compound (S)-1.5 (l=m=0, $R^1$=2,4-dimethylphenyl, $R^3$=—C(OH)Me$_2$, Z=—C(O)—, $R^2$=2-amino-5-(trifluoromethyl)phenyl, all other R=H; 10 mg). MS found: $(M+H)^+$=481.4.

Example 85

N-[2-[[(S)-1-[[[(2,4-dimethylphenyl)methyl]amino]methyl]-2-hydroxy-2-(ethyl)butyl]amino]-2-oxoethyl]-2-[[(1,1-dimethylethoxy)carbonyl]amino]-5-(trifluoromethyl)benzamide (85a) To a cooled (0° C.) solution of Weinreb amide (S)-11.2 (l=m=0, PGN=CbzHN, all other R=H; 0.25 g, 0.66 mmol) in THF (7 mL) was added ethylmagnesium bromide (2.0 mL of a 2.0 M solution in THF). The reaction was stirred for 3 h in the melting ice bath (during which time it warms to RT). The mixture was recooled to 0° C. and quenched with sat. $NH_4Cl$. The mixture was diluted with EtOAc, washed with sat. $NH_4Cl$ (2×) and brine (1×), and dried ($Na_2SO_4$), filtered, and concentrated in vacuo. The residue was resubjected to the identical procedure, including the aqueous workup, and the resultant residue was purified by flash chromatography to afford the desired (S)-11.4 (l=m=0, PGN=CbzHN, R=R"=ethyl, all other R=H; 125 mg).

(85b) The compound 1.2 (Z=—C(O)—, $R^2$=N-Boc 2-amino-5-(trifluoromethyl)benzoic acid, all other R=H; cf. procedure (47a); 140 mg, 0.39 mmol) and (S)-11.4 (l=m=0, PGN=CbzHN, R=R"=ethyl, all other R=H; cf. procedure (85a); 125 mg, 0.33 mmol) were combined in procedure (1c). The product was taken through procedure (1d), and the resultant product was purified by RP-HPLC to afford the title compound (S)-1.5 (l=m=0, $R^1$=2,4-dimethylphenyl, $R^3$=—C(OH)Et$_2$, Z=—C(O)—, $R^2$=N-Boc 2-amino-5-(trifluoromethyl)phenyl, all other R=H; 10 mg). Exact MS calcd for $C_{31}H_{44}F_3N_4O_5$, the formula for $(M+H)^+$=609.3264. Found: 609.3291.

Example 86

N-[2-[[(S)-1-[[[(2,4-dimethylphenyl)methyl]amino]methyl]-2-hydroxy-2-(ethyl)butyl]amino]-2-oxoethyl]-2-amino-5-(trifluoromethyl)benzamide (86a) A sample of (S)-1.5 (l=m=0, $R^1$=2,4-dimethylphenyl, $R^3$=—C(OH)Et$_2$, Z=—C(O)—, $R^2$=N-Boc 2-amino -5-(trifluoromethyl)phenyl, all other R=H; 11 mg) from procedure (85b) was taken through procedure (48a). The resultant product was purified by RP-HPLC to afford the title compound (S)-1.5 (l=m=0, $R^1$=2,4-dimethylphenyl, $R^3$=—C(OH)Et$_2$, Z=—C(O)—, $R^2$=2-amino-5-(trifluoromethyl)phenyl, all other R=H; 5 mg). MS found: $(M+H)^+$=509.4.

Example 87

N-[2-[[(S)-1-[[[(2,4-dimethylphenyl)methyl]amino]methyl]-2-hydroxy-2-(propyl)pentyl]amino]-2-oxoethyl]-2-[[(1,1-dimethylethoxy)carbonyl]amino]-5-(trifluoromethyl)benzamide (87a) To a cooled (0° C.) solution of Weinreb amide (S)-11.2 (l=m=0, PGN=CbzHN, all other R=H; 1.07 g, 2.8 mmol) in THF (25 mL) was added allylmagnesium bromide (17.0 mL of a 1.0 M solution in THF). The reaction was stirred for 3 h in the melting ice bath (during which time it warms to RT). The mixture was recooled to 0° C. and quenched with sat. $NH_4Cl$. The mixture was diluted with EtOAc, washed with sat. $NH_4Cl$ (2×) and brine (1×), and dried ($Na_2SO_4$), filtered, and concentrated in vacuo. The residue was resubjected to the identical procedure, including the aqueous workup, and the resultant residue was purified by flash chromatography to afford the desired (S)-11.4 (l=m=0, PGN=CbzHN, R=R"=allyl, all other R=H; 560 mg). MS found: $(M+Na)^+$=427.4.

(87b) The compound 1.2 (Z=—C(O)—, $R^2$=N-Boc 2-amino-5-(trifluoromethyl)benzoic acid, all other R=H; cf. procedure (47a); 176 mg, 0.49 mmol) and (2S, 3S)-11.4 (l=m=0, PGN=CbzHN, R=R"=allyl, all other R=H; cf. procedure (87a); 137 mg, 0.45 mmol) were combined in procedure (1c). The product was taken through procedure (1d), and the resultant product was purified by RP-HPLC to afford the title compound (S)-1.5 (l=m=0, $R^1$=2,4-dimethylphenyl, $R^3$=—C(OH)n-Pr$_2$, Z=—C(O)—, $R^2$=N-Boc 2-amino-5-(trifluoromethyl)phenyl, all other R=H; 10 mg). MS found: $(M+H)^+$=637.6.

Example 88

N-[2-[[(S)-1-[[[(2,4-dimethylphenyl)methyl]amino]methyl]-2-hydroxy-2-(propyl)pentyl]amino]-2-oxoethyl]-2-amino-5-(trifluoromethyl)benzamide (88a) A sample of (S)-1.5 (l=m=0, $R^1$=2,4-dimethylphenyl, $R^3$=—C(OH)n-Pr$_2$, Z=—C(O)—, $R^2$=N-

Boc 2-amino -5-(trifluoromethyl)phenyl, all other R=H; 11 mg) from procedure (87b) was taken through procedure (48a). The resultant product was purified by RP-HPLC to afford the title compound (S)-1.5 (l=m=0, $R^1$=2,4-dimethylphenyl, $R^3$=—C(OH)n-$Pr_2$, Z=—C(O)—, $R^2$=2-amino-5-(trifluoromethyl)phenyl, all other R=H; 5 mg). Exact MS calcd for $C_{28}H_{40}F_3N_4O_3$, the formula for $(M+H)^+$=537.3053. Found: 537.3065.

Example 89

N-[2-[[(S)-2-[[(2,4-dimethylphenyl)methyl]amino]-1-(hydroxycyclopentyl)ethyl]amino]-2-oxoethyl]-2-[[(1,1-dimethylethoxy)carbonyl]amino]-5-(trifluoromethyl)benzamide (89a) To a solution of (S)-11.4 (l=m=0, PGN=CbzHN, R=R"=allyl, all other R=H; 140 mg) in methylene chloride (4 mL) was added tricyclohexylphosphine[1,3-bis (2,4,6-trimethylphenyl)-4,5-dihydroimidazol-2-ylidene][benzylidene]ruthenium (IV) dichloride (Strem, Inc.; ca. 2 mg, catalytic amount). The reaction was stirred for 12 h at RT before being concentrated in vacuo. The residue was purified by flash chromatography to provide (S)-11.4 (l=m=0, PGN=CbzHN, R=R"=—$CH_2$C=$CCH_2$—, all other R=H; 31 mg). MS found: $(M+H)^+$=399.4.

(89b) The compound 1.2 (Z=—C(O)—, $R^2$=N-Boc 2-amino-5-(trifluoromethyl)benzoic acid, all other R=H; cf. procedure (47a); 92 mg, 0.25 mmol) and (S)-11.4 (l=m=0, PGN=CbzHN, R=R"=—$CH_2$C=$CCH_2$—, all other R=H; cf. procedure (89a); 59 mg, 0.16 mmol) were combined in procedure (1c). The product was taken through procedure (1d), and the resultant product was purified by RP-HPLC to afford the title compound (S)-1.5 (l=m=0, $R^1$=2,4-dimethylphenyl, $R^3$=—C(OH)c-$C_4H_8$, Z=—C(O)—, $R^2$=N-Boc 2-amino-5-(trifluoromethyl)phenyl, all other R=H; 15 mg). MS found: $(M+H)^+$=607.5.

Example 90

N-[2-[[(S)-1-[[(S)-2-[[(2,4-dimethylphenyl)methyl]amino]-1-(hydroxycyclopentyl)ethyl]amino]-2-oxoethyl]-2-amino-5-(trifluoromethyl)benzamide (90a) A sample of (S)-1.5 (l=m=0, $R^1$=2,4-dimethylphenyl, $R^3$=—C(OH)c-$C_4H_8$, Z=—C(O)—, $R^2$=N-Boc 2-amino -5-(trifluoromethyl)phenyl, all other R=H; 10 mg) from procedure (89b) was taken through procedure (48a). The resultant product was purified by RP-HPLC to afford the title compound (S)-1.5 (l=m=0, $R^1$=2,4-dimethylphenyl, $R^3$=—C(OH)c-$C_4H_8$, Z=—C(O)—, $R^2$=2-amino-5-(trifluoromethyl)phenyl, all other R=H; 3 mg). Exact MS calcd for $C_{26}H_{34}F_3N_4O_3$, the formula for $(M+H)^+$=507.2583. Found: 507.2588.

Example 91

(2S)-N-tert-Butyl-3-[[(2,4-dimethylphenyl)methyl]amino]-2-[[[[3-(trifluoromethoxy)benzoyl]amino]acetyl]amino]-propanamide (91a) The compound (S)-1.6 (l=m=0, PGN=CbzHN, $R^3$=CONHt-Bu, all other R=H; cf. procedure (33b); 1.4 g, 3.1 mmol) was incorporated into procedure (1d). The resultant secondary amine (1.1 g, 2.6 mmol) was dissolved in THF (39 mL). The solution was charged with triethylamine (0.69 mL, 5.2 mmol) and dibenzyldicarbonate (893 mg, 3.1 mmol) and stirred for 48 h before being concentrated in vacuo. The residue was dissolved in EtOAc, and the solution was washed successively with 1N HCl, water, and brine. The organic phase was dried ($Na_2SO_4$), filtered, and concentrated in vacuo to give (S)-1.6 (l=m=0, PGN=2,4-$Me_2$Ph (Cbz)N, $R^3$=CONHt-Bu, all other R=H; 0.7 g). MS found: $(M+H)^+$=569.3.

(91b) A solution of (S)-1.6 (l=m=0, PGN=2,4-$Me_2$Ph (Cbz)N, $R^3$=CONHt-Bu, all other R=H; 65 mg, 0.14 mmol) in DMF (3 mL) was charged successively with 3-trifluoromethoxybenzoic acid (29 mg, 0.14 mmol), N,N-diisopropylethylamine (0.06 mL, 0.35 mmol), and HATU (63 mg, 0.17 mmol). The mixture was stirred for 12 h and diluted with EtOAc. The organic phase was washed with water (2×), sat. $NaHCO_3$, water, and brine. The organic phase was then dried ($Na_2SO_4$), filtered, and concentrated in vacuo. The product was dissolved in MeOH (2 mL) and the solution was charged with 5% Pd/C, Degussa (13 mg). The reaction vessel was evacuated and back-filled with hydrogen several times over the course of 4 h. The mixture was filtered and the filtrate was concentrated in vacuo. Purification by RP-HPLC afforded the title compound (S)-1.5 ($R^1$=2,4-dimethylphenyl, $R^3$=—C(O)NHt-Bu, Z=—C(O)—, $R^2$=3-trifluoromethoxyphenyl, all other R=H; 3 mg). Exact MS calcd for $C_{26}H_{34}F_3N_4O_4$, the formula for $(M+H)^+$=523.2532. Found: 523.2521.

Example 92

(2S)-N-tert-Butyl-3-[[(2,4-dimethylphenyl)methyl]amino]-2-[[[3-(difluoromethyl)benzoyl]amino]acetyl]amino]-propanamide (92a) A solution of meta-cyanobenzaldehyde (1.3 g, 10 mmol) in methylene chloride (30 mL) was charged with DAST (1.3 mL, 10 mmol) and stirred for 3 h at RT. The mixture was poured into water and extracted with methylene chloride (2×). The organic extracts were combined, washed with brine, dried ($Na_2SO_4$), filtered, and concentrated in vacuo. The resultant 3-difluoromethyl-benzonitrile was dissolved in dioxane (15 mL) and 6N HCl (20 mL) and heated at 100° C. for 18 h. The mixture was cooled to RT and extracted with EtOAc (2×). The organic extracts were washed with brine, dried ($Na_2SO_4$), filtered, and concentrated in vacuo. Analysis by $^1$H-NMR showed 45% conversion to the benzoic acid. The residue was dissolved in $Et_2O$ and washed with 1N NaOH. The organic layer was discarded; the aqueous layer was acidified with 12M HCl and extracted with EtOAc (2×). The organic extracts were combined, washed with brine, dried ($Na_2SO_4$), filtered, and concentrated in vacuo to provide pure 3-(difluoromethyl) benzoic acid as a white solid (459 mg).

(92b) The compound 3-(difluoromethyl)benzoic acid (52 mg) was incorporated into procedure (91b). A portion (13.5 mg) of the resultant product was dissolved in ethanol (0.2 mL) and the solution was charged with 10% Pd/C (7 mg) and cyclohexene (0.01 mL). The reaction mixture was heated at 80° C. for 30 min, cooled to RT, and filtered. The filtrate was concentrated in vacuo. Purification by RP-HPLC afforded the title compound (S)-1.5 ($R^1$=2,4-dimethylphenyl, $R^3$=—C(O)NHt-Bu, Z=—C(O)—, $R^2$=3-difluoromethylphenyl, all other R=H; 5 mg). Exact MS calcd for $C_{26}H_{35}F_2N_4O_3$, the formula for $(M+H)^+$=489.2677. Found: 489.2665.

Example 93

(2S)-N-tert-Butyl-3-[[(2,4-dimethylphenyl)methyl]amino]-2-[[[[3-(trifluoromethylthio)benzoyl]amino]acetyl]amino]-propanamide (93a) The compound 3-(trifluoromethylthio)benzoic acid (25 mg, 0.11 mmol) was incorporated into procedure (91b).

Purification by RP-HPLC afforded the title compound (S)-1.5 ($R^1$=2,4-dimethylphenyl, $R^3$=—C(O)NHt-Bu, Z=—C(O)—, $R^2$=3-($F_3$CS)phenyl, all other R=H; 5 mg). Exact MS calcd for $C_{26}H_{34}S_1F_3N_4O_3$, the formula for $(M+H)^+$= 539.2304. Found: 539.2292.

Example 94

(2S)-N-tert-Butyl-3-[[(2,4-dimethylphenyl)methyl]amino]-2-[[[[3-(pentafluoroethyl)benzoyl]amino]acetyl]amino]-propanamide (94a) Methyl 3-iodobenzoate (1.0 g) was dissolved in DMF (10 mL) and toluene (4 mL) prior to the addition of CuI (1.34 g) and $CF_3CF_2CO_2Na$ (1.45 g). This mixture was heated at 130° C. and some toluene was removed via a Dean-Stark trap (Freskos, *J. Syn Comm.* 1988, 965). The mixture was then heat at 155° C. for 2 h. After cooling the solution was poured into water and $Et_2O$. The organic layer was dried and concentrated. The resulting residue was dissolved in THF (6 mL) and MeOH (1 mL) prior to the addition of 1M $LiOH/H_2O$ solution (9.3 mL). After 3 h, the solution was partially concentrated. The reaction was quenched with 1N HCl solution and extracted with EtOAc. The organic layer was dried and concentrated in vacuo. MS found: $(M-H)^-$=239.1.

(94b) The compound 3-(pentafluoroethyl)benzoic acid (29 mg, 0.12 mmol) was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=3-(pentafluoroethyl)phenyl, all other R=H; 5 mg). Exact MS calcd for $C_{27}H_{34}F_5N_4O_3$, the formula for $(M+H)^+$=557.2551. Found: 557.2524.

Example 95

(2S)-N-tert-Butyl-2-[[[[2-amino-5-(trifluoromethoxy)benzoyl]amino]acetyl]amino]-3-[[(2,4-dimethylphenyl)methyl]amino]-propanamide (95a) A cooled (−78° C.) solution of para-(trifluoromethoxy)aniline (3.2 mL, 24 mmol) in THF (200 mL) was charged with NaHMDS (53 mL of a 1.0 M THF solution) and stirred for 1 h. The mixture was then charged with a solution of di-(tert-butyl)dicarbonate (5.3 g, 24 mmol) in THF (40 mL) and stirred for 14 h, during which time it slowly warmed to RT. The reaction was concentrated in vacuo and the residue was dissolved in EtOAc. The organic phase was washed successively with 1N, water, and brine before being dried ($Na_2SO_4$), filtered, and concentrated in vacuo to provide N-Boc para-(trifluoromethoxy)aniline (6.2 g). The entirity of this product was dissolved in THF (112 mL), and the resultant solution was cooled to −78° C. before being charged with sec-butyllithium (38 mL of a 1.3 M solution). The solution was warmed to −40° C. and stirred at that temperature for 3 h. The reaction vessel was then evacuated and back-filled with carbon dioxide. The mixture was stirred for 14 h, during which time it slowly warmed to RT. The mixture was then treated with 1N HCl, stirred for 10 min, and extracted with EtOAc (2×). The organic extracts were washed with brine, dried ($Na_2SO_4$), filtered, and concentrated in vacuo. The residue was purified by flash chromatography to afford N-Boc 2-amino-3-(trifluoromethoxy)benzoic acid (3.4 g).

(95b) A solution of (S)-1.6 (l=m=0, PGN=2,4-$Me_2$Ph (Cbz)N, $R^3$=CONHt-Bu, all other R=H; cf. procedure (91a), 55 mg, 0.12 mmol) in 1:1 methylene chloride/DMF (3 mL) was charged successively with N-Boc 2-amino-3-(trifluoromethoxy)benzoic acid (37 mg, 0.12 mmol), N,N-diisopropylethylamine (0.05 mL, 0.21 mmol), and HATU (53 mg, 0.14 mmol). The mixture was stirred for 12 h and diluted with EtOAc. The organic phase was washed with water (2×), sat. $NaHCO_3$, water, and brine. The organic phase was then dried ($Na_2SO_4$), filtered, and concentrated in vacuo. The product was carried through procedure (48a) to provide (S)-1.5 ($R^1$=2,4-dimethylphenyl, $R^3$=—C(O)NHt-Bu, Z=—C(O)—, $R^2$=2-amino-3-(trifluoromethoxy)phenyl, all other R=H; 15 mg) after purification by RP-HPLC. MS found: $(M+H)^+$=672.3.

(95c) A sample of (S)-1.5 ($R^1$=2,4-dimethylphenyl, $R^3$=—C(O)NHt-Bu, Z=—C(O)—, $R^2$=2-amino-3-(trifluoromethoxy)phenyl, all other R=H; 15 mg) was dissolved in MeOH (2 mL) and the solution was charged with 5% Pd/C, Degussa (13 mg). The reaction vessel was evacuated and back-filled with hydrogen several times over the course of 4 h. The mixture was filtered and the filtrate was concentrated in vacuo. Purification by RP-HPLC afforded the title compound (S)-1.5 ($R^1$=2,4-dimethylphenyl, $R^3$=—C(O)NHt-Bu, Z=—C(O)—, $R^2$=2-amino-3-(trifluoromethoxy)phenyl, all other R=H; 4 mg). Exact MS calcd for $C_{26}H_{35}F_3N_3O_4$, the formula for $(M+H)^+$=538.2641. Found: 538.2644.

Example 96

(2S)-N-tert-Butyl-2-[[[[2-amino-5-(methyl)benzoyl]amino]acetyl]amino]-3-[[(2,4-dimethylphenyl)methyl]amino]-propanamide (96a) The compound 2-amino-5-(methyl)benzoic acid (65 mg, 0.14 mmol) was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-amino-5-(methyl)phenyl, all other R=H; 5 mg). Exact MS calcd for $C_{26}H_{38}N_5O_3$, the formula for $(M+H)^+$=468.2975. Found: 468.3002.

Example 97

(2S)-N-tert-Butyl-3-[[(2,4-dimethylphenyl)methyl]amino]-2-[[[[2-ethylamino-5-(trifluoromethyl)benzoyl]amino]acetyl]amino]-propanamide (97a) Iodoethane was incorporated into procedure (80a) to afford 2-ethylamino-5-trifluoromethylbenzoic acid, a portion (52 mg, 0.11 mmol) of which was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-ethylamino-5-(trifluoromethyl)phenyl, all other R=H; 5 mg). Exact MS calcd for $C_{28}H_{39}F_3N_5O_3$, the formula for $(M+H)^+$=550.3005. Found: 550.3013.

Example 98

(2S)-N-tert-Butyl-3-[[(2,4-dimethylphenyl)methyl]amino]-2-[[[[2-propylamino-5-(trifluoromethyl)benzoyl]amino]acetyl]amino]-propanamide (98a) Allyl iodide was incorporated into procedure (80a) to afford 2-allylamino-5-trifluoromethylbenzoic acid, a portion (20 mg, 0.08 mmol) of which was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-propylamino-5-(trifluoromethyl)phenyl, all other R=H; 5 mg). Exact MS calcd for $C_{29}H_{41}F_3N_5O_3$, the formula for $(M+H)^+$=564.3161. Found: 564.3187.

Example 99

(2S)-N-tert-Butyl-3-[[(2,4-dimethylphenyl)methyl]amino]-2-[[[[2-isobutylamino-5-(trifluoromethyl)benzoyl]amino]acetyl]amino]-propanamide (99a) The compound 2-methylpropenyl bromide was incorporated into procedure (80a) to afford 2-(methylpropenyl)amino-5-(trifluoromethyl) benzoic acid, a portion (17 mg, 0.07 mmol) of which was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-isobutylamino-5-(trifluoromethyl)phenyl, all other R=H; 5 mg). Exact MS calcd for $C_{30}H_{43}F_3N_5O_3$, the formula for $(M+H)^+$= 578.3318. Found: 578.3300.

Example 100

(2S)-N-tert-Butyl-2-[[[[2-butylamino-5-(trifluoromethyl)benzoyl]amino]acetyl]amino]-3-[[(2,4-dimethylphenyl)methyl]amino]-propanamide (100a) Butyl iodide was incorporated into procedure (80a) to afford 2-butylamino-5-(trifluoromethyl) benzoic acid, a portion (18 mg, 0.095 mmol) of which was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-butylamino-5-(trifluoromethyl)phenyl, all other R=H; 2 mg). Exact MS calcd for $C_{30}H_{43}F_3N_5O_3$, the formula for $(M+H)^+$= 578.3318. Found: 578.3325.

Example 101

(2S)-N-tert-Butyl-2-[[[[2-cyclohexylamino-5-(trifluoromethyl)benzoyl]amino]acetyl]amino]-3-[[(2,4-dimethylphenyl)methyl]amino]-propanamide (101a) Cyclohexylamine was incorporated into procedure (79a) to provide 2-cyclohexylamino-5-(trifluoromethyl) benzoic acid, which was carried through procedure (47a) to afford 1.2 (Z=—C(O)—, $R^2$=2-(methylaminocarbonyl)amino-5-(trifluoromethyl)phenyl, all other R=H). A portion (59 mg, 0.19 mmol) of this material was combined with (S)-2.3 (l=m=0, —C(O)N($R^{3a}$)$_2$=—C(O)NHt-Bu; cf. procedure (33a); 75 mg, 0.19 mmol) in procedure (1c). The product was carried through procedure (1d). The resultant crude product was purified by RP-HPLC to afford the title compound (S)-1.5 ($R^1$=2,4-dimethylphenyl, $R^3$=—C(O)NHt-Bu, Z=—C(O)—, $R^2$=2-cyclohexylamino-5-(trifluoromethyl)phenyl, all other R=H; 10 mg). Exact MS calcd for $C_{32}H_{45}F_3N_5O_3$, the formula for $(M+H)^+$= 604.3474. Found: 604.3452.

Example 102

(2S)-N-tert-Butyl-3-[[(2,4-dimethylphenyl)methyl]amino]-2-[[[[2-isopropylamino-5-(trifluoromethyl)benzoyl]amino]acetyl]amino]-propanamide (102a) The compounds (S)-2.3 (l=m=0,—C(O)N($R^{3a}$)$_2$=—C(O)NHt-Bu; cf. procedure (33a); 75 mg, 0.19 mmol) and 1.2 (Z=—C(O)—, $R^2$=2-isopropylamino-5-(trifluoromethyl)phenyl, all other R=H; cf. procedure (79b); 59 mg, 0.19 mmol) were combined in procedure (1c), and the product was taken through procedure (1d). The resultant crude product was purified by RP-HPLC to afford the title compound (S)-1.5 ($R^1$=2,4-dimethylphenyl, $R^3$=—C(O)NHt-Bu, Z=—C(O)—, $R^2$=2-isopropylamino-5-(trifluoromethyl)phenyl, all other R=H; 10 mg). Exact MS calcd for $C_{29}H_{41}F_3N_5O_3$, the formula for $(M+H)^+$= 564.3161. Found: 564.3172.

Example 103

(2S)-N-tert-Butyl-3-[[(2,4-dimethylphenyl)methyl]amino]-2-[[[[2-(tert-butyl)amino-5-(trifluoromethyl)benzoyl]amino]acetyl]amino]-propanamide (103a) The compounds (S)-2.3 (l=m=0, —C(O)N($R^{3a}$)$_2$=—C(O)NHt-Bu; cf. procedure (33a); 75 mg, 0.19 mmol) and 1.2 (Z=—C(O)—, $R^2$=2-(tert-butyl)amino-5-(trifluoromethyl)phenyl, all other R=H; cf. procedure (78b); 59 mg, 0.19 mmol) were combined in procedure (1c), and the product was taken through procedure (1d). The resultant crude product was purified by RP-HPLC to afford the title compound (S)-1.5 ($R^1$=2,4-dimethylphenyl, $R^3$=—C(O)NHt-Bu, Z=—C(O)—, $R^2$=2-(tert-butyl)amino-5-(trifluoromethyl)phenyl, all other R=H; 5 mg). Exact MS calcd for $C_{30}H_{43}F_3N_5O_3$, the formula for $(M+H)^+$= 578.3318. Found: 578.3319.

Example 104

(2S)-N-tert-Butyl-3-[[(2,4-dimethylphenyl)methyl]amino]-2-[[[[2-(methylaminocarbonyl)amino-5-(trifluoromethyl)benzoyl]amino]acetyl]amino]-propanamide (104a) The compounds (S)-2.3 (l=m=0, —C(O)N($R^{3a}$)$_2$=—C(O)NHt-Bu; cf. procedure (33a); 75 mg, 0.19 mmol) and 1.2 (Z=—C(O)—, $R^2$=2-(methylaminocarbonyl)amino-5-(trifluoromethyl)phenyl, all other R=H; cf. procedure (69a); 59 mg, 0.19 mmol) were combined in procedure (1c). The product was taken through procedure (1d). Purification by RP-HPLC afforded the title compound (S)-1.5 ($R^1$=2,4-dimethylphenyl, $R^3$=—C(O)NHt-Bu, Z=—C(O)—, $R^2$=2-(methylaminocarbonyl)amino-5-(trifluoromethyl)phenyl, all other R=H; 10 mg). Exact MS calcd for $C_{28}H_{38}F_3N_6O_4$, the formula for $(M+H)^+$=579.2907. Found: 579.2909.

Example 105

(2S)-N-tert-Butyl-3-[[(2,4-dimethylphenyl)methyl]amino]-2-[[[[2-(isopropoxycarbonyl)amino-5-(trifluoromethyl)benzoyl]amino]acetyl]amino]-propanamide (105a) 2-Amino-5-trifluoromethylbenzoic acid (110 mg) was dissolved in a THF (4 mL), water (1 mL), and Et$_3$N (0.25 mL) mixture prior to the addition of iso-propyl chloroformate (0.54 mL, 1M in toluene). The solution was stirred at rt for 18 h. The reaction was quenched with 1N HCl solution and extracted with EtOAc. The organic layer was dried (Na$_2$SO$_4$) and concentrated in vacuo.

(105b) The compound 2-(isopropoxycarbonyl)amino-5-(trifluoromethyl)benzoic acid was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-(isopropoxycarbonyl)amino-5-(trifluoromethyl)phenyl, all other R=H; 5 mg). Exact MS calcd for $C_{30}H_{41}F_3N_3O_5$, the formula for $(M+H)^+$= 608.3060. Found: 608.3080.

Example 106

(2S)-N-tert-Butyl-3-[[(2,4-dimethylphenyl)methyl]amino]-2-[[[[2-(isopropylaminocarbonyl)amino-5-(trifluoromethyl)benzoyl]amino]acetyl]amino]-propanamide (106a) The compound 2-(isopropylaminocarbonyl)amino-5-(trifluoromethyl)benzoic acid (cf. procedure (79a);

17 mg, 0.06 mmol) was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-(isopropylaminocarbonyl)amino-5-(trifluoromethyl)phenyl, all other R=H; 5 mg). Exact MS calcd for $C_{30}H_{42}F_3N_6O_4$, the formula for $(M+H)^+$= 607.3220. Found: 607.3235.

Example 107

(2S)-N-tert-Butyl-2-[[[[2-(cyclohexylcarbonyl) amino-5-(trifluoromethyl)benzoyl]amino]acetyl] amino]-3-[[(2,4-dimethylphenyl)methyl]amino]-propanamide (107a) 2-Amino-5-trifluorobenzoic acid (200 mg) was dissolved in THF (2.5 mL) and 2M $K_2CO_3/H_2O$ (1 mL) prior to the addition of cyclohexylcarbonyl chloride (0.2 mL). The solution was stirred at rt for 30 min. The reaction was quenched with 1N HCl solution and extracted with EtOAc. The organic layer was dried and concentrated (302 mg). MS found: $(2M–H)^−$=629.2.

(107b) The compound 2-(cyclohexylcarbonyl)amino-5-(trifluoromethyl)benzoic acid (42 mg, 0.13 mmol) was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-(cyclohexylcarbonyl)amino-5-(trifluoromethyl)phenyl, all other R=H; 3 mg). Exact MS calcd for $C_{33}H_{45}F_3N_3O_4$, the formula for $(M+H)^+$=632.3424. Found: 632.3442.

Example 108

(2S)-N-tert-Butyl-2-[[[[2-benzylamino-5-(trifluoromethyl)benzoyl]amino]acetyl]amino]-3-[[(2,4-dimethylphenyl)methyl]amino]-propanamide (108a) The compound 2-benzylamino-5-(trifluoromethyl) benzoic acid (cf. procedure (80a); 33 mg, 0.11 mmol) was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-benzylamino-5-(trifluoromethyl)phenyl, all other R=H; 5 mg). Exact MS calcd for $C_{33}H_{41}F_3N_5O_3$, the formula for $(M+H)^+$=612.3161. Found: 612.3143.

Example 109

(2S)-N-tert-Butyl-2-[[[[2-(para-chloro)benzylamino-5-(trifluoromethyl)benzoyl]amino]acetyl]amino]-3-[[(2,4-dimethylphenyl)methyl]amino]-propanamide (109a) The compound N-Boc 2-amino-5-(trifluoromethyl)benzoic acid (S. Takagishi, et al., Synlett 1992, 360) was transformed into its methyl ester as described in procedure (80a). A solution of this ester (125 mg, 0.39 mmol) in DMF (6 mL) was charged with $K_2CO_3$ (216 mg, 1.6 mmol) and para-chlorobenzyl bromide (160 mg, 0.78 mmol). After 1.5 h, the solution was diluted with EtOAc and was washed with brine solution followed by 1N HCl solution. The organic layer was then washed with $Na_2CO_3$ solution, water, and brine. The organic layer was dried ($MgSO_4$), filtered, and concentrated. Flash chromatography of the resulting residue provided the desired N-Boc benzylamine (69 mg), which was dissolved in THF (0.9 mL). The solution was charged with 1N LiOH (0.3 mL) and MeOH (0.3 mL). After stirring for 18 h, the THF was removed and the solution was made acidic (pH=5) with 1N HCl. This solution was extracted with EtOAc (2×). The organic layer was washed with brine, dried ($Na_2SO_4$), filtered, and concentrated to give N-Boc 2-(para-chlorobenzyl)amino-5-(trifluoromethyl)benzoic acid.

(109b) A solution of (S)-1.6 (1 m=0, PGN=2,4-Me$_2$Ph (Cbz)N, $R^3$=CONHt-Bu, all other R=H; 55 mg, 0.12 mmol) in 1:1 methylene chloride/DMF (3 mL) was charged successively with N-Boc 2-(para-chlorobenzyl)amino-5-(trifluoromethyl)benzoic acid (0.15 mmol), N,N-diisopropylethylamine (0.05 mL, 0.29 mmol), and HATU (53 mg, 0.14 mmol). The mixture was stirred for 12 h and diluted with EtOAc. The organic phase was washed with water (2×), sat. $NaHCO_3$, water, and brine. The organic phase was then dried ($Na_2SO_4$), filtered, and concentrated in vacuo. The product was dissolved in 2:1 methylene chloride/TFA, stirred for 3 h, and then concentrated in vacuo. The residue was dissolved in methylene chloride and concentrated in vacuo; this was repeated twice more. The resultant product was dissolved in ethanol (1 mL) and the solution was charged with 10% Pd/C (20 mg) and cyclohexene (0.02 mL). The reaction mixture was heated at 80° C. for 30 min, cooled to RT, and filtered. The filtrate was concentrated in vacuo. Purification by RP-HPLC afforded the title compound (S)-1.5 ($R^1$=2,4-dimethylphenyl, $R^3$=—C(O)NHt-Bu, Z=—C(O)—, $R^2$=2-(para-chloro)benzylamino-5-(trifluoromethyl)phenyl, all other R=H; 6 mg). Exact MS calcd for $C_{33}H_{40}Cl_1F_3N_5O_3$, the formula for $(M+H)^+$= 646.2772. Found: 646.2782.

Example 110

(2S)-N-tert-Butyl-2-[[[[2-[(beta-napthyl)methyl] amino-5-(trifluoromethyl)benzoyl]amino]acetyl] amino3-3-[[(2,4-dimethylphenyl)methyl]amino]-propanamide (110a) The compound (beta-napthyl)methyl bromide (176 mg, 0.8 mmol) was incorporated into procedure (80a) to provide 2-[(beta-napthyl)methyl]amino-5-(trifluoromethyl) benzoic acid, a portion (61 mg, 0.17 mmol) of which was incorporated into procedure (91b). Purification by RP-HPLC afforded the title compound (S)-1.5 ($R^1$=2,4-dimethylphenyl, $R^3$=—C(O)NHt-Bu, Z=—C(O)—$R^2$=2-((beta-napthyl)methyl)amino-5-(trifluoromethyl)phenyl, all other R=H; 3 mg). Exact MS calcd for $C_{37}H_{43}F_3N_5O_3$, the formula for $(M+H)^+$=662.3318. Found: 662.3311.

Example 111

(2S)-N-tert-Butyl-2-[[[[2-(meta-methyl) benzylamino-5-(trifluoromethyl)benzoyl]amino] acetyl]amino]-3-[[(2,4-dimethylphenyl)methyl] amino]-propanamide (111a) The compound meta-methylbenzyl bromide was incorporated into procedure (80a) to provide 2-(3-methyl) benzylamino-5-(trifluoromethyl)benzoic acid, a portion (43 mg, 0.14 mmol) of which was incorporated into procedure (91b). Purification by RP-HPLC afforded the title compound (S)-1.5 ($R^1$=2,4-dimethylphenyl, $R^3$=—C(O)NHt-Bu, Z=—C(O)—, $R^2$=2-(meta-methyl)benzylamino-5-(trifluoromethyl)phenyl, all other R=H; 5 mg). Exact MS calcd for $C_{34}H_{43}F_3N_5O_3$, the formula for $(M+H)^+$= 626.3318. Found: 626.3288.

Example 112

(2S)-N-tert-Butyl-2-[[[[2-(para-methyl)benzylamino-5-(trifluoromethyl)benzoyl]amino]acetyl]amino]-3-[[(2,4-dimethylphenyl)methyl]amino]-propanamide (112a) A solution of (S)-1.6 (l=m=0, PGN=2,4-Me$_2$Ph (Cbz)N, $R^3$=CONHt-Bu, all other R=H; cf. procedure (91a);

164 mg, 0.35 mmol) in 1:1 methylene chloride/DMF (5 mL) was charged successively with N-Boc 2-amino-5-(trifluoromethyl)benzoic acid (S. Takagishi, et al., *Synlett* 1992, 360; 107 mg, 0.35 mmol), N,N-diisopropylethylamine (0.06 mL, 0.35 mmol), and HATU (63 mg, 0.17 mmol). The mixture was stirred for 12 h and diluted with EtOAc. The organic phase was washed with water (2×), sat. NaHCO$_3$, water, and brine. The organic phase was then dried (Na$_2$SO$_4$), filtered, and concentrated in vacuo to provide (S)-1.3 (l=m=0, PGN=2,4-Me$_2$Ph(Cbz)N, R$^3$=CONHt-Bu, Z=—C(O)—, R$^2$ N-Boc 2-amino-5-(trifluoromethyl)phenyl, all other R=H; 249 mg). MS found: (M+H)$^+$=778.5.

(112b) A solution of (S)-1.3 (l=m=0, PGN=2,4-Me$_2$Ph (Cbz)N, R$^3$=CONHt-Bu, Z=—C(O)—, R$^2$=N-Boc 2-amino-5-(trifluoromethyl)phenyl, all other R=H; cf. procedure (112a); 83 mg, 0.11 mmol) in DMF (5 mL) was charged with K$_2$CO$_3$ and para-methylbenzyl bromide (41 mg, 0.22 mmol). After stirring for 1.5 h, the solution was diluted with EtOAc and was washed with brine solution followed by 1N HCl solution. The organic layer was then washed with Na$_2$CO$_3$ solution, water, and brine. The organic layer was dried (MgSO$_4$), filtered, and concentrated in vacuo. The product was dissolved in 2:1 methylene chloride/TFA (3 mL), stirred for 3 h, and then concentrated in vacuo. The product was dissolved in methylene chloride and concentrated in vacuo; this was repeated twice more. The resultant product was dissolved in ethanol (3 mL) and the solution was charged with 10% Pd/C (10 mg) and cyclohexene (0.04 mL). The reaction mixture was heated at 80° C. for 30 min, cooled to RT, and filtered. The filtrate was concentrated in vacuo. Purification by RP-HPLC afforded the title compound (S)-1.5 (R$^1$=2,4-dimethylphenyl, R$^3$=—C(O)NHt-Bu, Z=—C(O)—, R$^2$=2-(para-methyl)benzylamino-5-(trifluoromethyl)phenyl, all other R=H; 5 mg). Exact MS calcd for C$_{34}$H$_{43}$F$_3$N$_5$O$_3$, the formula for (M+H)$^+$=626.3318. Found: 626.3313.

Example 113

(2S)-N-tert-Butyl-2-[[[[2-(ortho-methyl) benzylamino-5-(trifluoromethyl)benzoyl]amino] acetyl]amino]-3-[[(2,4-dimethylphenyl)methyl] amino]-propanamide (113a) The compound ortho-methylbenzyl bromide (0.03 mL, 0.22 mmol) was incorporated intro procedure (112b). Purification by RP-HPLC afforded the title compound (S)-1.5 (R$^1$=2,4-dimethylphenyl, R$^3$=—C(O)NHt-Bu, Z=—C(O)—, R$^2$=2-(ortho-methyl)benzylamino-5-(trifluoromethyl)phenyl, all other R=H; 3 mg). MS found: (M+H)$^+$=626.4.

Example 114

(2S)-N-tert-Butyl-3-[[(2,4-dimethylphenyl)methyl] amino]-2-[[[[2-(para-trifluoromethyl)benzylamino-5-(trifluoromethyl)benzoyl]amino]acetyl]amino]-propanamide (114a) The compound para-(trifluoromethyl)benzyl bromide (0.03 mL, 0.22 mmol) was incorporated intro procedure (112b). Purification by RP-HPLC afforded the title compound (S)-1.5 (R$^1$=2,4-dimethylphenyl, R$^3$=—C(O)NHt-Bu, Z=—C(O)—, R$^2$=2-(para-trifluoromethyl)benzylamino-5-(trifluoromethyl)phenyl, all other R=H; 5 mg). Exact MS calcd for C$_{34}$H$_{40}$F$_6$N$_5$O$_3$, the formula for (M+H)$^+$=680.3035. Found: 680.3061.

Example 115

(2S)-N-tert-Butyl-2-[([[3-amino-5-(trifluoromethyl) benzoyl]amino]acetyl]amino]-3-[[(2,4-dimethylphenyl)methyl]amino]-propanamide (115a) The compound 3-nitro-5-(trifluoromethyl)benzoic acid (65 mg, 0.14 mmol) was incorporated into procedure (91b). Purification by RP-HPLC afforded the title compound (S)-1.5 (R$^1$=2,4-dimethylphenyl, R$^3$=—C(O)NHt-Bu, Z=—C(O)—, R$^2$=3-amino-5-(trifluoromethyl)phenyl, all other R=H; 10 mg). Exact MS calcd for C$_{26}$H$_{35}$F$_3$N$_5$O$_3$, the formula for (M+H)$^+$=522.2692. Found: 522.2702.

Example 116

(2S)-N-tert-Butyl-2-[[[[3-benzylamino-5-(trifluoromethyl)benzoyl]amino]acetyl]amino]-3-[[(2,4-dimethylphenyl)methyl]amino]-propanamide (116a) A solution of 3-nitro-5-(trifluoromethyl)benzoic acid (5.4 g, 23 mmol) in MeOH (115 mL) was charged with 5% Pd/C, Degussa (1.09 g). The reaction vessel was purged with hydrogen and stirred under a hydrogen atmosphere (1 atm) for 3 h. The mixture was filtered and the filtrate was concentrated in vacuo to provide 3-amino-5-(trifluoromethyl)benzoic acid (4.25 g). This material was incorporated into procedure (80a) to provide 3-benzylamino-5-(trifluoromethyl)benzoic acid, a portion (17 mg, 0.06 mmol) of which was incorporated into procedure (91b). Purification by RP-HPLC afforded the title compound (S)-1.5 (R$^1$=2,4-dimethylphenyl, R$^3$=—C(O)NHt-Bu, Z=—C(O)—, R$^2$=3-benzylamino-5-(trifluoromethyl)phenyl, all other R=H; 3 mg). Exact MS calcd for C$_{33}$H$_{41}$F$_3$N$_5$O$_3$, the formula for (M+H)$^+$=612.3161. Found: 612.3184.

Example 117

(2S)-N-tert-Butyl-2-[[[[3-methylamino-5-(trifluoromethyl)benzoyl]amino]acetyl]amino]-3-[[(2,4-dimethylphenyl)methyl]amino]-propanamide (117a) Methyl 3-(trifluoromethylcarbonyl)amino-5-(trifluoromethyl)benzoate (cf. procedures (116a) and (80a); 131 mg, 0.42 mmol) was dissolved in THF (5 mL), and the resultant solution was charged successively with KHMDS (0.83 mL of a 0.5 M solution) and iodomethane (0.03 mL, 0.42 mL). The mixture was stirred for 16 h, quenched with sat. NaHCO$_3$, and extracted with EtOAc (2×). The organic extracts were combined, washed with brine, dried (Na$_2$SO$_4$), filtered, and concentrated in vacuo. This product was dissolved in 3:1:1 THF/MeOH/water (5 mL) and the resultant solution was charged with lithium hydroxide (20 mg, 0.84 mmol). The reaction was stirred for 14 h, acidified with 1N HCl, and extracted with EtOAc (2×). The organic extracts were combined, washed with water, washed with brine, dried (Na$_2$SO$_4$), filtered, and concentrated in vacuo to provide 3-methylamino-5-(trifluoromethyl)benzoic acid.

(117b) The compound 3-methylamino-5-(trifluoromethyl)benzoic acid (55 mg, 0.25 mmol) was incorporated into procedure (91b). Purification by RP-HPLC afforded the title compound (S)-1.5 (R$^1$=2,4-dimethylphenyl, R$^3$=—C(O)NHt-Bu, Z=—C(O)—, R$^2$=3-methylamino-5-(trifluoromethyl)phenyl, all other R=H; 3 mg). Exact MS calcd for C$_{27}$H$_{37}$F$_3$N$_5$O$_3$, the formula for (M+H)$^+$=536.2848. Found: 536.2857.

Example 118

(2S)-N-tert-Butyl-2-[[[[3-ethylamino-5-(trifluoromethyl)benzoyl]amino]acetyl]amino]-3-[[(2,4-dimethylphenyl)methyl]amino]-propanamide (118a) Methyl 3-amino-5-(trifluoromethyl)benzoate (cf. procedures (116a) and (80a); 177 mg, 0.81 mmol) was dissolved in MeOH (12 mL) and the resulting solution was charged successively with acetaldehyde (0.045 mL, 0.81 mmol) and sodium cyanoborohydride (64 mg, 1.01 mmol). The reaction was stirred at RT for 12 h, concentrated in vacuo, and diluted with EtOAc. The organic phase was washed with sat. NaHCO$_3$, water (2×), and brine before being dried (Na$_2$SO$_4$), filtered, and concentrated in vacuo. This product was dissolved in 3:1 THF/MeOH (12 mL) and the resultant solution was charged with lithium hydroxide (3 mL of a 1N solution). The reaction was stirred for 14 h, acidified with 1N, and extracted with EtOAc (2×). The organic extracts were combined, washed with water, washed with brine, dried (Na$_2$SO$_4$), filtered, and concentrated in vacuo to provide 3-ethylamino-5-(trifluoromethyl)benzoic acid.

(118b) The compound 3-ethylamino-5-(trifluoromethyl)benzoic acid (35 mg, 0.15 mmol) was incorporated into procedure (91b). Purification by RP-HPLC afforded the title compound (S)-1.5 (R$^1$=2,4-dimethylphenyl, R$^3$=—C(O)NHt-Bu, Z=—C(O)—, R$^2$=3-ethylamino-5-(trifluoromethyl)phenyl, all other R=H; 10 mg). Exact MS calcd for C$_{28}$H$_{39}$F$_3$N$_5$O$_3$, the formula for (M+H)$^+$=550.3005. Found: 550.2999.

Example 119

(2S)-N-tert-Butyl-2-[[[[3-isobutylamino-5-(trifluoromethyl)benzoyl]amino]acetyl]amino]-3-[[(2,4-dimethylphenyl)methyl]amino]-propanamide (119a) Isobutyraldehyde (0.08 mL) was incorporated into procedure (118a) to provide 3-isobutylamino-5-(trifluoromethyl)benzoic acid (161 mg), a portion (27 mg, 0.1 mmol) of which was incorporated into procedure (91b). Purification by RP-HPLC afforded the title compound (S)-1.5 (R$^1$=2,4-dimethylphenyl, R$^3$=—C(O)NHt-Bu, Z=—C(O)—, R$^2$=3-isobutylamino-5-(trifluoromethyl)phenyl, all other R=H; 5 mg). Exact MS calcd for C$_{30}$H$_{43}$F$_3$N$_5$O$_3$, the formula for (M+H)$^+$=578.3318. Found: 578.3341.

Example 120

(2S)-N-tert-Butyl-2-[[[[3-propylamino-5-(trifluoromethyl)benzoyl]amino]acetyl]amino]-3-[[(2,4-dimethylphenyl)methyl]amino]-propanamide (120a) Propionaldehyde (0.1 mL) was incorporated into procedure (118a) to provide 3-propylamino-5-(trifluoromethyl)benzoic acid (103 mg), a portion (25 mg) of which was incorporated into procedure (91b). Purification by RP-HPLC afforded the title compound (S)-1.5 (R$^1$=2,4-dimethylphenyl, R$^3$=—C(O)NHt-Bu, Z=—C(O)—, R$^2$=3-propylamino-5-(trifluoromethyl)phenyl, all other R=H; 3 mg). Exact MS calcd for C$_{29}$H$_{41}$F$_3$N$_5$O$_3$, the formula for (M+H)$^+$=564.3161. Found: 564.3145.

Example 121

(2S)-N-tert-Butyl-2-[[[[3-butylamino-5-(trifluoromethyl)benzoyl]amino]acetyl]amino]-3-[[(2,4-dimethylphenyl)methyl]amino]-propanamide (121a) Butyraldehyde (0.09 mL) was incorporated into procedure (118a) to provide 3-butylamino-5-(trifluoromethyl)benzoic acid (172 mg), a portion (35 mg) of which was incorporated into procedure (91b). Purification by RP-HPLC afforded the title compound (S)-1.5 (R$^1$=2,4-dimethylphenyl, R$^3$=—C(O)NHt-Bu, Z=—C(O)—, R$^2$=3-butylamino-5-(trifluoromethyl)phenyl, all other R=H; 5 mg). Exact MS calcd for C$_{30}$H$_{43}$F$_3$N$_5$O$_3$, the formula for (M+H)$^+$=578.3318. Found: 578.3333.

Example 122

(2S)-N-tert-Butyl-2-[[[[3-(trifluoromethylcarbonyl)amino-5-(trifluoromethyl)benzoyl]amino]acetyl]amino]-3-[[(2,4-dimethylphenyl)methyl]amino]-propanamide (122a) A solution of (S)-1.5 (R$^1$=2,4-dimethylphenyl, R$^3$=—C(O)NHt-Bu, Z=—C(O)—, R$^2$=3-amino-5-(trifluoromethyl)phenyl, all other R=H; cf. procedure (115a); 14 mg, 0.03 mmol) in DMF (2 mL) was charged with pyridine (0.002 mL) and trifluoroacetic anhydride (0.004 mL). The reaction was stirred for 12 h, diluted with water, and extracted with EtOAc. The organic phase was washed with brine, dried (Na$_2$SO$_4$), filtered, and concentrated in vacuo. Purification by RP-HPLC afforded the title compound (S)-1.5 (R$^1$=2,4-dimethylphenyl, R$^3$=—C(O)NHt-Bu, Z=—C(O)—, R$^2$=3-(trifluoromethylcarbonyl)amino-5-(trifluoromethyl)phenyl, all other R=H; 5 mg). MS found: (M+H)$^+$=618.5.

Example 123

(2S)-N-tert-Butyl-2-[[[[3-(ethoxycarbonyl)amino-5-(trifluoromethyl)benzoyl]amino]acetyl]amino]-3-[[(2,4-dimethylphenyl)methyl]amino]-propanamide (123a) Methyl 3-amino-5-(trifluoromethyl)benzoate (cf. procedures (116a) and (80a); 236 mg, 1.01 mmol) was dissolved in THF (11 mL) and the resulting solution was charged successively with K$_2$CO$_3$ (1.6 mL of a 2.0 M aq. solution) and ethylchloroformate (258 mg, 2.7 mmol). The reaction was stirred at RT for 48 h, concentrated in vacuo, and diluted with EtOAc. The organic phase was washed with sat. NaHCO$_3$, water (2×), and brine before being dried (Na$_2$SO$_4$), filtered, and concentrated in vacuo. This product was dissolved in 3:1 THF/MeOH (8 mL) and the resultant solution was charged with lithium hydroxide (2 mL of a 1N solution). The reaction was stirred for 14 h, acidified with 1N HCl, and extracted with EtOAc (2×). The organic extracts were combined, washed with water, washed with brine, dried (Na$_2$SO4), filtered, and concentrated in vacuo to provide 3-(ethoxycarbonyl)amino-5-(trifluoromethyl)benzoic acid. MS found: (M−H)$^−$=276.1.

(123b) The compound 3-(ethoxycarbonyl)amino-5-(trifluoromethyl)benzoic acid (29 mg, 0.09 mmol) was incorporated into procedure (91b). Purification by RP-HPLC afforded the title compound (S)-1.5 (R$^1$=2,4-dimethylphenyl, R$^3$=—C(O)NHt-Bu, Z=—C(O)—, R$^2$=3-(ethoxycarbonyl)amino-5-(trifluoromethyl)phenyl, all other R=H; 5 mg). Exact MS calcd for C$_{29}$H$_{39}$F$_3$N$_5$O$_5$, the formula for (M+H)$^+$=594.2903. Found: 594.2917.

Example 124

(2S)-2-[[[[2-amino-5-(trifluoromethyl)benzoyl]amino]acetyl]amino]-3-[[(2-methyl-4-bromophenyl)methyl]amino]-propanamide (124a) The compound 2-methyl-4-bromobenzaldehyde (M. I. Dawson, et al., *J. Med. Chem.* 1984, 27, 1516–1531) was incorporated into procedure (27b). Purification by RP-HPLC afforded the title compound (S)-1.5 (R$^1$=2-methyl-4-bromophenyl, R$^3$=—C(O)NHt-Bu, Z=—C(O)—, R$^2$=2-amino-5-(trifluoromethyl)phenyl, all other R=H; 1.5 mg). MS found: (M+H)$^+$=530.0.

Example 125

(2S)-2-[[[[2-amino-5-(trifluoromethyl)benzoyl]amino]acetyl]amino]-3-[[(4-bromophenyl)methyl]amino]-propanamide (125a) The compound para-bromobenzaldehyde was incoporated into procedure (27b). Purification by RP-HPLC afforded the title compound (S)-1.5 ($R^1$=4-bromophenyl, $R^3$=—C(O)NHt-Bu, Z=—C(O)—, $R^2$=2-amino-5-(trifluoromethyl)phenyl, all other R=H; 5.0 mg). MS found: $(M+H)^+$=518.0.

Example 126

(2S)-N-tert-Butyl-3-[[(4-methylphenyl)methyl]amino]-2-[[[[3-(trifluoromethyl)benzoyl]amino]acetyl]amino]-propanamide (126a) The compound para-methylbenzaldehyde (0.015 mL, 0.13 mmol) was incorporated into procedure (1d). Purification by RP-HPLC afforded the title compound (S)-1.5 ($R^1$=4-methylphenyl, $R^3$=—C(O)NHt-Bu, Z=—C(O)—, $R^2$=3-(trifluoromethyl)phenyl, all other R=H; 15 mg). Exact MS calcd for $C_{25}H_{32}F_3N_4O_3$, the formula for $(M+H)^+$=493.2426. Found: 493.2445.

Example 127

(2S)-N-tert-Butyl-3-[[(4-bromophenyl)methyl]amino]-2-[[[[3-(trifluoromethyl)benzoyl]amino]acetyl]amino]-propanamide (127a) The compound para-bromobenzaldehyde (18 mg, 0.10 mmol) was incorporated into procedure (1d). Purification by RP-HPLC afforded the title compound (S)-1.5 ($R^1$=4-methylphenyl, $R^3$=—C(O)NHt-Bu, Z=—C(O)—, $R^2$=3-(trifluoromethyl)phenyl, all other R=H; 15 mg). MS found: $(M+H)^+$=557.1.

Example 128

(2S)-N-tert-Butyl-3-[[(4-bromo-2-methylphenyl)methyl]amino]-2-[[[[3-(trifluoromethyl)benzoyl]amino]acetyl]amino]-propanamide (128a) The compound 4-bromo-2-methylbenzaldehyde (M. I. Dawson, et al., *J. Med. Chem.* 1984, 27, 1516–1531; 0.025 mL, 0.13 mmol) was incorporated into procedure (1d). Purification by RP-HPLC afforded the title compound (S)-1.5 ($R^1$=4-bromo-2-methylphenyl, $R^3$=—C(O)NHt-Bu, Z=—C(O)—, $R^2$=3-(trifluoromethyl)phenyl, all other R=H; 20 mg). Exact MS calcd for $C_{25}H_{31}Br_1F_3N_4O_3$, the formula for $(M+H)^+$=571.1532. Found: 571.1536.

Example 129

(2S)-N-tert-Butyl-3-[[(4-methoxyphenyl)methyl]amino]-2-[[[[3-(trifluoromethyl)benzoyl]amino]acetyl]amino]-propanamide (129a) The compound para-methoxybenzaldehyde (0.015 mL, 0.12 mmol) was incorporated into procedure (1d). Purification by RP-HPLC afforded the title compound (S)-1.5 ($R^1$=4-methoxyphenyl, $R^3$=—C(O)NHt-Bu, Z=—C(O)—, $R^2$=3-(trifluoromethyl)phenyl, all other R=H; 10 mg). MS found: $(M+H)^+$=509.1.

Example 130

(2S)-N-tert-Butyl-3-[[(4-methoxy-2-methylphenyl)methyl]amino]-2-[[[[3-(trifluoromethyl)benzoyl]amino]acetyl]amino]-propanamide (130a) The compound 4-methoxy-2-methylbenzaldehyde (0.011 mL, 0.07 mmol) was incorporated into procedure (1d). Purification by RP-HPLC afforded the title compound (S)-1.5 ($R^1$=4-methoxy-2-methylphenyl, $R^3$=—C(O)NHt-Bu, Z=—C(O)—, $R^2$=3-(trifluoromethyl)phenyl, all other R=H; 20 mg). Exact MS calcd for $C_{26}H_{34}F_3N_4O_4$, the formula for $(M+H)^+$=523.2532. Found: 523.2546.

Example 131

(2S)-N-tert-Butyl-3-[[(2-methoxypyridin-5-yl)methyl]amino]-2-[[[[3-(trifluoromethyl)benzoyl]amino]acetyl]amino]-propanamide (131a) The compound 2-methoxy-5-formylpyridine (0.016 mL, 0.13 mmol) was incorporated into procedure (1d). Purification by RP-HPLC afforded the title compound (S)-1.5 ($R^1$=2-methoxypyridin-5-yl, $R^3$=—C(O)NHt-Bu, Z=—C(O)—, $R^2$=3-(trifluoromethyl)phenyl, all other R=H; 29 mg). Exact MS calcd for $C_{24}H_{31}F_3N_5O_4$, the formula for $(M+H)^+$=510.2328. Found: 510.2336.

Example 132

(2S)-N-tert-Butyl-3-[[(2,3-dimethyl-4-methoxyphenyl)methyl]amino]-2-[[[[3-(trifluoromethyl)benzoyl]amino]acetyl]amino]-propanamide (132a) The compound 2,3-dimethyl-4-methoxybenzaldehyde (0.025 mL, 0.13 mmol) was incorporated into procedure (1d). Purification by RP-HPLC afforded the title compound (S)-1.5 ($R^1$=2,3-dimethyl-4-methoxyphenyl, $R^3$=—C(O)NHt-Bu, Z=—C(O)—, $R^2$=3-(trifluoromethyl)phenyl, all other R=H; 10 mg). MS found: $(M+H)^+$=537.2.

Example 133

(2S)-N-tert-Butyl-3-[[(4-cyano-2-methylphenyl)methyl]amino]-2-[[[[3-(trifluoromethyl)benzoyl]amino]acetyl]amino]-propanamide (133a) The compound 4-cyano-2-methylbenzaldehyde (B. P. Clark, et al., *Biorg. & Med. Chem. Lett.* 1997, 7, 2777-2780; 8.2 mg, 0.06 mmol) was incorporated into procedure (1d). Purification by RP-HPLC afforded the title compound (S)-1.5 ($R^1$=4-cyano-2-methylphenyl, $R^3$=—C(O)NHt-Bu, Z=—C(O)—, $R^2$=3-(trifluoromethyl)phenyl, all other R=H; 7 mg). Exact MS calcd for $C_{26}H_{31}F_3N_5O_3$, the formula for $(M+H)^+$=518.2379. Found: 518.2374.

Example 134

(2S)-N-tert-Butyl-3-[[(4-ethylphenyl)methyl]amino]-2-[[[[3-(trifluoromethyl)benzoyl]amino]acetyl]amino]-propanamide (134a) The compound 4-ethylbenzaldehyde (0.015 mL, 0.11 mmol) was incorporated into procedure (1d). Purification by RP-HPLC afforded the title compound (S)-1.5 ($R^1$=4-ethylphenyl, $R^3$=—C(O)NHt-Bu, Z=—C(O)—, $R^2$=3-(trifluoromethyl)phenyl, all other R=H; 10 mg). Exact MS calcd for $C_{26}H_{34}F_3N_4O_3$, the formula for $(M+H)^+$=507.2583. Found: 507.2593.

Example 135

(2S)-N-tert-Butyl-3-[[(2-methyl-4-vinylphenyl)methyl]amino]-2-[[[[3-(trifluoromethyl)benzoyl]amino]acetyl]amino]-propanamide (135a) A solution of 4-bromo-2-methylbenzyl alcohol (M. I. Dawson, et al., *J. Med. Chem.* 1984, 27, 1516–1531; 0.81 g, 4.0 mmol) in toluene (10 mL) was charged successively with $Pd(PPh_3)_4$ (0.13 g, 0.11 mmol), BHT (few crystals, catalytic), and vinyltributyltin (1.3 mL, 4.4 mmol). The mixture was heated at 110° C. for 3.5 h, cooled, charged with aqueous KF and stirred for 12 h at RT. The mixture was diluted with EtOAc and the resultant white precipitate was removed via filtration. The organic phase was separated, dried ($Na_2SO_4$), filtered, and concentrated in vacuo. The residue was purified via flash chromatography to afford 2-methyl-4-vinylbenzyl alcohol (0.54 g). A portion (0.27 g) of this product in methylene chloride (5 mL) was added to a precooled (−78° C.) mixture of oxalyl chloride (1.3 mL, 2.6 mmol) and DMSO (0.3 mL, 4.3 mmol) in methylene chloride (10 mL). The reactoin was charged with triethylamine (1.0 mL, 7.2 mmol) and stirred in the cold bath for 2 h, at which point the bath was at RT. The reaction was stirred for an additional hour at RT and then quenched with sat. $NaHCO_3$. The mixture was extracted with EtOAc (2×), and the organic phase was dried ($Na_2SO_4$), filtered, and concentrated in vacuo to afford pure 2-methyl-4-vinylbenzaldehyde.

(135b) The compound 2-methyl-4-vinylbenzaldehyde (14 mg, 0.10 mmol) was incorporated into procedure (1d). Purification by RP-HPLC afforded the title compound (S)-1.5 ($R^1$=2-methyl-4-vinylphenyl, $R^3$=—C(O)NHt-Bu, Z=—C(O)—, $R^2$=3-(trifluoromethyl)phenyl, all other R=H; 5 mg). Exact MS calcd for $C_{27}H_{34}F_3N_4O_3$, the formula for $(M+H)^+$=519.2583. Found: 519.2580.

Example 136

(2S)-N-tert-Butyl-3-[[(4-ethyl-2-methylphenyl) methyl]amino]-2-[[[[3-(trifluoromethyl)benzoyl] amino]acetyl]amino]-propanamide (136a) The compound (S)-1.5 ($R^1$=2-methyl-4-vinylphenyl, $R^3$=—C(O)NHt-Bu, Z=—C(O)—, $R^2$=3-(trifluoromethyl)phenyl, all other R=H; cf. procedure (135b); 45 mg) was dissolved in MeOH and the solution was charged with 5% Pd/C, Degussa (ca. 3 mg, catalytic). The reaction vessel was purged with hydrogen and then maintained under a hydrogen atmosphere (1 atm pressure) for 2 h. The mixture was diluted with MeOH, filtered, and concentrated in vacuo. Purification by RP-HPLC afforded the title compound (S)-1.5 $R^1$=4-ethyl-2-methylphenyl, $R^3$=—C(O)NHt-Bu, Z=—C(O)—, $R^2$=3-(trifluoromethyl)phenyl, all other R=H; 7 mg). Exact MS calcd for $C_{27}H_{36}F_3N_4O_3$, the formula for $(M+H)^+$=521.2740. Found: 521.2758.

Example 137

(2S)-N-tert-Butyl-3-[[(4-isopropylphenyl)methyl] amino]-2-[[[[3-(trifluoromethyl)benzoyl]amino] acetyl]amino]-propanamide (137a) The compound 4-isopropylbenzaldehyde (0.02 mL, 0.13 mmol) was incorporated into procedure (1d). Purification by RP-HPLC afforded the title compound (S)-1.5 ($R^1$=4-isopropylphenyl, $R^3$=—C(O)NHt-Bu, Z=—C(O)—, $R^2$=3-(trifluoromethyl)phenyl, all other R=H; 5 mg). Exact MS calcd for $C_{27}H_{36}F_3N_4O_3$, the formula for $(M+H)^+$=521.2740. Found: 521.2759.

Example 138

(2S)-N-tert-Butyl-3-[[(4-butylphenyl)methyl] amino]-2-[[[[3-(trifluoromethyl)benzoyl]amino] acetyl]amino]-propanamide (138a) The compound 4-butylbenzaldehyde (0.022 mL, 0.13 mmol) was incorporated into procedure (1d). Purification by RP-HPLC afforded the title compound (S)-1.5 ($R^1$=4-butylphenyl, $R^3$=—C(O)NHt-Bu, Z=—C(O)—, $R^2$=3-(trifluoromethyl)phenyl, all other R=H; 28 mg). Exact MS calcd for $C_{28}H_{38}F_3N_4O_3$, the formula for $(M+H)^+$=535.2896. Found: 535.2901.

Example 139

(2S)-N-tert-Butyl-3-[[(4-dimethylaminophenyl) methyl]amino]-2-[[[[3-(trifluoromethyl)benzoyl] amino]acetyl]amino]-propanamide (139a) The compound 4-dimethylaminobenzaldehyde (11 mg, 0.07 mmol) was incorporated into procedure (1d). Purification by RP-HPLC afforded the title compound (S)-1.5 ($R^1$=4-dimethylaminophenyl, $R^3$=—C(O)NHt-Bu, Z=—C(O)—, $R^2$=3-(trifluoromethyl)phenyl, all other R=H; 5 mg). Exact MS calcd for $C_{26}H_{35}F_3N_5O_3$, the formula for $(M+H)^+$=522.2692. Found: 522.2721.

Example 140

(2S)-N-tert-Butyl-3-[[(4-dimethylamino-2-methylphenyl)methyl]amino]-2-[[[[3-(trifluoromethyl)benzoyl]amino]acetyl]amino]-propanamide (140a) The compound 4-dimethylamino-2-methylbenzaldehyde (23 mg, 0.14 mmol) was incorporated into procedure (1d). Purification by RP-HPLC afforded the title compound (S)-1.5 ($R^1$=4-dimethylamino-2-methylphenyl, $R^3$=—C(O)NHt-Bu, Z=—C(O)—, $R^2$=3-(trifluoromethyl)phenyl, all other R=H; 20 mg). Exact MS calcd for $C_{27}H_{37}F_3N_5O_3$, the formula for $(M+H)^+$=536.2848. Found: 536.2833.

Example 141

(2S)-N-tert-Butyl-3-[[(4-methylthiophenyl)methyl] amino]-2-[[[[3-(trifluoromethyl)benzoyl]amino] acetyl]amino]-propanamide (141a) The compound 4-methylthiobenzaldehyde (0.05 mL, 0.37 mmol) was incorporated into procedure (1d). Purification by RP-HPLC afforded the title compound (S)-1.5 ($R^1$=4-methylthiophenyl, $R^3$=—C(O)NHt-Bu, Z=—C(O)—, $R^2$=3-(trifluoromethyl)phenyl, all other R=H; 3 mg). Exact MS calcd for $C_{25}H_{32}F_3N_4O_3S_1$, the formula for $(M+H)^+$=525.2147. Found: 525.2129.

Example 142

(2S)-N-tert-Butyl-3-[[(4-methylsulfonylphenyl) methyl]amino]-2-[[[[3-(trifluoromethyl)benzoyl] amino]acetyl]amino]-propanamide (142a) The compound 4-methylsulfonylbenzaldehyde (13 mg, 0.07 mmol) was incorporated into procedure (1d). Purification by RP-HPLC afforded the title compound (S)-1.5 ($R^1$=4-methylsulfonylphenyl, $R^3$=—C(O)NHt-Bu, Z=—C(O)—, $R^2$=3-(trifluoromethyl)phenyl, all other R=H; 7 mg). Exact MS calcd for $C_{25}H_{32}F_3N_4O_5S_1$, the formula for $(M+H)^+$=557.2046. Found: 557.2052.

Example 143

(2S)-N-tert-Butyl-3-[[(4-trifluoromethoxyphenyl) methyl]amino]-2-[[[[3-(trifluoromethyl)benzoyl] amino]acetyl]amino]-propanamide (143a) The compound 4-trifluoromethoxybenzaldehyde (0.01 mL, 0.09 mmol) was incorporated into procedure (1d).

Purification by RP-HPLC afforded the title compound (S)-1.5 ($R^1$=4-trifluoromethoxyphenyl, $R^3$=—C(O)NHt-Bu, Z=—C(O)—, $R^2$=3-(trifluoromethyl)phenyl, all other R=H; 10 mg). Exact MS calcd for $C_{25}H_{29}F_6N_4O_4$, the formula for $(M+H)^+$=563.2093. Found: 563.2122.

Example 144

(2S)-N-tert-Butyl-3-[[(3-amino-4-methylphenyl)methyl]amino]-2-[[[[3-(trifluoromethyl)benzoyl]amino]acetyl]amino]-propanamide (144a) The compound 4-methyl-3-nitrobenzaldehyde (28 mg, 0.17 mmol) was incorporated into procedure (1d). The resultant product was then carried through procedure (136a). Purification by RP-HPLC afforded the title compound (S)-1.5 ($R^1$=3-amino-4-methylphenyl, $R^3$=—C(O)NHt-Bu, Z=—C(O)—, $R^2$=3-(trifluoromethyl)phenyl, all other R=H; 7 mg). Exact MS calcd for $C_{25}H_{33}F_3N_5O_3$, the formula for $(M+H)^+$=508.2535. Found: 508.2541.

Example 145

(2S)-N-tert-Butyl-3-[[(indol-3-yl)methyl]amino]-2-[[[[3-(trifluoromethyl)benzoyl]amino]acetyl]amino]-propanamide (145a) The compound indol-3-ylcarboxaldehyde (19 mg, 0.13 mmol) was incorporated into procedure (1d). Purification by RP-HPLC afforded the title compound (S)-1.5 ($R^1$=indol-3-yl, $R^3$=—C(O)NHt-Bu, Z=—C(O)—, $R^2$=3-(trifluoromethyl)phenyl, all other R=H; 5 mg). Exact MS calcd for $C_{26}H_{31}F_3N_5O_3$, the formula for $(M+H)^+$=518.2379. Found: 518.2374.

Example 146

(2S)-N-tert-Butyl-3-[[(2-methylphenyl)methyl]amino]-2-[[[[3-(trifluoromethyl)benzoyl]amino]acetyl]amino]-propanamide (146a) The compound 2-methylbenzaldehyde (0.02 mL, 0.15 mmol) was incorporated into procedure (1d). Purification by RP-HPLC afforded the title compound (S)-1.5 ($R^1$=2-methylphenyl, $R^3$=—C(O)NHt-Bu, Z=—C(O)—, $R^2$=3-(trifluoromethyl)phenyl, all other R=H; 15 mg). Exact MS calcd for $C_{25}H_{32}F_3N_4O_3$, the formula for $(M+H)^+$=493.2426. Found: 493.2417.

Example 147

(2S)-N-tert-Butyl-3-[[(2-ethylphenyl)methyl]amino]-2-[[[[3-(trifluoromethyl)benzoyl]amino]acetyl]amino]-propanamide (147a) The compound 2-ethylbenzaldehyde (0.02 mL, 0.15 mmol) was incorporated into procedure (1d). Purification by RP-HPLC afforded the title compound (S)-1.5 ($R^1$=2-ethylphenyl, $R^3$=—C(O)NHt-Bu, Z=—C(O)—, $R^2$=3-(trifluoromethyl)phenyl, all other R=H; 15 mg). Exact MS calcd for $C_{26}H_{34}F_3N_4O_3$, the formula for $(M+H)^+$=507.2583. Found: 507.2602.

Example 148

(2R)-N-Ethyl-3-[[(2,4-dimethylphenyl)methyl]amino]-2-[[[[3-(trifluoromethyl)benzoyl]amino]acetyl]amino]-propanamide (148a) Ethylamine (0.2 mL of a 2.0 M solution) and (R)-16.2 ($R^1$=2,4-dimethylphenyl, $R^2$=3-trifluoromethylphenyl, all other R=H; cf. procedure (6a); 36 mg) were incorporated into the above procedure (4a) to give the title amide (R)-16.3 $R^1$=2,4-dimethylphenyl, —C(O)N$(R^{3a})_2$=—C(O)NHEt, Z=—C(O)—, $R^2$=3-trifluoromethylphenyl, all other R=H; 10 mg). Exact MS calcd for $C_{24}H_{30}F_3N_4O_3$, the formula for $(M+H)^+$=479.2270. Found: 479.2265.

Example 149

(2R)-N-tert-Butyl-3-[[(2,4-dimethylphenyl)methyl]amino]-2-[[[3-(trifluoromethyl)benzoyl]amino]acetyl]amino]-propanamide (149a) tert-Butylamine (0.05 mL, 0.48 mmol) and (R)-16.2 ($R^1$=2,4-dimethylphenyl, $R^2$=3-trifluoromethylphenyl, all other R=H; cf. procedure (6a); 36 mg) were incorporated into the above procedure (4a) to give the title amide (R)-16.3 ($R^1$=2,4-dimethylphenyl, —C(O)N$(R^{3a})_2$=—C(O)NHt-Bu, Z=—C(O)—, $R^2$=3-trifluoromethylphenyl, all other R=H; 15 mg). Exact MS calcd for $C_{26}H_{34}F_3N_4O_3$, the formula for $(M+H)^+$=507.2583. Found: 507.2593.

Example 150

(2R)-N-[[(2-methyl)hydroxyprop-2-yl]-3-[[(2,4-dimethylphenyl)methyl]amino]-2-[[[3-(trifluoromethyl)benzoyl]amino]acetyl]amino]-propanamide (150a) The compounds 2-amino-2-methylpropanol (0.08 mL, 0.79 mmol) and (R)-16.2 ($R^1$=2,4-dimethylphenyl, $R^2$=3-trifluoromethylphenyl, all other R=H; cf. procedure (6a); 60 mg) were incorporated into the above procedure (4a) to give the title amide (R)-16.3 $R^1$=2,4-dimethylphenyl, —C(O)N$(R^{3a})_2$=—C(O)NHCMe$_2$CH$_2$OH, Z=—C(O)—, $R^2$=3-trifluoromethylphenyl, all other R=H; 20 mg). MS found: $(M+H)^+$=523.1.

Example 151

(2S)-N-tert-Amyl-3-[[(2,4-dimethylphenyl)methyl]amino]-2-[[[[3-(trifluoromethyl)benzoyl]amino]acetyl]amino]-propanamide (151a) tert-Amylamine (70 μL) was incorporated into the above procedure (4a) to give the title amide (S)-16.3 ($R^1$=2,4-dimethylphenyl, —C(O)N$(R^{3a})_2$=—C(O)NHCMe$_2$Et, Z=—C(O)—, $R^2$=3-trifluoromethylphenyl, all other R=H; 10 mg). Exact MS calcd for $C_{27}H_{36}F_3N_4O_3$, the formula for $(M+H)^+$=521.2740. Found: 521.2736.

Example 152

(2S)-N-[(2-methyl)hydroxyprop-2-yl]-3-[[(2,4-dimethylphenyl)methyl]amino]-2-[[[[3-(trifluoromethyl)benzoyl]amino]acetyl]amino]-propanamide (152a) The compound 2-amino-2-methylpropanol (50 μL) was incorporated into the above procedure (4a) to give the title amide (S)-16.3 ($R^1$=2,4-dimethylphenyl, —C(O)N$(R^{3a})_2$=—C(O)NHCMe$_2$CH$_2$OH, Z=—C(O)—, $R^2$=3-trifluoromethylphenyl, all other R=H; 7 mg). Exact MS calcd for $C_{26}H_{34}F_3N_4O_4$, the formula for $(M+H)^+$=523.2532. Found: 523.2537.

Example 153

(2S)-N-[(1methyl)cycloprop-1-yl]-3-[[(2,4-dimethylphenyl)methyl]amino]-2-[[[[3-(trifluoromethyl)benzoyl]amino]acetyl]amino]-propanamide (153a) The compound a-methylcyclopropylamine (*J. Org. Chem.* 1989, 54, 1815; 18 mg) was incorporated into the above procedure (4a) to give the title amide (S)-16.3 ($R^1$= 2,4-dimethylphenyl, —C(O)N($R^{3a}$)$_2$=—C(O)NH($\alpha$-Me)c-Pr, Z=—C(O)—, $R^2$=3-trifluoromethylphenyl, all other R=H; 7 mg). Exact MS calcd for $C_{26}H_{32}F_3N_4O_3$, the formula for (M+H)$^+$=505.2426. Found: 505.2405.

Example 154

(2S)-N-Cyclopentyl-3-[(2,4-dimethylphenyl)methyl]amino]-2-[[[[3-(trifluoromethyl)benzoyl]amino]acetyl]amino]-propanamide (154a) Cyclopentylamine (0.5 mL) was incorporated into the above procedure (4a) to give the title amide (S)-16.3 ($R^1$=2,4-dimethylphenyl, —C(O)N($R^{3a}$)$_2$=—C(O)NHc-$C_5H_9$, Z=—C(O)—, $R^2$=3-trifluoromethylphenyl, all other R=H; 5 mg). Exact MS calcd for $C_{27}H_{34}F_3N_4O_3$, the formula for (M+H)$^+$=519.2583. Found: 519.2572.

Example 155

(2S)-N-Cyclohexyl-3-[[(2,4-dimethylphenyl)methyl]amino]-2-[[[[3-(trifluoromethyl)benzoyl]amino]acetyl]amino]-propanamide (155a) Cyclohexylamine (0.05 mL) was incorporated into the above procedure (4a) to give the title amide (S)-16.3 ($R^1$=2,4-dimethylphenyl, —C(O)N($R^{3a}$)$_2$=—C(O)NHc-$C_6H_{11}$, Z=—C(O)—, $R^2$=3-trifluoromethylphenyl, all other R=H; 10 mg). Exact MS calcd for $C_{28}H_{36}F_3N_4O_3$, the formula for (M+H)$^+$=533.2740. Found: 533.2746.

Example 156

(2S)-N-($\beta\beta\beta$-Trifluoro)ethyl-3-[[(2,4-dimethylphenyl)methyl]amino]-2-[[[[3-(trifluoromethyl)benzoyl]aminolacetyl[amino]-propanamide (156a) $\beta$, $\beta$, $\beta$-Trifluoroethylamine (0.5 mL) was incorporated into the above procedure (4a) to give the title amide (S)-16.3 ($R^1$=2,4-dimethylphenyl, —C(O)N($R^{3a}$)$_2$=—C(O)NHCH$_2$CF$_3$, Z=—C(O)—, $R^2$=3-trifluoromethylphenyl, all other R=H; 5 mg). Exact MS calcd for $C_{24}H_{27}F_6N_4O_3$, the formula for (M+H)$^+$=533.1987. Found: 533.1987.

Example 157

(2S)-N-Allyl-3-[[(2,4-dimethylphenyl)methyl]amino]-2-[[[[3-(trifluoromethyl)benzoyl]amino]acetyl]amino]-propanamide (157a) Allylamine (0.02 mL) was incorporated into the above procedure (4a) to give the title amide (S)-16.3 ($^1$=2,4-dimethylphenyl, —C(O)N($R^{3a}$)$_2$=—C(O)NHallyl, Z=—C(O)—, $R^2$=3-trifluoromethylphenyl, all other R=H; 5 mg). Exact MS calcd for $C_{25}H_{30}F_3N_4O_3$, the formula for (M+H)$^+$=491.2270. Found: 491.2270.

Example 158

(2S)-N-Cyclopropylmethyl-3-[[(2,4-dimethylphenyl)methyl]amino]-2-[[[[3-(trifluoromethyl)benzoyl]amino]acetyl]amino]-propanamide (158a) Cyclopropylmethylamine (0.025 mL) was incorporated into the above procedure (4a) to give the title amide (S)-16.3 ($R^1$=2,4-dimethylphenyl, —C(O)N($R^{3a}$)$_2$=—C(O)NHCH$_2$c-Pr, Z=—C(O)—, $R^2$=3-trifluoromethylphenyl, all other R=H; 5 mg). Exact MS calcd for $C_{26}H_{32}F_3N_4O_3$, the formula for (M+H)$^+$=505.2426. Found: 505.2440.

Example 159

N-[2-[[(2S)-3-[[(2,4-dimethylphenyl)methyl]amino]-1-(pyrrolid-3-enyl)-1-oxopropyl-2-amino]-2-oxoethyl]-3-(trifluoromethyl)benzamide (159a) 3-Pyrrolidene (0.04 mL) was incorporated into the above procedure (4a) to give the title amide (S)-16.3 ($R^1$=2,4-dimethylphenyl, —C(O)N($R^{3a}$)$_2$=—C(O)c-NC$_4$H$_6$, Z=—C(O)—, $R^2$=3-trifluoromethylphenyl, all other R=H; 10 mg). MS found: (M+H)$^+$=503.1.

Example 160

N-[2-[[(2S)-3-[[(2,4-dimethylphenyl)methyl]amino]-1-(pyrrolidinyl)-1-oxopropyl-2-amino]-2-oxoethyl]-3-(trifluoromethyl)benzamide (160a) The compound (S)-16.3 ($R^1$=2,4-dimethylphenyl, —C(O)N($R^{3a}$)$_2$=—C(O)c-NC$_4$H$_6$, Z=—C(O)—, $R^2$=3-trifluoromethylphenyl, all other R=H; cf. procedure (159); 8 mg) was incorporated into procedure (136a) to give the title amide (S)-16.3 ($R^1$=2,4-dimethylphenyl, —C(O)N($R^{3a}$)$_2$=—C(O)c-NC$_4$H$_8$, Z=—C(O)—, $R^2$=3-trifluoromethylphenyl, all other R=H; 6 mg). MS found: (M+H)$^+$=505.3.

Example 161

N-[2-[[(2S)-3-[[(2,4-dimethylphenyl)methyl]amino]-1-(morpholinyl)-1-oxopropyl-2-amino]-2-oxoethyl]-3-(trifluoromethyl)benzamide (161a) Morpholine (0.02 mL) was incorporated into the above procedure (4a) to give the title amide (S)-16.3 ($R^1$=2,4-dimethylphenyl, —C(O)N($R^{3a}$)$_2$=—C(O)c-NC$_4$H$_8$O, Z=—C(O)—, $R^2$=3-trifluoromethylphenyl, all other R=H; 5 mg). MS found: (M+H)$^+$=521.3.

Example 162

(2S)-N-Isobutyl-3-[[(2,4-dimethylphenyl)methyl]amino]-2-[[[[3-(trifluoromethyl)benzoyl]amino]acetyl]amino]-propanamide (162a) Isobutylamine (0.15 mL) was incorporated into the above procedure (4a) to give the title amide (S)-16.3 ($R^1$=2,4-dimethylphenyl, —C(O)N($R^{3a}$)$_2$=—C(O)NHCH$_2$i-Pr, Z=—C(O)—, $R^2$=3-trifluoromethylphenyl, all other R=H; 7 mg). Exact MS calcd for $C_{26}H_{34}F_3N_4O_3$, the formula for (M+H)$^+$=507.2583. Found: 507.2604.

Example 163

(2S)-N-sec-Butyl-3-[[(2,4-dimethylphenyl)methyl]amino]-2-[[[[3-(trifluoromethyl)benzoyl]amino]acetyl]amino]-propanamide (163a) sec-Butylamine (0.07 mL) was incorporated into the above procedure (4a) to give the title amide (S)-16.3 ($R^1$=2,4-dimethylphenyl, —C(O)N($R^{3a}$)$_2$=—C(O)NHCH(Me)Et, Z=—C(O)—, $R^2$=3-trifluoromethylphenyl, all other R=H; 7 mg). Exact MS calcd for $C_{26}H_{34}F_3N_4O_3$, the formula for (M+H)$^+$=507.2583. Found: 507.2554.

Example 164

(2S)-N-tert-Butyl-4-[[(2,4-dimethylphenyl)methyl]amino]-3-[[[[3-(trifluoromethyl)benzoyl]amino]acetyl]amino]-butanamide (164a) A solution of (R)-1.3 (l=m=0, PGN=N$_3$, $R^3$=CH$_2$CO$_2$tBu, Z=—C(O)—, $R^2$=3-(trifluoromethyl)

phenyl, all other R=H; cf. procedure (31d); 388 mg, 0.9 mmol) was dissolved in 3:1 methylene chloride/TFA (12 mL) and stirred for 3 h before being concentrated in vacuo. The residue was dissolved in methylene chloride and concentrated in vacuo; this procedure was repeated to provide the carboxylic acid, which was carried through procedure (33a). The resultant amide (R)-1.3 (l=m=0, PGN=$N_3$, $R^3$=$CH_2CONHtBu$, Z=—C(O)—, $R^2$=3-(trifluoromethyl) phenyl, all other R=H; 0.3 mmol) was then carried through procedure (1d). Purification by RP-HPLC provided the title compound (R)-1.5 (l=m=0, $R^1$=2,4-dimethylphenyl, $R^3$=$CH_2CONHt$-Bu, Z=—C(O)—, $R^2$=3-trifluoromethylphenyl, all other R=H; 10 mg). Exact MS calcd for $C_{27}H_{36}F_3N_4O_3$, the formula for (M+H$^+$=521.2740. Found: 521.2755.

Example 165

(2S, 3R)-N-Ethyl-3-[[(2,4-dimethylphenyl)methyl] amino]-2-[[[[3-(trifluoromethyl)benzoyl]amino] acetyl]amino]-butanamide (165a) To a solution of $N_\alpha$-Boc threonine (2.19 g, 10 mmol) in $CH_2Cl_2$ (75 mL) was added BOP (4.65 g, 10.5 mmol) and ethylamine (11 mL of a 2.0 M solution). The reaction was stirred for 2.5 h at room temperature and partitioned between EtOAc and sat. $NH_4Cl$. The organic phase was separated, washed with sat. $NaHCO_3$ (1×), washed with brine (1×), dried ($MgSO_4$), filtered, and concentrated in vacuo. The residue was purified by flash chromatography to give (2S, 3R)-5.2 ($R^6$=methyl, $R^{3a}$=ethyl; 2.22 g). MS found: (M+Na+MeCN)$^+$=310.1.

(165b) The amide (2S, 3R)-5.2 ($R^6$=methyl, $R^{3a}$=ethyl; 588 mg) was dissolved in THF, and the resultant solution was cooled to 0° C. and charged with DEAD (511 μL, 3.23 mmol), para-nitrobenzoic acid (600 mg, 3.59 mmol), and triphenylphospine (785 mg, 2.99 mmol). The reaction was stirred at room temperature for 12 h, concentrated in vacuo, dissolved in $CH_2Cl_2$, and purified by flash chromatography to give the para-nitrobenzoate as a white solid. This material was dissolved in 25 mL of 2:2:1 THF/MeOH/$H_2O$ and treated with LiOH (192 mg of the monohydrate). The reaction was stirred at room temperature for 18 h and concentrated in vacuo. The residue was diluted with EtOAc and washed with 5% $NaHCO_3$ (1×) and brine (1×). The organic phase was dried ($MgSO_4$), filtered, and concentrated in vacuo to give (2S, 3S)-5.2 ($R^6$=methyl, $R^{3a}$=ethyl; 143 mg) as a white solid. $^1$H-NMR (300 MHz, $CD_3OD$)): δ 7.94 (bs, 1H), 6.57 (d, 1H), 3.98–3.92 (m, 2H), 3.27–3.18 (m, 2H), 1.44 (s, 9H), 1.17 (d, 3H, J=6.3 Hz), 1.12 (t, 3H, J=7.5 Hz).

(165c) To a solution of the alcohol (2S, 3S)-5.2 ($R^6$=methyl, $R^{3a}$=ethyl; 143 mg, 0.58 mmol) in $CH_2Cl_2$ (10 mL) was added N,N-diisopropylethylamine (121 μL, 0.7 mmol) and methanesulfonic anhydride (111 mg, 0.64 mmol). The reaction was stirred for 12 h at room temperature and partitioned between EtOAc and sat. $NH_4Cl$. The organic phase was washed with sat. $NH_4Cl$ (1×), washed with brine (1×), dried ($Na_2SO_4$), filtered, and concentrated in vacuo to give the mesylate as an off-yellow solid (175 mg). The mesylate was dissolved in DMSO (5 mL) and treated with sodium azide (176 mg, 2.7 mmol). The reaction was heated at 65° C. for 14 h and then partitioned between EtOAc and sat. $NaHCO_3$. The organic phase was washed with brine (1×), dried ($MgSO_4$), filtered, and concentrated in vacuo. The residue was purified via flash chromatography to give (2S, 3R)-5.3 ($R^6$=methyl, $R^{3a}$=ethyl; 75 mg) as a white solid. MS found: (M+Na+MeCN)$^+$=335.2.

(165d) The carbamate (2S, 3R)-5.3 ($R^6$=methyl, $R^{3a}$=ethyl; 75 mg) was dissolved in 2:1 $CH_2Cl_2$/TFA (10 mL), and the resultant mixture was stirred at room temperature for 4 h before being concentrated in vacuo. The residue was dissolved in $CH_2Cl_2$, and concentrated in vacuo; this procedure was repeated twice more. This residue was then dissolved in benzene and concentrated in vacuo to give the pure amine. The amine (0.276 mmol assumed) was dissolved in $CH_2Cl_2$ (10 mL), and the resultant solution was charged with N,N-diisopropylethylamine (0.24 mL, 1.38 mmol), 1.2 (Z=C(O)—, $R^2$=3-trifluoromethylphenyl, all other R=H; 75 mg, 0.304 mmol) and HATU (116 mg, 0.30 mmol). The reaction was stirred for 72 h at room temperature and then partitioned between EtOAc and sat. $NH_4Cl$. The organic phase was washed with brine (1×), dried ($MgSO_4$), filtered, and concentrated in vacuo to give (2S, 3R)-1.3 (l=m=0, PGN=$N_3$, $R^6$=methyl, $R^3$=—C(O)NHEt, Z=C(O)—, $R^2$=3-trifluoromethylphenyl, all other R=H; 175 mg). MS found: (M+Na)$^+$=423.0.

(165e) The azide (2S, 3R)-1.3 (l=m=0, PGN=$N_3$, $R^6$=methyl, $R^3$=—C(O)NHEt, Z=C(O)—, $R^2$=3-trifluoromethylphenyl, all other R=H; 175 mg) was dissolved in MeOH (15 mL), and the resultant solution was charged with 5% Pd/C, Degussa type (125 mg), purged with hydrogen gas, and then stirred under $H_2$ (1 atm) for 14 h. The mixture was filtered and concentrated in vacuo to give the amine (2S, 3R)-1.4 (l=m=0, $R^6$=methyl, $R^3$=—C(O)NHEt, Z=C(O)—, $R^2$=3-trifluoromethylphenyl, all other R=H; 155 mg). MS found: (M+H)$^+$=375.2.

(165f) The amine (2S, 3R)-1.4 (l=m=0, $R^6$=methyl, $R^3$=—C(O)NHEt, Z=C(O)—, $R^2$=3-trifluoromethylphenyl, all other R=H; 78 mg, 0.14 mmol) was dissolved in MeOH (8 mL), and the resultant solution was charged with 2,4-dimethylbenzaldehyde (24 μL, 0.17 mmol), stirred for 10 min, and charged with sodium cyanoborohydride (16 mg, 0.25 mmol). The reaction was stirred for 12 h at room temperature and partitioned between EtOAc and sat. $NaHCO_3$. The aqueous phase was back-extracted with EtOAc (1×), and the organic extracts were combined, washed with brine (1×), dried ($MgSO_4$), filtered, and concentrated in vacuo. The residue was purified via RP-HPLC to give the title compound (2S, 3R)-1.5 (l=m=0, $R^1$=2,4-dimethylphenyl, $R^6$=methyl, $R^3$=—C(O)NHEt, Z=C(O)—, $R^2$=3-trifluoromethylphenyl, all other R=H; 10 mg). Exact MS calcd for $C_{25}H_{32}F_3N_4O_3$, the formula for (M+H)$^+$= 493.2427. Found: 493.2441.

Example 166

(2S, 3R)-N-Ethyl-3-[[(4-bromophenyl)methyl] amino]-2-[[[[3-(trifluoromethyl)benzoyl]amino] acetyl]amino]-butanamide (166a) The compound para-bromobenzaldehyde (31 mg, 0.17 mmol) was incorporated into the above procedure (165f) to give the title compound (2S, 3R)-1.5 (l=m=0, $R^1$=4-bromophenyl, $R^6$=methyl, $R^3$=—C(O)NHEt, Z=C (O)—, $R^2$=3-trifluoromethylphenyl, all other R=H; 10 mg). Exact MS calcd for $C_{23}H_{27}Br_1F_3N_4O_3$, the formula for (M+H)$^+$=543.1219. Found: 543.1214.

Example 167

Methyl (2R)-2-[[(2,4-dimethylphenyl)methyl] amino]-3-[[[[3-(trifluoromethyl)benzoyl]amino] acetyl]amino]-propanoate (167a) (R)-$N_\alpha$-Boc,$N_\beta$-Cbz-diaminopropionic acid DCHA salt (R)-2.1 (l=m=0; 2.0 g, 3.9 mmol) was incorporated into the above procedure (1b) to give (R)-2.2 (l=m=0; 2.32 g). MS found: (M+Na)$^+$=375.1.

(167b) To a solution of (R)-2.2 (l=m=0; 2.32 g) in MeOH (40 mL) was added 5% Pd/C, Degussa (1.0 g). The vessel was purged with H$_2$, and the reaction was stirred under H$_2$ (1 atm) for 12 h before being filtered and concentrated in vacuo to provide the amine, MS found: (M+H)$^+$=219.3. The amine was dissolved in 40 mL of 3:1 CH$_2$Cl$_2$/DMF and the resulting solution was charged with N,N-diisopropylethylamine (1.4 mL), the acid 1.2 (Z=—C(O)—, R$^2$=3-trifluoromethylphenyl, all other R=H; 963 mg), and HATU (1.48 g). The reaction was stirred for 3.5 h and diluted with EtOAc. The organic phase was washed successively with sat. NH$_4$Cl, 5% NaHCO$_3$, and sat. NaCl. The organic phase was dried (Na$_2$SO$_4$), filtered, and concentrated in vacuo to provide amide (R)-23.1 (l=m=0, R$^6$=CO$_2$Me, Z=—C(O)—, R$^2$=3-trifluoromethylphenyl, all other R=H; 2.52 g). MS found: (M+Na)$^+$=470.1.

(167c) The carbamate (R)-23.1 (l=m=0, R$^6$=CO$_2$Me, Z=—C(O)—, R$^2$=3-trifluoromethylphenyl, all other R=H; 2.52 g) was dissolved in 3:2 CH$_2$Cl$_2$/TFA (75 mL) and stirred at room temperature for 80 min before being concentrated in vacuo. The residue was dissolved in CH$_2$Cl$_2$ and the solution was concentrated in vacuo. The residue was dissolved in benzene and the solution was concentrated in vacuo; this procedure was repeated once more to afford the amine as a yellow oil (3.5 g). MS found: (M+H)+=348.1. A portion of this amine (0.4 mmol) was dissolved in THF (6 mL) and the resultant solution was charged with N,N-diisopropylethylamine (430 μL) and 2,4-dimethylbenzaldehyde (67 μL). The reaction was stirred for 15 min and charged with sodium triacetoxyborohydride (254 mg). The reaction was stirred for 3 h at room temperature and partitioned between EtOAc and sat. NaHCO$_3$. The organic phase was washed with brine, dried (Na$_2$SO$_4$), filtered, and concentrated in vacuo. The resultant residue was purified by reverse phase HPLC to afford the title compound (R)-1.5 (l=m=0, R$^1$=2,4-dimethylphenyl, R$^6$=CO$_2$Me, Z=—C(O)—, R$^2$=3-trifluoromethylphenyl, all other R=H; 25 mg). MS found: (M+H)$^+$=466.3.

Example 168

(2R)-N-Ethyl-2-[[(2,4-dimethylphenyl)methyl] amino]-3-[[[[3-(trifluoromethyl)benzoyl]amino] acetyl]amino]-propanamide (168a) To a solution of (R)-1.5 (l=m=0, R$^1$=2,4-dimethylphenyl, R$^6$=CO$_2$Me, Z=—C(O)—, R$^2$=3-trifluoromethylphenyl, all other R=H; 19 mg) in 2:2:1 THF/MeOH/H$_2$O (10 mL) was added LiOH (40 mg). The reaction was stirred for 12 h at room temperature, quenched with 1 M HCl, and extracted with EtOAc (2×). The organic extracts were combined, washed with brine, dried (MgSO$_4$), filtered, and concentrated in vacuo to afford a white paste. This material was not characterized but rather dissolved in 3:1 CH$_2$Cl$_2$/DMF (8 mL) and treated with HATU (19 mg) and ethylamine (70 μL of a 2.0 M solution). The reaction was stirred for 3 h at room temperature and concentrated in vacuo. The residue was purified by reverse phase HPLC to afford the title compound (R)-1.5 (l=m=0, R$^1$=2,4-dimethylphenyl, R$^6$=CONHEt, Z=—C(O)—, R$^2$=3-trifluoromethylphenyl, all other R=H; 5 mg). MS found: (M+H)$^+$=479.4.

Example 169

Methyl (2S)-4-[[(2,4-dimethylphenyl)methyl] amino]-2-[[[[3-(trifluoromethyl)benzoyl]amino] acetyl]amino]-butanoate (169a) (S)-N$_\alpha$Boc,N$_{65}$-Cbz-diaminobutanoic acid DCHA salt (S)-2.1 (l=1, m=0; 4.93 g, 9.24 mmol) was incorporated into the above procedure (1b) to give (S)-2.2 (l=1, m=0, all R=H; 2.18 g). A portion (950 mg, 2.60 mmol) of this material was incorporated into procedures (1c) & (1d). Purification by RP-HPLC provided the title compound (S)-1.5 (l=1, m=0, R$^1$=2,4-dimethylphenyl, R$^3$=CO$_2$Me, Z=—C(O)—, R$^2$=3-trifluoromethylphenyl, all other R=H; 10 mg). MS found: (M+H)$^+$=480.3.

Example 170

(2S)-4-[[(2,4-dimethylphenyl)methyl]amino]-2-[[[[3-(trifluoromethyl)benzoyl]amino]acetyl]amino]-butanamide (170a) (S)-N$_\alpha$-Fmoc, Nγ-Alloc-diaminobutyric acid (0.64 g, 1.0 mmol), N$_\alpha$-Fmoc glycine (0.28 g, 1.0 mmol), and 3-(trifluoromethyl)benzoic acid were incorporated into the above procedure (27a) to afford the resin bound (S)-21.6 (l=1, m=0, R$^2$=3-(trifluoromethyl)phenyl, all other R=H; 700 mg).

(170b) The resin-bound (S)-21.6 (l=1, m=0, R$^2$=3-(trifluoromethyl)phenyl, all other R=H; 210 mg) was incorporated into the above procedure (27b) to afford the title compound (S)-21.8 (l=1, m=0, R$^1$=2,4-dimethylphenyl, R$^2$=3-(trifluoromethyl)phenyl, all other R=H; 4.0 mg). MS found: (M+H)$^+$=465.3.

Example 171

(2S)-N-Ethyl-4-[[(2,4-dimethylphenyl)methyl] amino]-2-[[[[3-(trifluoromethyl)benzoyl]amino] acetyl]amino]-butanamide (171a) (S)-N$_\alpha$-Boc,N$_\gamma$-Cbz-diaminobutanoic acid DCHA salt (S)-2.1 (l=1, m=0; 1.03g, 1.93 mmol) was dissolved in CH$_2$Cl$_2$ (17 mL), and the resultant solution was charged with ethylamine (5.0 mL of a 2.0 M solution, 10 mmol) and HATU (713 mg, 1.91 mmol). The reaction was stirred for 15 hours at room temperature, diluted with EtOAc (60 mL) and washed with 1N HCl (2×), water (1×), and brine (1×). The organic extracts were dried (Na$_2$SO$_4$), filtered, and concentrated in vacuo, and the resultant residue was purified via flash chromatography to give (S)-2.3 (l=1, m=0, —C(O)N(R$^{3a}$)$_2$=—C(O)NHEt; 398 mg). MS found: (M+Na)$^+$=402.2.

(171b) The amide (S)-2.3 (l=1, m=0, —C(O)N(R$^{3a}$)$_2$=—C(O)NHEt; 398 mg) was dissolved in 2:1 CH$_2$Cl$_2$/TFA (6 mL) and stirred at room temperature for 3 h. The volatiles were removed in vacuo. The residue was dissolved in CHCl$_3$ and concentrated in vacuo; this procedure was repeated once more. The residue was dissolved in EtOAc, washed with sat. NaHCO$_3$ (1×), water (1×), and brine (1×). The organic extracts were dried (Na$_2$SO$_4$), filtered, and concentrated in vacuo. The amine (217 mg, 0.77 mmol) was dissolved in CH$_2$Cl$_2$ (8 mL), and the resultant solution was charged with DMF (1.5 mL), N,N-diisopropylethylamine (0.4 mL, 2.31 mmol), N$_\alpha$-Boc glycine (142 mg, 0.81 mmol) and HATU (314 mg, 0.82 mmol). The reaction was stirred for 15 h at room temperature, diluted with EtOAc (60 mL) and washed with 1N HCl (2×), water (1×), sat. NaHCO$_3$ (1×), and brine (1×). The organic extracts were dried (Na$_2$SO$_4$), filtered, and concentrated in vacuo to give (S)-1.6 (l=1, m=0, PGN=CbzHN, R$^3$=—C(O)NHEt, all other R=H; >quantitative mass recovery). MS found: (M+Na)$^+$=459.2.

(171c) The bisamide (S)-1.6 (l=1, m=0, PGN=CbzHN, R$^3$=—C(O)NHEt, all other R=H; assumed to be 0.77 mmol) was dissolved in 2:1 CH$_2$Cl$_2$/TFA (6 mL) and stirred at room temperature for 3 h. The volatiles were removed in vacuo. The residue was dissolved in CH$_2$Cl$_2$ and concentrated in vacuo; this procedure was repeated twice more. The residue was dissolved in benzene and concentrated in vacuo; this procedure was repeated once more. The product amine (assumed to be 0.77 mmol) was dissolved in $CH_2Cl_2$ (4 mL), and the resultant solution was charged with DMF (3 mL), N,N-diisopropylethylamine (1.6 mL, 9.2 mmol), 3-trifluoromethylbenzoic acid (371 mg, 1.95 mmol) and HATU (690 mg, 1.82 mmol). The reaction was stirred for 15 h at room temperature, diluted with EtOAc and washed with 1N (2×), water (1×), sat. $NaHCO_3$ (1×), and brine (1×). The organic extracts were dried ($Na_2SO_4$), filtered, and concentrated in vacuo to give (S)-1.3 (l=1, m=0, PGN=CbzHN, $R^3$=—C(O)NHEt, Z=—C(O)—, $R^2$=trifluoromethylphenyl, all other R=H; 810 mg, >quantitative mass recovery). MS found: $(M-H+TFA)^-$=680.0.

(171d) The unpurified carbamate (S)-1.3 (l=1, m=0, PGN=CbzHN, $R^3$=—C(O)NHEt, Z=—C(O)—, $R^2$=trifluoromethylphenyl, all other R=H; 404 mg) was dissolved in 1:1 MeOH/THF (20 mL) and the resultant solution was charged with 5% Pd/C (Degussa type, 350 mg). The reaction was evacuated and then back-filled with $H_2$; this procedure was repeated twice more. The reaction was stirred for 12 h at room temperature and then filtered. The product was purified by RP-HPLC to give the free amine (S)-1.4 (l=1, m=0, $R^3$=—C(O)NHEt, Z=—C(O)—, $R^2$=trifluoromethylphenyl, all other R=H; 70 mg). MS found: $(M+H)^+$=375.2.

(171e) The amine (30 mg) was dissolved in MeOH (1 mL) and the resultant solution was charged with 2,4-dimethylbenzaldehyde (13 μL) and sodium cyanoborohydride (20 mg). The reaction was stirred at room temperature for 12 h, diluted with EtOAc, and washed with sat. $NaHCO_3$. The aqueous phase was back-extracted with EtOAc (2×), and the organic extracts were combined, washed with brine (1×), dried ($MgSO_4$), filtered, and concentrated in vacuo. The residue was purified by RP-HPLC to give the title compound (S)-1.5 (l=1, m=0, $R^1$=2,4-dimethylphenyl, $R^3$=—C(O)NHEt, Z=—C(O)—, $R^2$=3-trifluoromethylphenyl, all other R=H; 10 mg). Exact MS calcd for $C_{25}H_{32}F_3N_4O_3$, the formula for $(M+H)^+$= 493.2427. Found: 493.2443.

Example 172

(2S)-N-Ethyl-4-[[(2,4-dimethylphenyl)methyl]methylamino]-2-[[[[3-(trifluoromethyl)benzoyl]amino]acetyl]amino]-butanamide (172a) To a cooled (0° C.) solution of (S)-1.5 (l=1, m=0, $R^1$=2,4-dimethylphenyl, $R^3$=—C(O)NHEt, Z=—C(O)—, $R^2$=3-trifluoromethylphenyl, all other R=H; 6 mg) in 4:1 THF/1,2-dichloroethane (1 mL) was added N,N-diisopropylethylamine (2.0 μL) and formaldehyde (5 μL of a 37% aq. solution). The reaction was stirred at room temperature for 15 min and charged with sodium triacetoxyborohydride (5 mg). The reaction was stirred at room temperature for 2 h, quenched with sat. $NaHCO_3$, and extracted with EtOAc (3×). The organic extracts were combined, dried ($Na_2SO_4$), filtered, and concentrated in vacuo. The residue was purified by reverse phased HPLC to afford the title compound (S)-24.1 (l=1, m=0, $R^1$=2,4-dimethylphenyl, $R^{17}$=methyl, $R^3$=—C(O)NHEt, Z=—C(O)—, $R^2$=3-trifluoromethylphenyl, all other R=H; 3 mg). MS found: $(M+H)^+$=507.4.

Example 173

(2S)-N-tert-Butyl-2-[[[[2-[[(1,1-dimethylethoxy)carbonyl]amino]-5-(trifluoromethyl)benzoyl]amino]acetyl]amino]-4-[[(2,4-dimethylphenyl)methyl]amino]-butanamide (173a) tert-Butylamine (1.73 mL, 16.5 mmol) was incorporated into the above procedure (171a) to give (S)-2.3 (l=1, m=0, —C(O)N($R^{3a}$)$_2$=—C(O)NHt-Bu; assumed 5.49 mmol). This material was carried through procedure (171b) as described and then purified by flash chromatography to afford (S)-1.6 (l=1, m=0, PGN=CbzHN, $R^3$=—C(O)NHt-Bu, all other R=H; 2.14 g, 4.61 mmol). MS found: $(M+Na)^+$=487.

(173b) The compound (S)-1.6 (l=1, m=0, PGN=CbzHN, $R^3$=—C(O)NHt-Bu, all other R=H; 543 g, 1.17 mmol) and N-Boc 2-amino-5-(trifluoromethyl)benzoic acid (S. Takagishi, et al., *Synlett* 1992, 360; 375 mg, 1.23 mmol) were incorporated into the above procedure (171c) to afford (S)-1.3 (l=1, m=0, PGN=CbzHN, $R^3$=—C(O)NHt-Bu, Z=—C(O)—, $R^2$=N-Boc 2-amino-5-(trifluoromethyl)phenyl, all other R=H; 297 mg) after flash chromatography. MS found: $(M+Na)^+$=674.3.

(173c) The tris-amide (S)-1.3 (l=1, m=0, PGN=CbzHN, $R^3$=—C(O)NHt-Bu, Z=—C(O)—, $R^2$=N-Boc 2-amino-5-(trifluoromethyl)phenyl, all other R=H; 297 mg) was incorporated into procedure (171d) above, but the final product was not purified by HPLC; MS found: $(M+H)^+$=518.2. This material was immediately subjected to the conditions outlined in procedure (171e), and the crude product thus obtained was purified by RP-HPLC to afford the title compound (S)-1.5 (l=1, m=0, $R^1$=2,4-dimethylphenyl, $R^3$=—C(O)NHt-Bu, Z=—C(O)—, $R^2$=N-Boc 2-amino-5-trifluoromethylphenyl, all other R=H; 20 mg). Exact MS calcd for $C_{32}H_{45}F_3N_3O_5$, the formula for $(M+H)^+$= 636.3373. Found: 636.3392.

Example 174

(2S)-N-tert-Butyl-2-[[[[2-[[(1,1-dimethylethoxy)carbonyl]amino]-5-(trifluoromethyl)benzoyl]amino]acetyl]amino]-4-[[(2,4-dimethylphenyl)methyl]methylamino]-butanamide (174a) The material (S)-1.5 (l=1, m=0, $R^1$=2,4-dimethylphenyl, $R^3$=—C(O)NHt-Bu, Z=—C(O)—, $R^2$=N-Boc 2-amino-5-trifluoromethylphenyl, all other R=H; 0.275 mmol) was incorporated into the above procedure (172a) to afford the title compound (S)-24.1 (l=1, m=0, $R^1$=2,4-dimethylphenyl, $R^{17}$=methyl, $R^3$=—C(O)NHt-Bu, Z=—C(O)—, $R^2$=N-Boc 2-amino-5-trifluoromethylphenyl, all other R=H; 20 mg) as a white powder after RP-HPLC and lyopholization. Exact MS calcd for $C_{33}H_{47}F_3N_3O_5$, the formula for $(M+H)^+$=650.3529. Found: 650.3516.

Example 175

(2S)-N-tert-Butyl-2-[[[[2-amino-5-(trifluoromethyl)benzoyl]amino]acetyl]amino]-4-[[(2,4-dimethylphenyl)methyl]amino]-butanamide (175a) The compound (S)-1.5 (l=1, m=0, $R^1$=2,4-dimethylphenyl, $R^3$=—C(O)NHt-Bu, Z=—C(O)—, $R^2$=N-BoC 2-amino-5-trifluoromethylphenyl, all other R=H; 10 mg) was dissolved in 6 mL of 6:1 methylene chloride/TFA and stirred for 3 h at RT before being concentrated in vacuo. The residue was dissolved in methylene chloride and the solution was concentrated in vacuo; this procedure was repeated once more. The residue was purified by RP-HPLC to afford the title compound (S)-1.5 (l=1, m=0, $R^1$=2,4-dimethylphenyl, $R^3$=—C(O)NHt-Bu, Z=—C(O)—, $R^2$=2-amino-5-trifluoromethylphenyl, all other R=H; 5 mg) as a white powder after lyopholization. Exact MS calcd for $C_{27}H_{36}F_3N_5O_3$, the formula for $(M+H)^+$=536.2848. Found: 536.2855.

Example 176

(2S)-N-tert-Butyl-2-[[[[2-amino-5-(trifluoromethyl)benzoyl]amino]acetyl]amino]-4-[[(2,4-dimethylphenyl)methyl]methylamino]-butanamide (176a) The compound (S)-1.5 (l=1, m=0, $R^1$ 2,4-dimethylphenyl, $R^{17}$ methyl, $R^3$=—C(O)NHt-Bu, Z=—C (O)—$R^2$=N-Boc 2-amino-5-trifluoromethylphenyl, all other R=H; 20 mg) was incorporated into the above procedure (175a) to afford the title compound (S)-24.1 (l=1, m=0, $R^1$=2,4-dimethylphenyl, $R^{17}$=methyl, $R^3$=—C(O)NHt-Bu, Z=—C(O)—, $R^2$=2-amino-5-trifluoromethylphenyl, all other R=H; 10 mg) as a white powder after RP-HPLC and lyopholization. Exact MS calcd for $C_{28}H_{38}F_3N_5O_3$, the formula for $(M+H)^+$=550.3005. Found: 550.3003.

Example 177

(2S)-N-tert-Butyl-2-[[[[3-amino-5-(trifluoromethyl) benzoyl]amino]acetyl]amino]-4-[[(2,4-dimethylphenyl)methyl]amino]-butanamide (177a) The compound (S)-1.6 (l=1, m=0, PGN=CbzHN, $R^3$=—C(O)NHt-Bu, all other R=H; 0.61 mmol) and 3-nitro-5-(trifluoromethyl)benzoic acid (143 mg, 0.61 mmol) were incorporated into the above procedure (171c) to afford (S)-1.3 (l=1, m=0, PGN=CbzHN, $R^3$=—C(O)NHt-Bu, Z=—C(O)—, $R^2$=3-amino-5-(trifluoromethyl)phenyl, all other R=H; 279 mg) after flash chromatography.

(177b) The tris-amide (S)-1.3 (l=1, m=0, PGN=CbzHN, $R^3$=—C(O)NHt-Bu, Z=—C(O)—, $R^2$=3-amino-5-(trifluoromethyl)phenyl, all other R=H; 279 mg) was incorporated into procedure (171d) above, but the final product was not purified by HPLC; MS found: $(M+H)^+$=418.2. Half of this material (estimated 0.24 mmol) was immediately subjected to the conditions outlined in procedure (171e), and the crude product thus obtained was purified by RP-HPLC to afford the title compound (S)-1.5 (l=1, m=0, $R^1$=2,4-dimethylphenyl, $R^3$=—C(O)NHt-Bu, Z=—C(O)—, $R^2$=3-amino-5-trifluoromethylphenyl, all other R=H; 20 mg). Exact MS calcd for $C_{27}H_{37}F_3N_5O_3$, the formula for $(M+H)^+$=536.2848. Found: 536.2852.

Example 178

(2S)-N-tert-Butyl-2-[[[[3-amino-5-(trifluoromethyl) benzoyl]amino]acetyl]amino]-4-[[(4-ethylphenyl) methyl]amino]-butanamide (178a) The tris-amide (S)-1.3 (l=1, m=0, PGN=CbzHN, $R^3$=—C(O)NHt-Bu, Z=—C(O)—, $R^2$=3-amino-5-(trifluoromethyl)phenyl, all other R=H; 279 mg) was incorporated into procedure (171d) above, but the final product was not purified by HPLC; MS found: $(M+H)^+$=418.2. Half of this material (estimated 0.24 mmol) was immediately subjected to the conditions outlined in procedure (171e), substituting 4-ethylbenzaldehyde (0.033 mL, 0.24 mmol) for 2,4-dimethylbenzaldehyde. The crude product thus obtained was purified by RP-HPLC to afford the title compound (S)-1.5 (l=1, m=0, $R^1$=4-ethylphenyl, $R^3$=—C(O)NHt-Bu, Z=—C(O)—, $R^2$=3-amino-5-trifluoromethylphenyl, all other R=H; 15 mg). Exact MS calcd for $C_{27}H_{37}F_3N_5O_3$, the formula for $(M+H)^+$536.2848. Found: 536.2843.

Example 179

(2S)-N-tert-Butyl-4-[[(2,4-dimethylphenyl)methyl] amino]-2-[[[[3-(trifluoromethyl)benzoyl]amino] acetyl]amino]-butanamide (179a) The compound (S)-1.6 (l=1, m=0, PGN=CbzHN, $R^3$=—C(O)NHt-Bu, all other R=H; 2.42 mmol) and 3-(trifluoromethyl)benzoic acid (460 mg, 2.42 mmol) were incorporated into the above procedure (171c) to afford (S)-1.3 (l=1, m=0, PGN=CbzHN, $R^3$=—C(O)NHt-Bu, Z=—C(O)—, $R^2$=3-(trifluoromethyl)phenyl, all other R=H; 1.07 mg) after flash chromatography. MS found: $(M+Na)^+$=559.2.

(179b) The tris-amide (S)-1.3 (l=1, m=0, PGN=CbzHN, $R^3$=—C(O)NHt-Bu, Z=—C(O)—, $R^2$=3-(trifluoromethyl) phenyl, all other R=H; 1.43 mmol) was incorporated into procedure (171d) above, but the final product was not purified by HPLC. Half of this material (estimated 0.70 mmol) was immediately subjected to the conditions outlined in procedure (171e), and the crude product thus obtained was purified by RP-HPLC to afford the title compound (S)-1.5 (l=1, m=0, $R^1$=2,4-dimethylphenyl, $R^3$=—C(O) NHt-Bu, Z=—C(O)—, $R^2$=3-trifluoromethylphenyl, all other R=H; 10 mg). Exact MS calcd for $C_{27}H_{36}F_3N_4O_3$, the formula for $(M+H)^+$=521.2740. Found: 521.2739.

Example 180

(2S)-N-tert-Butyl-4-[[(4-ethylphenyl)methyl]amino]-2-[[[[3-(trifluoromethyl)benzoyl]amino]acetyl] amino]-butanamide (180a) The tris-amide (S)-1.3 (l=1, m=0, PGN=CbzHN, $R^3$=—C(O)NHt-Bu, Z=—C(O)—, $R^2$=3-(trifluoromethyl) phenyl, all other R=H; 1.43 mmol) was incorporated into procedure (171d) above, but the final product was not purified by HPLC. Half of this material (estimated 0.70 mmol) was immediately subjected to the conditions outlined in procedure (171e), substituting 4-ethylbenzaldehyde (0.096 mL, 0.7 mmol) for 2, 4-dimethylbenzaldehyde. The crude product thus obtained was purified by RP-HPLC to afford the title compound (S)-1.5 (l=1, m=0, $R^1$=4-ethylphenyl, $R^3$=—C(O)NHt-Bu, Z=—C(O)—, $R^2$=3-trifluoromethylphenyl, all other R=H; 9 mg). Exact MS calcd for $C_{27}H_{36}F_3N_4O_3$, the formula for $(M+H)^+$= 521.2740. Found: 521.2741.

Example 181

(2S)-N-Ethyl-5-[[(2,4-dimethylphenyl)methyl] amino]-2-[[[[3-(trifluoromethyl)benzoyl]amino] acetyl]amino]-pentanamide (181a) (S)-$N_\alpha$-Boc,N5-Cbz-ornithine (S)-2.1 (l=m=1; 1.56g, 4.23 mmol) was incorporated into the above procedure (171a) to give (S)-2.3 (l=m=1,—C(O)N($R^{3a}$)$_2$=—C(O) NHEt; 1.02 g). MS found: $(M+Na)^+$=416.2. This material was carried through procedures (171b)–(171e) to give the title compound (S)-1.5 (l=m=1, $R^1$=2,4-dimethylphenyl, $R^3$=—C(O)NHEt, Z=—C(O)—, $R^2$=3-trifluoromethylphenyl, all other R=H; 15 mg). Exact MS calcd for $C_{26}H_{34}F_3N_4O_3$, the formula for $(M+H)^+$507.2583. Found: 507.2599.

Example 182

N-[2-[[(1S, 2S/R)-1-[[[(2,4-dimethylphenyl)methyl] methylamino]methyl]-2-hydroxy-3-(methyl)butyl] amino]-2-oxoethyl]-3-(trifluoromethyl)benzamide (182a) The compound (1S, 2S/R)-1.5 (l=m=0, $R^1$=2,4-dimethylphenyl, $R^3$=—CH(OH)i-Pr, Z=—C(O)—, $R^2$=3-(trifluoromethyl)phenyl, all other R=H; 31 mg, 0.05 mmol) was incorporated into procedure (172a) above. The residue was purified by RP-HPLC to separate starting material and the title compound (1S, 2S/R)-24.1 (l=m=0, $R^1$=2,4-dimethylphenyl, $R^{17}$=Me, $R^3$=—CH(OH)i-Pr, Z=—C(O)—, $R^2$=3-(trifluoromethyl)phenyl, all other R=H; 5 mg), which was obtained as white powder after lyopholization. Exact MS calcd for $C_{26}H_{35}F_3N_3O_3$, the formula for $(M+H)^+$= 494.2631. Found: 494.2643.

Example 183

N-[2-[[(1S, 2S)-1-[[[(2,4-dimethylphenyl)methyl] methylamino]methyl]-2-(hydroxy)pentyl]amino]-2-oxoethyl]-2-[[(isopropylamino) carbonyl]amino]-5-(trifluoromethyl)benzamide (183a) The compound (1S, 2S)-1.5 (l=m=0, $R^1$=2,4-dimethylphenyl, $R^3$=—CH(OH)n-propyl, Z=—C(O)—, $R^2$=2-(isopropylaminocarbonyl)amino-5-(trifluoromethyl)phenyl, all other R=H; cf. procedure (65a); 23 mg, 0.043 mmol) was dissolved in MeOH (0.5 mL), and the solution was charged with formaldehyde (37% aq. solution, 0.003 mL, 0.043 mmol) and acetic acid (0.005 mL). The reaction was stirred for 15 min at RT and then charged with sodium cyanoborohydride (3.4 mg, 0.054 mmol). The reaction was stirred for 48 h at RT and then partitioned between EtOAc and sat. $NaHCO_3$. The organic phase was washed with brine, dried ($Na_2SO_4$), filtered, and concentrated in vacuo. The residue was purified by RP-HPLC to provide the title compound (S)-24.1 (l=1, m=0, $R^1$=2,4-dimethylphenyl, $R^{17}$=methyl, $R^3$=—CH (OH) n-Pr, Z=—C(O)—, $R^2$=2-(isopropylaminocarbonyl)amino-5-trifluoromethylphenyl, all other R=H; 3 mg). Exact MS calcd for $C_{30}H_{43}F_3N_3O_4$, the formula for $(M+H)^+$=594.3267. Found: 594.3276.

Example 184

N-[2-[[(1S, 2S)-1-[[[(2,4-dimethylphenyl)methyl]isopropylamino]methyl]-2-(hydroxy)pentyl]amino]-2-oxoethyl]-2-[[(isopropylamino) carbonyl]amino]-5-(trifluoromethyl)benzamide (184a) The compound (1S, 2S)-1.5 (l=m=0, $R^1$=2,4-dimethylphenyl, $R^3$=—CH(OH)n-propyl, Z=—C(O)—, $R^2$=2-(isopropylaminocarbonyl)amino-5-(trifluoromethyl)phenyl, all other R=H; cf. procedure (65a); 25 mg, 0.043 mmol) was combined with acetone (0.003 mL, 0.043 mmol) in procedure (183a). The product was purified by RP-HPLC to provide the title compound (S)-24.1 (l=1, m=0, $R^1$=2,4-dimethylphenyl, $R^{17}$=isopropyl, $R^3$=—CH(OH)n-Pr, Z=—C(O)—, $R^2$=2-(isopropylaminocarbonyl)amino-5-trifluoromethylphenyl, all other R=H; 3 mg). Exact MS calcd for $C_{32}H_{47}F_3N_3O_4$, the formula for $(M+H)^+$=622.3580. Found: 622.3588.

Example 185

N-[2-[[(1S, 2S)-1-[[[(4-ethylphenyl)methyl]methylamino]methyl]-2-(hydroxy)pentyl]amino]-2-oxoethyl]-2-[[(isopropylamino) carbonyl]amino1-5-(trifluoromethyl)benzamide (185a) The compound (1S, 2S)-1.5 (l=m=0, $R^1$=4-ethylphenyl, $R^3$=—CH(OH)n-propyl, Z=—C(O)—, $R^2$=2-(isopropylaminocarbonyl)amino-5-(trifluoromethyl)phenyl, all other R=H; cf. procedure (74a); 25 mg, 0.043 mmol) was incorporated into procedure (183a). Purification by RP-HPLC provided the title compound (S)-24.1 (l=1, m=0, $R^1$=4-ethylphenyl, $R^{17}$=Me, $R^3$=—CH(OH) n-Pr, Z=—C(O)—, $R^2$=2-(isopropylaminocarbonyl)amino-5-trifluoromethylphenyl, all other R=H; 3 mg). Exact MS calcd for $C_{30}H_{43}F_3N_3O_4$, the formula for $(M+H)^+$=594.3267. Found: 594.3273.

Example 186

N-[2-[[(1S, 2S)-1-[[[(4-ethylphenyl)methyl]isopropylamino]methyl]-2-(hydroxy)pentyl]amino]-2-oxoethyl]-2-[[(isopropylamino) carbonyl]amino]-5-(trifluoromethyl)benzamide (186a) The compound (1S, 2S)-1.5 (l=m=0, $R^1$=4-ethylphenyl, $R^3$=—CH(OH)n-propyl, Z=—C(O)—, $R^2$=2-(isopropylaminocarbonyl)amino-5-(trifluoromethyl)phenyl, all other R=H; cf. procedure (74a); 23 mg, 0.041 mmol) was combined with acetone (0.003 mL, 0.041 mmol) and incorporated into procedure (183a). Purification by RP-HPLC provided the title compound (S)-24.1 (l=1, m=0, $R^1$=4-ethylphenyl, $R^{17}$=isopropyl, $R^3$=—CH(OH)n-Pr, Z=—C(O)—, $R^2$=2-(isopropylaminocarbonyl)amino-5-trifluoromethylphenyl, all other R=H; 3 mg). Exact MS calcd for $C_{32}H_{47}F_3N_5O_4$, the formula for $(M+H)^+$=622.3592. Found: 622.3588.

Example 187

(2S)-N-tert-Butyl-3-[[(2,4-dimethylphenyl)methyl]methylamino]-2-[[[[3-(trifluoromethyl)benzoyl]amino]acetyl]amino]-propanamide (187a) The compound (S)-16.3 ($R^1$=2,4-dimethylphenyl, —C(O)N($R^{3a}$)_2=—C(O)NHt-Bu, Z=—C(O)—, $R^2$=3-trifluoromethylphenyl, all other R=H; cf. procedure (10a); 11 mg, 0.02 mmol) was carried through procedure (172a). The product was purified by RP-HPLC to afford the title compound (S)-24.1 (l=m=0, $R^1$=2,4-dimethylphenyl, $R^{17}$=methyl, $R^3$=—C(O)NHt-Bu, Z=—C(O)—$R^2$=3-trifluoromethylphenyl, all other R=H; 6 mg). MS found: $(M+H)^+$=521.2.

Example 188

N-[2-[[1-[[[(2,4-dimethylphenyl)methyl]amino]methyl]cyclohexyl]amino]-2-oxoethyl]-3-(trifluoromethyl)benzamide (188a) A solution of 1-amino-1-cyanocyclohexane (T. A. Keating and R. W. Armstrong, *J. Am. Chem. Soc.* 1996, 118, 2574; 0.55 g, 4.4 mmol) in DMF (15 mL) was charged sequentially with the acid 1.2 (all R=H, Y=3-trifluoromethylphenyl; 1.09 g, 4.4 mmol), BOP (2.15 g, 4.9 mmol), and N,N-diisopropylethylamine (1.9 mL, 11.1 mmol). The reaction was stirred for 12 h at room temperature and partitioned between EtOAc and brine. The organic phase was dried ($Na_2SO_4$), filtered, and concentrated in vacuo. The resultant residue was purified by flash chromatography to afford the product N-[2-[(1-cyanocyclohexyl)amino]-2-oxoethyl]-3-(trifluoromethyl)benzamide (300 mg). MS found: $(M+Na)^+$=376.2.

(188b) A solution of N-[2-[(1-cyanocyclohexyl)amino]-2-oxoethyl]-3-(trifluoromethyl)benzamide (300 mg) in 7:2 MeOH/$CHCl_3$ (9 mL) was charged with 5% Pd/C, Degussa (100 mg) and transferred to a Parr vessel. The reaction was shaken under 50 psi of $H_2$ for 12 h, charged with another 100 mg of Pd catalyst, and shaken for another 5 h at 50 psi of $H_2$. The reaction mixture was filtered and concentrated in vacuo to afford the crude amine 1.4 (l=m=0, ($R^3$, $R^{12}$)=—($CH_2$)_4—, Z=—C(O)—, $R^2$=3-trifluoromethylphenyl, all other R=H; 120 mg). MS found: $(M+H)^+$=358.2.

(188c) A solution of the amine 1.4 (l=m=0, ($R^3$, $R^{12}$)=—($CH_2$)_4—, Z=—C(O)—, $R^2$=3-trifluoromethylphenyl, all other R=H; 57 mg, 0.15 mmol) in THF (4 mL) was charged with N,N-diisopropylethylamine (0.12 mL, 0.72 mmol), 2,4-dimethylbenzaldehyde (22 mg, 0.15 mmol), 4 Å molecular sieves (powdered, 60 mg), and glacial acetic acid (8 mL, 0.15 mmol). The reaction was stirred at room temperature for 3 h, charged with sodium triacetoxyborohydride (46 mg, 0.22 mmol), stirred for another 1 h at room temperature, and filtered. The filtrate was partitioned between EtOAc and sat. $NaHCO_3$, and the organic phase was concentrated in vacuo. The residue was purified by reverse phase HPLC to give the title compound 1.5 (l=m =0, $R^1$=2,4-dimethylphenyl, ($R^3$, $R^{12}$)=—($CH_2$)_4—, Z=—C(O)—, $R^2$=3-trifluoromethylphenyl, all other R=H; 8.0 mg). MS found: $(M+H)^+$=476.4.

Example 189

N-[2-[[1-[[[(4-chlorophenyl)methyl]amino]methyl]
cyclohexyl]amino]-2-oxoethyl]-3-(trifluoromethyl)
benzamide (189a) para-Chlorobenzaldehyde (14 mg) was incorporated into the above procedure (188c) to give the title compound 1.5 (l=m=0, $R^1$=4-chlorophenyl, ($R^3$, $R^{12}$)=—(CH$_2$)$_4$—, Z=—C(O)—, $R^2$=3-trifluoromethylphenyl, all other R=H; 7.0 mg). MS found: (M+H)$^+$=482.2.

Example 190

N-[2-[[1-[[[(2,4-dimethylphenyl)methyl]amino]
methyl]cyclopentyl]amino]-2-oxoethyl]-3-
(trifluoromethyl)benzamide (190a) To a solution of 1-[1,1-(dimethyl)ethoxycarbonyl] aminocyclopentyl carboxaldehyde (D. Braghiroli and M. Di Bella, *Tetrahedron Lett.* 1996, 37, 7319; 1.10 g, 5.16 mmol) in trimethyl orthoformate (20 mL) was added 2,4-dimethylbenzylamine (1.4 g) and the reaction mixture stirred at room temperature for 8 h. Sodium cyanoborohydride (0.96 g) and methanol (2.5 mL) were added consecutively and the suspension stirred at room temperature for 12 h. The mixture was quenched with water and extracted with dichloromethane (2×). The organic extracts were washed with brine, dried (Na$_2$SO$_4$), and concentrated in vacuo. Purification by flash chromatography (SiO$_2$) provided N-Boc 1-[[(2,4-dimethylphenyl)methyl]amino] methylcyclopentylamine (974 mg, 57%) MS found: (M+H)$^+$=333. To a solution of this amine (500 mg, 1.63 mmol) and triethylamine (0.5 mL, 3.58 mmol) in CH$_2$Cl$_2$ (50 mL) was added benzyl chloroformate (512 μL, 3.58 mmol) and the reaction mixture stirred at room temperature for 20 h. The mixture was washed consecutively with water (10 mL), saturated aqueous NaHCO$_3$ (10 mL), and brine (20 mL), dried over magnesium sulfate/sodium sulfate, and concentrated in vacuo to give the product carbamate 1.1 (l=m=0, PGN=2,4-Me$_2$Ph(Cbz)N, $R^3$, $R^{12}$=c-C$_4$H$_8$, all other R=H, 599 mg) as a yellow oil. $^1$H NMR (300 MHz, CDCl$_3$) δ 7.45–7.38 (m, 5H), 7.20–7.05 (m, 2H), 7.00–6.85 (m, 3H), 5.06 (s, 2H), 4.52 (s, 2H), 3.63 (s, 2H), 2.30 (s, 6H), 1.95–1.50 (m, 8H), 1.38 (s, 9H).

(190b) The carmbamate 1.1 (l=m=0, PGN=2,4-Me$_2$Ph (Cbz)N, $R^3$, $R^{12}$=c-C$_4$H$_8$, all other R=H, 0.68 mmol) was incorporated into procedure (1c). The product (70 mg, 0.10 mmol) was dissolved in pyridine (0.2 mL) and methanol, and the solution was charged with 10% Pd/C (50 mg). The reaction mixture was stirred vigorously under an atmosphere of H$_2$(g) at room temperature for 1 h. The mixture was filtered through a pad of diatomaceous earth and the filtrate concentrated in vacuo. The residue was dissolved in CH$_2$Cl$_2$ (20 mL) at 0° C., then trifluoroacetic acid was added and the mixture stirred for 5 min at 0° C. Purification by RP-HPLC provided the title compound 1.5 (l=m=0, $R^1$=2,4-dimethylphenyl, $R^3$, $R^{12}$=c-C$_4$H$_8$, Z=—C(O)—, $R^2$=3-trifluoromethylphenyl, all other R=H; 77 mg). MS found: (M+H)$^+$=462.

Example 191

N-[2-[[1-[[[(2,4-dimethylphenyl)methyl]amino]
methyl]cyclopentyl]amino]-2-oxoethyl]-2-[[(1,1-
dimethylethoxy)carbonyl]amino]-5-(trifluoromethyl)
benzamide (191a) The carmbamate 1.1 (l=m=0, PGN=2,4-Me$_2$Ph (Cbz)N, $R^3$, $R^{12}$=c-C$_4$H$_8$, all other R=H, 270 mg, 0.74 mmol) was combined with 1.2 (Z=—C(O)—, $R^2$=N-Boc 2-amino-5-(trifluoromethyl)benzoic acid, all other R=H; 0.74 mmol) and incorporated into procedure (1c). The product (60 mg, 0.08 mmol) was dissolved in pyridine (0.2 mL) and methanol, and the solution was charged with 10% Pd/C (50 mg). The reaction mixture was stirred vigorously under an atmosphere of H$_2$ (g) at room temperature for 1 h. The mixture was filtered through a pad of diatomaceous earth and the filtrate concentrated in vacuo. The residue was dissolved in CH$_2$Cl$_2$ (20 mL) at 0° C., then trifluoroacetic acid was added and the mixture stirred for 5 min at 0° C. Purification by RP-HPLC provided the title compound 1.5 (l=m=0, $R^1$=2,4-dimethylphenyl, $R^3$, $R^{12}$=c-C$_4$H$_8$, Z=—C(O)—, $R^2$=N-Boc 2-amino-5-trifluoromethylphenyl, all other R=H; 36 mg). MS found: (M+H)$^+$=577.

Example 192

N-[2-[[1-[[[(2,4-dimethylphenyl)methyl]amino]
methyl]cyclopropyl]amino]-2-oxoethyl]-2-[[(1,1-
dimethylethoxy)carbonyl]amino]-5-(trifluoromethyl)
benzamide (192a) 1-[1,1-(Dimethyl)ethoxycarbonyl] aminocyclopropyl carboxaldehyde (D. Braghiroli and M. Di Bella, *Tetrahedron Lett.* 1996, 37, 7319; 3.6 g, 19.4 mmol) was incorporated into procedure (190a) to provide the carbamate X (949 mg), which was incorporated into procedure (191a). Purification by RP-HPLC provided the title compound 1.5 (l=m=0, $R^1$=2,4-dimethylphenyl, $R^3$, $R^{12}$=c-C$_2$H$_4$, Z=—C(O)—, $R^2$=N-Boc 2-amino-5-trifluoromethylphenyl, all other R=H; 43 mg). MS found: (M+H)$^+$=549.

Example 193

N-[2-[[1[[[(2,4-dimethylphenyl)methyl]amino]
methyl]cyclopropyl]amino]-2-oxoethyl]-2-amino-5-
(trifluoromethyl)benzamide (193a) The compound 1.5 (l=m=0, $R^1$=2,4-dimethylphenyl, $R^3$, $R^{12}$=c-C$_2$H$_4$, Z=—C(O)—, $R^2$=N-Boc 2-amino-5-trifluoromethylphenyl, all other R=H; 15 mg) was carried through procedure (48a). Purification by RP-HPLC provided the title compound 1.5 (l=m=0, $R^1$=2, 4-dimethylphenyl, $R^3_1$, $R^{12}$=c-C$_2$H$_4$, Z=—C(O)—, $R^2$=2-amino-5-trifluoromethylphenyl, all other R=H; 13 mg). MS found: (M+H)$^+$=449.

Example 194

(2S)-N-Ethyl-3-[[(2,4-dimethylphenyl)methyl]
amino]-2-[[[[2-amino-5-(trifluoromethyl)benzoyl]
amino]acetyl]amino]-2-methyl-propanamide (194a) A solution of racemic alpha-methylserine (2.33 g) was dissolved in 1:1 THF/water (160 mL) and charged successively with triethylamine (3.0 mL) and dibenzyldicarbonate (6.0 g). The reaction was stirred for 48 h at RT, quenched with 50 mL of 1 N NaOH, and extracted with Et$_2$O (2×50 mL). The aqueous phase was acidified with 1N (solution pH now <2) and extracted with EtOAc (3×100 mL). The organic extracts were combined, washed with brine, dried (Na$_2$SO$_4$), filtered, and concentrated in vacuo to afford the carbamate as a colorless oil (2.93 g). The entirity of the carbamate was dissolved in methylene chloride (100 mL) and the solution was charged with HATU (3.99 g), ethylamine (19 mL of a 2.0 M solution), and DMAP (117 mg). The reaction was stirred at RT for 16 h and partitioned between EtOAc and sat. NH₄Cl. The organic phase was washed with sat. NaHCO3, brine, dried (Na₂SO₄), filtered, and concentrated in vacuo. Flash chromatography provided rac- N-ethyl-2-(benzyloxycarbonyl)amino-3-hydroxy-2-methyl-propanamide (900 mg). MS found: $(M+Na)^+=303$.

(194b) A solution of rac- N-ethyl-2-(benzyloxycarbonyl)amino-3-hydroxy-2-methyl-propanamide (900 mg) in methylene chloride (40 mL) was charged with pyridine (1.3 mL) and Dess-Martin periodinane (1.36 g). The reaction was stirred at RT for 16 h and then partitioned between EtOAc and sat. NaHCO₃. The organic phase was washed with successively with sat. Na₂S₂O₃ and brine, and then dried (Na₂SO₄), filtered, and concentrated in vacuo to provide the aldehyde. The aldehyde (assumed 3.2 mmol) was dissolved in THF (30 mL) and the solution was charged with 2,4-dimethylbenzylamine (0.45 mL), acetic acid (0.55 mL), and sodium triacetoxyborohydride (2.0 g). The reaction was stirred for 16 h at RT and then partitioned between EtOAc and sat. NaHCO₃. The aqueous phase was extracted with EtOAc (2×), and the combined organic extracts were washed with brine, dried (Na₂SO₄), filtered, and concentrated in vacuo. Flash chromatography provided the amine as a yellow oil (785 mg), which was dissolved in 1:1 THF/water (20 mL) and then treated with triethylamine (0.275 mL) and di-(tert-butyl)dicarbonate. The mixture was stirred at RT for 16 h and then partitioned between EtOAc and sat. NH₄Cl. The organic phase was washed with brine, dried (Na₂SO₄), filtered, and concentrated in vacuo. residue was purified via flash chromatography (SiO₂) to afford the biscarbamate as a colorless oil (650 mg). The product was dissolved in MeOH (13 mL) and the resultant solution was charged with Pd/BaSO₄ (350 mg). The vessel was purged with hydrogen and stirred under an atmosphere of hydrogen for 2 h before being filtered. The filtrate was concentrated in vacuo to afford the primary amine as a colorless oil. MS found: $(M+H)^+=364.5$.

(194c) The primary amine (1.4 mmol) from procedure (194b) was dissolved in methylene chloride (15 mL) and the resultant solution was charged with N-Cbz glycine (300 mg), HATU (600 mg), and N,N-diisopropylethylamine (0.58 mL). The reaction was stirred at RT for 16 h and partitioned between EtOAc and sat. NH₄Cl. The organic phase was washed with sat. NaHCO₃, brine, dried (Na₂SO₄), filtered, and concentrated in vacuo. A portion (525 mg, 0.95 mmol) of the product was dissolved in MeOH (10 mL) and the resultant solution was charged with 5% Pd/C (150 mg). The vessel was purged with hydrogen and stirred under an atmosphere of hydrogen for 1.5 h before being filtered. The filtrate was concentrated in vacuo to afford the primary amine as a colorless oil. MS found: $(M+H)^+=421.4$.

(194d) The primary amine (0.95 mmol) from procedure (194c) was dissolved in methylene chloride (10 mL) and the resultant solution was charged with N-Boc-2-amino-5-(trifluoromethyl)benzoic acid (S. Takagishi, et al., *Synlett* 1992, 360; 290 mg), HATU (361 mg), and N,N-diisopropylethylamine (0.50 mL). The reaction was stirred at RT for 16 h and partitioned between EtOAc and sat. NH₄Cl. The organic phase was washed with sat. NaHCO₃, brine, dried (Na₂SO₄), filtered, and concentrated in vacuo. The product was dissolved in 2:1 methylene chloride/TFA (12 mL) and stirred at RT for 2.5 h. The reaction was concentrated in vacuo; the residue was dissolved in benzene and concentrated in vacuo. Purification by RP-HPLC afforded the title compound rac-1.5 ($R^1$=2,4-dimethylphenyl, $R^3$=—C(O)NHEt, $R^{12}$=Me, Z=—C(O)—, $R^2$=2-amino-5-trifluoromethylphenyl, all other R=H; 30 mg). Exact MS calcd for $C_{25}H_{33}F_3N_5O_3$, the formula for $(M+H)^+=508.2535$. Found: 508.2537.

Table of Examples

The following tables illustrate examples of the present invention. The data in the "MS" columns represent the values observed for the $(M+H)^+$ ions in electrospray mass spectroscopy experiments; "NMR" indicates that ¹H-NMR spectroscopy was used in lieu of mass spectroscopy for characterization purposes. The substituents listed in each table are to be paired with the structure embedded in the table heading. The synthesis of all of these compounds has been described in detail in the previous section (Examples).

TABLE 1 examples 1–164

| No. | $R^1$ | $R^{16}$ | * | $R^3$ | $R^2$ | MS |
|---|---|---|---|---|---|---|
| 1 | 2,4-dimethylphenyl | H | (S) | methoxycarbonyl | 3-CF₃-phenyl | 466 |
| 2 | 2,4-dimethylphenyl | H | (R) | methoxycarbonyl | 3-CF₃-phenyl | 466 |

TABLE 1-continued
examples 1–164
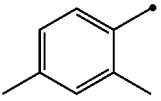
| No. | R¹ | R¹⁶ | * | R³ | R² | MS |
|---|---|---|---|---|---|---|
| 3 |  | H | (S) | 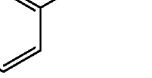 | 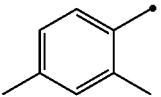 | 452 |
| 4 | 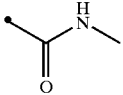 | H | (S) | 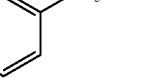 | 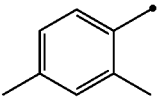 | 465 |
| 5 | 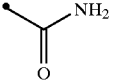 | H | (S) | 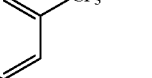 | 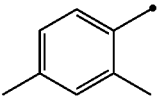 | 451 |
| 6 | 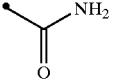 | H | (R) | 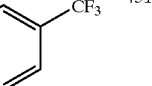 | 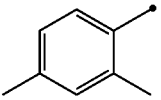 | 451 |
| 7 | 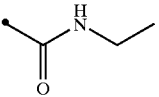 | H | (S) | 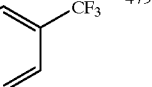 | 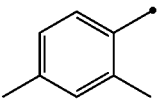 | 479 |
| 8 | 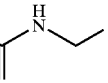 | H | (S) | 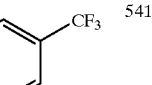 |  | 541 |
| 9 | 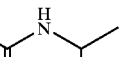 | H | (S) | 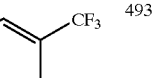 |  | 493 |
| 10 | 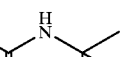 | H | (S) | 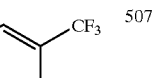 | 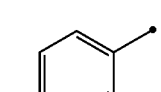 | 507 |
| 11 | 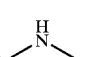 | H | (S) | 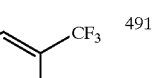 | 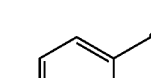 | 491 |
| 12 | 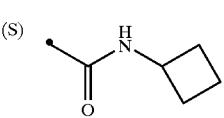 | H | (S) | 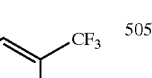 | 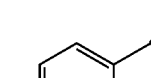 | 505 |
| 13 |  | H | (S) | 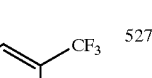 |  | 527 |

TABLE 1-continued
examples 1–164
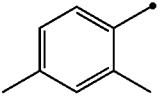
| No. | R¹ | R¹⁶ | * | R³ | R² | MS |
|---|---|---|---|---|---|---|
| 14 | 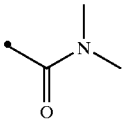 | H | (S) | 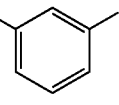 | 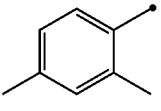 | 479 |
| 15 | 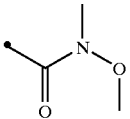 | H | (S) | 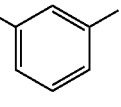 | 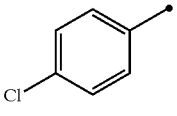 | 495 |
| 16 | 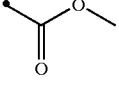 | H | (S) | 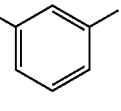 | 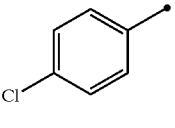 | 472 |
| 17 | 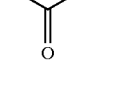 | H | (S) | 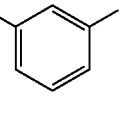 | 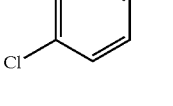 | 457 |
| 18 | 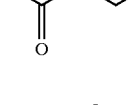 | H | (S) | 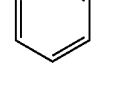 | 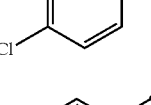 | 485 |
| 19 | 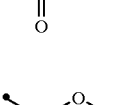 | Me | (S) | 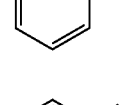 | 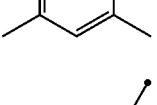 | 486 |
| 20 | 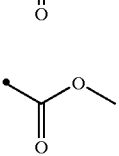 | Me | (S) | 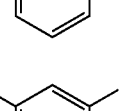 | 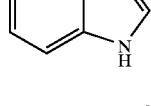 | 480 |
| 21 |  | H | (S) | 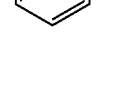 | 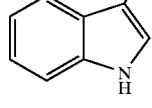 | NMR |
| 22 |  | H | (S) | 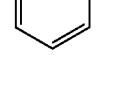 | 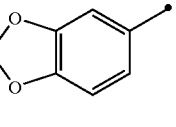 | 462 |
| 23 | 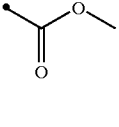 | H | (S) | 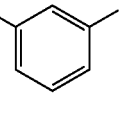 | | 482 |

TABLE 1-continued examples 1–164

| No. | R¹ | R¹⁶ | * | R³ | R² | MS |
|---|---|---|---|---|---|---|
| 24 | 4-Br-phenyl | H | (S) | CH₂CO₂Me | 3-CF₃-phenyl | 516 |
| 25 | 2,4-diMe-phenyl | H | (S) | CH₂CO₂Me | 2-NHBoc-4-CF₃-phenyl | 581 |
| 26 | 2,4-diMe-phenyl | H | (S) | CH₂CO₂Me | 2-NH₂-4-CF₃-phenyl | 481 |
| 27 | 2,4-diMe-phenyl | H | (S) | CH₂C(O)NH₂ | 2-NH₂-4-CF₃-phenyl | 466 |
| 28 | 2,4-diMe-phenyl | H | (S) | CH₂OH | 3-CF₃-phenyl | 438 |
| 29 | 2,4-diMe-phenyl | H | (R) | CH₂OH | 3-CF₃-phenyl | 438 |
| 30 | 2,4-diMe-phenyl | H | (S) | CH(OH)CH₃ | 3-CF₃-phenyl | 452 |
| 31 | 2,4-diMe-phenyl | H | (R) | CH₂CH₂CO₂t-Bu | 3-CF₃-phenyl | 522 |
| 32 | 2,4-diMe-phenyl | H | (R) | CH₂-phenyl | 3-CF₃-phenyl | 498 |

TABLE 1-continued
examples 1–164
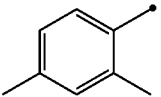
| No. | R¹ | R¹⁶ | * | R³ | R² | MS |
|---|---|---|---|---|---|---|
| 33 |  | H | (S) | 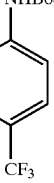 | 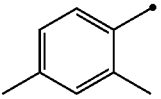 | 622 |
| 34 |  | H | (S) | 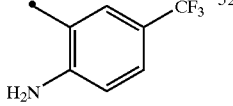 | 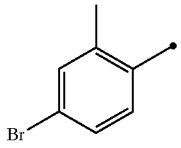 | 522 |
| 35 | 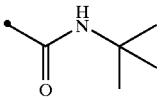 | H | (S) | 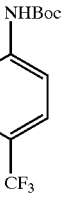 | 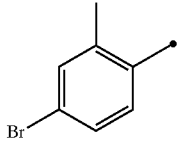 | 686 |
| 36 | 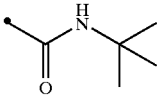 | H | (S) | 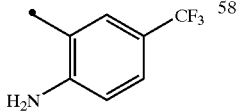 | 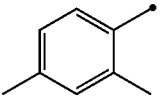 | 586 |
| 37 | 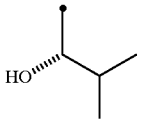 | H | (S) | 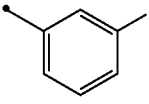 | 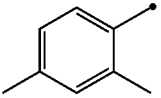 | 480 |
| 38 | 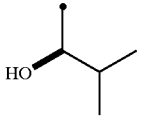 | H | (S) | 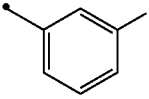 | 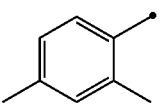 | 480 |
| 39 | 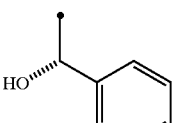 | H | (S) | 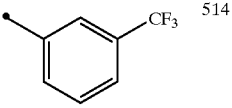 | 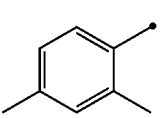 | 514 |
| 40 | 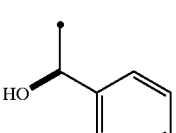 | H | (S) | 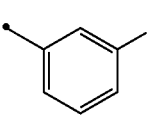 | | 514 |

TABLE 1-continued
examples 1–164
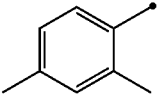
| No. | R¹ | R¹⁶ | * | R³ | R² | MS |
|---|---|---|---|---|---|---|
| 41 | 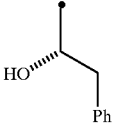 | H | (S) | 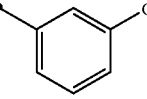 | 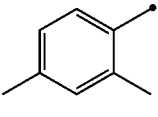 | 528 |
| 42 | 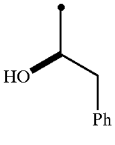 | H | (S) | 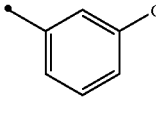 | 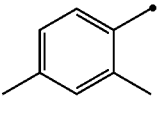 | 528 |
| 43 | 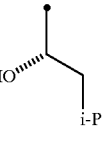 | H | (S) | 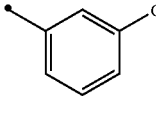 | 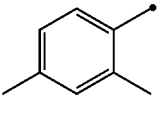 | 494 |
| 44 | 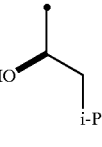 | H | (S) | 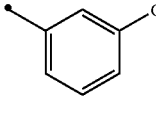 | 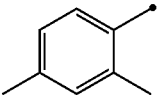 | 494 |
| 45 | 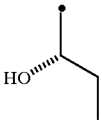 | H | (S) | 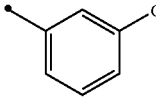 | 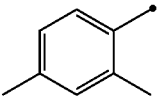 | 466 |
| 46 | 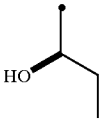 | H | (S) | 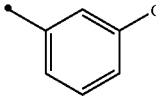 | 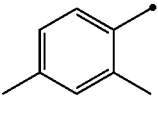 | 466 |
| 47 | 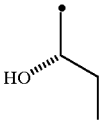 | H | (S) | 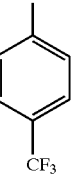 | 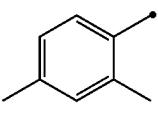 | 581 |
| 48 | 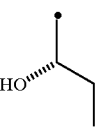 | H | (S) | 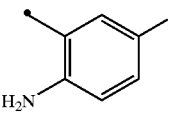 | | 481 |

TABLE 1-continued
examples 1–164
| No. | R¹ | R¹⁶ | * | R³ | R² | MS |
|---|---|---|---|---|---|---|
| 49 | 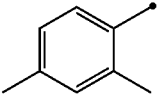 | H | (S) | 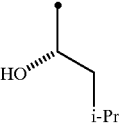 | 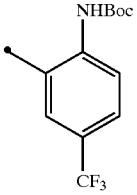 | 609 |
| 50 | 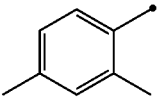 | H | (S) | 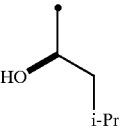 | 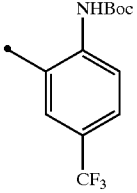 | 609 |
| 51 | 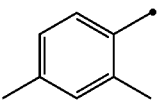 | H | (S) | 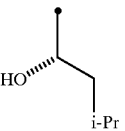 | 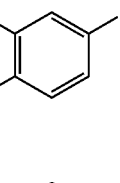 | 509 |
| 52 | 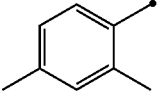 | H | (S) | 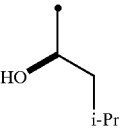 | 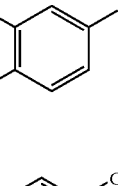 | 509 |
| 53 | 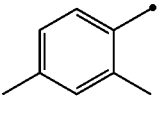 | H | (S) | 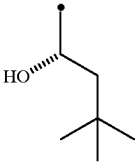 | 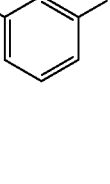 | 508 |
| 54 | 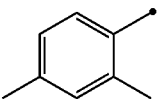 | H | (S) | 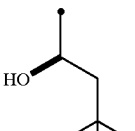 | 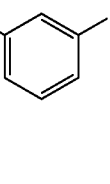 | 508 |
| 55 | 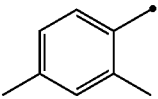 | H | (S) | 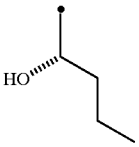 | 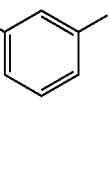 | 480 |

TABLE 1-continued
examples 1–164
| No. | R¹ | R¹⁶ | * | R³ | R² | MS |
|---|---|---|---|---|---|---|
| 56 | 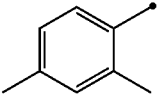 | H | (S) | 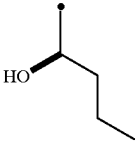 | 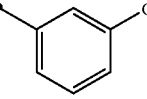 | 480 |
| 57 | 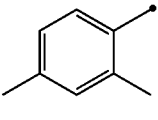 | H | (S) | 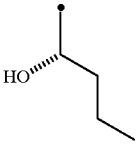 | 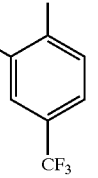 | 595 |
| 58 | 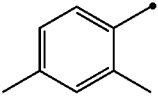 | H | (S) | 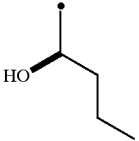 | 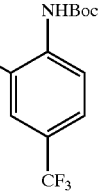 | 595 |
| 59 | 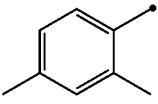 | H | (S) | 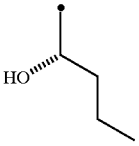 | 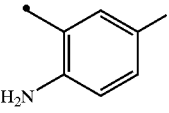 | 495 |
| 60 | 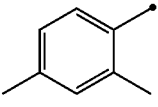 | H | (S) | 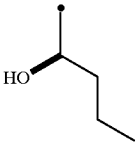 | 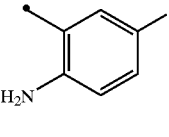 | 495 |
| 61 | 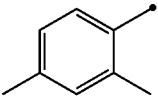 | H | (S) | 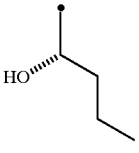 | 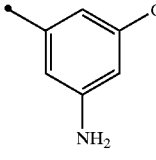 | 495 |
| 62 | 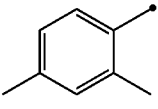 | H | (S) | 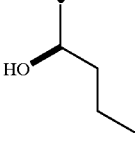 | 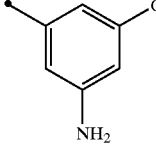 | 495 |

TABLE 1-continued examples 1–164

| No. | R¹ | R¹⁶ | * | R³ | R² | MS |
|---|---|---|---|---|---|---|
| 63 | 2,4-dimethylphenyl | H | (S) | (R)-1-hydroxybutyl | 2-methyl-4-trifluoromethyl-NHCONHEt-phenyl | 566 |
| 64 | 2,4-dimethylphenyl | H | (S) | (S)-1-hydroxybutyl | 2-methyl-4-trifluoromethyl-NHCONHEt-phenyl | 566 |
| 65 | 2,4-dimethylphenyl | H | (S) | (R)-1-hydroxybutyl | 2-methyl-4-trifluoromethyl-NHCONHi-Pr-phenyl | 580 |
| 66 | 2,4-dimethylphenyl | H | (S) | (S)-1-hydroxybutyl | 2-methyl-4-trifluoromethyl-NHCONHi-Pr-phenyl | 580 |
| 67 | 2,4-dimethylphenyl | H | (S) | (R)-1-hydroxybutyl | 2-methyl-4-trifluoromethyl-phenyl pyrrolidine-1-carboxamide | 592 |
| 68 | 2,4-dimethylphenyl | H | (S) | (S)-1-hydroxybutyl | 2-methyl-4-trifluoromethyl-phenyl azetidine-1-carboxamide | 578 |

TABLE 1-continued
examples 1–164
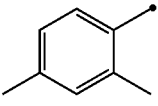
| No. | R¹ | R¹⁶ | * | R³ | R² | MS |
|---|---|---|---|---|---|---|
| 69 | 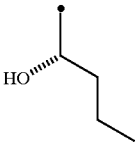 | H | (S) | 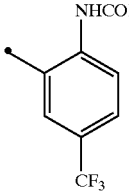 | 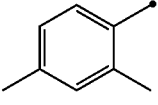 | 552 |
| 70 | 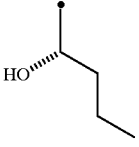 | H | (S) | 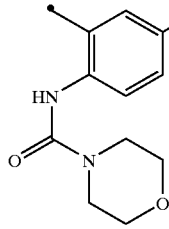 | 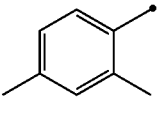 | 608 |
| 71 | 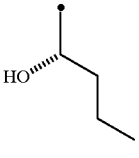 | H | (S) | 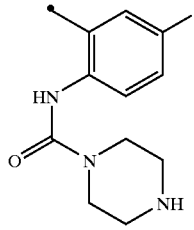 | 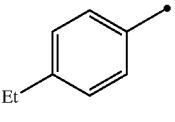 | 607 |
| 72 | 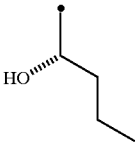 | H | (S) | 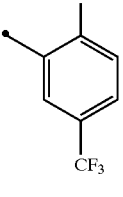 | 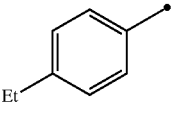 | 595 |
| 73 | 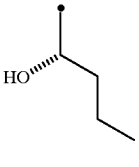 | H | (S) | 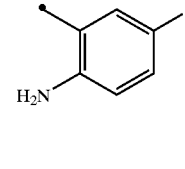 | 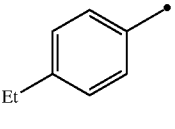 | 495 |
| 74 | 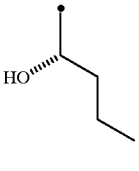 | H | (S) | 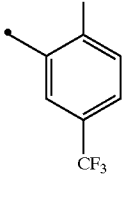 | | 580 |

TABLE 1-continued
examples 1–164
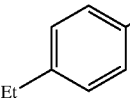
| No. | R¹ | R¹⁶ | * | R³ | R² | MS |
|---|---|---|---|---|---|---|
| 75 | 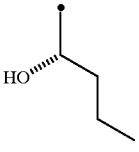 | H | (S) | 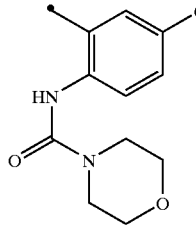 | 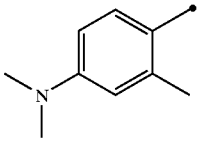 | 608.5 |
| 76 | 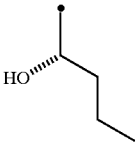 | H | (S) | 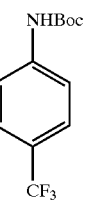 | 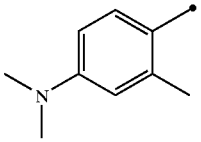 | 624.6 |
| 77 | 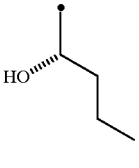 | H | (S) | 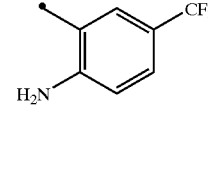 | 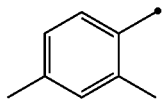 | 524 |
| 78 | 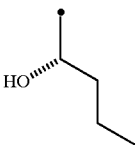 | H | (S) | 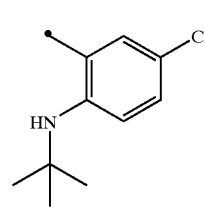 | 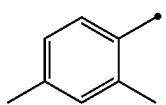 | 551 |
| 79 | 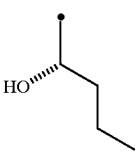 | H | (S) | 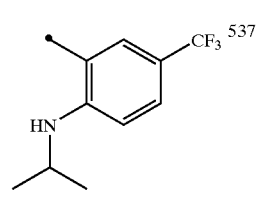 | 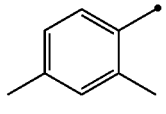 | 537 |
| 80 | 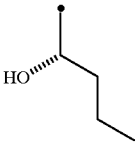 | H | (S) | 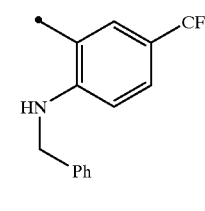 | | 585.6 |

TABLE 1-continued examples 1–164

| No. | R¹ | R¹⁶ | * | R³ | R² | MS |
|---|---|---|---|---|---|---|
| 81 | 2,4-dimethylphenyl | H | (S) | (S)-MeO-pentyl | 2-methyl-4-CF₃-NHBoc-phenyl | 609 |
| 82 | 2,4-dimethylphenyl | H | (S) | (S)-MeO-pentyl | 2-methyl-4-CF₃-H₂N-phenyl | 509 |
| 83 | 2,4-dimethylphenyl | H | (S) | (S)-HO,Me-methyl | 2-methyl-4-CF₃-NHBoc-phenyl | 581 |
| 84 | 2,4-dimethylphenyl | H | (S) | (S)-HO,Me-methyl | 2-methyl-4-CF₃-H₂N-phenyl | 481 |
| 85 | 2,4-dimethylphenyl | H | (S) | (S)-HO,diethyl | 2-methyl-4-CF₃-NHBoc-phenyl | 609 |
| 86 | 2,4-dimethylphenyl | H | (S) | (S)-HO,diethyl | 2-methyl-4-CF₃-H₂N-phenyl | 509 |
| 87 | 2,4-dimethylphenyl | H | (S) | (S)-HO,dipropyl | 2-methyl-4-CF₃-NHBoc-phenyl | 637.6 |

TABLE 1-continued examples 1–164

| No. | R¹ | R¹⁶ | * | R³ | R² | MS |
|---|---|---|---|---|---|---|
| 88 | 2,4-dimethylphenyl | H | (S) | (S)-3-hydroxy-3-propylhexyl | 2-methyl-4-trifluoromethylaniline | 537 |
| 89 | 2,4-dimethylphenyl | H | (S) | (S)-1-hydroxycyclopentyl | 2-NHBoc-4-CF₃-phenyl | 607.5 |
| 90 | 2,4-dimethylphenyl | H | (S) | (S)-1-hydroxycyclobutyl | 2-methyl-4-trifluoromethylaniline | 507 |
| 91 | 2,4-dimethylphenyl | H | (S) | N-tert-butylacetamido | 3-OCF₃-phenyl | 523 |
| 92 | 2,4-dimethylphenyl | H | (S) | N-tert-butylacetamido | 3-CF₂H-phenyl | 489 |
| 93 | 2,4-dimethylphenyl | H | (S) | N-tert-butylacetamido | 3-SCF₃-phenyl | 539 |
| 94 | 2,4-dimethylphenyl | H | (S) | N-tert-butylacetamido | 3-CF₂CF₃-phenyl | 557 |
| 95 | 2,4-dimethylphenyl | H | (S) | N-tert-butylacetamido | 2-amino-4-OCF₃-phenyl | 538 |
| 96 | 2,4-dimethylphenyl | H | (S) | N-tert-butylacetamido | 2-amino-4-methylphenyl | 468 |

TABLE 1-continued examples 1–164

| No. | R¹ | R¹⁶ | * | R³ | R² | MS |
|---|---|---|---|---|---|---|
| 97 | 2,4-dimethylphenyl | H | (S) | -C(=O)NH-t-Bu | 2-methyl-4-CF₃-phenyl-NH-Et | 550 |
| 98 | 2,4-dimethylphenyl | H | (S) | -C(=O)NH-t-Bu | 2-methyl-4-CF₃-phenyl-NH-CH₂Et | 564 |
| 99 | 2,4-dimethylphenyl | H | (S) | -C(=O)NH-t-Bu | 2-methyl-4-CF₃-phenyl-NH-CH₂-i-Pr | 578 |
| 100 | 2,4-dimethylphenyl | H | (S) | -C(=O)NH-t-Bu | 2-methyl-4-CF₃-phenyl-NH-CH₂-n-Pr | 578 |
| 101 | 2,4-dimethylphenyl | H | (S) | -C(=O)NH-t-Bu | 2-methyl-4-CF₃-phenyl-NH-c-Hex | 604 |
| 102 | 2,4-dimethylphenyl | H | (S) | -C(=O)NH-t-Bu | 2-methyl-4-CF₃-phenyl-NH-i-Pr | 564 |
| 103 | 2,4-dimethylphenyl | H | (S) | -C(=O)NH-t-Bu | 2-methyl-4-CF₃-phenyl-NH-t-Bu | 578 |

TABLE 1-continued
examples 1–164
| No. | R¹ | R¹⁶ | * | R³ | R² | MS |
|-----|----|----|---|----|----|----|
| 104 | 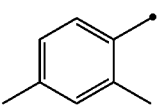 | H | (S) |  | 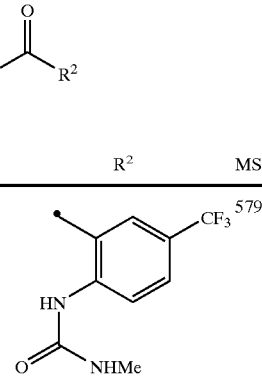 | 579 |
| 105 |  | H | (S) |  | 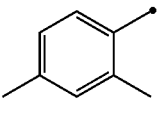 | 608 |
| 106 | 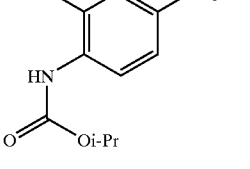 | H | (S) |  | 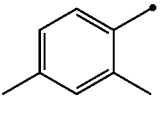 | 607 |
| 107 |  | H | (S) | 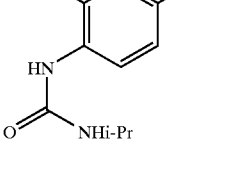 |  | 632 |
| 108 | 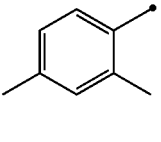 | H | (S) |  | 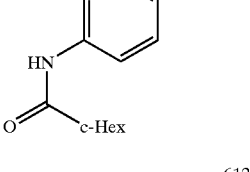 | 612 |
| 109 |  | H | (S) | 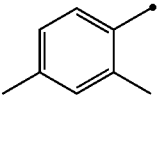 |  | 646 |
| 110 | 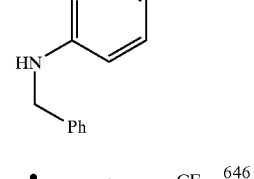 | H | (S) |  | 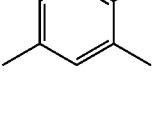 | 662 |

TABLE 1-continued examples 1–164

| No. | R¹ | R¹⁶ | * | R³ | R² | MS |
|---|---|---|---|---|---|---|
| 111 | 2,4-diMePh | H | (S) | C(=O)NH-tBu | 2-Me-4-CF₃-Ph with HN-CH₂-(m-MePh) | 626 |
| 112 | 2,4-diMePh | H | (S) | C(=O)NH-tBu | 2-Me-4-CF₃-Ph with HN-CH₂-(p-MePh) | 626 |
| 113 | 2,4-diMePh | H | (S) | C(=O)NH-tBu | 2-Me-4-CF₃-Ph with HN-CH₂-(o-MePh) | 626 |
| 114 | 2,4-diMePh | H | (S) | C(=O)NH-tBu | 2-Me-4-CF₃-Ph with HN-CH₂-(p-CF₃Ph) | 680 |
| 115 | 2,4-diMePh | H | (S) | C(=O)NH-tBu | 3-CF₃-5-NH₂-Ph | 522 |
| 116 | 2,4-diMePh | H | (S) | C(=O)NH-tBu | 3-CF₃-5-BnHN-Ph | 612 |
| 117 | 2,4-diMePh | H | (S) | C(=O)NH-tBu | 3-CF₃-5-MeHN-Ph | 536 |

TABLE 1-continued examples 1–164

| No. | R¹ | R¹⁶ | * | R³ | R² | MS |
|-----|----|----|----|----|----|----|
| 118 | 2,4-dimethylphenyl | H | (S) | C(=O)NH-t-Bu | 3-CF₃-5-(EtHN)-phenyl | 550 |
| 119 | 2,4-dimethylphenyl | H | (S0) | C(=O)NH-t-Bu | 3-CF₃-5-(i-BuHN)-phenyl | 578 |
| 120 | 2,4-dimethylphenyl | H | (S) | C(=O)NH-t-Bu | 3-CF₃-5-(n-PrHN)-phenyl | 564 |
| 121 | 2,4-dimethylphenyl | H | (S) | C(=O)NH-t-Bu | 3-CF₃-5-(n-BuHN)-phenyl | 578 |
| 122 | 2,4-dimethylphenyl | H | (S) | C(=O)NH-t-Bu | 3-CF₃-5-((TFA)HN)-phenyl | 618.5 |
| 123 | 2,4-dimethylphenyl | H | (S) | C(=O)NH-t-Bu | 3-CF₃-5-(EtO₂CHN)-phenyl | 594 |
| 124 | 4-Br-2-methylphenyl | H | (S) | C(=O)NH₂ | 2-NH₂-4-CF₃-phenyl | 530 |
| 125 | 4-Br-phenyl | H | (S) | C(=O)NH₂ | 2-NH₂-4-CF₃-phenyl | 518 |

TABLE 1-continued
examples 1–164
| No. | R¹ | R¹⁶ | * | R³ | R² | MS |
|---|---|---|---|---|---|---|
| 126 |  | H | (S) |  |  | 493 |
| 127 |  | H | (S) |  |  | 557 |
| 128 |  | H | (S) |  |  | 571 |
| 129 |  | H | (S) |  | 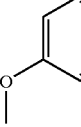 | 509 |
| 130 |  | H | (S) |  | 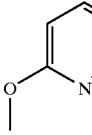 | 523 |
| 131 |  | H | (S) |  | 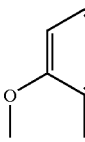 | 510 |
| 132 |  | H | (S) |  |  | 537 |
| 133 |  | H | (S) |  |  | 518 |
| 134 |  | H | (S) |  |  | 507 |

TABLE 1-continued
examples 1–164
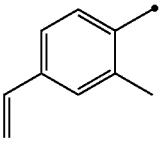
| No. | R¹ | R¹⁶ | * | R³ | R² | MS |
|---|---|---|---|---|---|---|
| 135 | 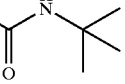 | H | (S) | 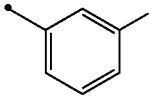 | 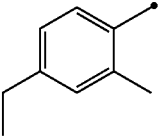 | 519 |
| 136 | 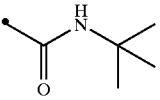 | H | (S) | 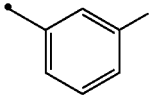 | 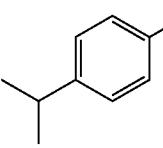 | 521 |
| 137 | 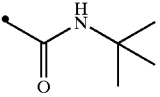 | H | (S) | 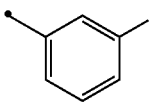 | 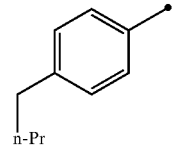 | 521 |
| 138 | 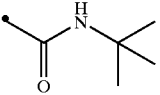 | H | (S) | 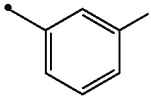 | 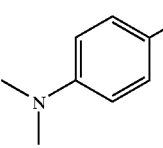 | 535 |
| 139 | 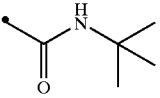 | H | (S) | 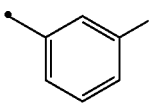 | 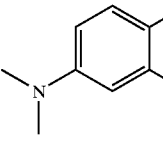 | 522 |
| 140 | 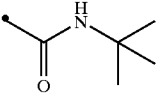 | H | (S) | 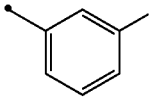 | 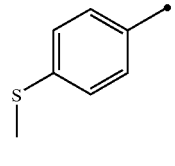 | 536 |
| 141 | 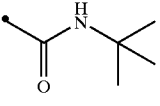 | H | (S) | 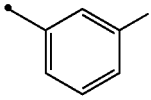 | 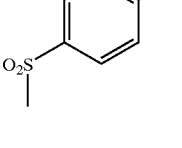 | 525 |
| 142 | 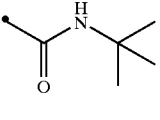 | H | (S) | 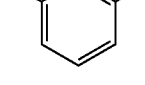 |  | 557 |

TABLE 1-continued examples 1–164

| No. | R¹ | R¹⁶ | * | R³ | R² | MS |
|---|---|---|---|---|---|---|
| 143 | 4-(OCF₃)-phenyl | H | (S) | C(O)NH-tBu | 3-CF₃-phenyl | 563 |
| 144 | 4-NH₂-2-methylphenyl... (2-H₂N, position) | H | (S) | C(O)NH-tBu | 3-CF₃-phenyl | 508 |
| 145 | 1H-indol-3-yl | H | (S) | C(O)NH-tBu | 3-CF₃-phenyl | 518 |
| 146 | 2-methylphenyl | H | (S) | C(O)NH-tBu | 3-CF₃-phenyl | 493 |
| 147 | 2-ethylphenyl | H | (S) | C(O)NH-tBu | 3-CF₃-phenyl | 507 |
| 148 | 2,4-dimethylphenyl | H | (R) | C(O)NHEt | 3-CF₃-phenyl | 479 |
| 149 | 2,4-dimethylphenyl | H | (R) | C(O)NH-tBu | 3-CF₃-phenyl | 507 |
| 150 | 2,4-dimethylphenyl | H | (R) | C(O)NHC(CH₃)₂CH₂OH | 3-CF₃-phenyl | 523 |
| 151 | 2,4-dimethylphenyl | H | (S) | C(O)NHC(CH₃)₂Et | 3-CF₃-phenyl | 521 |

TABLE 1-continued
examples 1–164
| No. | R¹ | R¹⁶ | * | R³ | R² | MS |
|---|---|---|---|---|---|---|
| 152 | 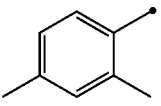 | H | (S) | 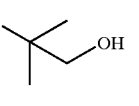 | 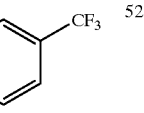 | 523 |
| 153 | 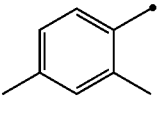 | H | (S) |  | 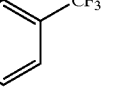 | 505 |
| 154 | 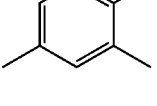 | H | (S) | 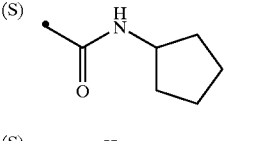 | 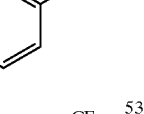 | 519 |
| 155 | 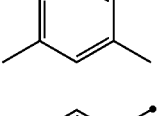 | H | (S) |  | 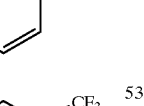 | 533 |
| 156 | 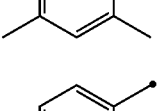 | H | (S) |  | 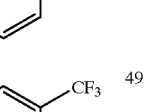 | 533 |
| 157 | 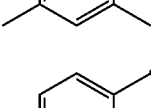 | H | (S) |  | 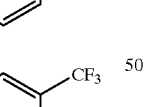 | 491 |
| 158 | 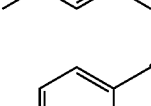 | H | (S) | 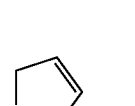 | 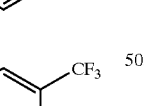 | 505 |
| 159 | 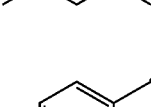 | H | (S) |  | 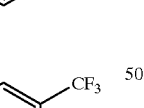 | 503 |
| 160 | 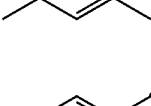 | H | (S) | 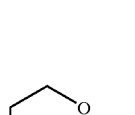 | 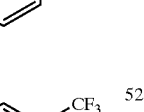 | 505 |
| 161 | 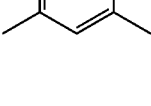 | H | (S) | 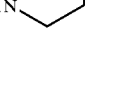 | 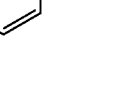 | 521 |

TABLE 1-continued examples 1–164

| No. | R¹ | R¹⁶ | * | R³ | R² | MS |
|---|---|---|---|---|---|---|
| 162 | 2,4-dimethylphenyl | H | (S) | -C(O)NH-iBu | 3-CF₃-phenyl | 507 |
| 163 | 2,4-dimethylphenyl | H | (S) | -C(O)NH-sBu | 3-CF₃-phenyl | 507 |
| 164 | 2,4-dimethylphenyl | H | (R) | -CH₂CH₂CONHt-Bu | 3-CF₃-phenyl | 521 |

TABLE 2 examples 165–168

| No. | R¹ | * | R⁶ | R³ | R² | MS |
|---|---|---|---|---|---|---|
| 165 | 2,4-dimethylphenyl | (R) | Me | -C(O)NHEt | 3-CF₃-phenyl | 493 |
| 166 | 4-Br-phenyl | (R) | Me | -C(O)NHEt | 3-CF₃-phenyl | 543 |
| 167 | 2,4-dimethylphenyl | (R) | -C(O)OMe | H | 3-CF₃-phenyl | 466 |
| 168 | 2,4-dimethylphenyl | (R) | -C(O)NHEt | H | 3-CF₃-phenyl | 479 |

TABLE 3 examples 169–187

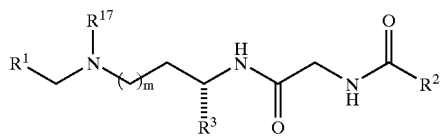

| No. | R¹ | R¹⁷ | m | R³ | R² | MS |
|-----|----|----|---|----|----|-----|
| 169 | 2,4-dimethylphenyl | H | 1 | -C(=O)OMe | 3-CF₃-phenyl | 480 |
| 170 | 2,4-dimethylphenyl | H | 1 | -C(=O)NH₂ | 3-CF₃-phenyl | 465 |
| 171 | 2,4-dimethylphenyl | H | 1 | -C(=O)NHEt | 3-CF₃-phenyl | 493 |
| 172 | 2,4-dimethylphenyl | Me | 1 | -C(=O)NHEt | 3-CF₃-phenyl | 507 |
| 173 | 2,4-dimethylphenyl | H | 1 | -C(=O)NHtBu | 2-NHBoc-4-CF₃-phenyl | 636 |
| 174 | 2,4-dimethylphenyl | Me | 1 | -C(=O)NHtBu | 2-NHBoc-4-CF₃-phenyl | 650 |
| 175 | 2,4-dimethylphenyl | H | 1 | -C(=O)NHtBu | 2-NH₂-4-CF₃-phenyl | 536 |
| 176 | 2,4-dimethylphenyl | Me | 1 | -C(=O)NHtBu | 2-NH₂-4-CF₃-phenyl | 550 |
| 177 | 2,4-dimethylphenyl | H | 1 | -C(=O)NHtBu | 3-CF₃-5-NH₂-phenyl | 536 |

TABLE 3-continued examples 169–187

| No. | R¹ | R¹⁷ | m | R³ | R² | MS |
|---|---|---|---|---|---|---|
| 178 | 4-ethylphenyl | H | 1 | C(=O)NH-tBu | 3-CF₃-5-NH₂-phenyl | 536 |
| 179 | 2,4-dimethylphenyl | H | 1 | C(=O)NH-tBu | 3-CF₃-phenyl | 521 |
| 180 | 4-ethylphenyl | H | 1 | C(=O)NH-tBu | 3-CF₃-phenyl | 521 |
| 181 | 2,4-dimethylphenyl | H | 2 | C(=O)NHEt | 3-CF₃-phenyl | 507 |
| 182 | 2,4-dimethylphenyl | Me | 0 | CH(OH)iPr | 3-CF₃-phenyl | 494 |
| 183 | 2,4-dimethylphenyl | Me | 0 | (R)-CH(OH)Pr | 2-NHCONHi-Pr-4-CF₃-phenyl | 594 |
| 184 | 2,4-dimethylphenyl | i-Pr | 0 | (R)-CH(OH)Pr | 2-NHCONHi-Pr-4-CF₃-phenyl | 622 |
| 185 | 4-ethylphenyl | Me | 0 | (R)-CH(OH)Pr | 2-NHCONHi-Pr-4-CF₃-phenyl | 594 |

TABLE 3-continued examples 169–187

| No. | R¹ | R¹⁷ | m | R³ | R² | MS |
|---|---|---|---|---|---|---|
| 186 | 4-ethylphenyl | i-Pr | 0 | (R)-CH(OH)-propyl | 2-(NHCONHi-Pr)-4-CF₃-phenyl | 622 |
| 187 | 2,4-dimethylphenyl | Me | 0 | CH₂-NH-C(=O)-t-Bu | 3-CF₃-phenyl | 521 |

TABLE 4 examples 188–194

| No. | R¹ | R¹⁶ | R¹⁷ | G | R² | MS |
|---|---|---|---|---|---|---|
| 188 | 2,4-dimethylphenyl | H | H | 1,1-cyclohexyl | 3-CF₃-phenyl | 476 |
| 189 | 4-Cl-phenyl | H | H | 1,1-cyclohexyl | 3-CF₃-phenyl | 482 |
| 190 | 2,4-dimethylphenyl | H | H | 1,1-cyclopentyl | 3-CF₃-phenyl | 462 |
| 191 | 2,4-dimethylphenyl | H | H | 1,1-cyclopentyl | 2-NHBoc-4-CF₃-phenyl | 577 |

TABLE 4-continued examples 188–194

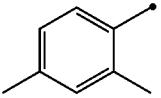

| No. | R¹ | R¹⁶ | R¹⁷ | G | R² | MS |
|---|---|---|---|---|---|---|
| 192 |  | H | H | 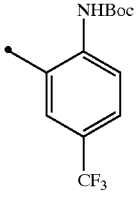 | 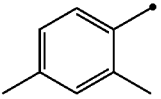 | 549 |
| 193 |  | H | H | 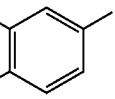 | 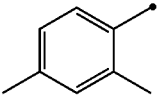 | 449 |
| 194 |  | H | H | 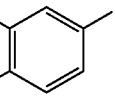 racemic | (see structure) | 508 |

UTILITY

Compounds of formula I are shown to be modulators of chemokine and chemokine receptor activity using assays known by those skilled in the art. In this section, we describe these assays and give their literature reference. By displaying activity in these assays of MCP-1 antagonism, compounds of formula I are expected to be useful in the treatment of human diseases associated with chemokines and their cognate receptors.

Antagonism of MCP-1 Binding to Human PBMC
(Yoshimura et al., *J. Immunol.* 1990, 145, 292)

All examples of the present invention have activity in the antagonism of MCP-1 binding to human PBMC (human peripheral blood mononuclear cells) described here. The definition of activity in this assay is a compound demonstrating 50% inhibition of MCP-1 binding ($IC_{50}$) at a concentration of 20 μM or lower.

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration compound, is combined with 50 μl of $^{125}$-I labeled human MCP-1 (to give a final concentration of 150 pM radioligand) and 50 μl of binding buffer containing 5×10⁵ cells. Cells used for such binding assays can include human peripheral blood mononuclear cells isolated by Ficoll-Hypaque gradient centrifugation, human monocytes (Weiner et al., *J. Immunol. Methods.* 1980, 36, 89), or the THP-1 cell line which expresses the endogenous receptor. The mixture of compound, cells and radioligand are incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MCP-1 in place of the test compound.

Antagonism of MCP-1-Induced Calcium Influx
(Sullivan, et al. *Methods Mol. Biol.* 1999, 114, 125–133)

Calcium mobilization is measured using the fluorescent $Ca^{2+}$ indicator dye, Fluo-3. Cells are incubated at 8×10⁵ cells/ml in phosphate-buffered saline containing 0.1% bovine serum albumin, 20 mM HEPES buffer, 5 mM glucose, 1% fetal bovine serum, 4 μM Fluo-3 AM and 2.5 mM probenecid for 60 minutes at 37° C. Cells used for such calcium assays can include human monocytes (Weiner et al., *J. Immunol. Methods.* 1980, 36, 89) or cell lines which express the endogenous $CCR^2$ receptor, such as THP-1 and MonoMac-6. The cells are then washed three times in phosphate-buffered saline containing 0.1% bovine serum albumin, 20 mM HEPES, 5 mM glucose and 2.5 mM probenecid. The cells are resuspended in phosphate-buffered saline containing 0.5% bovine serum albumin, 20 mM HEPES and 2.5 mM probenecid at a final concentration of 2–4×10⁶ cells/ml. Cells are plated into 96-well, black-wall microplates (100 μl/well) and the plates centrifuged at 200×g for 5 minutes. Various concentrations of compound are added to the wells (50 μl/well) and after 5 minutes, 50 μl/well of MCP-1 is added to give a final concentration of 10 nM. Calcium mobilization is detected by using a fluorescent-imaging plate reader. The cell monolayer is excited with an argon laser (488 nM) and cell-associated fluorescence measured for 3 minutes, (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MCP-1 alone.

Antagonism of MCP-1-Induced Human PBMC Chemotaxis (Bacon et al., *Brit. J. Pharmacol.* 1988, 95, 966)

Neuroprobe MBA96-96-well chemotaxis chamber, Polyfiltronics MPC 96 well plate, and Neuroprobe polyvinylpyrrolidone-free polycarbonate PFD5 8-micron filters are warmed in a 37° C. incubator. Human Peripheral Blood Mononuclear Cells (PBMCs) (Boyum et al., *Scand. J. Clin. Lab Invest. Suppl.* 1968, 97, 31), freshly isolated via the standard ficoll density separation method, are suspended in DMEM at $1 \times 10^7$ c/ml and warmed at 37° C. A 60 nM solution of human MCP-1 is also warmed at 37° C. Dilutions of test compounds are made up at 2x the concentration needed in DMEM. The PBMC suspension and the 60 nm MCP-1 solution are mixed 1:1 in polypropylene tubes with prewarmed DMEM with or without a dilution of the test compounds. These mixtures are warmed in a 37° C. tube warmer. In order to initiate the assay, the MCP-1/compound mixture (400 $\mu$L) is added into the wells of the Polyfiltronics MPC 96 well plate that has been placed into the bottom part of the Neuroprobe chemotaxis chamber. The 8 micron filter is placed on top of the 96 well plate, a rubber gasket is attached to the bottom of the upper chamber, and the chamber is assembled. The cell suspension/compound mixture (200 $\mu$l) is added to the appropriate wells of the upper chamber. The upper chamber is covered with a plate sealer, and the assembled unit is placed in a 37° C. incubator for 45 min. After incubation, the plate sealer is removed and all the remaining cell suspension is aspirated off. The chamber is disassembled and the filter is removed. The unmigrated cells are washed away using a gentle stream of phosphate buffered saline, and the top of the filter is wiped with the tip of a rubber squeegee. This wash is repeated twice more. The filter is air dried and then immersed completely in Wright Geimsa stain for 45 sec. The filter is washed by soaking in distilled water for 7 min, and the filter is soaked again for 15 sec in fresh distilled water. The filter is air dried. Migrated cells on the filter are quantified by visual microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte migration, adhesion, chemotaxis, exocytosis (e.g., of enzymes, histamine) or inflammatory mediator release, is inhibited.

In addition, an instant compound that promotes internalization/desensitization of a mammalian chemokine receptor without also inducing its primary function may be administered to inhibit (i.e., reduce or prevent) disease. If one contemplates the delivery of sufficient compound to cause the loss of receptor expression on cells through the induction of chemokine receptor internalization, than one can imagine that such a compound would also be useful for the treatment of the aforementioned inflammatory, allergic and autoimmune diseases.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV. The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for compounds that promote chemokine receptor internalization without stimulating chemokine receptor function, particularly if one contemplates the delivery of sufficient compound to cause the loss of receptor expression on cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurism, fever, cardiovascular effects, haemodynamic shock, sepsis syndrom, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes melitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

Furthermore, the compounds are used to treat or prevent inflammatory disorders selected from osteoarthritis, aneurism, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

In another aspect of the invention, the compounds are used to treat or prevent inflammatory disorders selected from rheumatoid arthritis, atherosclerosis, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selecting, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2a, interferon-2B, interferon alpha-N3, interferon beta-la, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is also meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:
1. A compound of Formula (I):

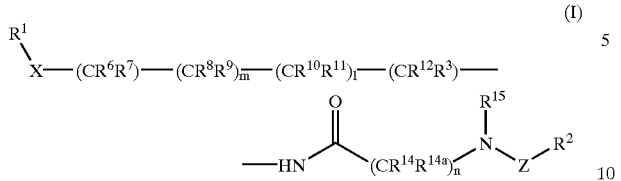

or a stereoisomer or a pharmaceutically acceptable salt thereof, wherein:

Z is selected from a bond, —C(O)—, —C(O)NH—, —C(S)NH—, —SO$_2$—, and —SO$_2$NH—;

X is selected from —NR$^{17}$—, —O—, and —CHR$^{16}$NR$^{17}$—;

R$^1$ is selected from a C$_{6-10}$ aryl group substituted with 0–5 R$^4$;

R$^2$ is selected from a C$_{6-10}$ aryl group substituted with 0–5 R$^5$;

R$^3$ is selected from (CRR)$_q$OH, (CRR)$_q$SH, (CRR)$_q$OR$^{3d}$, (CRR)$_q$S(O)$_p$R$^{3d}$, (CRR)$_q$C(O)R$^{3b}$, (CRR)$_q$NR$^{3a}$R$^{3a}$, (CRR)$_q$C(O)NR$^{3a}$R$^{3a}$, (CRR)$_r$C(O)NR$^{3a}$OR$^{3d}$, (CRR)$_q$SO$_2$NR$^{3a}$R$^{3a}$, (CRR)$_r$C(O)OR$^{3d}$, a (CRR)$_r$—C$_{3-10}$ carbocyclic residue substituted with 0–5 R$^{3e}$, and a (CRR)$_r$-5–10 membered heterocyclic system containing 1–4 heteroatoms selected from N, O, and S, substituted with 0–3 R$^{3e}$;

R$^{3a}$, at each occurrence, is independently selected from H, methyl substituted with 0–1 R$^{3c}$, C$_{2-6}$ alkyl substituted with 0–3 R$^{3e}$, C$_{3-8}$ alkenyl substituted with 0–3 R$^{3e}$, C$_{3-8}$ alkynyl substituted with 0–3 R$^{3e}$, (CH$_2$)$_r$C$_{3-6}$ cycloalkyl, a (CH$_2$)$_r$—C$_{3-10}$ carbocyclic residue substituted with 0–5 R$^{3e}$, and a (CH$_2$)$_r$-5–10 membered heterocyclic system containing 1–4 heteroatoms selected from N, O, and S, substituted with 0–3 R$^{3e}$;

R$^{3b}$, at each occurrence, is independently selected from C$_{1-6}$ alkyl substituted with 0–3 R$^{3e}$, C$_{2-8}$ alkenyl substituted with 0–3 R$^{3e}$, C$_{2-8}$ alkynyl substituted with 0–3 R$^{3e}$, a (CH$_2$)$_r$—C$_{3-6}$ carbocyclic residue substituted with 0–2 R$^{3e}$, and a (CH$_2$)$_r$-5–6 membered heterocyclic system containing 1–4 heteroatoms selected from N, O, and S, substituted with 0–3 R$^{3e}$;

R$^{3c}$ is independently selected from —C(O)R$^{3b}$, —C(O)OR$^{3d}$, —C(O)NR$^{3f}$R$^{3f}$, and (CH$_2$)$_r$phenyl;

R$^{3d}$, at each occurrence, is independently selected from H, methyl, —CF$_3$, C$_{2-6}$ alkyl substituted with 0–3 R$^{3e}$, C$_{3-6}$ alkenyl substituted with 0–3 R$^{3e}$, C$_{3-6}$ alkynyl substituted with 0–3 R$^{3e}$, a C$_{3-10}$ carbocyclic residue substituted with 0–3 R$^{3e}$, and a (CH$_2$)$_r$-5–6 membered heterocyclic system containing 1–4 heteroatoms selected from N, O, and S, substituted with 0–3 R$^{3e}$;

R$^{3e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{3f}$R$^{3f}$, and (CH$_2$)$_r$phenyl;

R$^{3f}$, at each occurrence, is selected from H, C$_{1-6}$ alkyl, and C$_{3-6}$ cycloalkyl;

R, at each occurrence, is independently selected from H, C$_{1-6}$ alkyl, C$_{2-8}$ alkenyl, C$_{2-8}$ alkynyl, (CH$_2$)$_r$C$_{3-6}$ cycloalkyl, (CHR)$_r$C(O)NR$^{3a}$R$^{3a}$, and (CHR)$_r$C(O)OR$^{3d}$, and (CH$_2$)$_r$phenyl substituted with R$^{3e}$;

R$^4$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CR'R')$_r$NR$^{4a}$R$^{4a}$, (CR'R')$_r$OH, (CR'R')$_r$O(CR'R')$_r$R$^{4d}$, (CR'R')$_r$SH, (CR'R')$_r$C(O)H, (CR'R')$_r$S(CR'R')$_r$R$^{4d}$, (CR'R')$_r$C(O)OH, (CR'R')$_r$C(O)(CR'R')$_r$R$^{4b}$, (CR'R')$_r$C(O)NR$^{4a}$R$^{4a}$, (CR'R')$_r$NR$^{4f}$C(O)(CR'R')$_r$R$^{4b}$, (CR'R')$_r$C(O)O(CR'R')$_r$R$^{4d}$, (CR'R')$_r$OC(O)(CR'R')$_r$R$^{4b}$, (CR'R')$_r$NR$^{4f}$C(O)O(CR'R')$_r$R$^{4d}$, (CR'R')$_r$OC(O)NR$^{4a}$R$^{4a}$, (CR'R')$_r$NR$^{6a}$C(S)NR$^{6a}$(CR'R')$_r$R$^{6d}$, (CR'R')$_r$NR$^{4a}$C(O)NR$^{4a}$R$^{4a}$, (CR'R')$_r$C(=NR$^{4f}$)NR$^{4a}$R$^{4a}$, (CR'R')$_r$NHC(=NR$^{4f}$)NR$^{4f}$R$^{4f}$, (CR'R')$_r$S(O)$_p$(CR'R')$_r$R$^{4b}$, (CR'R')$_r$S(O)$_2$NR$^{4a}$R$^{4a}$, (CR'R')$_r$NR$^{6f}$S(O)$_2$NR$^{6a}$R$^{6a}$, (CR'R')$_r$NR$^{4f}$S(O)$_2$(CR'R')$_r$R$^{4b}$, C$_{1-6}$ haloalkyl, C$_{2-8}$ alkenyl substituted with 0–3 R', C$_{2-8}$ alkynyl substituted with 0–3 R', and (CR'R')$_r$phenyl substituted with 0–3 R$^{4e}$;

alternatively, two R$^4$ on adjacent atoms on R$^1$ may join to form a cyclic acetal;

R$^{4a}$, at each occurrence, is independently selected from H, methyl substituted with 0–1R$^{4g}$, C$_{2-6}$ alkyl substituted with 0–2 R$^{5e}$, C$_{3-8}$ alkenyl substituted with 0–2 R$^{5e}$, C$_{3-8}$ alkynyl substituted with 0–2 R$^{5e}$, a (CH$_2$)$_r$—C$_{3-10}$ carbocyclic residue substituted with 0–5 R$^{4e}$, and a (CH$_2$)$_r$-5–10 membered heterocyclic system containing 1–4 heteroatoms selected from N, O, and S, substituted with 0–2 R$^{4e}$;

R$^{4b}$, at each occurrence, is selected from C$_{1-6}$ alkyl substituted with 0–2 R$^{5e}$, C$_{3-8}$ alkenyl substituted with 0–2 R$^{5e}$, C$_{3-8}$ alkynyl substituted with 0–2 R$^{5e}$, a (CH$_2$)$_r$C$_{3-6}$ carbocyclic residue substituted with 0–3 R$^{4e}$, and a (CH$_2$)$_r$-5–6 membered heterocyclic system containing 1–4 heteroatoms selected from N, O, and S, substituted with 0–2 R$^{4e}$;

R$^{4d}$, at each occurrence, is selected from C$_{3-8}$ alkenyl substituted with 0–2 R$^{5e}$, C$_{3-8}$ alkynyl substituted with 0–2 R$^{5e}$, methyl, CF$_3$, C$_{2-6}$ alkyl substituted with 0–3 R$^{4e}$, a (CH$_2$)$_r$—C$_{3-10}$ carbocyclic residue substituted with 0–3 R$^{4e}$, and a (CH$_2$)$_r$-5–6 membered heterocyclic system containing 1–4 heteroatoms selected from N, O, and S, substituted with 0–3 R$^{4e}$;

R$^{4e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{4f}$R$^{4f}$, and (CH$_2$)$_r$phenyl;

R$^{4f}$, at each occurrence, is selected from H, C$_{1-5}$ alkyl, and C$_{3-6}$ cycloalkyl, and phenyl;

R$^{4g}$ is independently selected from —C(O)R$^{4b}$, —C(O)OR$^{4d}$, —C(O)NR$^{4f}$R$^{4f}$, and (CH$_2$)$_r$phenyl;

R$^5$, at each occurrence, is selected from C$_{1-8}$ alkyl, C2-8 alkenyl, C$_{2-8}$ alkynyl, (CH$_2$)$_r$C$_{3-6}$ cycloalkyl, Cl, Br, I, F, NO$_2$, CN, (CR'R')$_r$NR$^{5a}$R$^{5a}$, (CR'R')$_r$OH, (CR'R')$_r$O(CR'R')$_r$R$^{5d}$, (CR'R')$_r$SH, (CR'R')$_r$C(O)H, (CR'R')$_r$S(CR'R')$_r$R$^{5d}$, (CR'R')$_r$C(O)OH, (CR'R')$_r$C(O)(CR'R')$_r$R$^{5b}$, (CR'R')$_r$C(O)NR$^{5a}$R$^{5a}$, (CR'R')$_r$NR$^{5f}$C(O)(CR'R')$_r$R$^{5b}$, (CR'R')$_r$C(O)O(CR'R')$_r$R$^{5d}$, (CR'R')$_r$OC(O)(CR'R')$_r$R$^{5b}$, (CR'R')$_r$NR$^{5f}$C(O)O(CR'R')$_r$R$^{5d}$, (CR'R')$_r$OC(O)NR$^{5a}$R$^{5a}$, (CR'R')$_r$NR$^{5a}$C(O)NR$^{5a}$R$^{5a}$, (CR'R')$_r$C(=NR$^{5f}$)NR$^{5a}$R$^{5a}$, (CR'R')$_r$NHC(=NR$^{5f}$)NR$^{5f}$R$^{5f}$, (CR'R')$_r$S(O)$_p$(CR'R')$_r$R$^{5b}$, (CR'R')$_r$S(O)$_2$NR$^{5a}$R$^{5a}$, (CR'R')$_r$NR$^{5a}$S(O)$_2$NR$^{5a}$R$^{5a}$, (CR'R')$_r$NR$^{5f}$S(O)$_2$(CR'R')$_r$R$^{5b}$, C$_{1-6}$ haloalkyl, C$_{2-8}$ alkenyl substituted with 0–3 R', C$_{2-8}$ alkynyl substituted with 0–3 R', and (CR'R')$_r$phenyl substituted with 0–3 R$^{5e}$;

alternatively, two R$^5$ on adjacent atoms on R$^2$ may join to form a cyclic acetal;

R$^{5a}$, at each occurrence, is independently selected from H, methyl substituted with 0–1 R$^{5g}$, C$_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_r$—$C_{3-10}$ carbocyclic residue substituted with 0–5 $R^{5e}$, and a $(CH_2)_r$-5–10 membered heterocyclic system containing 1–4 heteroatoms selected from N, O, and S, substituted with 0–2 $R^{5e}$;

$R^{5b}$, at each occurrence, is independently selected from $C_{1-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_r C_{3-6}$ carbocyclic residue substituted with 0–3 $R^{5e}$, and a $(CH_2)_r$-5–6 membered heterocyclic system containing 1–4 heteroatoms selected from N, O, and S, substituted with 0–2 $R^{5e}$;

$R^{5d}$, at each occurrence, is independently selected from $C_{3-8}$ alkenyl substituted with 0–2 $R^{5e}$, $C_{3-8}$ alkynyl substituted with 0–2 $R^{5e}$, methyl, $CF_3$, $C_{2-6}$ alkyl substituted with 0–3 $R^{5e}$, a $(CH_2)_r$—$C_{3-10}$ carbocyclic residue substituted with 0–3 $R^{5e}$, and a $(CH_2)_r$-5–6 membered heterocyclic system containing 1–4 heteroatoms selected from N, O, and S, substituted with 0–3 $R^{5e}$;

$R^{5e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{5f}R^{5f}$, and $(CH_2)_r$phenyl;

$R^{5f}$, at each occurrence, is selected from H, $C_{1-5}$ alkyl, and $C_{3-6}$ cycloalkyl, and phenyl;

$R^{5g}$ is independently selected from —$C(O)R^{5b}$, —$C(O)OR^{5d}$, —$C(O)NR^{5f}R^{5f}$, and $(CH_2)_r$phenyl;

R', at each occurrence, is selected from H, $C_{1-6}$ alkyl, $C_{2-8}$ alkenyl, $C_{2-8}$ alkynyl, $(CH_2)_r C_{3-6}$ cycloalkyl, and $(CH_2)_r$phenyl substituted with $R^{5e}$;

$R^6$, is selected from H, $C_{1-6}$ alkyl, $C_{2-6}$ alkenyl, $C_{2-6}$ alkynyl, $(CRR)_q OH$, $(CRR)_q SH$, $(CRR)_q OR^{6d}$, $(CRR)_q S(O)_p R^{6d}$, $(CRR)_r C(O)R^{6b}$, $(CRR)_r NR^{6a}R^{6a}$, $(CRR)_r C(O)NR^{6a}R^{6a}$, $(CRR)_r C(O)NR^{6a}OR^{6d}$, $(CRR)_r SO_2 NR^{6a}R^{6a}$, $(CRR)_r C(O)OR^{6d}$, a $(CRR)_r$—$C_{3-10}$ carbocyclic residue substituted with 0–5 $R^{6e}$, and a $(CRR)_r$-5–10 membered heterocyclic system containing 1–4 heteroatoms selected from N, O, and S, substituted with 0–3 $R^{6e}$;

$R^{6a}$, at each occurrence, is independently selected from H, methyl, $C_{2-6}$ alkyl substituted with 0–3 $R^{6e}$, $C_{3-8}$ alkenyl substituted with 0–3 $R^{6e}$, $C_{3-8}$ alkynyl substituted with 0–3 $R^{6e}$, $(CH_2)_r C_{3-6}$ cycloalkyl, a $(CH_2)_r$—$C_{3-10}$ carbocyclic residue substituted with 0–5 $R^{6e}$, and a $(CH_2)_r$-5–10 membered heterocyclic system containing 1–4 heteroatoms selected from N, O, and S, substituted with 0–3 $R^{6e}$;

$R^{6b}$, at each occurrence, is independently selected from $C_{1-6}$ alkyl substituted with 0–3 $R^{6e}$, $C_{2-8}$ alkenyl substituted with 0–3 $R^{6e}$, $C_{2-8}$ alkynyl substituted with 0–3 $R^{6e}$, a $(CH_2)_r$—$C_{3-6}$ carbocyclic residue substituted with 0–2 $R^{6e}$, and a $(CH_2)_r$-5–6 membered heterocyclic system containing 1–4 heteroatoms selected from N, O, and S, substituted with 0–3 $R^{6e}$;

$R^{6d}$, at each occurrence, is independently selected from H, methyl, —$CF_3$, $C_{2-6}$ alkyl substituted with 0–3 $R^{6e}$, $C_{3-6}$ alkenyl substituted with 0–3 $R^{6e}$, $C_{3-6}$ alkynyl substituted with 0–3 $R^{6e}$, a $C_{3-10}$ carbocyclic residue substituted with 0–3 $R^{6e}$, and a $(CH_2)_r$-5–6 membered heterocyclic system containing 1–4 heteroatoms selected from N, O, and S, substituted with 0–3 $R^{6e}$;

$R^{6e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, —O—$C_{1-6}$ alkyl, SH, $(CH_2)_r SC_{1-5}$ alkyl, $(CH_2)_r NR^{6f}R^{6f}$, and $(CH_2)_r$phenyl;

$R^{6f}$, at each occurrence, is independently selected from H, $C_{1-6}$ alkyl, and $C_{3-6}$ cycloalkyl;

$R^{6g}$ is selected from $(CHR)_q OH$, $(CHR)_q SH$, $(CHR)_q OR^{6d}$, $(CHR)_q S(O)_p R^{6d}$, $(CHR)_r C(O)R^{6b}$, $(CHR)_q NR^{6a}R^{6a}$, $(CHR)_r C(O)NR^{6a}R^{6a}$, $(CHR)_r C(O)NR^{6a}OR^{6d}$, $(CHR)_q SO_2 NR^{6a}R^{6a}$, $(CHR)_r C(O)OR^{6d}$, and a $(CHR)_r$—$C_{3-10}$ carbocyclic residue substituted with 0–5 $R^{6e}$;

$R^7$, is selected from H, $C_{1-6}$ alkyl, $C_{2-6}$ alkenyl, $C_{2-6}$ alkynyl, $(CRR)_q OH$, $(CRR)_q SH$, $(CRR)_q OR^{7d}$, $(CRR)_q S(O)_p R^{7d}$, $(CRR)_r C(O)R^{7b}$, $(CRR)_r NR^{7a}R^{7a}$, $(CRR)_r C(O)NR^{7a}R^{7a}$, $(CRR)_r C(O)NR^{7a}OR^{7d}$, $(CRR)_q SO_2 NR^{7a}R^{7a}$, $(CRR)_r C(O)OR^{7d}$, a $(CRR)_r$—$C_{3-10}$ carbocyclic residue substituted with 0–5 $R^{7e}$, and a $(CRR)_r$-5–10 membered heterocyclic system containing 1–4 heteroatoms selected from N, O, and S, substituted with 0–3 $R^{7e}$;

$R^{7a}$, at each occurrence, is independently selected from H, methyl, $C_{2-6}$ alkyl substituted with 0–3 $R^{7e}$, $C_{3-8}$ alkenyl substituted with 0–3 $R^{7e}$, $C_{3-8}$ alkynyl substituted with 0–3 $R^{7e}$, $(CH_2)_r C_{3-6}$ cycloalkyl, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–3 $R^{7e}$;

$R^{7b}$, at each occurrence, is independently selected from $C_{1-6}$ alkyl substituted with 0–3 $R^{7e}$, $C_{2-8}$ alkenyl substituted with 0–3 $R^{7e}$, $C_{2-8}$ alkynyl substituted with 0–3 $R^{7e}$, a $(CH_2)_r$—$C_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7d}$, at each occurrence, is independently selected from H, methyl, —$CF_3$, $C_{2-6}$ alkyl substituted with 0–3 $R^{7e}$, $C_{3-6}$ alkenyl substituted with 0–3 $R^{7e}$, $C_{3-6}$ alkynyl substituted with 0–3 $R^{7e}$, a $C_{3-10}$ carbocyclic residue substituted with 0–3 $R^{7e}$, and a $(CH_2)_r$-5–6 membered heterocyclic system containing 1–4 heteroatoms selected from N, O, and S, substituted with 0–3 $R^{7e}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_r CF_3$, $(CH_2)_r OC_{1-5}$ alkyl, OH, —O—$C_{1-6}$ alkyl, SH, $(CH_2)_r SC_{1-5}$ alkyl, $(CH_2)_r NR^{7f}R^{7f}$, and $(CH_2)_r$phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{2-6}$ alkenyl, $C_{2-6}$ alkynyl, $(CRR)_r OH$, $(CRR)_r SH$, $(CRR)_r OR^{8d}$, $(CRR)_r S(O)_p R^{8d}$, $(CRR)_r C(O)R^{8b}$, $(CRR)_r NR^{8a}R^{8a}$, $(CRR)_r C(O)NR^{8a}R^{8a}$, $(CRR)_r C(O)NR^{8a}OR^{8d}$, $(CRR)_r SO_2 NR^{8a}R^{8a}$, $(CRR)_r C(O)OR^{8d}$, a $(CRR)_r$—$C_{3-10}$ carbocyclic residue substituted with 0–5 $R^{8e}$, and a $(CRR)_r$-5–10 membered heterocyclic system containing 1–4 heteroatoms selected from N, O, and S, substituted with 0–3 $R^{8e}$;

$R^{8a}$, at each occurrence, is independently selected from H, methyl, $C_{2-6}$ alkyl substituted with 0–3 $R^{8e}$, $C_{3-8}$ alkenyl substituted with 0–3 $R^{8e}$, $C_{3-8}$ alkynyl substituted with 0–3 $R^{8e}$, $(CH_2)_r C_{3-6}$ cycloalkyl, a $(CH_2)_r$—$C_{3-10}$ carbocyclic residue substituted with 0–5 $R^{8e}$, and a $(CH_2)_r$-5–10 membered heterocyclic system containing 1–4 heteroatoms selected from N, O, and S, substituted with 0–3 $R^{8e}$;

$R^{8b}$, at each occurrence, is independently selected from $C_{1-6}$ alkyl substituted with 0–3 $R^{8e}$, $C_{2-8}$ alkenyl substituted with 0–3 $R^{8e}$, $C_{2-8}$ alkynyl substituted with 0–3 $R^{8e}$, a $(CH_2)_r$—$C_{3-6}$ carbocyclic residue substituted with 0–2 $R^{8e}$, and a $(CH_2)_r$-5–6 membered heterocyclic system containing 1–4 heteroatoms selected from N, O, and S, substituted with 0–3 $R^{8e}$;

$R^{8d}$, at each occurrence, is independently selected from H, methyl, —$CF_3$, $C_{2-6}$ alkyl substituted with 0–3 $R^{8e}$, $C_{3-6}$ alkenyl substituted with 0–3 $R^{8e}$, $C_{3-6}$ alkynyl substituted with 0–3 $R^{8e}$, a $C_{3-10}$ carbocyclic residue substituted with 0–3 $R^{8e}$, and a $(CH_2)_r$-5–6 membered heterocyclic system containing 1–4 heteroatoms selected from N, O, and S, substituted with 0–3 $R^{8e}$;

$R^{8e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{8f}R^{8f}$, and $(CH_2)_r$phenyl;

$R^{8f}$, at each occurrence, is independently selected from H, $C_{1-6}$ alkyl, and $C_{3-6}$ cycloalkyl;

$R^{8g}$ is selected from $(CHR)_qOH$, $(CHR)_qSH$, $(CHR)_qOR^{8d}$, $(CHR)_qS(O)_pR^{8d}$, $(CHR)_qC(O)R^{8b}$, $(CHR)_qNR^{8a}R^{8a}$, $(CHR)_rC(O)NR^{8a}R^{8a}$, $(CHR)_rC(O)NR^{8a}OR^{8d}$, $(CHR)_qSO_2NR^{8a}R^{8a}$, $(CHR)_rC(O)OR^{8d}$, and a $(CHR)_r$—$C_{3-10}$ carbocyclic residue substituted with 0–5 $R^{8e}$;

$R^9$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{9d}$, $(CRR)_rS(O)_pR^{9d}$, $(CRR)_rC(O)R^{9b}$, $(CRR)_rNR^{9a}R^{9a}$, $(CRR)_rC(O)NR^{9a}R^{9a}$, $(CRR)_rC(O)NR^{9a}OR^{9d}$, $(CRR)_rSO_2NR^{9a}R^{9a}$, $(CRR)_rC(O)OR^{9d}$, a $(CRR)_r$—$C_{3-10}$ carbocyclic residue substituted with 0–5 $R^{9e}$, and a $(CRR)_r$-5–10 membered heterocyclic system containing 1–4 heteroatoms selected from N, O, and S, substituted with 0–3 $R^{9e}$;

$R^{9a}$, at each occurrence, is independently selected from H, methyl, $C_{2-6}$ alkyl substituted with 0–3 $R^{9e}$, $C_{3-8}$ alkenyl substituted with 0–3 $R^{9e}$, $C_{3-8}$ alkynyl substituted with 0–3 $R^{9e}$, $(CH_2)_rC_{3-6}$ cycloalkyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–3 $R^{9e}$;

$R^{9b}$, at each occurrence, is independently selected from $C_{1-6}$ alkyl substituted with 0–3 $R^{9e}$, $C_{2-8}$ alkenyl substituted with 0–3 $R^{9e}$, $C_{2-8}$ alkynyl substituted with 0–3 $R^{9e}$, a $(CH_2)_r$—$C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9d}$, at each occurrence, is independently selected from H, methyl, —$CF_3$, $C_{2-6}$ alkyl substituted with 0–3 $R^{9e}$, $C_{3-6}$ alkenyl substituted with 0–3 $R^{9e}$, $C_{3-6}$ alkynyl substituted with 0–3 $R^{9e}$, a $C_{3-10}$ carbocyclic residue substituted with 0–3 $R^{9e}$, and a $(CH_2)_r$-5–6 membered heterocyclic system containing 1–4 heteroatoms selected from N, O, and S, substituted with 0–3 $R^{9e}$;

$R^{9e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{9f}R^{9f}$, and $(CH_2)_r$phenyl;

$R^{9f}$, at each occurrence, is independently selected from H, $C_{1-6}$ alkyl, and $C_{3-6}$ cycloalkyl;

$R^{10}$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{10d}$, $(CRR)_rS(O)_pR^{10d}$, $(CRR)_rC(O)R^{10b}$, $(CRR)_rNR^{10a}R^{10a}$, $(CRR)_rC(O)NR^{10a}R^{10a}$, $(CRR)_rC(O)NR^{10a}OR^{10d}$, $(CRR)_rSO_2NR^{10a}R^{10a}$, $(CRR)_rC(O)OR^{10d}$, a $(CRR)_r$—$C_{3-10}$ carbocyclic residue substituted with 0–5 $R^{10e}$, and a $(CRR)_r$-5–10 membered heterocyclic system containing 1–4 heteroatoms selected from N, O, and S, substituted with 0–3 $R^{10e}$;

$R^{10a}$, at each occurrence, is independently selected from H, methyl, $C_{2-6}$ alkyl substituted with 0–3 $R^{10e}$, $C_{3-8}$ alkenyl substituted with 0–3 $R^{10e}$, $C_{3-8}$ alkynyl substituted with 0–3 $R^{10e}$, $(CH_2)_rC_{3-6}$ cycloalkyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

$R^{10b}$, at each occurrence, is independently selected from $C_{1-6}$ alkyl substituted with 0–3 $R^{10e}$, $C_{2-8}$ alkenyl substituted with 0–3 $R^{10e}$, $C_{2-8}$ alkynyl substituted with 0–3 $R^{10e}$, a $(CH_2)_r$—$C_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10d}$, at each occurrence, is independently selected from H, methyl, —$CF_3$, $C_{2-6}$ alkyl substituted with 0–3 $R^{10e}$, $C_{3-6}$ alkenyl substituted with 0–3 $R^{10e}$, $C_{3-6}$ alkynyl substituted with 0–3 $R^{10e}$, a $C_{3-10}$ carbocyclic residue substituted with 0–3 $R^{10e}$, and a $(CH_2)_r$-5–6 membered heterocyclic system containing 1–4 heteroatoms selected from N, O, and S, substituted with 0–3 $R^{10e}$;

$R^{10e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{10f}R^{10f}$, and $(CH_2)_r$phenyl;

$R^{10f}$, at each occurrence, is independently selected from H, $C_{1-6}$ alkyl, and $C_{3-6}$ cycloalkyl;

$R^{10g}$ is selected from $(CHR)_qOH$, $(CHR)_qSH$, $(CHR)_qOR^{10d}$, $(CHR)_qS(O)_pR^{10d}$, $(CHR)_qC(O)R^{10b}$, $(CHR)_qNR^{10a}R^{10a}$, $(CHR)_rC(O)NR^{10a}R^{10a}$, $(CHR)_rC(O)NR^{10a}OR^{10d}$, $(CHR)_qSO_2NR^{10a}R^{10a}$, $(CHR)_rC(O)OR^{10d}$, and a $(CHR)_r$—$C_{3-10}$ carbocyclic residue substituted with 0–5 $R^{10e}$;

$R^{11}$, is selected from H, $C_{1-6}$ alkyl, $C_{2-6}$ alkenyl, $C_{2-6}$ alkynyl, $(CRR)_rOH$, $(CRR)_rSH$, $(CRR)_rOR^{11d}$, $(CRR)_rS(O)_pR^{11d}$, $(CRR)_rC(O)R^{11b}$, $(CRR)_rNR^{11a}R^{11a}$, $(CRR)_rC(O)NR^{11a}R^{11a}$, $(CRR)_rC(O)NR^{11a}OR^{11d}$, $(CRR)_rSO_2NR^{11a}R^{11a}$, $(CRR)_rC(O)OR^{11d}$, a $(CRR)_r$—$C_{3-10}$ carbocyclic residue substituted with 0–5 $R^{11e}$, and a $(CRR)_r$-5–10 membered heterocyclic system containing 1–4 heteroatoms selected from N, O, and S, substituted with 0–3 $R^{11e}$;

$R^{11a}$, at each occurrence, is independently selected from H, methyl, $C_{2-6}$ alkyl substituted with 0–3 $R^{11e}$, $C_{3-8}$ alkenyl substituted with 0–3 $R^{11e}$, $C_{3-8}$ alkynyl substituted with 0–3 $R^{11e}$, $(CH_2)_rC_{3-6}$ cycloalkyl, a $(CH_2)_r$—$C_{3-10}$ carbocyclic residue substituted with 0–5 $R^{11e}$, and a $(CH_2)_r$-5–10 membered heterocyclic system containing 1–4 heteroatoms selected from N, O, and S, substituted with 0–3 $R^{11e}$;

$R^{11b}$, at each occurrence, is independently selected from $C_{1-6}$ alkyl substituted with 0–3 $R^{11e}$, $C_{2-8}$ alkenyl substituted with 0–3 $R^{11e}$, $C_{2-8}$ alkynyl substituted with 0–3 $R^{11e}$, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11d}$, at each occurrence, is independently selected from H, methyl, —$CF_3$, $C_{2-6}$ alkyl substituted with 0–3 $R^{11e}$, $C_{3-6}$ alkenyl substituted with 0–3 $R^{11e}$, $C_{3-6}$ alkynyl substituted with 0–3 $R^{11e}$, a $C_{3-10}$ carbocyclic residue substituted with 0–3 $R^{11e}$, and a $(CH_2)_r$-5–6 membered heterocyclic system containing 1–4 heteroatoms selected from N, O, and S, substituted with 0–3 $R^{11e}$;

$R^{11e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_r$ $NR^{11f}R^{11f}$, and $(CH_2)_r$phenyl;

$R^{11f}$, at each occurrence, is independently selected from H, $C_{1-6}$ alkyl, and $C_{3-6}$ cycloalkyl;

$R^{12}$ is selected from H, $C_{1-6}$ alkyl, $C_{2-6}$ alkenyl, $C_{2-6}$ alkynyl, $(CRR)_qOH$, $(CRR)_qSH$, $(CRR)_qOR^{12d}$, $(CRR)_qS(O)_pR^{12d}$, $(CRR)_rC(O)R^{12b}$, $(CRR)_r$ $NR^{12a}R^{12a}$, $(CRR)_rC(O)NR^{12a}R^{12a}$, $(CRR)_rC(O)$ $NR^{12a}OR^{12d}$, $(CRR)_qSO_2NR^{12a}R^{12a}$, $(CRR)_rC(O)$ $OR^{12d}$, a $(CRR)_r$—$C_{3-10}$ carbocyclic residue substituted with 0–5 $R^{12e}$, and a $(CRR)_r$-5–10 membered heterocyclic system containing 1–4 heteroatoms selected from N, O, and S, substituted with 0–3 $R^{12e}$;

$R^{12a}$, at each occurrence, is independently selected from H, methyl, $C_{2-6}$ alkyl substituted with 0–3 $R^{12e}$, $C_{3-8}$ alkenyl substituted with 0–3 $R^{12e}$, $C_{3-8}$ alkynyl substituted with 0–3 $R^{12e}$, $(CH_2)_rC_{3-6}$ cycloalkyl, a $(CH_2)_r$—$C_{3-10}$ carbocyclic residue substituted with 0–5 $R^{12e}$, and a $(CH_2)_r$-5–10 membered heterocyclic system containing 1–4 heteroatoms selected from N, O, and S, substituted with 0–3 $R^{12e}$;

$R^{12b}$, at each occurrence, is independently selected from $C_{1-6}$ alkyl substituted with 0–3 $R^{12e}$, $C_{2-8}$ alkenyl substituted with 0–3 $R^{12e}$, $C_{2-8}$ alkynyl substituted with 0–3 $R^{12e}$, a $(CH_2)_r$—$C_{3-6}$ carbocyclic residue substituted with 0–2 $R^{12e}$, and a $(CH_2)_r$-5–6 membered heterocyclic system containing 1–4 heteroatoms selected from N, O, and S, substituted with 0–3 $R^{12e}$;

$R^{12d}$, at each occurrence, is independently selected from H, methyl, —$CF_3$, $C_{2-6}$ alkyl substituted with 0–3 $R^{12e}$, $C_{3-6}$ alkenyl substituted with 0–3 $R^{12e}$, $C_{3-6}$ alkynyl substituted with 0–3 $R^{12e}$, a $C_{3-10}$ carbocyclic residue substituted with 0–3 $R^{12e}$, and a $(CH_2)_r$-5–6 membered heterocyclic system containing 1–4 heteroatoms selected from N, O, and S, substituted with 0–3 $R^{12e}$;

$R^{12e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_r$ $NR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{14}$ and $R^{14a}$ are H, $R^{15}$ is H;

$R^{16}$ is selected from H, $C_{1-4}$ alkyl substituted with 0–3 $R^{16a}$, and $C_{3-6}$ cycloalkyl substituted with 0–3 $R^{16a}$;

$R^{16a}$ is selected from $C_{1-4}$ alkyl, —OH, —SH, —$NR^{16c}R^{16c}$, —$C(O)NR^{16c}R^{16c}$, and —$NHC(O)R^{16c}$;

$R^{16c}$ is selected from H, $C_{1-4}$ alkyl and $C_{3-6}$ cycloalkyl;

$R^{17}$ is selected from H, $C_{1-4}$ alkyl, and $C_{3-4}$ cycloalkyl;

n is 1;

l is selected from 0 and 1;

m is selected from 0 and 1;

p, at each occurrence, is selected from 0, 1, or 2;

q, at each occurrence, is selected from 1, 2, 3, or 4; and r, at each occurrence, is selected from 0, 1, 2, 3, or 4.

2. A compound of claim 1, wherein:

Z is selected from a bond, —C(O)—, —C(O)NH—, —C(S)NH—, —$SO^2$—, and —$SO_2NH$—;

X is selected from —$NR^{17}$—, —O—, and —$CHR^{16}NR^{17}$—;

$R^1$ is selected from a $C_{6-10}$ aryl group substituted with 0–5 $R^4$;

$R^2$ is selected from a $C_{6-10}$ aryl group substituted with 0–5 $R^5$;

$R^3$ is selected from $(CRR)_qOH$, $(CRR)_qSH$, $(CRR)_qOR^{3d}$, $(CRR)_qS(O)_pR^{3d}$, $(CRR)_rC(O)R^{3b}$, $(CRR)_qNR^{3a}R^{3a}$, $(CRR)_rC(O)NR^{3a}R^{3a}$, $(CRR)_rC(O)NR^{3a}OR^{3d}$, $(CRR)_qSO_2NR^{3a}R^{3a}$, $(CRR)_rC(O)OR^{3d}$, a $(CRR)_r$—$C_{3-10}$ carbocyclic residue substituted with 0–5 $R^{3e}$, and a $(CRR)_r$-5–10 membered heterocyclic system containing 1–4 heteroatoms selected from N, O, and S, substituted with 0–3 $R^{3e}$;

$R^{3a}$, at each occurrence, is independently selected from H, methyl substituted with 0–1 $R^{3c}$, $C_{2-6}$ alkyl substituted with 0–3 $R^{3e}$, $C_{3-8}$ alkenyl substituted with 0–3 $R^{3e}$, $C_{3-8}$ alkynyl substituted with 0–3 $R^{3e}$, $(CH_2)_rC_{3-6}$ cycloalkyl, a $(CH_2)_r$—$C_{3-10}$ carbocyclic residue substituted with 0–5 $R^{3e}$, and a $(CH_2)_r$-5–10 membered heterocyclic system containing 1–4 heteroatoms selected from N, O, and S, substituted with 0–3 $R^{3e}$;

$R^{3b}$, at each occurrence, is independently selected from $C_{1-6}$ alkyl substituted with 0–3 $R^{3e}$, $C_{2-8}$ alkenyl substituted with 0–3 $R^{3e}$, $C_{2-8}$ alkynyl substituted with 0–3 $R^{3e}$, a $(CH_2)_r$—$C_{3-6}$ carbocyclic residue substituted with 0–2 $R^{3e}$, and a $(CH_2)_r$-5–6 membered heterocyclic system containing 1–4 heteroatoms selected from N, O, and S, substituted with 0–3 $R^{3e}$;

$R^{3c}$ is independently selected from —$C(O)R^{3b}$, —$C(O)OR^{3d}$, —$C(O)NR^{3f}R^{3f}$, and $(CH_2)_r$phenyl;

$R^{3d}$, at each occurrence, is independently selected from H, methyl, —$CF_3$, $C_{2-6}$ alkyl substituted with 0–3 $R^{3e}$, $C_{3-6}$ alkenyl substituted with 0–3 $R^{3e}$, $C_{3-6}$ alkynyl substituted with 0–3 $R^{3e}$, a $C_{3-10}$ carbocyclic residue substituted with 0–3 $R^{3e}$, and a $(CH_2)_r$-5–6 membered heterocyclic system containing 1–4 heteroatoms selected from N, O, and S, substituted with 0–3 $R^{3e}$;

$R^{3e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{3f}R^{3f}$, and $(CH_2)_r$phenyl;

$R^{3f}$, at each occurrence, is selected from H, $C_{1-6}$ alkyl, and $C_{3-6}$ cycloalkyl;

R, at each occurrence, is independently selected from H, $C_{1-6}$ alkyl, $C_{2-8}$ alkenyl, $C_{2-8}$ alkynyl, $(CH_2)_rC_{3-6}$ cycloalkyl, $(CHR)_rC(O)NR^{3a}R^{3a}$, and $(CHR)_rC(O)$ $OR^{3d}$, and $(CH_2)_r$phenyl substituted with $R^{3e}$;

$R^4$, at each occurrence, is selected from $C_{1-8}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CR'R')_rNR^{4a}R^{4a}$, $(CR'R')_rOH$, $(CR'R')_rO$ $(CR'R')_rR^{4d}$, $(CR'R')_rSH$, $(CR'R')_rC(O)H$, $(CR'R')_rS$ $(CR'R')_rR^{4d}$, $(CR'R')_rC(O)OH$, $(CR'R')_rC(O)(CR'R')_r$ $R^{4b}$, $(CR'R')_rC(O)NR^{4a}R^{4a}$, $(CR'R')_rNR^{4f}C(O)$ $(CR'R')_rR^{4b}$, $(CR'R')_rC(O)O(CR'R')_rR^{4d}$, $(CR'R')_rOC$ $(O)(CR'R')_rR^{4b}$, $(CR'R')_rNR^{4f}C(O)O(CR'R')_rR^{4d}$, $(CR'R')_rOC(O)NR^{4a}R^{4a}$, $(CR'R')_rNR^{6a}C(S)NR^{6a}$ $(CR'R')_rR^{6d}$, $(CR'R')_rNR^{4a}C(O)NR^{4a}R^{4a}$, $(CR'R')_rC(=NR^{4f})NR^{4a}R^{4a}$, $(CR'R')_rNHC(=NR^{4f})NR^{4f}R^{4f}$, $(CR'R')_rS(O)_p(CR'R')_rR^{4b}$, $(CR'R')_rS(O)_2NR^{4a}R^{4a}$, $(CR'R')_rNR^{6f}S(O)_2NR^{6a}R^{6a}$, $(CR'R')_rNR^{4f}S(O)_2(CR'R')_rR^{4b}$, $C_{1-6}$ haloalkyl, $C_{2-8}$ alkenyl substituted with 0–3 R', $C_{2-8}$ alkynyl substituted with 0–3 R', and $(CR'R')_r$phenyl substituted with 0–3 $R^{4e}$;

alternatively, two $R^4$ on adjacent atoms on $R^1$ may join to form a cyclic acetal;

$R^{4a}$, at each occurrence, is independently selected from H, methyl substituted with 0–1$R^{4g}$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_r$—$C_{3-10}$ carbocyclic residue substituted with 0–5 $R^{4e}$, and a $(CH_2)_r$-5–10 membered heterocyclic system containing 1–4 heteroatoms selected from N, O, and S, substituted with 0–2 $R^{4e}$;

$R^{4b}$, at each occurrence, is selected from $C_{1-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_rC_{3-6}$ carbocyclic residue substituted with 0–3 $R^{4e}$, and a $(CH_2)_r$-5–6 membered heterocyclic system containing 1–4 heteroatoms selected from N, O, and S, substituted with 0–2 $R^{4e}$;

$R^{4d}$, at each occurrence, is selected from $C_{3-8}$ alkenyl substituted with 0–2 $R^{5e}$, $C_{3-8}$ alkynyl substituted with 0–2 $R^{5e}$, methyl, $CF_3$, $C_{2-6}$ alkyl substituted with 0–3 $R^{4e}$, a $(CH_2)_r$—$C_{3-10}$ carbocyclic residue substituted with 0–3 $R^{4e}$, and a $(CH_2)_r$-5–6 membered heterocyclic system containing 1–4 heteroatoms selected from N, O, and S, substituted with 0–3 $R^{4e}$;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, and $(CH_2)_r$phenyl;

$R^{4f}$, at each occurrence, is selected from H, $C_{1-5}$ alkyl, and $C_{3-6}$ cycloalkyl, and phenyl;

$R^{4g}$ is independently selected from —C(O)$R^{4b}$, —C(O)OR$^{4d}$, —C(O)NR$^{4f}R^{4f}$, and $(CH_2)_r$phenyl;

$R^5$, at each occurrence, is selected from $C_{1-8}$ alkyl, C2-8 alkenyl, $C_{2-8}$ alkynyl, $(CH_2)_rC_{3-6}$ cycloalkyl, Cl, Br, I, F, $NO_2$, CN, $(CR'R')_rNR^{5a}R^{5a}$, $(CR'R')_rOH$, $(CR'R')_rO(CR'R')_rR^{5d}$, $(CR'R')_rSH$, $(CR'R')_rC(O)H$, $(CR'R')_rS(CR'R')_rR^{5d}$, $(CR'R')_rC(O)OH$, $(CR'R')_rC(O)(CR'R')_rR^{5b}$, $(CR'R')_rC(O)NR^{5a}R^{5a}$, $(CR'R')_rNR^{5f}C(O)(CR'R')_r$ $R^{5b}$, $(CR'R')_rC(O)O(CR'R')_rR^{5d}$, $(CR'R')_rOC(O)(CR'R')_rR^{5b}$, $(CR'R')_rNR^{5f}C(O)O(CR'R')_rR^{5d}$, $(CR'R')_r$ $OC(O)NR^{5a}R^{5a}$, $(CR'R')_rNR^{5a}C(O)NR^{5a}R^{5a}$, $(CR'R')_r$ $C(=NR^{5f})NR^{5a}R^{5a}$, $(CR'R')_rNHC(=NR^{5f})NR^{5f}R^{5f}$, $(CR'R')_rS(O)_p(CR'R')_rR^{5b}$, $(CR'R')_rS(O)_2NR^{5a}R^{5a}$, $(CR'R')_rNR^{5a}S(O)_2NR^{5a}R^{5a}$, $(CR'R')_rNR^{5f}S(O)_2(CR'R')_rR^{5b}$, $C_{1-6}$ haloalkyl, $C_{2-8}$ alkenyl substituted with 0–3 R', $C_{2-8}$ alkynyl substituted with 0–3 R', and $(CR'R')_r$phenyl substituted with 0–3 $R^{5e}$;

alternatively, two $R^5$ on adjacent atoms on $R^2$ may join to form a cyclic acetal;

$R^{5a}$, at each occurrence, is independently selected from H, methyl substituted with 0–1 $R^{5g}$, $C_{2-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_r$—$C_{3-10}$ carbocyclic residue substituted with 0–5 $R^{5e}$, and a $(CH_2)_r$-5–10 membered heterocyclic system containing 1–4 heteroatoms selected from N, O, and S, substituted with 0–2 $R^{5e}$;

$R^{5b}$, at each occurrence, is independently selected from $C_{1-6}$ alkyl substituted with 0–2 $R^{5e}$, $C_{3-8}$ alkenyl substituted with 0–2 $R^{5e}$, $C_{3-8}$ alkynyl substituted with 0–2 $R^{5e}$, a $(CH_2)_rC_{3-6}$ carbocyclic residue substituted with 0–3 $R^{5e}$, and a $(CH_2)_r$-5–6 membered heterocyclic system containing 1–4 heteroatoms selected from N, O, and S, substituted with 0–2 $R^{5e}$;

$R^{5d}$, at each occurrence, is independently selected from $C_{3-8}$ alkenyl substituted with 0–2 $R^{5e}$, $C_{3-8}$ alkynyl substituted with 0–2 $R^{5e}$, methyl, $CF_3$, $C_{2-6}$ alkyl substituted with 0–3 $R^{5e}$, a $(CH_2)_r$—$C_{3-10}$ carbocyclic residue substituted with 0–3 $R^{5e}$, and a $(CH_2)_r$-5–6 membered heterocyclic system containing 1–4 heteroatoms selected from N, O, and S, substituted with 0–3 $R^{5e}$;

$R^{5e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{5f}R^{5f}$, and $(CH_2)_r$phenyl;

$R^{5f}$, at each occurrence, is selected from H, $C_{1-5}$ alkyl, and $C_{3-6}$ cycloalkyl, and phenyl;

$R^{5g}$ is independently selected from —C(O)$R^{5b}$, —C(O)OR$^{5d}$, —C(O)NR$^{5f}R^{5f}$, and $(CH_2)_r$phenyl;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{5e}$;

$R^6$, is selected from H, $C_{1-6}$ alkyl, $C_{2-6}$ alkenyl, $C_{2-6}$ alkynyl, $(CRR)_qOH$, $(CRR)_qSH$, $(CRR)_qOR^{6d}$, $(CRR)_qS(O)_pR^{6d}$, $(CRR)_rC(O)R^{6b}$, $(CRR)_rNR^{6a}R^{6a}$, $(CRR)_rC(O)NR^{6a}R^{6a}$, $(CRR)_rC(O)NR^{6a}OR^{6d}$, $(CRR)_rSO_2NR^{6a}R^{6a}$, $(CRR)_rC(O)OR^{6d}$, a $(CRR)_r$—$C_{3-10}$ carbocyclic residue substituted with 0–5 $R^{6e}$, and a $(CRR)_r$-5–10 membered heterocyclic system containing 1–4 heteroatoms selected from N, O, and S, substituted with 0–3 $R^{6e}$;

$R^{6a}$, at each occurrence, is independently selected from H, methyl, $C_{2-6}$ alkyl substituted with 0–3 $R^{6e}$, $C_{3-8}$ alkenyl substituted with 0–3 $R^{6e}$, $C_{3-8}$ alkynyl substituted with 0–3 $R^{6e}$, $(CH_2)_rC_{3-6}$ cycloalkyl, a $(CH_2)_r$—$C_{3-10}$ carbocyclic residue substituted with 0–5 $R^{6e}$, and a $(CH_2)_r$-5–10 membered heterocyclic system containing 1–4 heteroatoms selected from N, O, and S, substituted with 0–3 $R^{6e}$;

$R^{6b}$, at each occurrence, is independently selected from $C_{1-6}$ alkyl substituted with 0–3 $R^{6e}$, $C_{2-8}$ alkenyl substituted with 0–3 $R^{6e}$, $C_{2-8}$ alkynyl substituted with 0–3 $R^{6e}$, a $(CH_2)_r$—$C_{3-6}$ carbocyclic residue substituted with 0–2 $R^{6e}$, and a $(CH_2)_r$-5–6 membered heterocyclic system containing 1–4 heteroatoms selected from N, O, and S, substituted with 0–3 $R^{6e}$;

$R^{6d}$, at each occurrence, is independently selected from H, methyl, —$CF_3$, $C_{2-6}$ alkyl substituted with 0–3 $R^{6e}$, $C_{3-6}$ alkenyl substituted with 0–3 $R^{6e}$, $C_{3-6}$ alkynyl substituted with 0–3 $R^{6e}$, a $C_{3-10}$ carbocyclic residue substituted with 0–3 $R^{6e}$, and a $(CH_2)_r$-5–6 membered heterocyclic system containing 1–4 heteroatoms selected from N, O, and S, substituted with 0–3 $R^{6e}$;

$R^{6e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{6f}R^{6f}$, and $(CH_2)_r$phenyl;

$R^{6f}$, at each occurrence, is independently selected from H, $C_{1-6}$ alkyl, and $C_{3-6}$ cycloalkyl;

$R^{6g}$ is selected from $(CHR)_qOH$, $(CHR)_qSH$, $(CHR)_qOR^{6d}$, $(CHR)_qS(O)_pR^{6d}$, $(CHR)_rC(O)R^{6b}$, $(CHR)_qNR^{6a}R^{6a}$, $(CHR)_rC(O)NR^{6a}R^{6a}$, $(CHR)_rC(O)$ $NR^{6a}OR^{6d}$, $(CHR)_qSO_2NR^{6a}R^{6a}$, $(CHR)_rC(O)OR^{6d}$, and a $(CHR)_r$—$C_{3-10}$ carbocyclic residue substituted with 0–5 $R^{6e}$;

$R^7$, is selected from H, $C_{1-6}$ alkyl, $C_{2-6}$ alkenyl, $C_{2-6}$ alkynyl, $(CRR)_qOH$, $(CRR)_qSH$, $(CRR)_qOR^{7d}$, $(CRR)_qS(O)_pR^{7d}$, $(CRR)_rC(O)R^{7b}$, $(CRR)_rNR^{7a}R^{7a}$, $(CRR)_rC(O)NR^{7a}R^{7a}$, $(CRR)_rC(O)NR^{7a}OR^{7d}$, $(CRR)_qSO_2NR^{7a}R^{7a}$, $(CRR)_rC(O)OR^{7d}$, a $(CRR)_r$—$C_{3-10}$ carbocyclic residue substituted with 0–5 $R^{7e}$, and a $(CRR)_r$-5–10 membered heterocyclic system containing 1–4 heteroatoms selected from N, O, and S, substituted with 0–3 $R^{7e}$;

$R^{7a}$, at each occurrence, is independently selected from H, methyl, $C_{2-6}$ alkyl substituted with 0–3 $R^{7e}$, $C_{3-8}$ alkenyl substituted with 0–3 $R^{7e}$, $C_{3-8}$ alkynyl substituted with 0–3 $R^{7e}$, $(CH_2)_rC_{3-6}$ cycloalkyl, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–3 $R^{7e}$;

$R^{7b}$, at each occurrence, is independently selected from $C_{1-6}$ alkyl substituted with 0–3 $R^{7e}$, $C_{2-8}$ alkenyl substituted with 0–3 $R^{7e}$, $C_{2-8}$ alkynyl substituted with 0–3 $R^{7e}$, a $(CH_2)_r$—$C_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7d}$, at each occurrence, is independently selected from H, methyl, —$CF_3$, $C_{2-6}$ alkyl substituted with 0–3 $R^{7e}$, $C_{3-6}$ alkenyl substituted with 0–3 $R^{7e}$, $C_{3-6}$ alkynyl substituted with 0–3 $R^{7e}$, a $C_{3-10}$ carbocyclic residue substituted with 0–3 $R^{7e}$, and a $(CH_2)_r$-5–6 membered heterocyclic system containing 1–4 heteroatoms selected from N, O, and S, substituted with 0–3 $R^{7e}$;

$R^{7e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{7f}R^{7f}$, and $(CH_2)_r$phenyl;

$R^{7f}$, at each occurrence, is independently selected from H, $C_{1-6}$ alkyl, and $C_{3-6}$ cycloalkyl;

$R^8$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{8d}$, $(CRR)_rS(O)_pR^{8d}$, $(CRR)_rC(O)R^{8b}$, $(CRR)_rNR^{8a}R^{8a}$, $(CRR)_rC(O)NR^{8a}R^{8a}$, $(CRR)_rC(O)NR^{8a}OR^{8d}$, $(CRR)_rSO_2NR^{8a}R^{8a}$, $(CRR)_rC(O)OR^{8d}$, a $(CRR)_r$—$C_{3-10}$ carbocyclic residue substituted with 0–5 $R^{8e}$, and a $(CRR)_r$-5–10 membered heterocyclic system containing 1–4 heteroatoms selected from N, O, and S, substituted with 0–3 $R^{8e}$;

$R^{8a}$, at each occurrence, is independently selected from H, methyl, $C_{2-6}$ alkyl substituted with 0–3 $R^{8e}$, $C_{3-8}$ alkenyl substituted with 0–3 $R^{8e}$, $C_{3-8}$ alkynyl substituted with 0–3 $R^{8e}$, $(CH_2)_rC_{3-6}$ cycloalkyl, a $(CH_2)_r$—$C_{3-10}$ carbocyclic residue substituted with 0–5 $R^{8e}$, and a $(CH_2)_r$-5–10 membered heterocyclic system containing 1–4 heteroatoms selected from N, O, and S, substituted with 0–3 $R^{8e}$;

$R^{8b}$, at each occurrence, is independently selected from $C_{1-6}$ alkyl substituted with 0–3 $R^{8e}$, $C_{2-8}$ alkenyl substituted with 0–3 $R^{8e}$, $C_{2-8}$ alkynyl substituted with 0–3 $R^{8e}$, a $(CH_2)_r$—$C_{3-6}$ carbocyclic residue substituted with 0–2 $R^{8e}$, and a $(CH_2)_r$-5–6 membered heterocyclic system containing 1–4 heteroatoms selected from N, O, and S, substituted with 0–3 $R^{8e}$;

$R^{8d}$, at each occurrence, is independently selected from H, methyl, —$CF_3$, $C_{2-6}$ alkyl substituted with 0–3 $R^{8e}$, $C_{3-6}$ alkenyl substituted with 0–3 $R^{8e}$, $C_{3-6}$ alkynyl substituted with 0–3 $R^{8e}$, a $C_{3-10}$ carbocyclic residue substituted with 0–3 $R^{8e}$, and a $(CH_2)_r$-5–6 membered heterocyclic system containing 1–4 heteroatoms selected from N, O, and S, substituted with 0–3 $R^{8e}$;

$R^{8e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{8f}R^{8f}$, and $(CH_2)_r$phenyl;

$R^{8f}$, at each occurrence, is independently selected from H, $C_{1-6}$ alkyl, and $C_{3-6}$ cycloalkyl;

$R^{8g}$ is selected from $(CHR)_qOH$, $(CHR)_qSH$, $(CHR)_qOR^{8d}$, $(CHR)_qS(O)_pR^{8d}$, $(CHR)_rC(O)R^{8b}$, $(CHR)_qNR^{8a}R^{8a}$, $(CHR)_rC(O)NR^{8a}R^{8a}$, $(CHR)_rC(O)NR^{8a}OR^{8d}$, $(CHR)_qSO_2NR^{8a}R^{8a}$, $(CHR)_rC(O)OR^{8d}$, and a $(CHR)_r$—$C_{3-10}$ carbocyclic residue substituted with 0–5 $R^{8e}$;

$R^9$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{9d}$, $(CRR)_rS(O)_pR^{9d}$, $(CRR)_rC(O)R^{9b}$, $(CRR)_rNR^{9a}R^{9a}$, $(CRR)_rC(O)NR^{9a}R^{9a}$, $(CRR)_rC(O)NR^{9a}OR^{9d}$, $(CRR)_rSO_2NR^{9a}R^{9a}$, $(CRR)_rC(O)OR^{9d}$, a $(CRR)_r$—$C_{3-10}$ carbocyclic residue substituted with 0–5 $R^{9e}$, and a $(CRR)_r$-5–10 membered heterocyclic system containing 1–4 heteroatoms selected from N, O, and S, substituted with 0–3 $R^{9e}$;

$R^{9a}$, at each occurrence, is independently selected from H, methyl, $C_{2-6}$ alkyl substituted with 0–3 $R^{9e}$, $C_{3-8}$ alkenyl substituted with 0–3 $R^{9e}$, $C_{3-8}$ alkynyl substituted with 0–3 $R^{9e}$, $(CH_2)_rC_{3-6}$ cycloalkyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–3 $R^{9e}$;

$R^{9b}$, at each occurrence, is independently selected from $C_{1-6}$ alkyl substituted with 0–3 $R^{9e}$, $C_{2-8}$ alkenyl substituted with 0–3 $R^{9e}$, $C_{2-8}$ alkynyl substituted with 0–3 $R^{9e}$, a $(CH_2)_r$—$C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9d}$, at each occurrence, is independently selected from H, methyl, —$CF_3$, $C_{2-6}$ alkyl substituted with 0–3 $R^{9e}$, $C_{3-6}$ alkenyl substituted with 0–3 $R^{9e}$, $C_{3-6}$ alkynyl substituted with 0–3 $R^{9e}$, a $C_{3-10}$ carbocyclic residue substituted with 0–3 $R^{9e}$, and a $(CH_2)_r$-5–6 membered heterocyclic system containing 1–4 heteroatoms selected from N, O, and S, substituted with 0–3 $R^{9e}$;

$R^{9e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_rNR^{9f}R^{9f}$, and $(CH_2)_r$phenyl;

$R^{9f}$, at each occurrence, is independently selected from H, $C_{1-6}$ alkyl, and $C_{3-6}$ cycloalkyl;

$R^{10}$ is selected from H, $C_{1-6}$ alkyl, $C_{2-6}$ alkenyl, $C_{2-6}$ alkynyl, $(CRR)_rOH$, $(CRR)_rSH$, $(CRR)_rOR^{10d}$, $(CRR)_rS(O)_pR^{10d}$, $(CRR)_rC(O)R^{10b}$, $(CRR)_rNR^{10a}R^{10a}$, $(CRR)_rC(O)NR^{10a}R^{10a}$, $(CRR)_rC(O)NR^{10a}OR^{10d}$, $(CRR)_rSO_2NR^{10a}R^{10a}$, $(CRR)_rC(O)OR^{10d}$, a $(CRR)_r$—$C_{3-10}$ carbocyclic residue substituted with 0–5 $R^{10e}$, and a $(CRR)_r$-5–10 membered heterocyclic system containing 1–4 heteroatoms selected from N, O, and S, substituted with 0–3 $R^{10e}$;

$R^{10a}$, at each occurrence, is independently selected from H, methyl, $C_{2-6}$ alkyl substituted with 0–3 $R^{10e}$, $C_{3-8}$ alkenyl substituted with 0–3 $R^{10e}$, $C_{3-8}$ alkynyl substituted with 0–3 $R^{10e}$, $(CH_2)_r C_{3-6}$ cycloalkyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

$R^{10b}$, at each occurrence, is independently selected from $C_{1-6}$ alkyl substituted with 0–3 $R^{10e}$, $C_{2-8}$ alkenyl substituted with 0–3 $R^{10e}$, $C_{2-8}$ alkynyl substituted with 0–3 $R^{10e}$, a $(CH_2)_r$—$C_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10d}$, at each occurrence, is independently selected from H, methyl, —$CF_3$, $C_{2-6}$ alkyl substituted with 0–3 $R^{10e}$, $C_{3-6}$ alkenyl substituted with 0–3 $R^{10e}$, $C_{3-6}$ alkynyl substituted with 0–3 $R^{10e}$, a $C_{3-10}$ carbocyclic residue substituted with 0–3 $R^{10e}$, and a $(CH_2)_r$-5–6 membered heterocyclic system containing 1–4 heteroatoms selected from N, O, and S, substituted with 0–3 $R^{10e}$;

$R^{10e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_r$ $NR^{10f}R^{10f}$, and $(CH_2)_r$phenyl;

$R^{10f}$, at each occurrence, is independently selected from H, $C_{1-6}$ alkyl, and $C_{3-6}$ cycloalkyl;

$R^{10g}$ is selected from $(CHR)_qOH$, $(CHR)_qSH$, $(CHR)_qOR^{10d}$, $(CHR)_qS(O)_pR^{10d}$, $(CHR)_rC(O)R^{10b}$, $(CHR)_qNR^{10a}R^{10a}$, $(CHR)_rC(O)NR^{10a}R^{10a}$, $(CHR)_rC(O)NR^{10a}OR^{10d}$, $(CHR)_qSO_2NR^{10a}R^{10a}$, $(CHR)_rC(O)OR^{10d}$, and a $(CHR)_r$—$C_{3-10}$ carbocyclic residue substituted with 0–5 $R^{10e}$;

$R^{11}$, is selected from H, $C_{1-6}$ alkyl, $C_{2-6}$ alkenyl, $C_{2-6}$ alkynyl, $(CRR)_rOH$, $(CRR)_rSH$, $(CRR)_rOR^{11d}$, $(CRR)_rS(O)_pR^{11d}$, $(CRR)_rC(O)R^{11b}$, $(CRR)_rNR^{11a}R^{11a}$, $(CRR)_rC(O)NR^{11a}R^{11a}$, $(CRR)_rC(O)NR^{11a}OR^{11d}$, $(CRR)_rSO_2NR^{11a}R^{11a}$, $(CRR)_rC(O)OR^{11d}$, a $(CRR)_r$—$C_{3-10}$ carbocyclic residue substituted with 0–5 $R^{11e}$, and a $(CRR)_r$-5–10 membered heterocyclic system containing 1–4 heteroatoms selected from N, O, and S, substituted with 0–3 $R^{11e}$;

$R^{11a}$, at each occurrence, is independently selected from H, methyl, $C_{2-6}$ alkyl substituted with 0–3 $R^{11e}$, $C_{3-8}$ alkenyl substituted with 0–3 $R^{11e}$, $C_{3-8}$ alkynyl substituted with 0–3 $R^{11e}$, $(CH_2)_rC_{3-6}$ cycloalkyl, a $(CH_2)_r$—$C_{3-10}$ carbocyclic residue substituted with 0–5 $R^{11e}$, and a $(CH_2)_r$-5–10 membered heterocyclic system containing 1–4 heteroatoms selected from N, O, and S, substituted with 0–3 $R^{11e}$;

$R^{11b}$, at each occurrence, is independently selected from $C_{1-6}$ alkyl substituted with 0–3 $R^{11e}$, $C_{2-8}$ alkenyl substituted with 0–3 $R^{11e}$, $C_{2-8}$ alkynyl substituted with 0–3 $R^{11e}$, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11d}$, at each occurrence, is independently selected from H, methyl, —$CF_3$, $C_{2-6}$ alkyl substituted with 0–3 $R^{11e}$, $C_{3-6}$ alkenyl substituted with 0–3 $R^{11e}$, $C_{3-6}$ alkynyl substituted with 0–3 $R^{11e}$, a $C_{3-10}$ carbocyclic residue substituted with 0–3 $R^{11e}$, and a $(CH_2)_r$-5–6 membered heterocyclic system containing 1–4 heteroatoms selected from N, O, and S, substituted with 0–3 $R^{11e}$;

$R^{11e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_r$ $NR^{11f}R^{11f}$, and $(CH_2)_r$phenyl;

$R^{11f}$, at each occurrence, is independently selected from H, $C_{1-6}$ alkyl, and $C_{3-6}$ cycloalkyl;

$R^{12}$ is selected from H, $C_{1-6}$ alkyl, $C_{2-6}$ alkenyl, $C_{2-6}$ alkynyl, $(CRR)_qOH$, $(CRR)_qSH$, $(CRR)_qOR^{12d}$, $(CRR)_q S(O)_pR^{12d}$, $(CRR)_rC(O)R^{12b}$, $(CRR)_r R^{12a}R^{12a}$, $(CRR)_rC(O)NR^{12a}R^{12a}$, $(CRR)_rC(O) NR^{12a}OR^{12d}$, $(CRR)_qSO_2NR^{12a}R^{12a}$, $(CRR)_rC(O) OR^{12d}$, a $(CRR)_r$—$C_{3-10}$ carbocyclic residue substituted with 0–5 $R^{12e}$, and a $(CRR)_r$-5–10 membered heterocyclic system containing 1–4 heteroatoms selected from N, O, and S, substituted with 0–3 $R^{12e}$;

$R^{12a}$, at each occurrence, is independently selected from H, methyl, $C_{2-6}$ alkyl substituted with 0–3 $R^{12e}$, $C_{3-8}$ alkenyl substituted with 0–3 $R^{12e}$, $C_{3-8}$ alkynyl substituted with 0–3 $R^{12e}$, $(CH_2)_rC_{3-6}$ cycloalkyl, a $(CH_2)_r$—$C_{3-10}$ carbocyclic residue substituted with 0–5 $R^{12e}$, and a $(CH_2)_r$-5–10 membered heterocyclic system containing 1–4 heteroatoms selected from N, O, and S, substituted with 0–3 $R^{12e}$;

$R^{12b}$, at each occurrence, is independently selected from $C_{1-6}$ alkyl substituted with 0–3 $R^{12e}$, $C_{2-8}$ alkenyl substituted with 0–3 $R^{12e}$, $C_{2-8}$ alkynyl substituted with 0–3 $R^{12e}$, a $(CH_2)_r$—$C_{3-6}$ carbocyclic residue substituted with 0–2 $R^{12e}$, and a $(CH_2)_r$-5–6 membered heterocyclic system containing 1–4 heteroatoms selected from N, O, and S, substituted with 0–3 $R^{12e}$;

$R^{12d}$, at each occurrence, is independently selected from H, methyl, —$CF_3$, $C_{2-6}$ alkyl substituted with 0–3 $R^{12e}$, $C_{3-6}$ alkenyl substituted with 0–3 $R^{12e}$, $C_{3-6}$ alkynyl substituted with 0–3 $R^{12e}$, a $C_{3-10}$ carbocyclic residue substituted with 0–3 $R^{12e}$, and a $(CH_2)_r$-5–6 membered heterocyclic system containing 1–4 heteroatoms selected from N, O, and S, substituted with 0–3 $R^{12e}$;

$R^{12e}$, at each occurrence, is independently selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, —O—$C_{1-6}$ alkyl, SH, $(CH_2)_rSC_{1-5}$ alkyl, $(CH_2)_r$ $NR^{12f}R^{12f}$, and $(CH_2)_r$phenyl;

$R^{12f}$, at each occurrence, is selected from H, $C_{1-6}$ alkyl, and $C_{3-6}$ cycloalkyl;

$R^{14}$ and $R^{14a}$ are H, $R^{15}$ is H;

$R^{16}$ is selected from H, $C_{1-4}$ alkyl substituted with 0–3 $R^{16a}$, and $C_{3-6}$ cycloalkyl substituted with 0–3 $R^{16a}$;

$R^{16a}$ is selected from $C_{1-4}$ alkyl, —OH, —SH, —$NR^{16c}R^{16c}$, —$C(O)NR^{16c}R^{16c}$, and —$NHC(O)R^{16}c$;

$R^{16c}$ is selected from H, $C_{1-4}$ alkyl and $C_{3-6}$ cycloalkyl;

$R^{17}$ is selected from H, $C_{1-4}$ alkyl, and $C_{3-4}$ cycloalkyl;

n is 1;

l is selected from 0 and 1;

m is selected from 0 and 1;

p, at each occurrence, is selected from 0, 1, or 2;

q, at each occurrence, is selected from 1, 2, 3, or 4; and r, at each occurrence, is selected from 0, 1, 2, 3, or 4.

3. The compound of claim 2, wherein:

$R^{16}$ is selected from H, $C_{1-4}$ alkyl substituted with 0–1 $R^{16a}$, wherein the alkyl is selected from methyl, ethyl, propyl, i-propyl, butyl, i-butyl, and s-butyl, and $C_{3-4}$ cycloalkyl substituted with 0–3 $R^{16a}$ wherein the cycloalkyl is selected from cyclopropyl and cyclobutyl;

$R^{16a}$ is selected from methyl, ethyl, propyl, i-propyl, —OH, —SH, —$NR^{16c}R^{16c}$, —$C(O)NR^{16c}R^{16c}$, and —$NHC(O)R^{16c}$; and $R^{17}$ is selected from H, methyl, ethyl, propyl, and i-propyl.

4. The compound of claim 3, wherein:

$R^9$ and $R^{11}$ are H; and $R^8$ and $R^{10}$ are independently selected from H, $C_{1-6}$ alkyl, $C_{2-6}$ alkenyl, $C_{2-6}$ alkynyl, a $(CH_2)_r$—$C_{3-10}$ carbocyclic residue wherein the carbocyclic residue is selected from cyclopropyl, cyclobutyl, cyclopentyl, cyclohexyl, phenyl and naphthyl.

5. The compound of claim 4, wherein:

$R^3$ is selected from $(CRR)_qOH$, $(CRR)_qSH$, $(CRR)_qOR^{3d}$, $(CRR)_qS(O)_pR^{3d}$, $(CRR)_rC(O)R^{3b}$, $(CRR)_qNR^{3a}R^{3a}$, $(CRR)_rC(O)NR^{3a}R^{3a}$, $(CRR)_rC(O)NR^{3a}OR^{3d}$, $(CRR)_qSO_2NR^{3a}R^{3a}$, $(CRR)_rC(O)$ $OR^{3d}$, a $(CRR)_r$—$C_{3-10}$ carbocyclic residue substituted with 0–5 $R^{3e}$, and a $(CRR)_r$-5–10 membered heterocyclic system containing 1–4 heteroatoms selected from N, O, and S, substituted with 0–3 $R^{3e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, pyrrolidinyl, tetrahydrofuranyl, tetrahydrothiophenyl, 1,2,4-triazolyl, 1,2,3-triazolyl, tetrazolyl, thiadiazolyl, thiazolyl, oxazolyl, pyrazinyl, and pyrimidinyl;

$R^6$ is selected from H, $(CRR)_qOH$, $(CRR)_qSH$, $(CRR)_qOR^{6d}$, $(CRR)_qS(O)_pR^{6d}$, $(CRR)_rC(O)R^{6b}$, $(CRR)_qNR^{6a}R^{6a}$, $(CRR)_rC(O)NR^{6a}R^{6a}$, $(CRR)_rC(O)NR^{6a}OR^{6d}$, $(CRR)_qSO_2NR^{6a}R^{6a}$, $(CRR)_rC(O)OR^{6d}$, a $(CRR)_r$—$C_{6-10}$ carbocyclic residue substituted with 0–5 $R^{6e}$, and a $(CRR)_r$-5–10 membered heterocyclic system containing 1–4 heteroatoms selected from N, O, and S, substituted with 0–6 $R^{6e}$ wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, pyrrolidinyl, tetrahydrofuranyl, tetrahydrothiophenyl, 1,2,4-triazolyl, 1,2,6-triazolyl, tetrazolyl, thiadiazolyl, thiazolyl, oxazolyl, pyrazinyl, and pyrimidinyl;

$R^7$ is H;

$R^{12}$ is selected from H, methyl, ethyl, and propyl.

6. The compound of claim 5, wherein:

$R^1$ is selected from phenyl substituted with 0–3 $R^4$;

$R^2$ is selected from phenyl substituted with 0–3 $R^5$.

7. The compound of claim 6, wherein:

X is —$CHR^{16}NR^{17}$—;

$R^4$, at each occurrence, is selected from $C_{1-8}$ alkyl, $C_{2-8}$ alkenyl, $C_{2-8}$ alkynyl, $(CR'R')_rC_{3-6}$ cycloalkyl, Cl, Br, I, F, $NO_2$, CN, $(CR'R')_rNR^{4a}R^{4a}$, $(CR'R')_rOH$, $(CR'R')_rOR^{4d}$, $(CR'R')_rSH$, $(CR'R')_rSR^{4d}$, $(CR'R')_rC(O)OH$, $(CR'R')_rC(O)R^{4b}$, $(CR'R')_rC(O)NR^{4a}R^{4a}$, $(CR'R')_rNR^{4f}C(O)R^{4b}$, $(CR'R')_rC(O)OR^{4d}$, $(CR'R')_rOC(O)R^{4b}$, $(CR'R')_rNR^{4f}C(O)OR^{4d}$, $(CR'R')_rOC(O)NR^{4a}R^{4a}$, $(CR'R')_rNR^{4a}C(O)NR^{4a}R^{4a}$, $(CR'R')_rS(O)_pR^{4b}$, $(CR'R')_rNR^{4a}R^{4a}$, $(CR'R')_rNR^{4f}S(O)_2R^{4b}$, $(CR'R')_rNR^{4f}S(O)_2$ $NR^{4a}R^{4a}$, $C_{1-6}$ haloalkyl, and $(CR'R')_r$phenyl substituted with 0–3 $R^{4e}$;

alternatively, two $R^4$ on adjacent atoms join to form —O—$(CH_2)$—O—;

$R^{4a}$, at each occurrence, is independently selected from H, methyl, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{4b}$, at each occurrence, is selected from methyl, ethyl, propyl, i-propyl, butyl, s-butyl, i-butyl, t-butyl, pentyl, hexyl, allyl, propargyl, a $(CH_2)_r$—$C_{3-6}$ carbocyclic residue substituted with 0–3 $R^{4e}$, wherein the carbocyclic residue is selected from cyclopropyl, cyclobutyl, cyclopentyl and cyclohexyl, and a $(CH_2)_r$-5–6 membered heterocyclic system containing 1–4 heteroatoms selected from N, O, and S, substituted with 0–2 $R^{4e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{4d}$, at each occurrence, is selected from H, methyl, $CF_3$, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{4e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{4f}R^{4f}$, and $(CH_2)_r$phenyl;

$R^{4f}$, at each occurrence, is selected from H, methyl, ethyl, propyl, i-propyl, butyl, and cyclopropyl, cyclobutyl, and phenyl;

$R^5$, at each occurrence, is selected from methyl, ethyl, propyl, i-propyl, butyl, i-butyl, s-butyl, t-butyl, pentyl, hexyl, $(CR'R')_rC_{3-6}$ cycloalkyl, Cl, Br, I, F, $NO_2$, CN, $(CR'R')_rNR^{5a}R^{5a}$, $(CR'R')_rOH$, $(CR'R')_rOR^{5d}$, $(CR'R')_rSH$, $(CR'R')_rC(O)H$, $(CR'R')_rSR^{5d}$, $(CR'R')_rC(O)OH$, $(CR'R')_rC(O)R^{5b}$, $(CR'R')_rC(O)NR^{5a}R^{5a}$, $(CR'R')_rNR^{5f}C(O)R^{5b}$, $(CR'R')_rC(O)OR^{5d}$, $(CR'R')_rOC(O)R^{5b}$, $(CR'R')_rNR^{5f}C(O)OR^{5d}$, $(CR'R')_rOC(O)NR^{5a}R^{5a}$, $(CR'R')_rNR^{5a}C(O)NR^{5a}R^{5a}$, $(CR'R')_rNR^{5a}C(O)$ $NR^{5a}R^{5a}$, $(CR'R')_rNR^{5a}C(O)O(CR'R')_rR^{5d}$, $(CR'R')_rS(O)_pR^{5b}$, $(CR'R')_rS(O)_2NR^{5a}R^{5a}$, $(CR'R'')_rNR^{5f}S(O)_2$ $R^{5b}$, $C_{1-6}$ haloalkyl, and $(CHR')_r$phenyl substituted with 0–3 $R^{5e}$;

alternatively, two $R^5$ on adjacent atoms join to form —O—$(CH_2)$—O—;

$R^{5a}$, at each occurrence, is independently selected from H, methyl, ethyl, propyl, i-propyl, butyl, s-butyl, i-butyl, t-butyl, pentyl, hexyl, allyl, propargyl, and a $(CH_2)_r$—$C_{3-10}$ carbocyclic residue substituted with 0–1 $R^{5e}$, wherein the carbocyclic residue is selected from cyclopropyl, cyclobutyl, cyclopentyl, cyclohexyl, phenyl and naphthyl;

$R^{5b}$, at each occurrence, is selected from methyl, ethyl, propyl, i-propyl, butyl, s-butyl, i-butyl, t-butyl, pentyl, hexyl, allyl, propargyl, a $(CH_2)_r$—$C_{3-6}$ carbocyclic residue selected from cyclopropyl, cyclobutyl, cyclopentyl, cyclohexyl, and phenyl; and a $(CH_2)_r$-5–6 membered heterocyclic system containing 1–4 heteroatoms selected from N, O, and S, wherein the heterocyclic system is selected from pyridinyl, thiophenyl, furanyl, indazolyl, azetidinyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, morphlinyl, piperidinyl, pyrrolyl, 2,5-dihydropyrrolyl, pyrrazolyl, 1,2,4-triazolyl, 1,2,3-triazolyl, tetrazolyl, thiadiazolyl, thiazolyl, oxazolyl, pyrazinyl, and pyrimidinyl;

$R^{5d}$, at each occurrence, is selected from H, methyl, $CF_3$, ethyl, propyl, i-propyl, butyl, s-butyl, i-butyl, t-butyl, pentyl, hexyl, allyl, propargyl, and a $(CH_2)_r$—$C_{3-6}$ carbocyclic residue selected from cyclopropyl, cyclobutyl, cyclopentyl and cyclohexyl;

$R^{5e}$, at each occurrence, is selected from $C_{1-6}$ alkyl, $C_{2-8}$ alkenyl, $C_{2-8}$ alkynyl, $(CH_2)_r C_{3-6}$ cycloalkyl, Cl, F, Br, I, CN, $NO_2$, $(CF_2)_r CF_3$, $(CH_2)_r OC_{1-5}$ alkyl, OH, SH, $(CH_2)_r SC_{1-5}$ alkyl, $(CH_2)_r NR^{5f}R^{5f}$, and $(CH_2)_r$phenyl; and $R^{5f}$, at each occurrence, is selected from H, methyl, ethyl, propyl, i-propyl, butyl, and cyclopropyl, cyclobutyl, and phenyl.

8. The compound of claim 7, wherein:

$R^5$ is selected from methyl, ethyl, propyl, i-propyl, butyl, i-butyl, s-butyl, pentyl, hexyl, $CF_3$, $CF_2CF_3$, $CF_2H$, $OCF_3$, Cl, Br, I, F, $SCF_3$, $NR^{5a}R^{5a}$, $NHC(O)OR^{5a}$, $NHC(O)R^{5b}$, and $NHC(O)NHR^{5a}$; and $R^{12}$ is selected from H and methyl.

9. A compound of claim 8, wherein:

Z is —C(O)—;

X is —$CHR^{16}NR^{17}$—;

$R^1$ is selected from phenyl substituted with 0–3 $R^4$;

$R^2$ is phenyl substituted with 0–2 $R^5$;

$R^3$ is selected from $(CRR)_q OH$, $(CRR)_q OR^{3d}$, $(CH_2)_r C(O)OH$, $(CH_2)_r C(O)NR^{3a}R^{3a}$, $(CHR)_r C(O)NR^{3a}OR^{3d}$, $(CH_2)C(O)R^{3b}$, $(CH_2)_r C(O)OR^{3d}$, and $(CH_2)$-phenyl;

$R^{3a}$ is selected from H, methyl, ethyl, propyl, i-propyl, butyl, i-butyl, s-butyl, t-butyl, allyl, $CH_2CF_3$, $C(CH_3)CH_2CH_2OH$, cyclopropyl, 1-methylcyclopropyl, cyclobutyl, cyclopentyl, cyclohexyl, phenyl, and benzyl;

$R_{3b}$ is selected from pyrrolidinyl, pyrrolid-3-enyl, and morpholinyl;

$R_{3d}$ is selected from methyl, ethyl, propyl, i-propyl, butyl, i-butyl, t-butyl and benzyl;

R is selected from H, methyl, ethyl, propyl, i-propyl, butyl, i-butyl, s-butyl, pentyl, neopentyl, phenyl and benzyl;

$R^4$ is selected from methyl, ethyl, propyl, i-propyl, butyl, ethylene, $OCH_3$, $OCF_3$, $SCH_3$, $SO_2CH_3$, Cl, F, Br, CN; alternatively, two $R^4$ join to form —O—$(CH_2)$—O—;

$R^6$ is selected from H, methyl, ethyl, propyl, i-propyl, butyl, $C(O)OCH_3$, $C(O)NHCH_2CH_3$;

$R^7$, $R^9$, and $R^{11}$ are H;

$R^8$ is H;

$R^{10}$ is selected from H and methyl;

$R^{16}$ is selected from H and methyl;

$R^{17}$ is selected from H and methyl;

m is 0 or 1;

l is 0 or 1 r is 0 or 1; and q is 1.

10. The compound of claim 1, wherein the compound is selected from:

Methyl (2S)-3-[[(2,4-dimethylphenyl)methyl]amino]-2-[[[[3-(trifluoromethyl)benzoyl]amino]acetyl]amino]-propanoate;

Methyl (2R)-3-[[(2,4-dimethylphenyl)methyl]amino]-2-[[[[3-(trifluoromethyl)benzoyl]amino]acetyl]amino]-propanoate;

(2S)-3-[[(2,4-dimethylphenyl)methyl]amino]-2-[[[[3-(trifluoromethyl)benzoyl]amino]acetyl]amino]-propanoic acid;

(2S)-N-Methyl-3-[[(2,4-dimethylphenyl)methyl]amino]-2-[[[[3-(trifluoromethyl)benzoyl]amino]acetyl]amino]-propanamide;

(2S)-3-[[(2,4-dimethylphenyl)methyl]amino]-2-[[[[3-(trifluoromethyl)benzoyl]amino]acetyl]amino]-propanamide;

(2R)-3-[[(2,4-dimethylphenyl)methyl]amino]-2-[[[[3-(trifluoromethyl)benzoyl]amino]acetyl]amino]-propanamide;

(2S)-N-Ethyl-3-[[(2,4-dimethylphenyl)methyl]amino]-2-[[[[3-(trifluoromethyl)benzoyl]amino]acetyl]amino]-propanamide;

(2S)-N-Benzyl-3-[[(2,4-dimethylphenyl)methyl]amino]-2-[[[[3-(trifluoromethyl)benzoyl]amino]acetyl]amino]-propanamide;

(2S)-N-Isopropyl-3-[[(2,4-dimethylphenyl)methyl]amino]-2-[[[[3-(trifluoromethyl)benzoyl]amino]acetyl]amino]-propanamide;

(2S)-N-tert-Butyl-3-[[(2,4-dimethylphenyl)methyl]amino]-2-[[[[3-(trifluoromethyl)benzoyl amino]acetyl]amino]-propanamide;

(2S)-N-Cyclopropyl-3-[[(2,4-dimethylphenyl)methyl]amino]-2-[[[[3-(trifluoromethyl)benzoyl]amino]acetyl]amino]-propanamide;

(2S)-N-Cyclobutyl-3-[[(2,4-dimethylphenyl)methyl]amino]-2-[[[[3-(trifluoromethyl)benzoyl]amino]acetyl]amino]-propanamide;

(2S)-N-Phenyl-3-[[(2,4-dimethylphenyl)methyl]amino]-2-[[[[3-(trifluoromethyl)benzoyl]amino]acetyl]amino]-propanamide;

(2S)-N,N-Dimethyl-3-[[(2,4-dimethylphenyl)methyl]amino]-2-[[[[3-(trifluoromethyl)benzoyl]amino]acetyl]amino]-propanamide;

(2S)-N-Methyl,N-methoxy-3-[[(2,4-dimethylphenyl)methyl]amino]-2-[[[[3-(trifluoromethyl)benzoyl]amino]acetyl]amino]-propanamide;

Methyl (2S)-3-[[(4-chlorophenyl)methyl]amino]-2-[[[[3-(trifluoromethyl)benzoyl]amino]acetyl]amino]-propanoate;

(2S)-3-[[(4-chlorophenyl)methyl]amino]-2-[[[[3-(trifluoromethyl)benzoyl]amino]acetyl]amino]-propanamide;

(2S)-N-Ethyl-3-[[(4-chlorophenyl)methyl]amino]-2-[[[[3-(trifluoromethyl)benzoyl]amino]acetyl]amino]-propanamide;

Methyl (2S)-3-[[(1S/R)-1-(4-chlorophenyl)ethyl]amino]-2-[[[[3-(trifluoromethyl)benzoyl]amino]acetyl]amino]-propanoate;

Methyl (2S)-3-[[(1S/R)-1-(2,4-dimethylphenyl)ethyl]amino]-2-[[[[3-(trifluoromethyl)benzoyl]amino]acetyl]amino]-propanoate;

Methyl (2S)-3-[(1,3-benzodioxol-5-ylmethyl)amino]-2-[[[[3-(trifluoromethyl)benzoyl]amino]acetyl]amino]-propanoate;

Methyl (2S)-3-[[(4-bromophenyl)methyl]amino]-2-[[[[3-(trifluoromethyl)benzoyl]amino]acetyl]amino]-propanamide;

Methyl (2S)-2-[[[[2-[[(1,1-dimethylethoxy)carbonyl]amino]-5-(trifluoromethyl)benzoyl]amino]acetyl]amino]-3-[[(2,4-dimethylphenyl)methyl]amino]-propanoate;

Methyl (2S)-2-[[[[2-amino-5-(trifluoromethyl)benzoyl]amino]acetyl]amino]-3-[[(2,4-dimethylphenyl)methyl]amino]-propanoate;

(2S)-2-[[[[2-amino-5-(trifluoromethyl)benzoyl]amino]acetyl]amino]-3-[[(2,4-dimethylphenyl)methyl]amino]-propanamide;

N-[2-[[(1S)-2-[[(2,4-dimethylphenyl)methyl]amino]-1-(hydroxymethyl)ethyl]amino]-2-oxoethyl]-3-(trifluoromethyl)benzamide;

N-[2-[[(1R)-2-[[(2,4-dimethylphenyl)methyl]amino]-1-(hydroxymethyl)ethyl]amino]-2-oxoethyl]-3-(trifluoromethyl)benzamide;

N-[2-[[(1S, 2S/R)-1-[[[(2,4-dimethylphenyl)methyl]amino]methyl]-2-hydroxypropyl]amino]-2-oxoethyl]-3-(trifluoromethyl)benzamide;

tert-Butyl (3R)-4-[[(2,4-dimethylphenyl)methyl]amino]-3-[[[[3-(trifluoromethyl)benzoyl]amino]acetyl]amino]-butanoate;

N-[2-[[(1R)-2-[[(2,4-dimethylphenyl)methyl]amino]-1-(phenylmethyl)ethyl]amino]-2-oxoethyl]-3-(trifluoromethyl)benzamide;

(2S)-N-tert-Butyl-2-[[[[2-[[(1,1-dimethylethoxy)carbonyl]amino]-5-(trifluoromethyl)benzoyl]amino]acetyl]amino]-3-[[(2,4-dimethylphenyl)methyl]amino]-propanamide;

(2S)-N-tert-Butyl-2-[[[[2-amino-5-(trifluoromethyl)benzoyl]amino]acetyl]amino]-3-[[(2,4-dimethylphenyl)methyl]amino]-propanamide;

(2S)-N-tert-Butyl-3-[[(4-bromo, 2-methylphenyl)methyl]amino]-2-[[[[2-[[(1,1-dimethylethoxy)carbonyl]amino]-5-(trifluoromethyl)benzoyl]amino]acetyl]amino]-propanamide;

(2S)-N-tert-Butyl-2-[[[[2-amino-5-(trifluoromethyl)benzoyl]amino]acetyl]amino]-3-[[(4-bromo, 2-methylphenyl)methyl]amino]-propanamide;

N-[2-[[(1S, 2S)-1-[[[(2,4-dimethylphenyl)methyl]amino]methyl]-2-hydroxy-3-(methyl)butyl]amino]-2-oxoethyl]-3-(trifluoromethyl)benzamide;

N-[2-[[(1S, 2R)-]-[[[(2,4-dimethylphenyl)methyl]amino]methyl]-2-hydroxy-3-(methyl)butyl]amino]-2-oxoethyl]-3-(trifluoromethyl)benzamide;

N-[2-[[(1S, 2S)-1-[[[(2,4-dimethylphenyl)methyl]amino]methyl]-2-hydroxy-2-(phenyl)ethyl]amino]-2-oxoethyl]-3-(trifluoromethyl)benzamide;

N-[2-[[(1S, 2R)-1-[[[(2,4-dimethylphenyl)methyl]amino]methyl]-2-hydroxy-2-(phenyl) ethyl]amino]-2-oxoethyl]-3-(trifluoromethyl)benzamide;

N-[2-[[(1S, 2S)-1-[[[(2,4-dimethylphenyl)methyl]amino]methyl]-2-hydroxy-3-(phenyl)propyl]amino]-2-oxoethyl]-3-(trifluoromethyl)benzamide;

N-[2-[[(1S, 2R)-1-[[[(2,4-dimethylphenyl)methyl]amino]methyl]-2-hydroxy-3-(phenyl)propyl]amino]-2-oxoethyl]-3-(trifluoromethyl)benzamide;

N-[2-[[(1S, 2S)-1-[[[(2,4-dimethylphenyl)methyl]amino]methyl]-2-hydroxy-4-(methyl)pentyl]amino]-2-oxoethyl]-3-(trifluoromethyl)benzamide;

N-[2-[[(1S, 2R)-1-[[[(2,4-dimethylphenyl)methyl]amino]methyl]-2-hydroxy-4-(methyl)pentyl]amino]-2-oxoethyl]-3-(trifluoromethyl)benzamide;

N-[2-[[(1S, 2S)-1-[[[(2,4-dimethylphenyl)methyl]amino]methyl]-2-(hydroxy)butyl]amino]-2-oxoethyl]-3-(trifluoromethyl)benzamide;

N-[2-[[(1S, 2R)-1-[[[(2,4-dimethylphenyl)methyl]amino]methyl]-2-(hydroxy)butyl]amino]-2-oxoethyl]-3-(trifluoromethyl)benzamide;

N-[2-[[(1S, 2S)-1-[[[(2,4-dimethylphenyl)methyl]amino]methyl]-2-(hydroxy)butyl]amino]-2-oxoethyl]-2-[[(1,1-dimethylethoxy)carbonyl]amino]-5-(trifluoromethyl)benzamide;

N-[2-[[(1S, 2S)-1-[[[(2,4-dimethylphenyl)methyl]amino]methyl]-2-(hydroxy)butyl]amino]-2-oxoethyl]-2-amino-5-(trifluoromethyl)benzamide;

N-[2-[[(1S, 2S)-1-[[[(2,4-dimethylphenyl)methyl]amino]methyl]-2-hydroxy-4-(methyl)pentyl]amino]-2-oxoethyl]-2-[[(1,1-dimethylethoxy)carbonyl]amino]-5-(trifluoromethyl)benzamide;

N-[2-[[(1S, 2R)-1-[[[(2,4-dimethylphenyl)methyl]amino]methyl]-2-hydroxy-4-(methyl)pentyl]amino]-2-oxoethyl]-2-[[(1,1-dimethylethoxy)carbonyl]amino]-5-(trifluoromethyl)benzamide;

N-[2-[[(1S, 2S)-1-[[[(2,4-dimethylphenyl)methyl]amino]methyl]-2-hydroxy-4-(methyl)pentyl]amino]-2-oxoethyl]-2-amino-5-(trifluoromethyl)benzamide;

N-[2-[[(1S, 2R)-1-[[[(2,4-dimethylphenyl)methyl]amino]methyl]-2-hydroxy-4-(methyl)pentyl]amino]-2-oxoethyl]-2-amino-5-(trifluoromethyl)benzamide;

N-[2-[[(1S, 2S)-]-[[[(2,4-dimethylphenyl)methyl]amino]methyl]-4,4-dimethyl-2-(hydroxy)pentyl]amino]-2-oxoethyl]-3-(trifluoromethyl)benzamide;

N-[2-[[(1S, 2R)-1-[[[(2,4-dimethylphenyl)methyl]amino]methyl]-4,4-dimethyl-2-(hydroxy)pentyl]amino]-2-oxoethyl]-3-(trifluoromethyl)benzamide;

N-[2-[[(1S, 2S)-1-[[[(2,4-dimethylphenyl)methyl]amino]methyl]-2-(hydroxy)pentyl]amino]-2-oxoethyl]-3-(trifluoromethyl)benzamide;

N-[2-[[(1S, 2R)-1-[[[(2,4-dimethylphenyl)methyl]amino]methyl]-2-(hydroxy)pentyl]amino]-2-oxoethyl]-3-(trifluoromethyl)benzamide;

N-[2-[[(1S, 2S)-1-[[[(2,4-dimethylphenyl)methyl]amino]methyl]-2-(hydroxy)pentyl]amino]-2-oxoethyl]-2-[[(1,1-dimethylethoxy)carbonyl]amino]-5-(trifluoromethyl)benzamide;

N-[2-[[(1S, 2R)-1-[[[(2,4-dimethylphenyl)methyl]amino]methyl]-2-(hydroxy)pentyl]amino]-2-oxoethyl]-2-[[(1,1-dimethylethoxy)carbonyl]amino]-5-(trifluoromethyl)benzamide;

N-[2-[[(1S, 2S)-1-[[[(2,4-dimethylphenyl)methyl]amino]methyl]-2-(hydroxy)pentyl]amino]-2-oxoethyl]-2-amino-5-(trifluoromethyl)benzamide;

N-[2-[[(1S, 2R)-1-[[[(2,4-dimethylphenyl)methyl]amino]methyl]-2-(hydroxy)pentyl]amino]-2-oxoethyl]-2-amino-5-(trifluoromethyl)benzamide;

N-[2-[[(1S, 2S)-1-[[[(2,4-dimethylphenyl)methyl]amino]methyl]-2-(hydroxy)pentyl]amino]-2-oxoethyl]-3-amino-5-(trifluoromethyl)benzamide;

N-[2-[[(1S, 2R)-1-[[[(2,4-dimethylphenyl)methyl]amino]methyl]-2-(hydroxy)pentyl]amino]-2-oxoethyl]-3-amino-5-(trifluoromethyl)benzamide;

N-[2-[[(1S, 2R)-1-[[[(2,4-dimethylphenyl)methyl]amino]methyl]-2-(hydroxy)pentyl]amino]-2-oxoethyl]-3-amino-5-(trifluoromethyl)benzamide;

N-[2-[[(1S, 2S)-1-[[[(2,4-dimethylphenyl)methyl]amino]
methyl]-2-(hydroxy)pentyl]amino]-2-oxoethyl]-2-
[[(ethylamino) carbonyl]amino]-5-(trifluoromethyl)
benzamide;

N-[2-[[(1S, 2R)-1-[[[(2,4-dimethylphenyl)methyl]amino]
methyl]-2-(hydroxy)pentyl]amino]-2-oxoethyl]-2-
[[(ethylamino) carbonyl]amino]-5-(trifluoromethyl)
benzamide;

N-[2-[[(1S, 2S)-1-[[[(2,4-dimethyiphenyl)methyl]amino]
methyl]-2-(hydroxy) pentyl]amino]-2-oxoethyl]-2-
[[(isopropylamino)carbonyl]amino]-5-
(trifluoromethyl)benzamide;

N-[2-[[(1S, 2R)-1-[[[(2,4-dimethyiphenyl)methyl]amino]
methyl]-2-(hydroxy)pentyl]amino]-2-oxoethyl]-2-
[[(isopropylamino)carbonyl]amino]-5-
(trifluoromethyl)benzamide;

N-[2-[[(1S, 2S)-1-[[[(2,4-dimethyiphenyl)methyl]amino]
methyl]-2-(hydroxy)pentyl]amino)-2-oxoethyl]-2-[(1-
pyrrolidinylcarbonyl)amino]-5-(trifluoromethyl)
benzamide;

N-[2-[[(1S, 2S)-1-[[[(2,4-dimethyiphenyl)methyl]amino]
methyl]-2-(hydroxy)pentyl]amino]-2-oxoethyl]-2-[(1-
azetidinylcarbonyl)amino]-5-(trifluoromethyl)
benzamide;

N-[2-[[(1S, 2S)-1-[[[(2,4-dimethyiphenyl)methyl]amino]
methyl]-2-(hydroxy)pentyl]amino]-2-oxoethyl]-2-
[[(methylamino)carbonyl]amino]-5-(trifluoromethyl)
benzamide;

N-[2-[[(1S, 2R)-1-[[[(2,4-dimethyiphenyl)methyl]amino]
methyl]-2-(hydroxy)pentyl]amino]-2-oxoethyl]-2-[[(4-
mopholinylcarbonyl)]amino]-5-(trifluoromethyl)
benzamide;

N-[2-[[(1S, 2R)-1-[[[(2,4-dimethyiphenyl)methyl]amino]
methyl]-2-(hydroxy)pentyl]amino]-2-oxoethyl]-2-[[(1-
piperazinylcarbonyl)]amino]-5-(trifluoromethyl)
benzamide;

N-[2-[[(1S, 2S)-1-[[[(4-ethylphenyl)methyl]amino]
methyl]-2-(hydroxy)pentyl]amino]-2-oxoethyl]-2-[[(1,
1-dimethylethoxy)carbonyl]amino]-5-
(trifluoromethyl)benzamide;

N-[2-[[(1S, 2S)-1-[[[(4-ethylphenyl)methyl]amino]
methyl]-2-(hydroxy)pentyl]amino]-2-oxoethyl]-2-
amino-5-(trifluoromethyl)benzamide;

N-[2-[[(1S, 2S)-1-[[[(4-ethylphenyl)methyl]amino]
methyl]-2-(hydroxy)pentyl]amino]-2-oxoethyl]-2-
[[(isopropylamino)carbonyl]amino]-5-
(trifluoromethyl)benzamide;

N-[2-[[(1S, 2S)-1-[[[(4-ethylphenyl)methyl]amino]
methyl]-2-(hydroxy)pentyl]amino]-2-oxoethyl]-2-[(4-
morpholinylcarbonyl)amino]-5-(trifluoromethyl)
benzamide;

N-[2-[[(1S, 2S)-1-[[[(4-dimethylamino-2-methylphenyl)
methyl]amino]methyl]-2-(hydroxy)pentyl]amino]-2-
oxoethyl]-2-[[(1,1-dimethylethoxy)carbonyl]amino]-
5-(trifluoromethyl)benzamide;

N-[2-[[(1S, 2S)-1-[[[(4-dimethylamino-2-methylphenyl)
methyl]amino]methyl]-2-(hydroxy)pentyl]amino]-2-
oxoethyl]-2-amino-5-(trifluoromethyl)benzamide;

N-[2-[[(1S, 2S)-1-[[[(2,4-dimethyiphenyl)methyl]amino]
methyl]-2-(hydroxy)pentyl]amino]-2-oxoethyl]-2-
(tert-butyl)amino-5- (trifluoromethyl)benzamide;

N-[2-[[(1S, 2S)-1-[[[(2,4-dimethyiphenyl)methyl]amino]
methyl]-2-(hydroxy)pentyl]amino]-2-oxoethyl]-2-
isopropylamino-5-(trifluoromethyl)benzamide;

N-[2-[[(1S, 2S)-1-[[[(2,4-dimethylphenyl)methyl]amino]
methyl]-2-(hydroxy)pentyl]amino]-2-oxoethyl]-2-
benzylamino -5-(trifluoromethyl)benzamide;

N-[2-[[(1S, 2S)-1-[[[(2,4-dimethylphenyl)methyl]amino]
methyl]-2-(methoxy)pentyl]amino]-2-oxoethyl]-2-
[[(1,1-dimethylethoxy)carbonyl]amino]-5-
(trifluoromethyl)benzamide;

N-[2-[[(1S, 2S)-1-[[[(2,4-dimethylphenyl)methyl]amino]
methyl]-2-(methoxy)pentyl]amino]-2-oxoethyl]-2-
amino-5-(trifluoromethyl)benzamide;

N-[2-[[(S)-1-[[[(2,4-dimethyiphenyl)methyl]amino]
methyl]-2-hydroxy-2-(methyl)propyl]amino]-2-
oxoethyl]-2-[[(1,1-dimethylethoxy)carbonyl]amino]-
5-(trifluoromethyl)benzamide;

N-[2-[[(S)-1-[[[(2,4-dimethylphenyl)methyl]amino]
methyl]-2-hydroxy-2 -(methyl)propyl]amino]-2-
oxoethyl]-2-amino-5-(trifluoromethyl)benzamide;

N-[2-[[(S)-1-[[[(2,4-dimethyiphenyl)methyl]amino]
methyl]-2-hydroxy-2 -(ethyl)butyl]amino]-2-
oxoethyl]-2-[[(1,1-dimethylethoxy)carbonyl]amino]-
5-(trifluoromethyl)benzamide;

N-[2-[[(S)-1-[[[(2,4-dimethyiphenyl)methyl]amino]
methyl]-2-hydroxy-2-(ethyl)butyl]amino]-2-oxoethyl]-
2-amino-5-(trifluoromethyl)benzamide;

N-[2-[[(S)-1-[[[(2,4-dimethylphenyl)methyl]amino]
methyl]-2-hydroxy-2-(propyl)pentyl]amino]-2-
oxoethyl]-2-[[(1,1-dimethylethoxy)carbonyl]amino]-
5-(trifluoromethyl)benzamide;

N-[2-[[(S)-1-[[[(2,4-dimethylphenyl)methyl]amino]
methyl]-2-hydroxy-2-(propyl)pentyl]amino]-2-
oxoethyl]-2-amino-5-(trifluoromethyl)benzamide;

N-[2-[[(S)-2-[[(2,4-dimethylphenyl)methyl]amino]-1-
(hydroxycyclopentyl)ethyl]amino]-2-oxoethyl]-2-[[(1,
1-dimethylethoxy)carbonyl]amino]-5-
(trifluoromethyl)benzamide;

N-[2-[[(S)-1-[[(S)-2-[[(2,4-dimethylphenyl)methyl]
amino]-1-(hydroxycyclopentyl)ethyl]amino]-2-
oxoethyl]-2-amino-5-(trifluoromethyl)benzamide;

(2S)-N-tert-Butyl-3-[[(2,4-dimethylphenyl)methyl]
amino]-2-[[[3-(trifluoromethoxy)benzoyl]amino]
acetyl]amino]-propanamide;

(2S)-N-tert-Butyl-3-[[(2,4-dimethylphenyl)methyl]
amino]-2-[[[3-(difluoromethyl)benzoyl]amino]acetyl]
amino]-propanamide;

(2S)-N-tert-Butyl-3-[[(2,4-dimethylphenyl)methyl]
amino]-2-[[[3-(trifluoromethylthio)benzoyl]amino]
acetyl]amino]-propanamide;

(2S)-N-tert-Butyl-3-[[(2,4-dimethylphenyl)methyl]
amino]-2-[[[3-(pentafluoroethyl)benzoyl]amino]
acetyl]amino]-propanamide;

(2S)-N-tert-Butyl-2-[[[2-amino-5-(trifluoromethoxy)
benzoyl]amino]acetyl]amino]-3-[[(2,4-
dimethylphenyl)methyl]amino]-propanamide;

(2S)-N-tert-Butyl-2-[[[2-amino-5-(methyl)benzoyl]
amino]acetyl]amino]-3-[[(2,4-dimethylphenyl)methyl]
amino]-propanamide;

(2S)-N-tert-Butyl-3-[[(2,4-dimethylphenyl)methyl]
amino]-2-[[[2-ethylamino-5-(trifluoromethyl)
benzoyl]amino]acetyl]amino]-propanamide;

(2S)-N-tert-Butyl-3-[[(2,4-dimethylphenyl)methyl]
amino]-2-[[[2-propylamino-5-(trifluoromethyl)
benzoyl]amino]acetyl]amino]-propanamide;

(2S)-N-tert-Butyl-3-[[(2,4-dimethylphenyl)methyl]
amino]-2-[[[2-isobutylamino-5-(trifluoromethyl)
benzoyl]amino]acetyl]amino]-propanamide;

(2S)-N-tert-Butyl-2-[[[[2-butylamino-5-(trifluoromethyl)benzoyl]amino]acetyl]amino]-3-[[(2,4-dimethylphenyl)methyl]amino]-propanamide;

(2S)-N-tert-Butyl-2-[[[[2-cyclohexylamino-5-(trifluoromethyl)benzoyl]amino]acetyl]amino]-3-[[(2,4-dimethylphenyl)methyl]amino]-propanamide;

(2S)-N-tert-Butyl-3-[[(2,4-dimethylphenyl)methyl]amino]-2-[[[[2-isopropylamino-5-(trifluoromethyl)benzoyl]amino]acetyl]amino]-propanamide;

(2S)-N-tert-Butyl-3-[[(2,4-dimethylphenyl)methyl]amino]-2-[[[[2-(tert-butyl)amino-5-(trifluoromethyl)benzoyl]amino]acetyl]amino]-propanamide;

(2S)-N-tert-Butyl-3-[[(2,4-dimethylphenyl)methyl]amino]-2-[[[[2-(methylaminocarbonyl)amino-5-(trifluoromethyl)benzoyl]amino]acetyl]amino]-propanamide;

(2S)-N-tert-Butyl-3-[[(2,4-dimethylphenyl)methyl]amino]-2-[[[[2-(isopropoxycarbonyl)amino-5-(trifluoromethyl)benzoyl]amino]acetyl]amino]-propanamide;

(2S)-N-tert-Butyl-3-[[(2,4-dimethylphenyl)methyl]amino]-2-[[[[2-(isopropylaminocarbonyl)amino-5-(trifluoromethyl)benzoyl]amino]acetyl]amino]-propanamide;

(2S)-N-tert-Butyl-2-[[[[2-(cyclohexylcarbonyl)amino-5-(trifluoromethyl)benzoyl]amino]acetyl]amino]-3-[[(2,4-dimethylphenyl)methyl]amino]-propanamide;

(2S)-N-tert-Butyl-2-[[[[2-benzylamino-5-(trifluoromethyl)benzoyl]amino]acetyl]amino]-3-[[(2,4-dimethylphenyl)methyl]amino]-propanamide;

(2S)-N-tert-Butyl-2-[[[[2-(para-chloro)benzylamino-5-(trifluoromethyl)benzoyl]amino]acetyl]amino]-3-[[(2,4-dimethylphenyl)methyl]amino]-propanamide;

(2S)-N-tert-Butyl-2-[[[[2-[(beta-napthyl)methyl]amino-5-(trifluoromethyl)benzoyl]amino]acetyl]amino]-3-[[(2,4-dimethylphenyl)methyl]amino]-propanamide;

(2S)-N-tert-Butyl-2-[[[[2-(meta-methyl)benzylamino-5-(trifluoromethyl)benzoyl]amino]acetyl]amino]-3-[[(2,4-dimethylphenyl)methyl]amino]-propanamide;

(2S)-N-tert-Butyl-2-[[[[2-(para-methyl)benzylamino-5-(trifluoromethyl)benzoyl]amino]acetyl]amino]-3-[[(2,4-dimethylphenyl)methyl]amino]-propanamide;

(2S)-N-tert-Butyl-2-[[[[2-(ortho-methyl)benzylamino-5-(trifluoromethyl)benzoyl]amino]acetyl]amino]-3-[[(2,4-dimethylphenyl)methyl]amino]-propanamide;

(2S)-N-tert-Butyl-3-[[(2,4-dimethylphenyl)methyl]amino]-2-[[[[2-(para-trifluoromethyl)benzylamino-5-(trifluoromethyl)benzoyl]amino]acetyl]amino]-propanamide;

(2S)-N-tert-Butyl-2-[[[[3-amino-5-(trifluoromethyl)benzoyl]amino]acetyl]amino]-3-[[(2,4-dimethylphenyl)methyl]amino]-propanamide;

(2S)-N-tert-Butyl-2-[[[[3-benzylamino-5-(trifluoromethyl)benzoyl]amino]acetyl]amino]-3-[[(2,4-dimethylphenyl)methyl]amino]-propanamide;

(2S)-N-tert-Butyl-2-[[[[3-methylamino-5-(trifluoromethyl)benzoyl]amino]acetyl]amino]-3-[[(2,4-dimethylphenyl)methyl]amino]-propanamide;

(2S)-N-tert-Butyl-2-[[[[3-ethylamino-5-(trifluoromethyl)benzoyl]amino]acetyl]amino]-3-[[(2,4-dimethylphenyl)methyl]amino]-propanamide;

(2S)-N-tert-Butyl-2-[[[[3-isobutylamino-5-(trifluoromethyl)benzoyl]amino]acetyl]amino]-3-[[(2,4-dimethylphenyl)methyl]amino]-propanamide;

(2S)-N-tert-Butyl-2-[[[[3-propylamino-5-(trifluoromethyl)benzoyl]amino]acetyl]amino]-3-[[(2,4-dimethylphenyl)methyl]amino]-propanamide;

(2S)-N-tert-Butyl-2-[[[[3-butylamino-5-(trifluoromethyl)benzoyl]amino]acetyl]amino]-3-[[(2,4-dimethylphenyl)methyl]amino]-propanamide;

(2S)-N-tert-Butyl-2-[[[[3-(trifluoromethylcarbonyl)amino-5-(trifluoromethyl)benzoyl]amino]acetyl]amino]-3-[[(2,4-dimethylphenyl)methyl]amino]-propanamide;

(2S)-N-tert-Butyl-2-[[[[3-(ethoxycarbonyl)amino-5-(trifluoromethyl)benzoyl]amino]acetyl]amino]-3-[[(2,4-dimethylphenyl)methyl]amino]-propanamide;

(2S)-2-[[[[2-amino-5-(trifluoromethyl)benzoyl]amino]acetyl]amino]-3-[[(2-methyl-4-bromophenyl)methyl]amino]-propanamide;

(2S)-2-[[[[2-amino-5-(trifluoromethyl)benzoyl]amino]acetyl]amino]-3-[[(4-bromophenyl)methyl]amino]-propanamide;

(2S)-N-tert-Butyl-3-[[(4-methylphenyl)methyl]amino]-2-[[[[3-(trifluoromethyl)benzoyl]amino]acetyl]amino]-propanamide;

(2S)-N-tert-Butyl-3-[[(4-bromophenyl)methyl]amino]-2-[[[[3-(trifluoromethyl)benzoyl]amino]acetyl]amino]-propanamide;

(2S)-N-tert-Butyl-3-[[(4-bromo-2-methylphenyl)methyl]amino]-2-[[[[3-(trifluoromethyl)benzoyl]amino]acetyl]amino]-propanamide;

(2S)-N-tert-Butyl-3-[[(4-methoxyphenyl)methyl]amino]-2-[[[[3-(trifluoromethyl)benzoyl]amino]acetyl]amino]-propanamide;

(2S)-N-tert-Butyl-3-[[(4-methoxy-2-methylphenyl)methyl]amino]-2-[[[[3-(trifluoromethyl)benzoyl]amino]acetyl]amino]-propanamide;

(2S)-N-tert-Butyl-3-[[(2,3-dimethyl-4-methoxy-phenyl)methyl]amino]-2-[[[[3-(trifluoromethyl)benzoyl]amino]acetyl]amino]-propanamide;

(2S)-N-tert-Butyl-3-[[(4-cyano-2-methylphenyl)methyl]amino]-2-[[[[3-(trifluoromethyl)benzoyl]amino]acetyl]amino]-propanamide;

(2S)-N-tert-Butyl-3-[[(4-ethylphenyl)methyl]amino]-2-[[[[3-(trifluoromethyl)benzoyl]amino]acetyl]amino]-propanamide;

(2S)-N-tert-Butyl-3-[[(2-methyl-4-vinylphenyl)methyl]amino]-2-[[[[3-(trifluoromethyl)benzoyl]amino]acetyl]amino]-propanamide;

(2S)-N-tert-Butyl-3-[[(4-ethyl-2-methylphenyl)methyl]amino]-2-[[[[3-(trifluoromethyl)benzoyl]amino]acetyl]amino]-propanamide;

(2S)-N-tert-Butyl-3-[[(4-isopropylphenyl)methyl]amino]-2-[[[[3-(trifluoromethyl)benzoyl]amino]acetyl]amino]-propanamide;

(2S)-N-tert-Butyl-3-[[(4-butylphenyl)methyl]amino]-2-[[[[3-(trifluoromethyl)benzoyl]amino]acetyl]amino]-propanamide;

(2S)-N-tert-Butyl-3-[[(4-dimethylaminophenyl)methyl]amino]-2-[[[[3-(trifluoromethyl)benzoyl]amino]acetyl]amino]-propanamide;

(2S)-N-tert-Butyl-3-[[(4-dimethylamino-2-methylphenyl)methyl]amino]-2-[[[[3-(trifluoromethyl)benzoyl]amino]acetyl]amino]-propanamide;

(2S)-N-tert-Butyl-3-[[(4-methylthiophenyl)methyl]amino]-2-[[[[3-(trifluoromethyl)benzoyl]amino]acetyl]amino]-propanamide;

(2S)-N-tert-Butyl-3-[[(4-methylsulfonylphenyl)methyl]amino]-2-[[[[3-(trifluoromethyl)benzoyl]amino]acetyl]amino]-propanamide;

(2S)-N-tert-Butyl-3-[[(4-trifluoromethoxyphenyl)methyl]amino]-2-[[[[3-(trifluoromethyl)benzoyl]amino]acetyl]amino]-propanamide;

(2S)-N-tert-Butyl-3-[[(3-amino-4-methylphenyl)methyl]amino]-2-[[[[3-(trifluoromethyl)benzoyl]amino]acetyl]amino]-propanamide;

(2S)-N-tert-Butyl-3-[[(2-methylphenyl)methyl]amino]-2-[[[[3-(trifluoromethyl)benzoyl]amino]acetyl]amino]-propanamide;

(2S)-N-tert-Butyl-3-[[(2-ethylphenyl)methyl]amino]-2-[[[[3-(trifluoromethyl)benzoyl]amino]acetyl]amino]-propanamide;

(2R)-N-Ethyl-3-[[(2,4-dimethylphenyl)methyl]amino]-2-[[[[3-(trifluoromethyl)benzoyl]amino]acetyl]amino]-propanamide;

(2R)-N-tert-Butyl-3-[[(2,4-dimethylphenyl)methyl]amino]-2-[[[[3-(trifluoromethyl)benzoyl]amino]acetyl]amino]-propanamide;

(2R)-N-[(2-methyl)hydroxyprop-2-yl]-3-[[(2,4-dimethylphenyl)methyl]amino]-2-[[[[3-(trifluoromethyl)benzoyl]amino]acetyl]amino]-propanamide;

(2S)-N-tert-Amyl-3-[[(2,4-dimethylphenyl)methyl]amino]-2-[[[[3-(trifluoromethyl)benzoyl]amino]acetyl]amino]-propanamide;

(2S)-N-[(2-methyl)hydroxyprop-2-yl]-3-[[(2,4-dimethylphenyl)methyl]amino]-2-[[[[3-(trifluoromethyl)benzoyl]amino]acetyl]amino]-propanamide;

(2S)-N-[(1-methyl)cycloprop-1-yl]-3-[[(2,4-dimethylphenyl)methyl]amino]-2-[[[[3-(trifluoromethyl)benzoyl]amino]acetyl]amino]-propanamide;

(2S)-N-Cyclopentyl-3-[[(2,4-dimethylphenyl)methyl]amino]-2-[[[[3-(trifluoromethyl)benzoyl]amino]acetyl]amino]-propanamide;

(2S)-N-Cyclohexyl-3-[[(2,4-dimethylphenyl)methyl]amino]-2-[[[[3-(trifluoromethyl)benzoyl]amino]acetyl]amino]-propanamide;

(2S)-N-(β,β,β-Trifluoro)ethyl-3-[[(2,4-dimethylphenyl)methyl]amino]-2-[[[[3-(trifluoromethyl)benzoyl]amino]acetyl]amino]-propanamide;

(2S)-N-Allyl-3-[[(2,4-dimethylphenyl)methyl]amino]-2-[[[[3-(trifluoromethyl)benzoyl]amino]acetyl]amino]-propanamide;

(2S)-N-Cyclopropylmethyl-3-[[(2,4-dimethylphenyl)methyl]amino]-2-[[[[3-(trifluoromethyl)benzoyl]amino]acetyl]amino]-propanamide;

N-[2-[[(2S)-3-[[(2,4-dimethylphenyl)methyl]amino]-1-(pyrrolid-3-enyl)-1-oxopropyl-2-amino]-2-oxoethyl]-3-(trifluoromethyl)benzamide;

N-[2-[[(2S)-3-[[(2,4-dimethylphenyl)methyl]amino]-1-(pyrrolidinyl)-1-oxopropyl-2-amino]-2-oxoethyl]-3-(trifluoromethyl)benzamide;

N-[2-[[(2S)-3-[[(2,4-dimethylphenyl)methyl]amino]-1-(morpholinyl)-1-oxopropyl-2-amino]-2-oxoethyl]-3-(trifluoromethyl)benzamide;

(2S)-N-Isobutyl-3-[[(2,4-dimethylphenyl)methyl]amino]-2-[[[[3-(trifluoromethyl)benzoyl]amino]acetyl]amino]-propanamide;

(2S)-N-sec-Butyl-3-[[(2,4-dimethylphenyl)methyl]amino]-2-[[[[3-(trifluoromethyl)benzoyl]amino]acetyl]amino]-propanamide;

(2S)-N-tert-Butyl-4-[[(2,4-dimethylphenyl)methyl]amino]-3-[[[[3-(trifluoromethyl)benzoyl]amino]acetyl]amino]-butanamide;

(2S, 3R)-N-Ethyl-3-[[(2,4-dimethylphenyl)methyl]amino]-2-[[[[3-(trifluoromethyl)benzoyl]amino]acetyl]amino]-butanamide;

(2S, 3R)-N-Ethyl-3-[[(4-bromophenyl)methyl]amino]-2-[[[[3-(trifluoromethyl)benzoyl]amino]acetyl]amino]-butanamide;

Methyl (2R)-2-[[(2,4-dimethylphenyl)methyl]amino]-3-[[[[3-(trifluoromethyl)benzoyl]amino]acetyl]amino]-propanoate;

(2R)-N-Ethyl-2-[[(2,4-dimethylphenyl)methyl]amino]-3-[[[[3-(trifluoromethyl)benzoyl]amino]acetyl]amino]-propanamide;

Methyl (2S)-4-[[(2,4-dimethylphenyl)methyl]amino]-2-[[[[3-(trifluoromethyl)benzoyl]amino]acetyl]amino]-butanoate;

(2S)-4-[[(2,4-dimethylphenyl)methyl]amino]-2-[[[[3-(trifluoromethyl)benzoyl]amino]acetyl]amino]-butanamide;

(2S)-N-Ethyl-4-[[(2,4-dimethylphenyl)methyl]amino]-2-[[[[3-(trifluoromethyl)benzoyl]amino]acetyl]amino]-butanamide;

(2S)-N-Ethyl-4-[[(2,4-dimethylphenyl)methyl]methylamino]-2-[[[[3-(trifluoromethyl)benzoyl]amino]acetyl]amino]-butanamide;

(2S)-N-tert-Butyl-2-[[[[2-[[(1,1-dimethylethoxy)carbonyl]amino]-5-(trifluoromethyl)benzoyl]amino]acetyl]amino]-4-[[(2,4-dimethylphenyl)methyl]amino]-butanamide;

(2S)-N-tert-Butyl-2-[[[[2-[[(1,1-dimethylethoxy)carbonyl]amino]-5-(trifluoromethyl)benzoyl]amino]acetyl]amino]-4-[[(2,4-dimethylphenyl)methyl]methylamino]-butanamide;

(2S)-N-tert-Butyl-2-[[[[2-amino-5-(trifluoromethyl)benzoyl]amino]acetyl]amino]-4-[[(2,4-dimethylphenyl)methyl]amino]-butanamide;

(2S)-N-tert-Butyl-2-[[[[2-amino-5-(trifluoromethyl)benzoyl]amino]acetyl]amino]-4-[[(2,4-dimethylphenyl)methyl]methylamino]-butanamide;

(2S)-N-tert-Butyl-2-[[[[3-amino-5-(trifluoromethyl)benzoyl]amino]acetyl]amino]-4-[[(2,4-dimethylphenyl)methyl]amino]-butanamide;

(2S)-N-tert-Butyl-2-[[[[3-amino-5-(trifluoromethyl)benzoyl]amino]acetyl]amino]-4-[[(4-ethylphenyl)methyl]amino]-butanamide;

(2S)-N-tert-Butyl-4-[[(2,4-dimethylphenyl)methyl]amino]-2-[[[[3-(trifluoromethyl)benzoyl]amino]acetyl]amino]-butanamide;

(2S)-N-tert-Butyl-4-[[(4-ethylphenyl)methyl]amino]-2-[[[[3-(trifluoromethyl)benzoyl]amino]acetyl]amino]-butanamide;

(2S)-N-Ethyl-5-[[(2,4-dimethylphenyl)methyl]amino]-2-[[[[3-(trifluoromethyl)benzoyl]amino]acetyl]amino]-pentanamide;

N-[2-[[(1S, 2S/R)-1-[[[(2,4-dimethylphenyl)methyl]methylamino]methyl]-2-hydroxy-3-(methyl)butyl]amino]-2-oxoethyl]-3-(trifluoromethyl)benzamide;

N-[2-[[(1S, 2S)-1-[[[(2,4-dimethylphenyl)methyl]methylamino]methyl]-2-(hydroxy)pentyl]amino]-2-oxoethyl]-2-[[(isopropylamino) carbonyl]amino]-5-(trifluoromethyl)benzamide;

N-[2-[[(1S, 2S)-1-[[[(2,4-dimethylphenyl)methyl]isopropylamino]methyl]-2-(hydroxy)pentyl]amino]-2- oxoethyl]-2-[[(isopropylamino) carbonyl]amino]-5-(trifluoromethyl)benzamide;

N-[2-[[(1S, 2S)-1-[[[(4-ethylphenyl)methyl]methylamino]methyl]-2-(hydroxy)pentyl]amino]-2-oxoethyl]-2-[[(isopropylamino) carbonyl]amino]-5-(trifluoromethyl)benzamide;

N-[2-[[(1S, 2S)-1-[[[(4-ethylphenyl)methyl]isopropylamino]methyl]-2-(hydroxy)pentyl]amino]-2-oxoethyl]-2-[[(isopropylamino) carbonyl]amino]-5-(trifluoromethyl)benzamide;

(2S)-N-tert-Butyl-3-[[(2,4-dimethylphenyl)methyl]methylamino]-2-[[[[3-(trifluoromethyl)benzoyl]amino]acetyl]amino]-propanamide; and (2S)-N-Ethyl-3-[[(2,4-dimethylphenyl)methyl]amino]-2-[[[[2-amino-5-(trifluoromethyl)benzoyl]amino]acetyl]amino]2-methyl-propanamide.

11. A pharmaceutical composition, comprising a pharmaceutically acceptable carrier and a therapeutically effective amount of a compound of claim 1.

12. A method for antagonizing MCP-1 activity comprising administering to a patient in need thereof a therapeutically effective amount of a compound of claim 1.

13. The method for treating disorders, comprising administering to a patient in need thereof a therapeutically effective amount of a compound of claim 1, wherein said disorders being selected from psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, and rheumatoid arthritis.

14. The method for treating disorders, of claim 13, wherein said disorders being selected from alveolitis, colitis, systemic lupus erythematosus, nephrotoxic serum nephritis, glomerularnephritis, asthma, multiple sclerosis, artherosclerosis, and rheumatoid arthritis.

15. The method for treating disorders, of claim 14, wherein said disorders being selected from asthma, multiple sclerosis, artherosclerosis, and rheumatoid arthritis.

16. A method for treating rheumatoid arthritis, comprising administering to a patient in need thereof a therapeutically effective amount of a compound of claim 1.

17. A method for treating multiple sclerosis, comprising administering to a patient in need thereof a therapeutically effective amount of a compound of claim 1.

18. A method for treating atherosclerosis, comprising administering to a patient in need thereof a therapeutically effective amount of a compound of claim 1.

19. A method for treating asthma, comprising administering to a patient in need thereof a therapeutically effective amount of a compound of claim 1.

20. A method for antagonizing CCR2 activity comprising administering to a patient in need thereof a therapeutically effective amount of a compound of claim 1.

21. A method for treating disorders, comprising administering to a patient in need thereof a therapeutically effective amount of a compound of claim 9, said disorders being selected from asthma, multiple sclerosis, artherosclerosis, and rheumatoid arthritis.

22. A method for treating rheumatoid arthritis, comprising administering to a patient in need thereof a therapeutically effective amount of a compound of claim 9.

23. A method for treating multiple sclerosis, comprising administering to a patient in need thereof a therapeutically effective amount of a compound of claim 9.

24. A method for treating atherosclerosis, comprising administering to a patient in need thereof a therapeutically effective amount of a compound of claim 9.

25. A method for treating asthma, comprising administering to a patient in need thereof a therapeutically effective amount of a compound of claim 9.

26. A method for antagonizing CCR2 activity comprising administering to a patient in need thereof a therapeutically effective amount of a compound of claim 9.

* * * * *

UNITED STATES PATENT AND TRADEMARK OFFICE
CERTIFICATE OF CORRECTION

| | | |
|---|---|---|
| PATENT NO. | : 6,974,836 B2 | Page 1 of 1 |
| APPLICATION NO. | : 10/027505 | |
| DATED | : December 13, 2005 | |
| INVENTOR(S) | : Percy Carter and Robert Cherney | |

It is certified that error appears in the above-identified patent and that said Letters Patent is hereby corrected as shown below:

At column 196, line 49, delete the "C2-8" and insert -- $C_{2-8}$ --;
at column 196, line 56, delete the "$(CR'R')_rNR^{5f}C(O)O(CR'R')_rR^{5d}$," and insert -- $(CR'R')_rNR^{5f}C(O)O(CR'R')_rR^{5d}$, --;
at column 201, line 62, delete the "and --NHC(O)$R^{16c}$;" and insert -- and --NHC(O)$R^{16c}$; --;
at column 202, line 8, delete the "-$SO^2$-," and insert -- -$SO_2$-, --;
at column 203, line 41, delete the "C2-8" and insert -- $C_{2-8}$ --;
at column 212, line 34, delete the "[[[[3-(trifluoromethyl)benzoyl amino] acetyl]" and insert -- [[[[3-(trifluoromethyl)benzoyl]amino] acetyl] --.

Signed and Sealed this

Twenty-second Day of August, 2006

JON W. DUDAS
*Director of the United States Patent and Trademark Office*